(12) United States Patent
Kern

(10) Patent No.: US 12,241,114 B2
(45) Date of Patent: Mar. 4, 2025

(54) BIOPHYSICAL PLATFORM FOR DRUG DEVELOPMENT BASED ON ENERGY LANDSCAPE

(71) Applicant: BRANDEIS UNIVERSITY, Waltham, MA (US)

(72) Inventor: Dorothee Kern, Waltham, MA (US)

(73) Assignee: Brandeis University, Waltham, MA (US)

(*) Notice: Subject to any disclaimer, the term of this patent is extended or adjusted under 35 U.S.C. 154(b) by 1490 days.

(21) Appl. No.: 15/524,181

(22) PCT Filed: Nov. 4, 2015

(86) PCT No.: PCT/US2015/059086
§ 371 (c)(1),
(2) Date: May 3, 2017

(87) PCT Pub. No.: WO2016/073639
PCT Pub. Date: May 12, 2016

(65) Prior Publication Data
US 2017/0356024 A1 Dec. 14, 2017

Related U.S. Application Data

(60) Provisional application No. 62/075,043, filed on Nov. 4, 2014.

(51) Int. Cl.
| | | |
|---|---|---|
| *C12Q 1/48* | (2006.01) | |
| *G01N 33/557* | (2006.01) | |
| *G01N 33/573* | (2006.01) | |
| *G16C 10/00* | (2019.01) | |

(52) U.S. Cl.
CPC ............ *C12Q 1/485* (2013.01); *G01N 33/557* (2013.01); *G01N 33/573* (2013.01); *G16C 10/00* (2019.02); *G01N 2333/91205* (2013.01); *G01N 2500/00* (2013.01); *G01N 2500/04* (2013.01); *G01N 2500/20* (2013.01)

(58) Field of Classification Search
None
See application file for complete search history.

(56) References Cited

U.S. PATENT DOCUMENTS

| | | |
|---|---|---|
| 2009/0005356 A1 | 1/2009 | Blaney et al. |
| 2009/0092961 A1 | 4/2009 | Agarwal |
| 2011/0268713 A1 | 11/2011 | Gaucher |
| 2013/0123281 A1 | 5/2013 | Vankayalapati et al. |
| 2014/0134647 A1 | 5/2014 | Benedict et al. |
| 2014/0229150 A1 | 8/2014 | Tsumura et al. |

OTHER PUBLICATIONS

International Search Report and Written Opinion, for corresponding PCT/US2015/059086, dated Jan. 29, 2016 (14 pages).

*Primary Examiner* — Lori A. Clow
(74) *Attorney, Agent, or Firm* — Karen A. LeCuyer; DeWitt LLP

(57) ABSTRACT

In one aspect, the present invention provides a method of selecting or identifying an agent that inhibits a target protein having an active site. In another aspect, the invention provides a method of selecting an agent that inhibits a target protein having an active site for further optimization. In some embodiments, the methods comprise measuring or predicting stability of an induced fit conformation of an agent contacted to an active site of the protein, wherein the agent is selected if the stability of the induced fit conformation of the agent contacted to the active site of the protein is increased relative to a reference stability.

14 Claims, 109 Drawing Sheets
Specification includes a Sequence Listing.

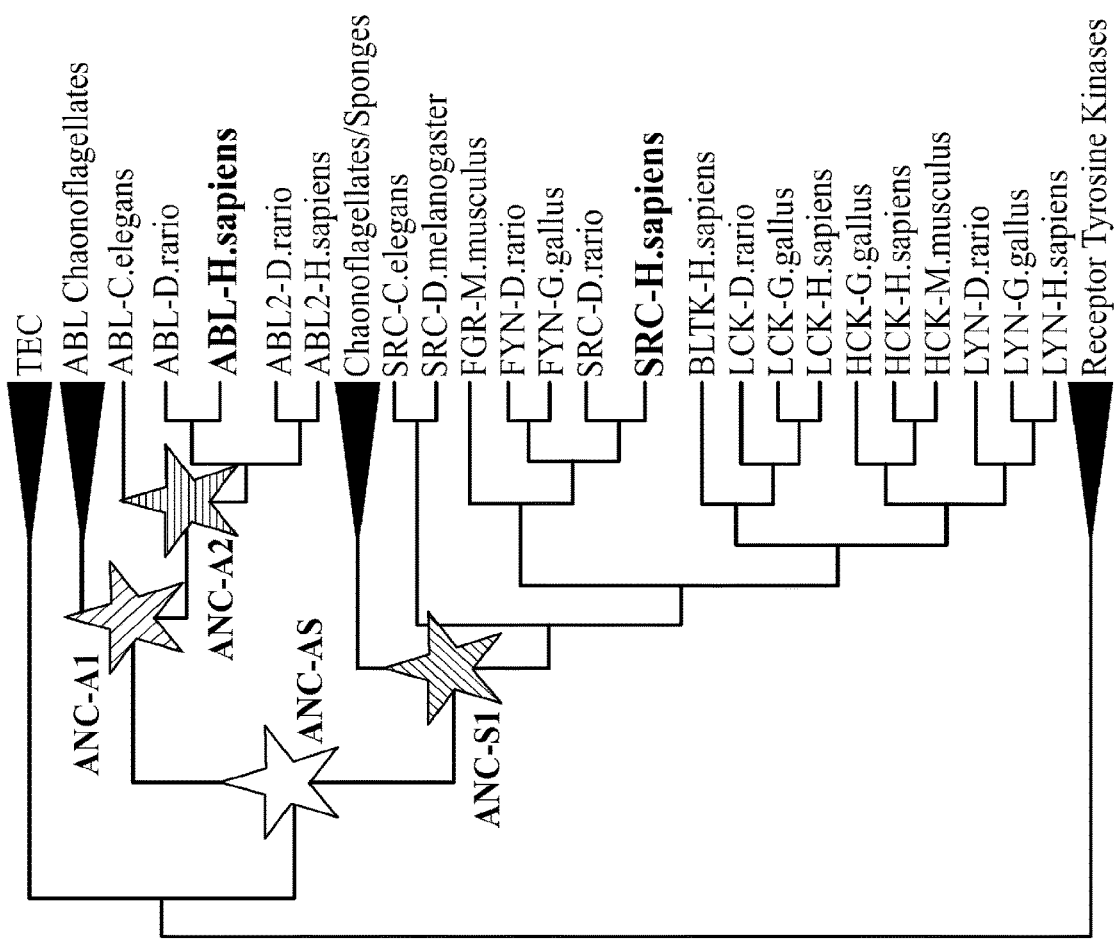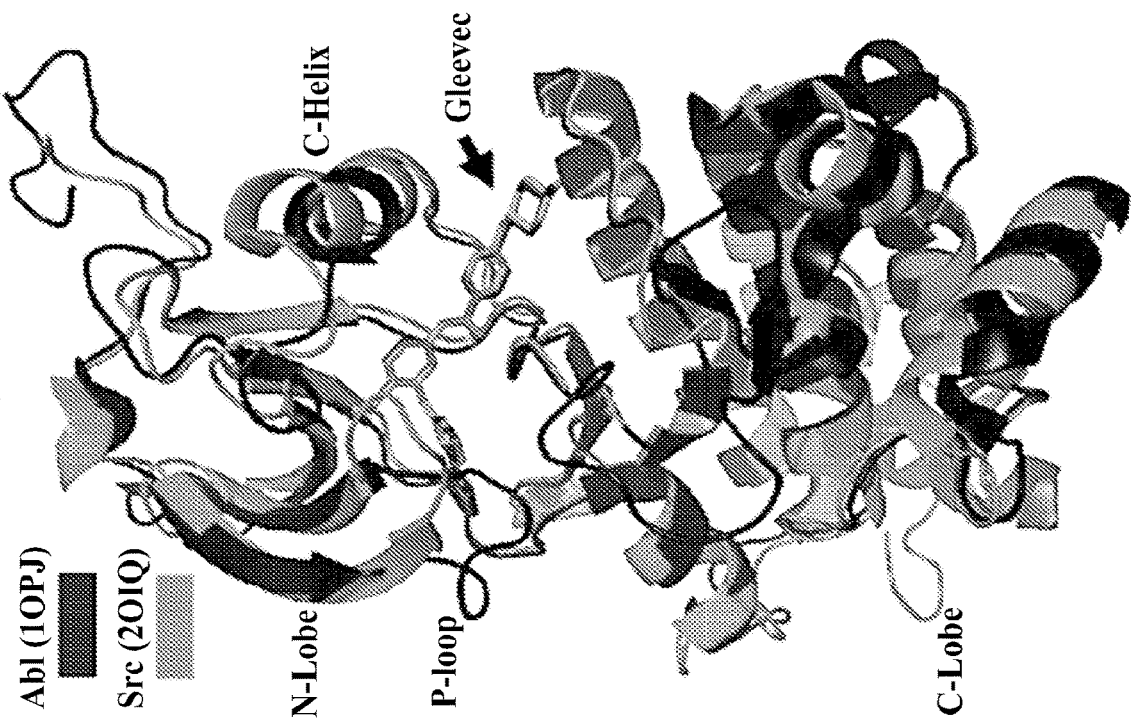
FIG. 1A
FIG. 1B

FIG. 3A
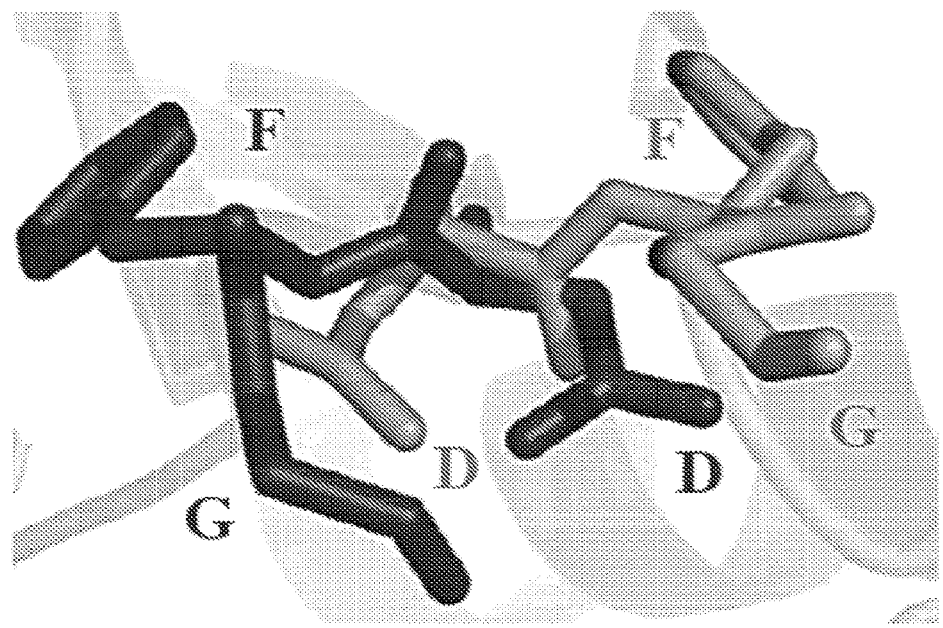
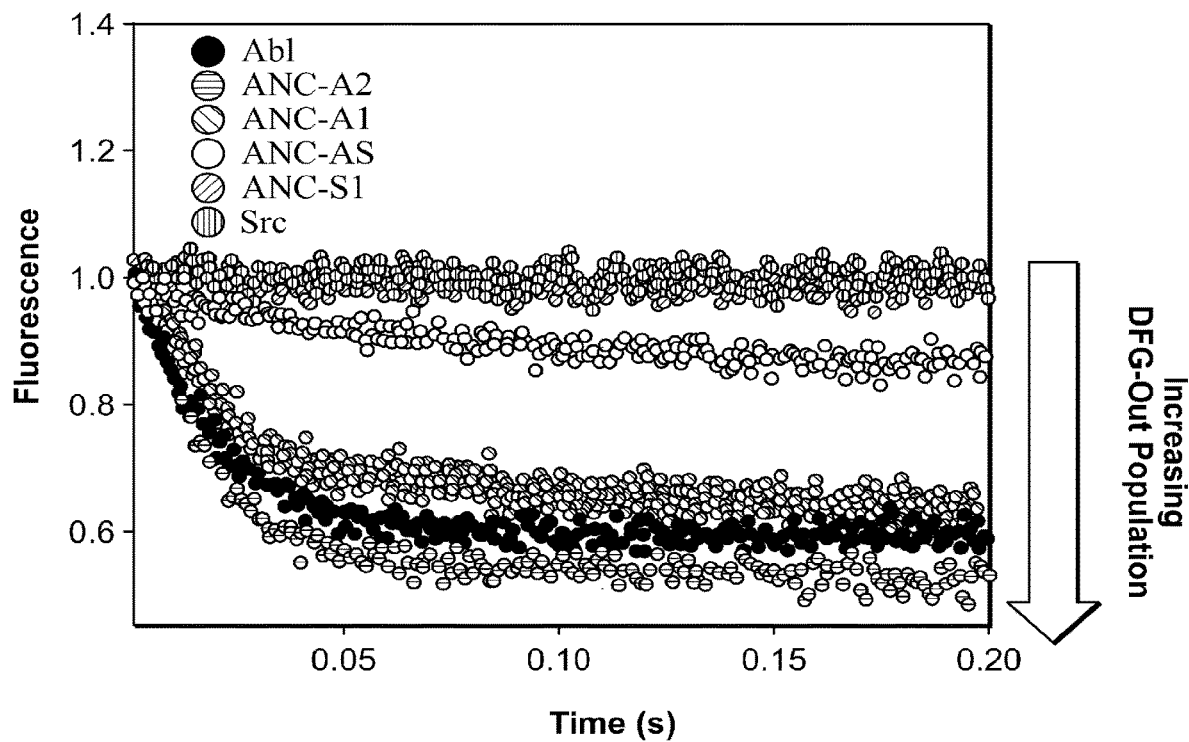

FIG. 3B
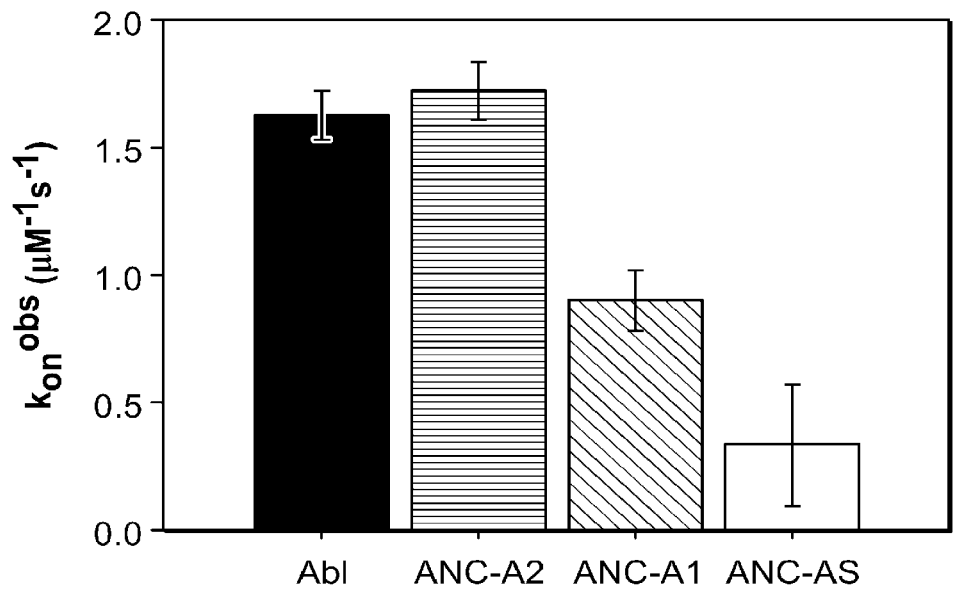
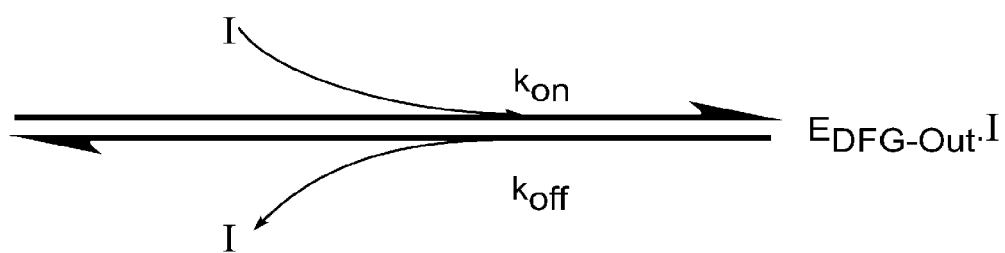
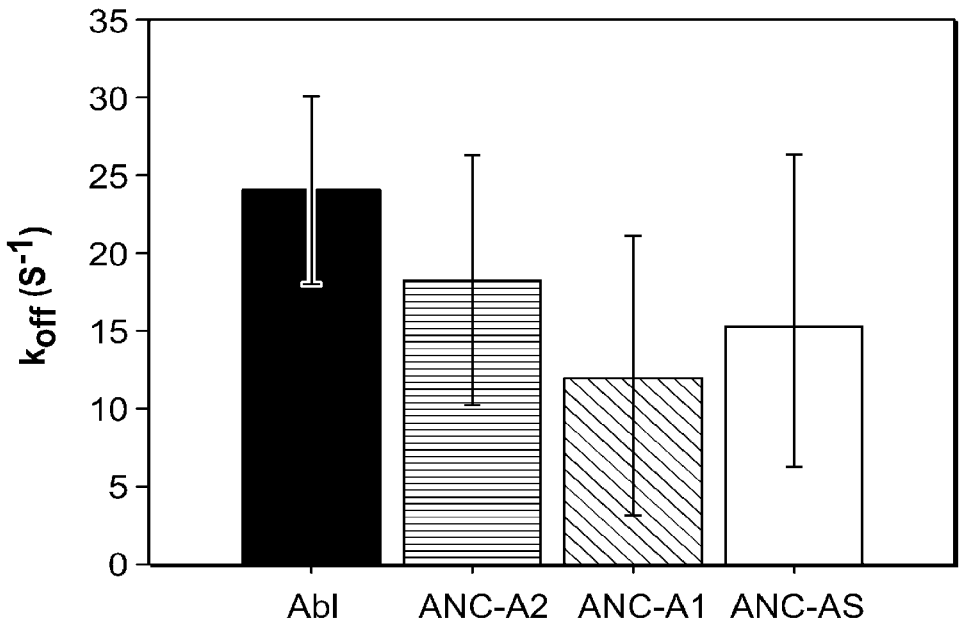

FIG. 3C
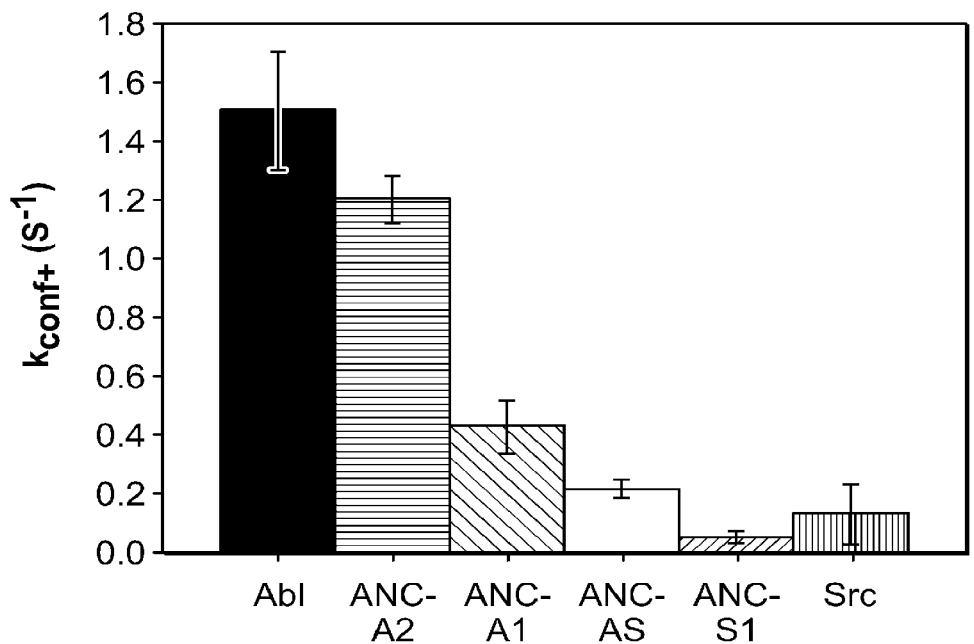
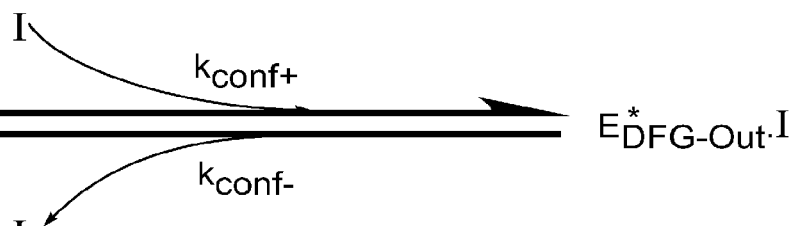
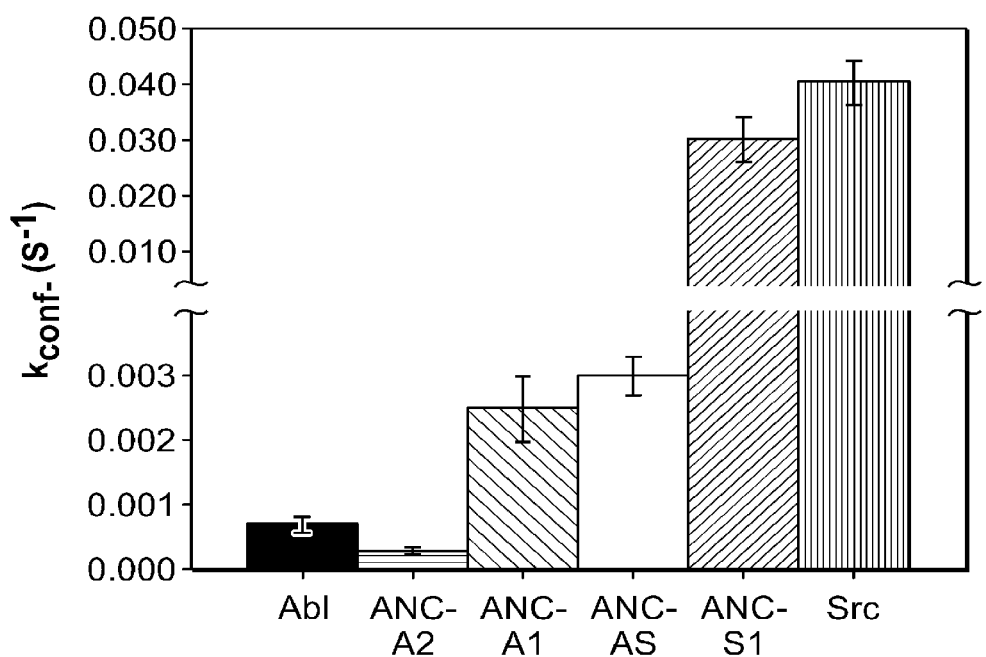

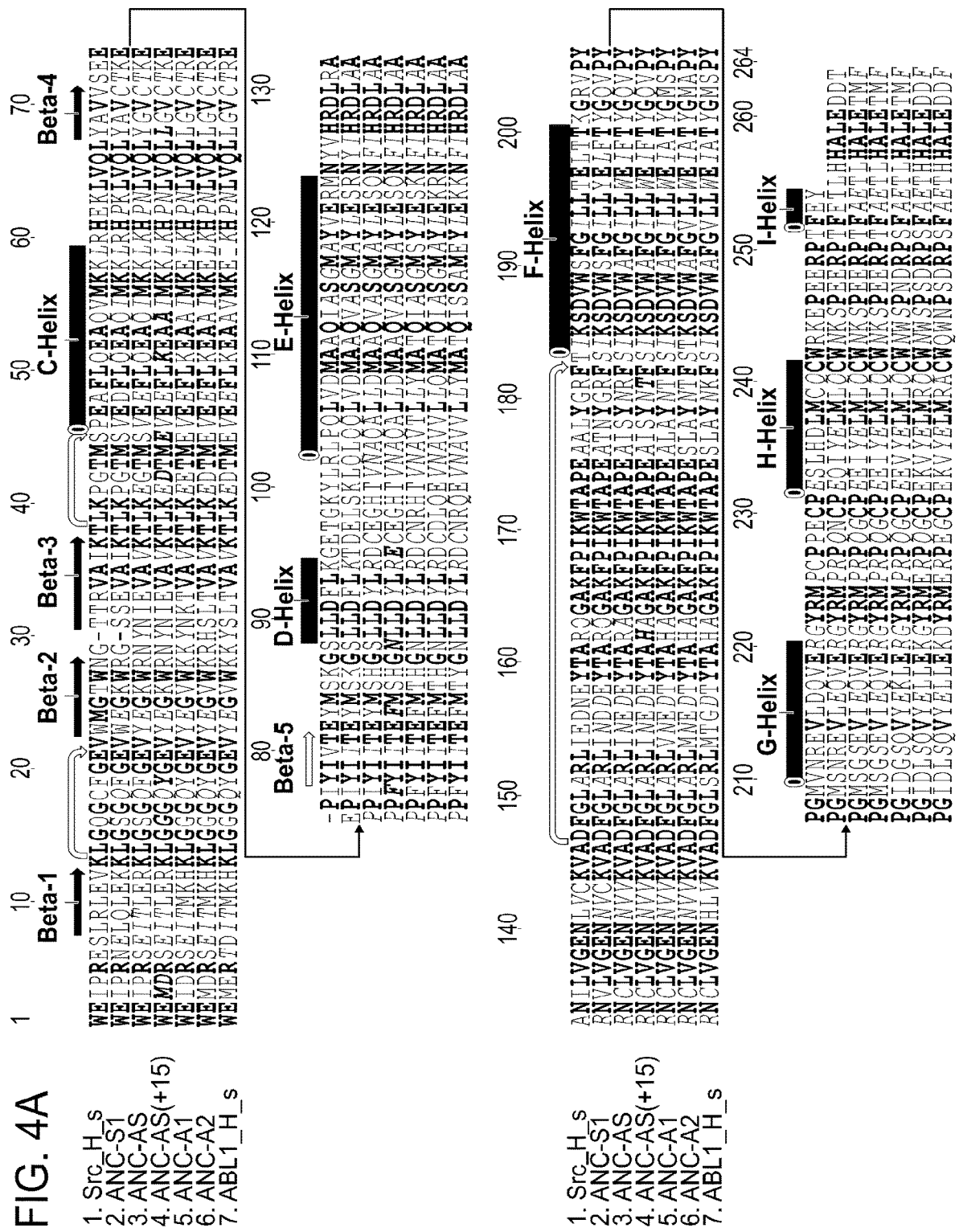

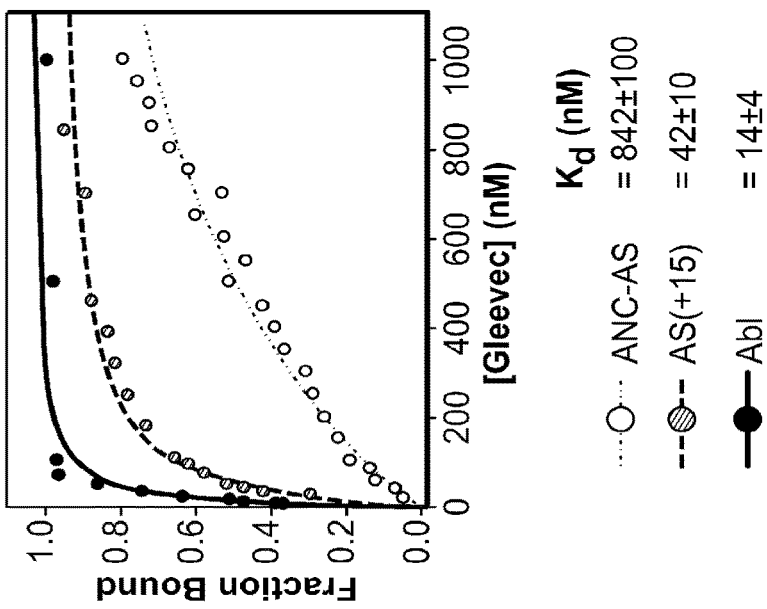
FIG. 4D
FIG. 4C
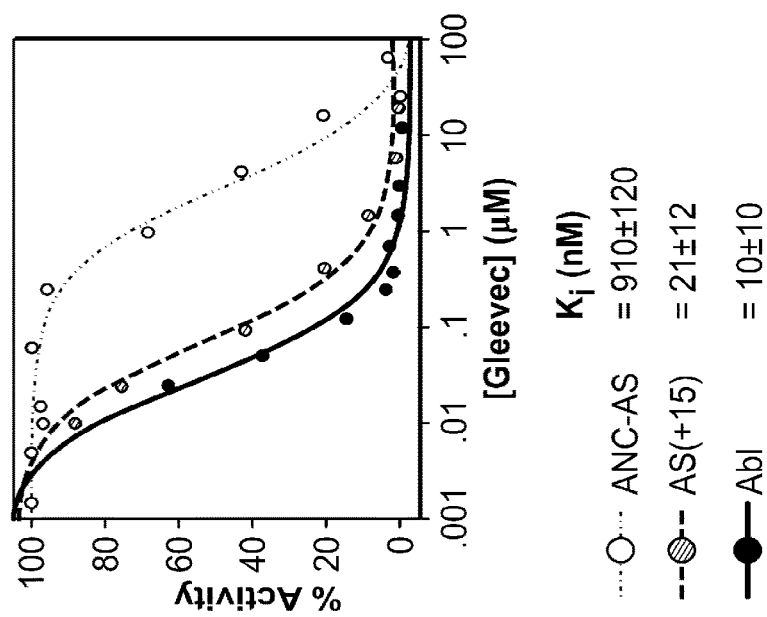
FIG. 4B
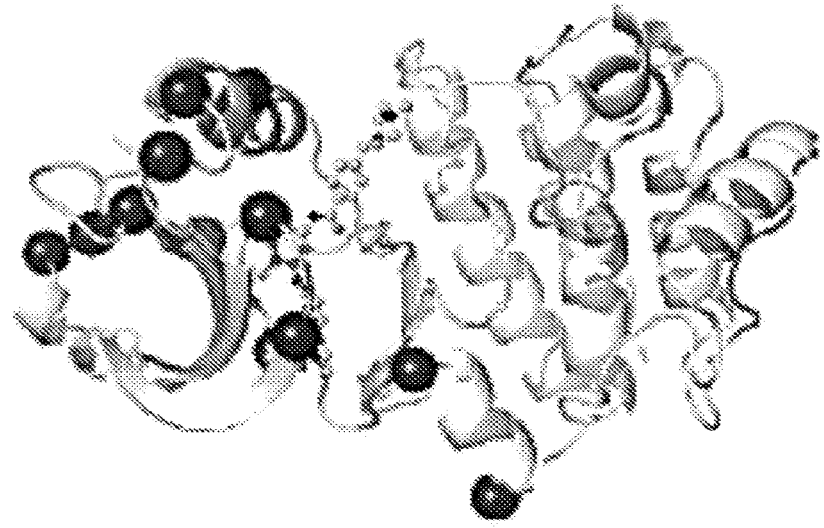

| Src | ANC-AS (AS+15) | Abl |
|---|---|---|
| Q275 | S16 (G) | G269 |
| F278 | F19 (Y) | Y272 |
| G300 | G42 (D) | D295 |
| S303 | S45 (E) | E298 |
| Q309 | Q51 (K) | K304 |
| Q312 | Q54 (A) | A307 |
| Y326 | Y68 (L) | L321 |
| I335 | I77 (F) | F330 |
| Y341 | Y83 (F) | F336 |
| S346 | S88 (N) | N341 |

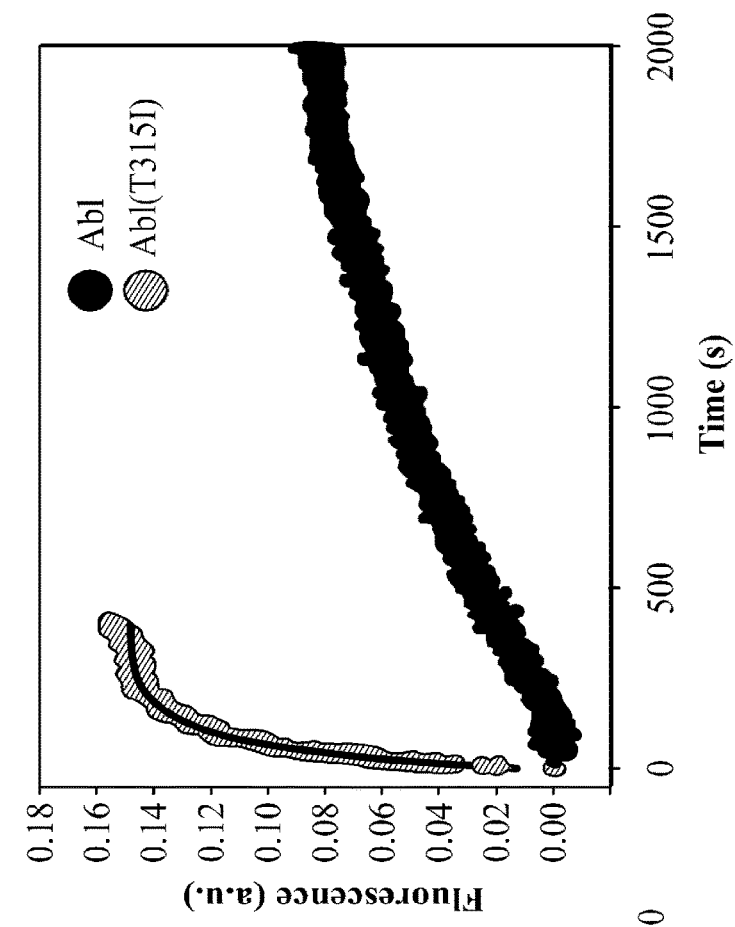
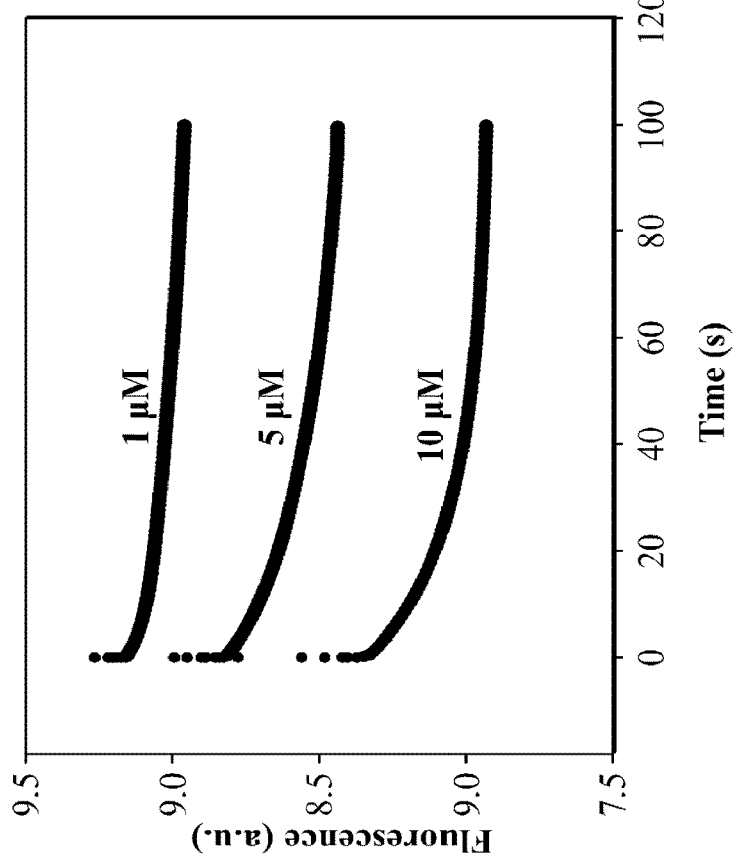
FIG. 5A
FIG. 5B

FIG. 5E
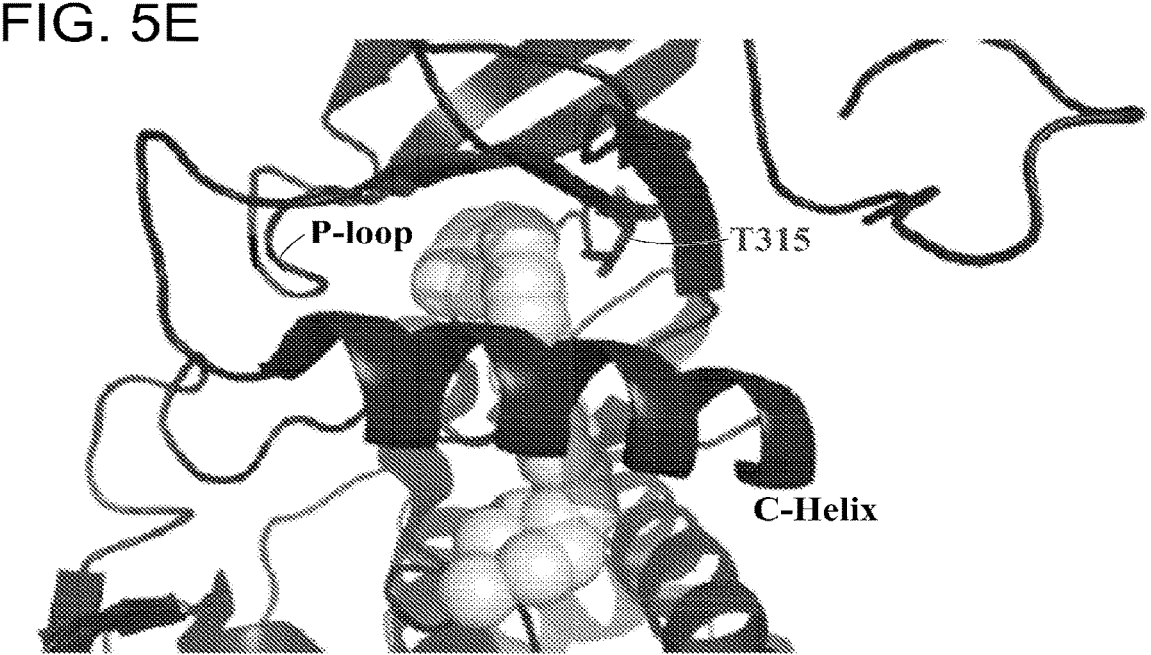
FIG. 5F
|  | Abl | Abl (T315I) |
|---|---|---|
| $k_{on}^{obs}$ ($\mu M^{-1} s^{-1}$) | $1.6 \pm 0.1$ | $0.96 \pm 0.05$ |
| $k_{off}$ ($s^{-1}$) | $24 \pm 6$ | $15.0 \pm 0.8$ |
| $k_{conf+}$ ($s^{-1}$) | $1.5 \pm 0.2$ | $0.06 \pm 0.01$ |
| $k_{conf-}$ ($s^{-1}$) | $0.0007 \pm 1E-4$ | $0.015 \pm 0.003$ |
FIG. 5G
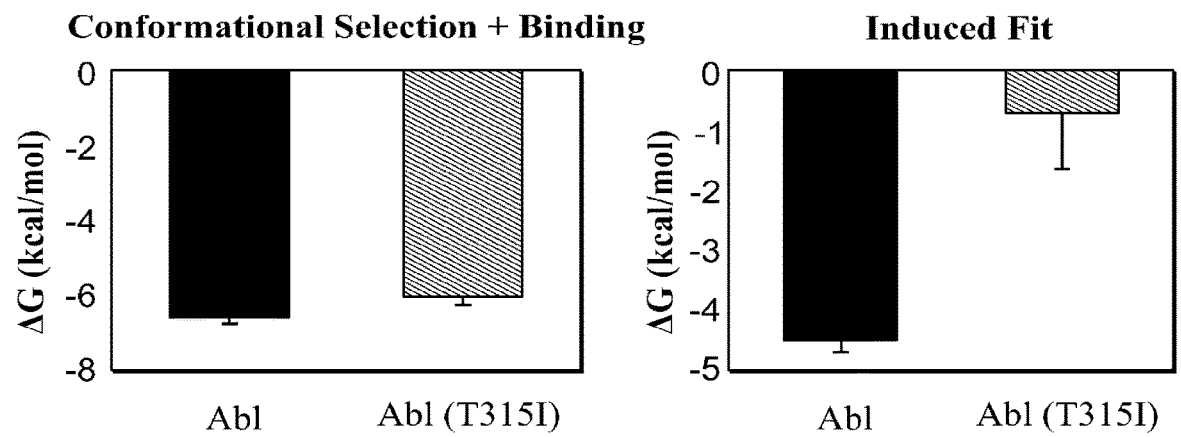

FIG. 6A cont.

Legend:

1a TK-S.raphanus
2 FGRF1
3 HER1
4 CSK-M.ovata
5 CSK-E.fuviatiis
6 CSK-A.queenslandica
7 CSK-S.rosetta
8 CSK-H.vulgaris
9 TEC-C.gracilis
10 TEC-H.magnipapiliata
11 TEC-S.domuncula
12 TEC-A. queenslandica
13 TEC-D.melanogaster
14 BTK-H.sapien
15 BMX-G.gallus
16 BMX-H.sapien
17 ITK-D.rario
18 ITK-G.gallus
19 ITK-H.sapien
20 TEC-D.rario
21 TEC-G.gallus
22 TEC-H.sapien
23 ABL-M.brevicolis
24 ABL-M.ovata
25 ABL-C.graclis
26 ABL-S.rosetta
27 ABL-N.vectensis
28 ABL1-C.elegans
29 ABL1-D.rario
30 ABL1-H.sapien
31 ABL2-D.rario
32 ABL2-H.sapien
33 SRMA-H.sapien
34 PK6-D.rario
35 PK6-H.sapien
36 SRC-S.saipingoeca
37 SRK3-S.spongila
38 STK-A.queenslandica
39 SRC-S.domuncula
40 SRK-H.sapien
41 FYN-H.magnipapilata
42 SRK-A. queenslandica
43 SRC2-S.domuncula
44 SRK4-S.lacustris
45 SRK1-S. lacustris
46 SRK-E.fluviatilis
47 SRC-A. queenslandica
48 SRC-E.fluviatilis
49 SRC3-S. domuncula
50 SRC-T.adhaerens
51 SRK2-S. lacustris
52 SRC4-A. queenslandica
53 SRC-S.diplocostata
54 SRC2-S.saipingoeca
55 SRC2-M.ovata
56 SRC-M.ovata
57 SRC-M.brevicolis
58 SRC2-M.brevicolis
59 SRC-H.magnipapilata
60 SRC-C.elegans
61 SRC-D.melanogaster
62 FGR-M.musculus
63 FYN-D.rario
64 FYN-G.gallus
65 SRC-D.rario
66 SRC-H.sapien
67 BLTK_H.sapien
68 LCK-D.rario
69 LCK-G.gallus
70 LCK-H.sapien
71 HCK-G.gallus
72 HCK-H.sapien
73 HCK-M.musculus
74 LYN-D.rario
75 LYN-G.gallus
76 LYN-H.sapien

Mutational Screen ANC-AS -> ANC-A2

| Location | Construct | Soluble? | kcat (s⁻¹) | $K_i$ (nM) |
|---|---|---|---|---|
| | ANC-AS | Yes | 8.0 ± 1.0 | 910 ± 120 |
| | N-lobe Buried (AS+15) | Yes | 3.3 ± 0.5 | 21 ± 12 |
| | N-lobe Mutations | Yes | 0.74 ± 0.2 | 16 ± 9 |
| | C-lobe Buried | Yes | 0.26 ± 0.3 | 850 ± 98 |
| | C-lobe Mutations | No | x | x |
| | C-lobe Buried +N-lobe Mutations | Yes | 0.07 ± 0.09 | x |
| | Abl | Yes | 13 ± 1.0 | 10 ± 10 |

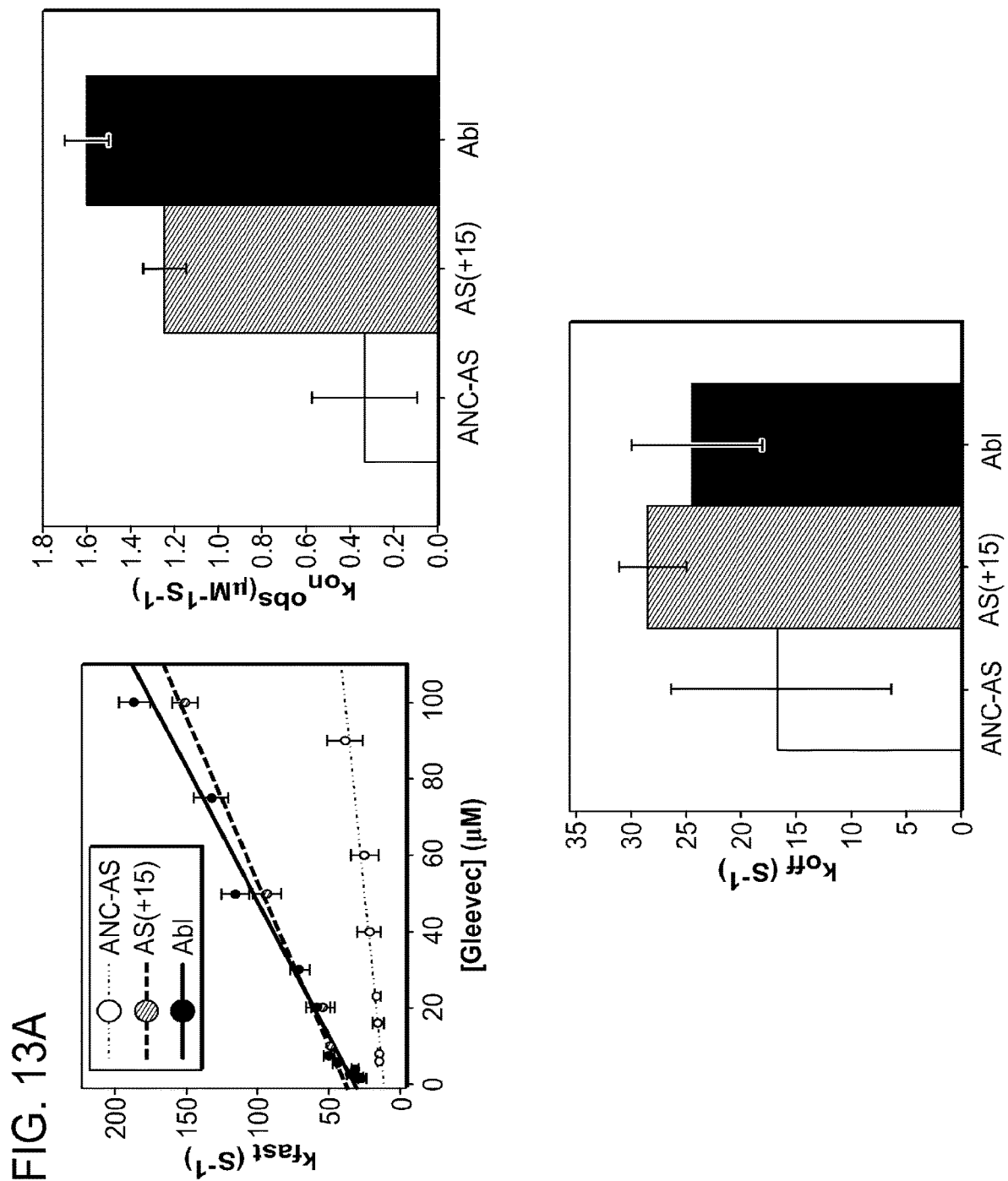

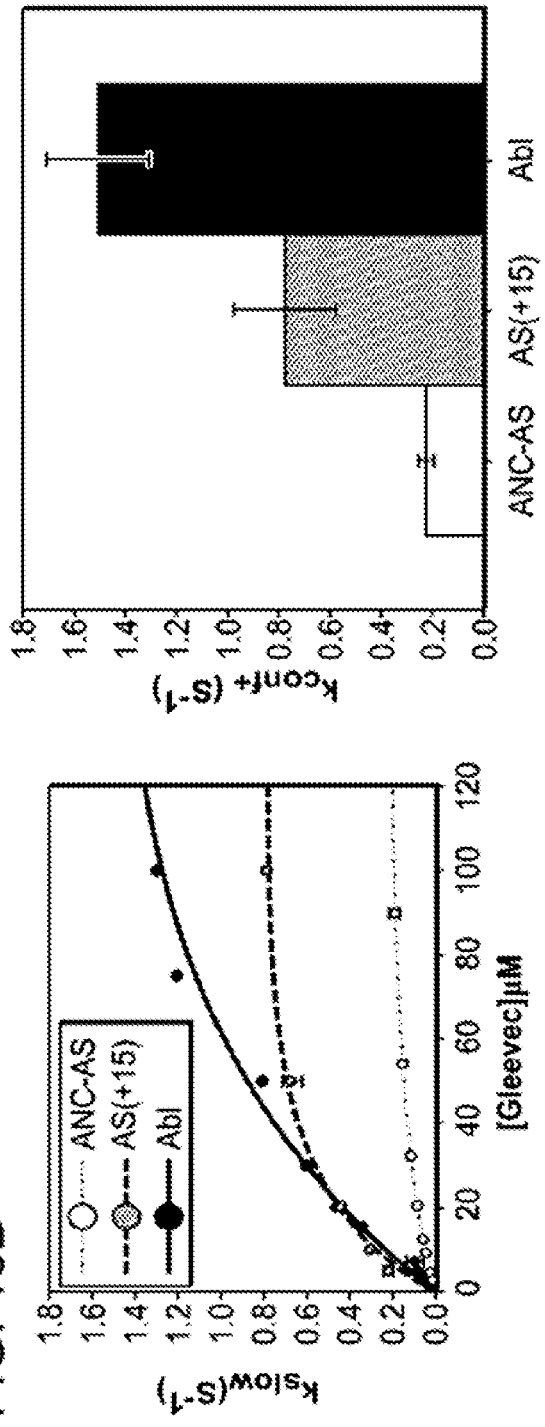
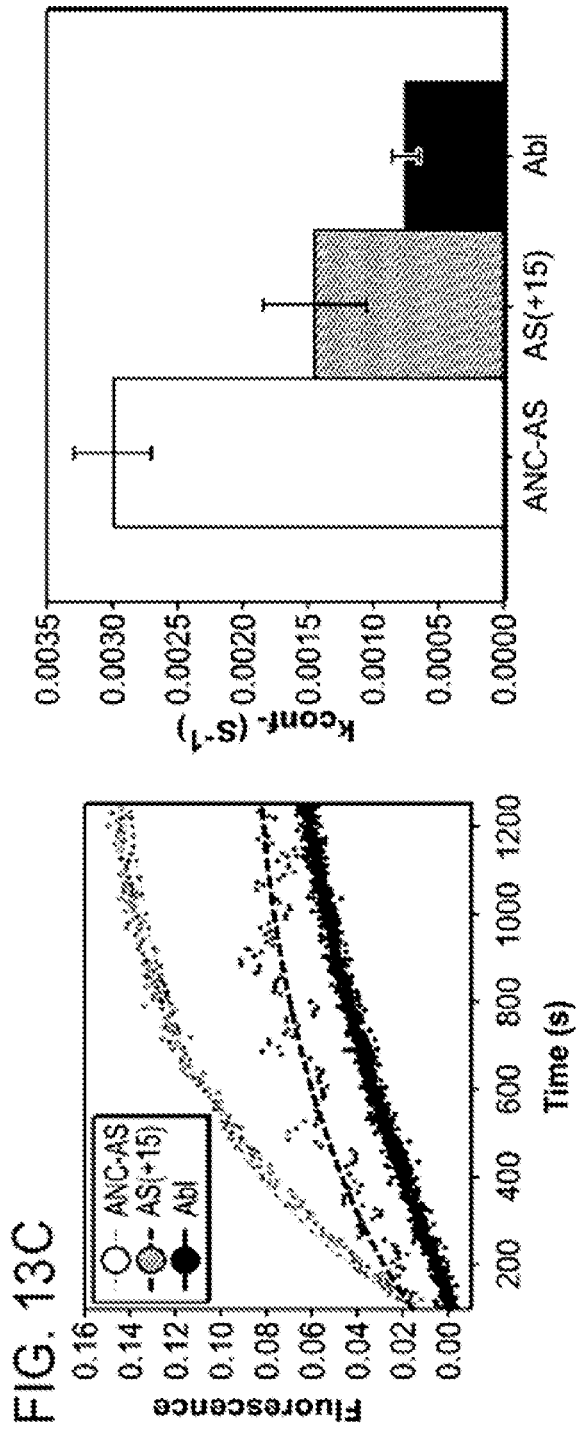

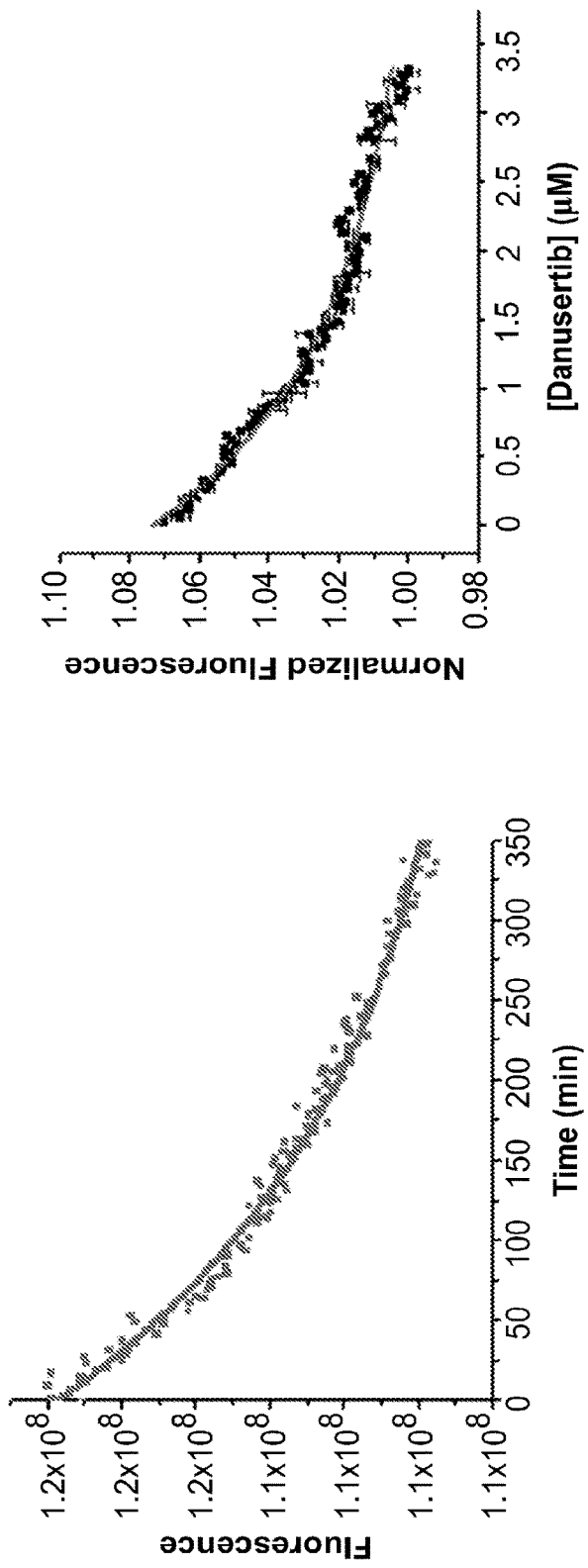
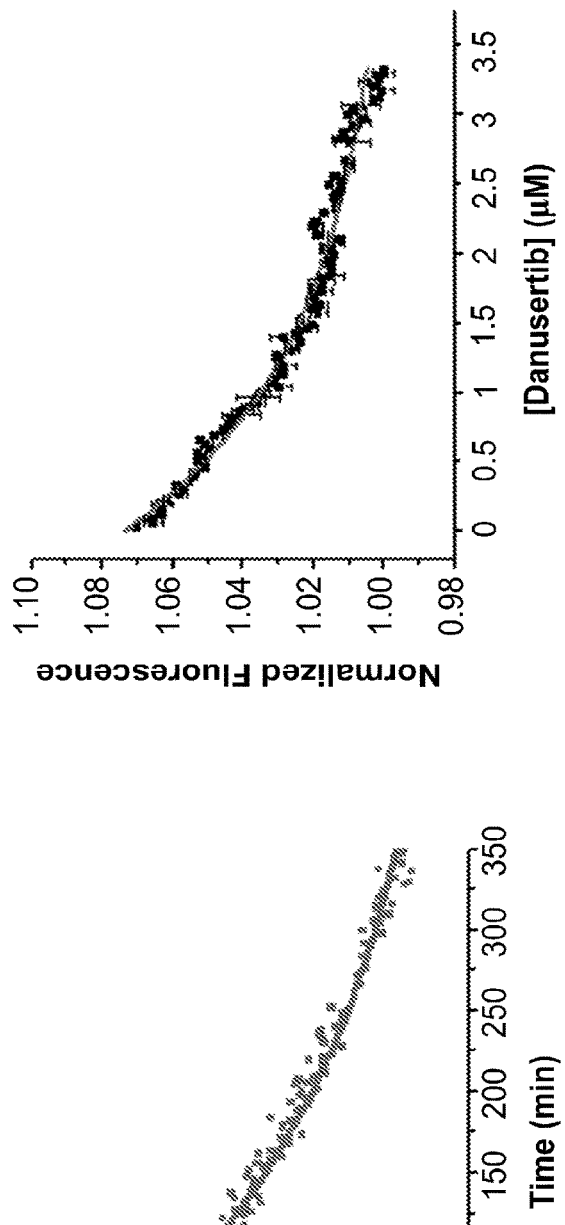
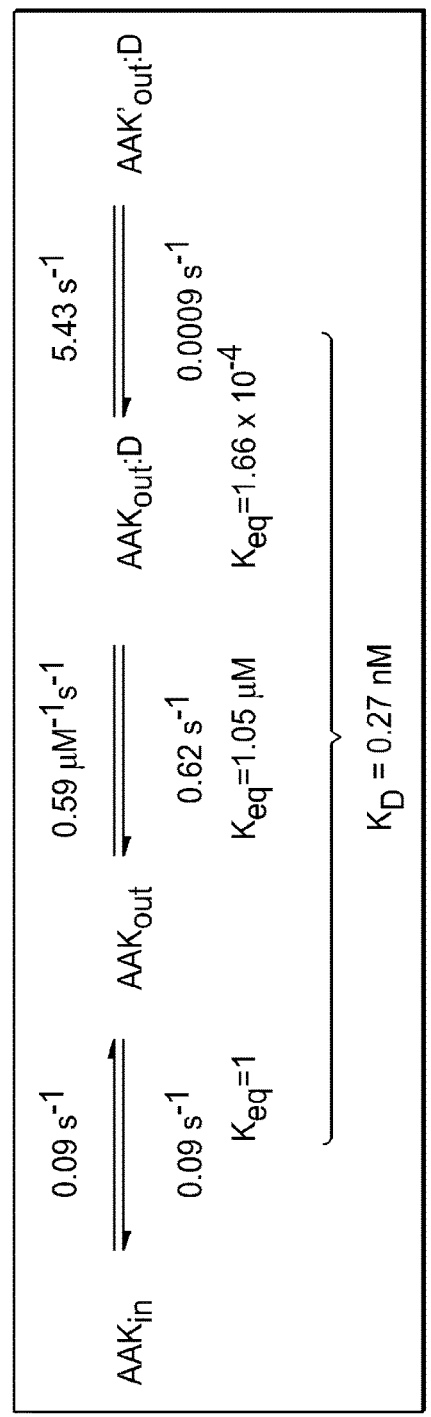
FIG. 16E
FIG. 16F
FIG. 16G

FIG. 20A

| Data Collection | | |
|---|---|---|
| Space group | P 6$_1$ 2 2 | P 6$_1$ 2 2 |
| Cell dimensions a, b, c (Å) | 81.80, 81.80, 172.69 | 80.68, 80.68, 170.07 |
| α, β, γ (°) | 90, 90, 120 | 90, 90, 120 |
| Resolution (Å) | 86.34-2.36 | 44.02-2.41 |
| R$_{merge}$ | 0.154 | 0.076 |
| I/σ(I) | 13.2 | 22.4 |
| Completeness (%) | 100.0 | 99.7 |
| Redundancy | 22.0 | 18.8 |
| | | |
| Refinement | | |
| Resolution (Å) | 65.54-2.36 | 44.06-2.41 |
| No. reflections | 13722 | 12232 |
| R$_{work}$/R$_{free}$ | 0.227/0.282 | 0.234/0.301 |
| No. atoms | | |
| Protein | 2169 | 2169 |
| Lingand/ion | 32 | 40 |
| Water | 15 | 28 |
| B-factors | | |
| Protein | 59.7 | 72.0 |
| Lingand/ion | 70.8 | 135.3 |
| Water | 59.9 | 65.0 |
| R.m.s deviations | | |
| Bond lengths (Å) | 0.015 | 0.010 |
| Bond angles (°) | 1.702 | 1.381 |
| | | |
| PDB ID | 4UTD | 4UTE |

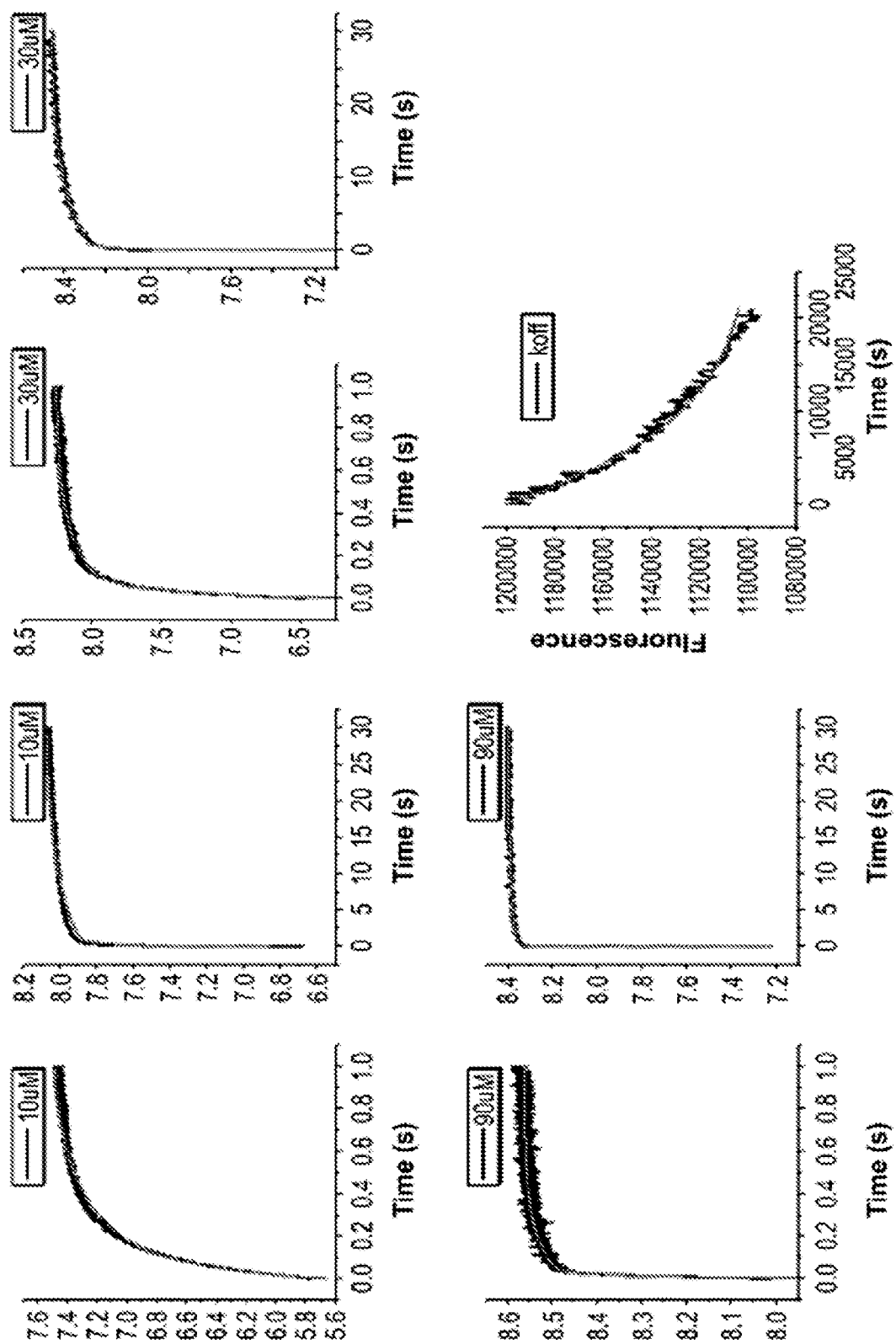

FIG. 25A
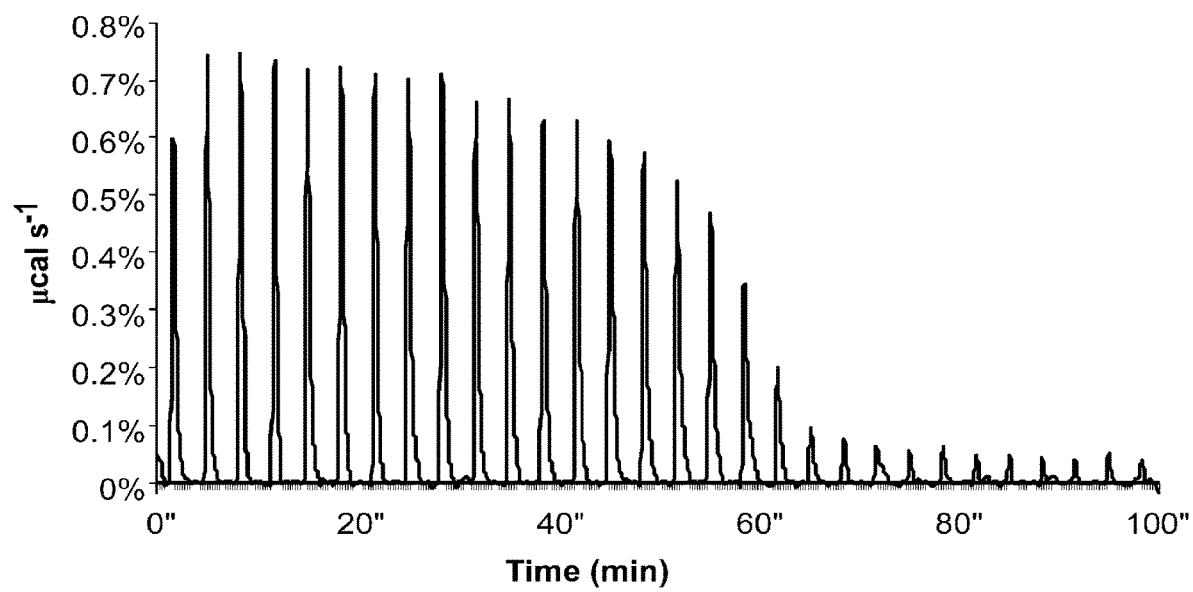
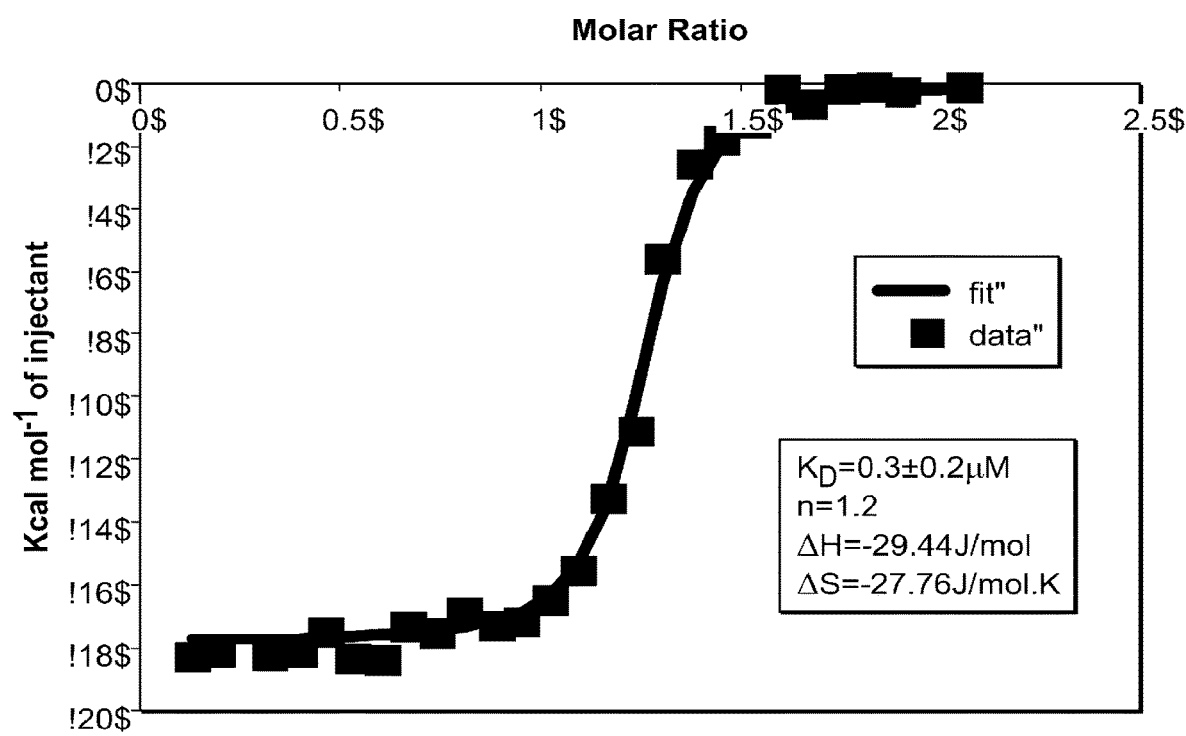

$k_{cat} = (1.2 \pm 0.2)\,s^{-1}$

FIG. 26D
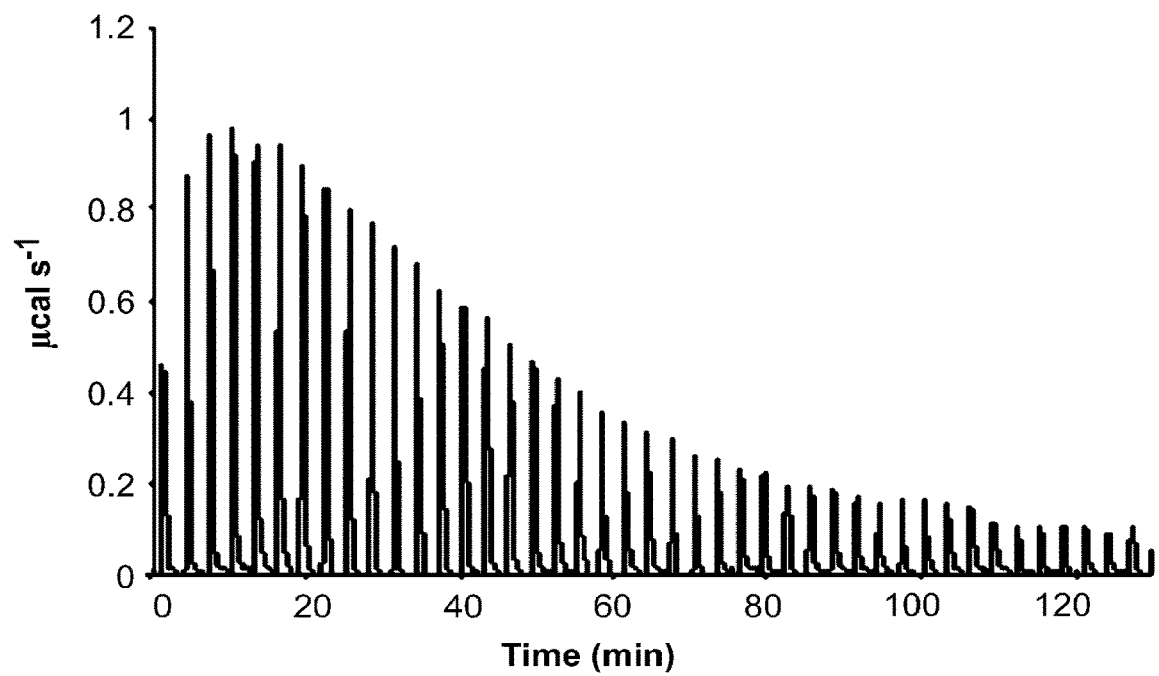
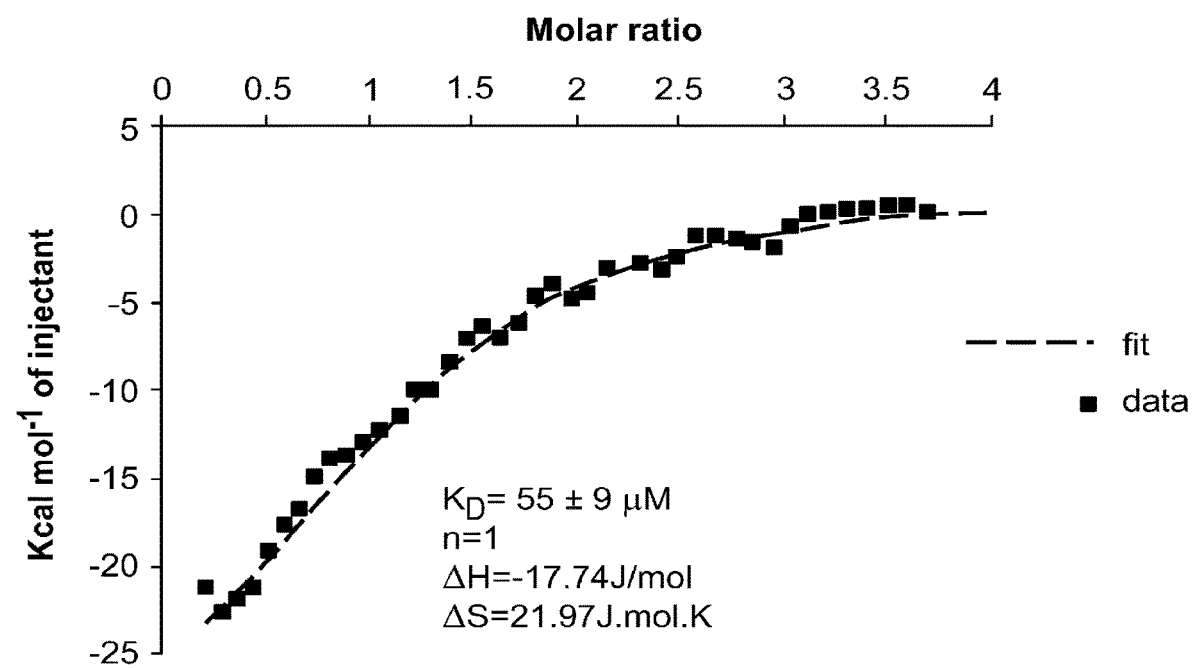

FIG. 27A
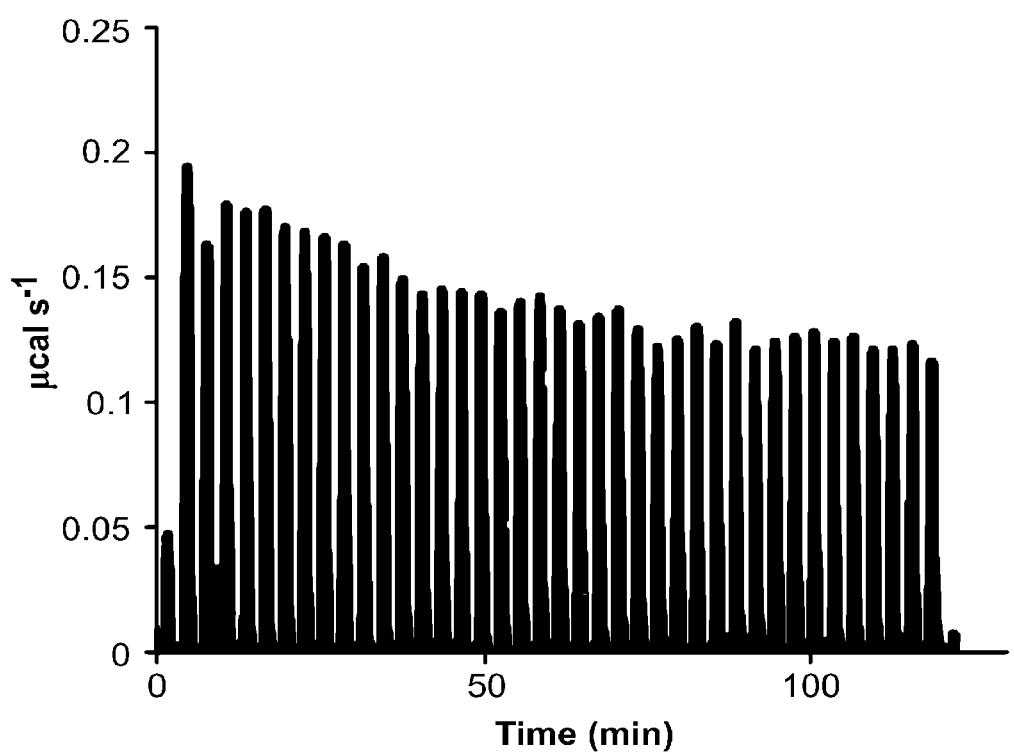
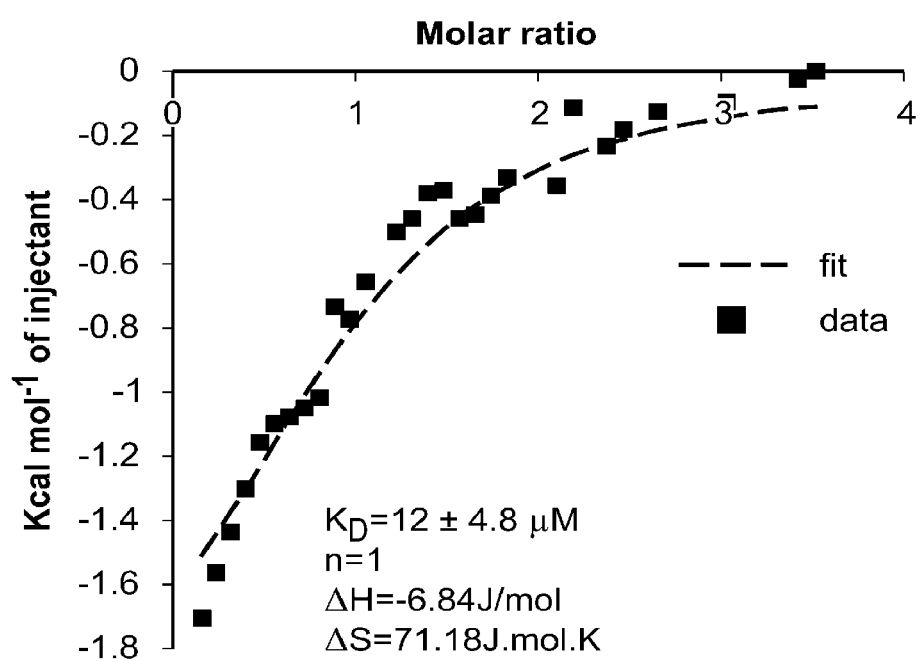

| | $K_D$ Kinetics (nM) | $K_D$ Measured (nM) | Temp (°C) |
|---|---|---|---|
| AurA/Danusertib | 0.5 ± 0.7 | 0.9 ± 0.4 | 25 |
| AurA/Gleevec | 62 ± 13 | 55 ± 10 | 10 |
| Abl/Danusertib | 0.06 ± 0.07 | 0.1 ± 0.02 | 25 |
| AblT315I/Gleevec | 89000 ± 3700 | 12000 ± 4800 | 5 |
| AblT315I/Danusertib | 0.1 ± 0.08 | 0.1 ± 0.01 | 25 |

FIG. 29A
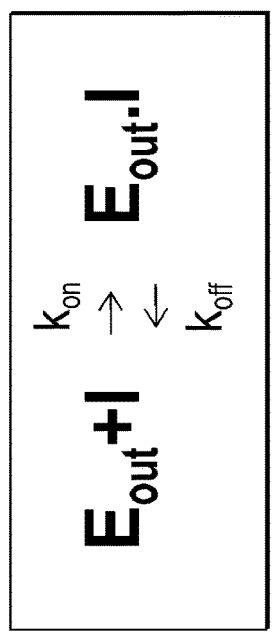
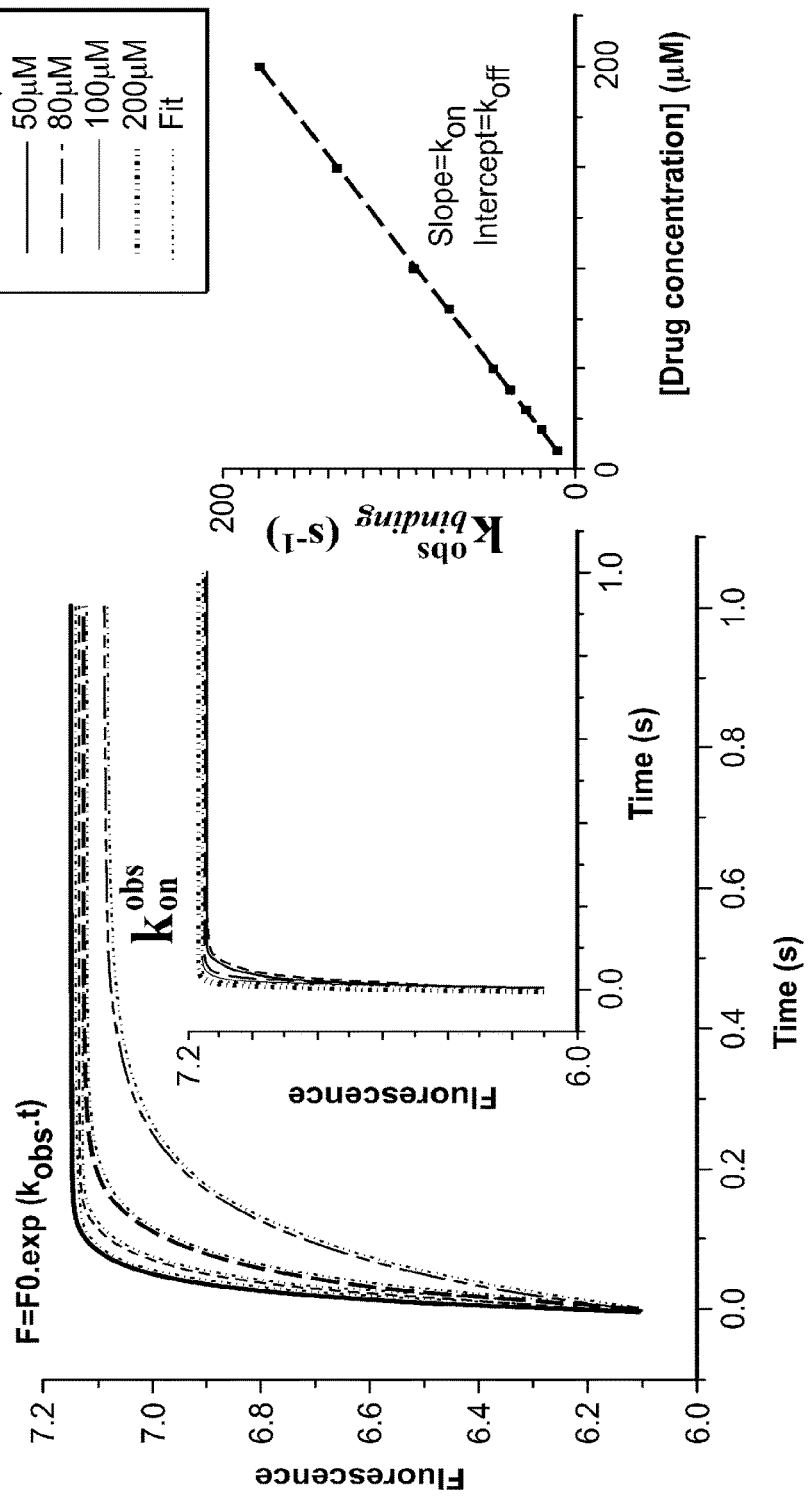

FIG. 29B
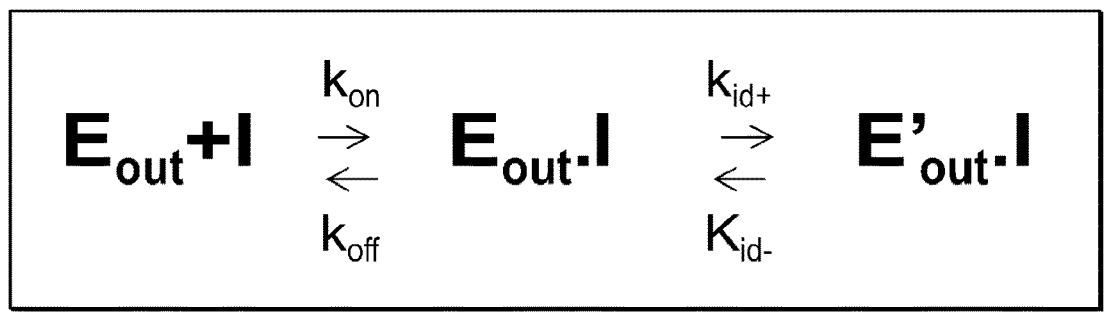
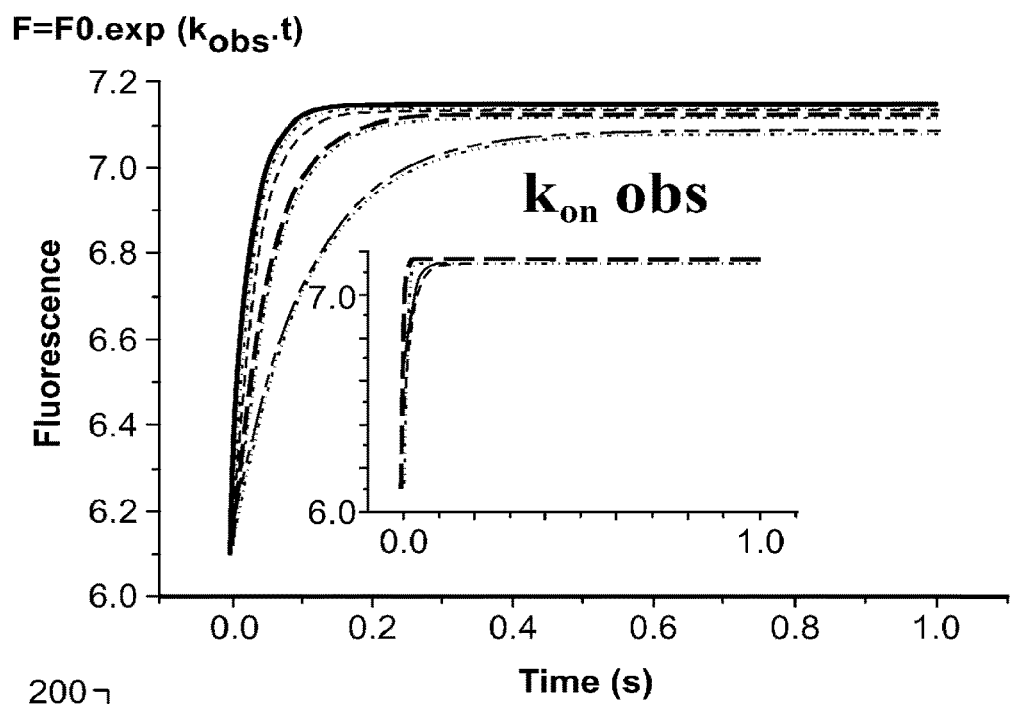
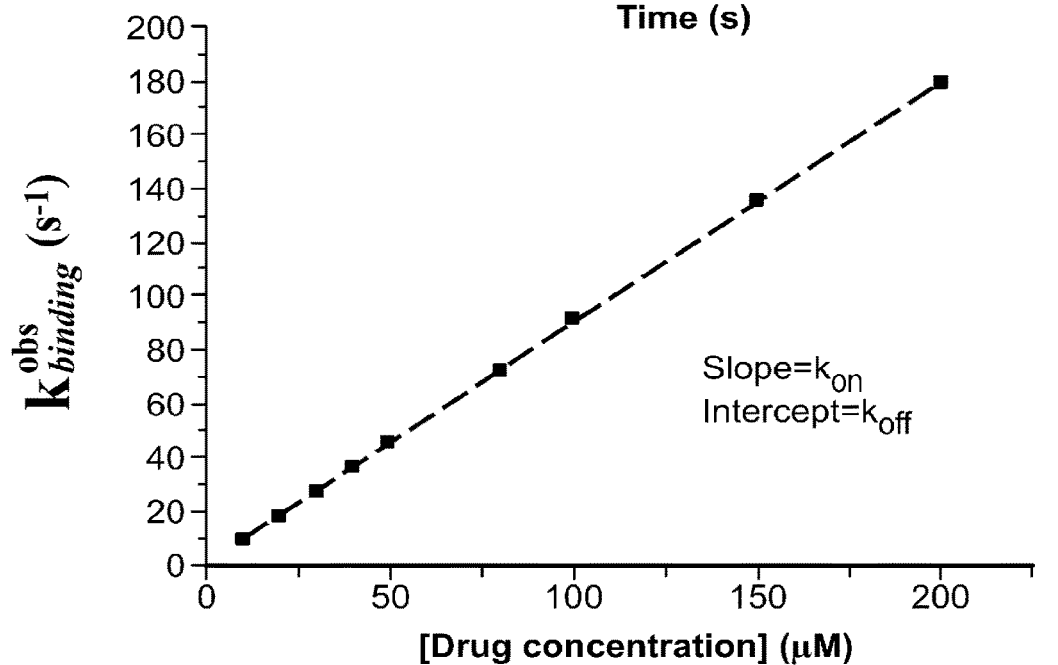

FIG. 29B cont.
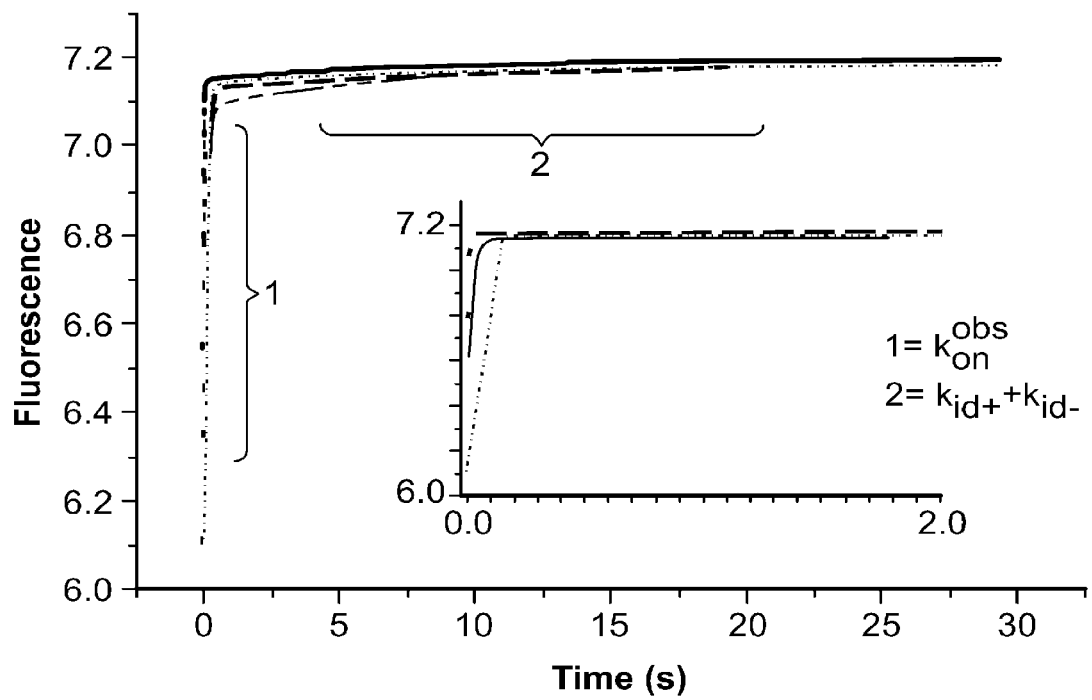
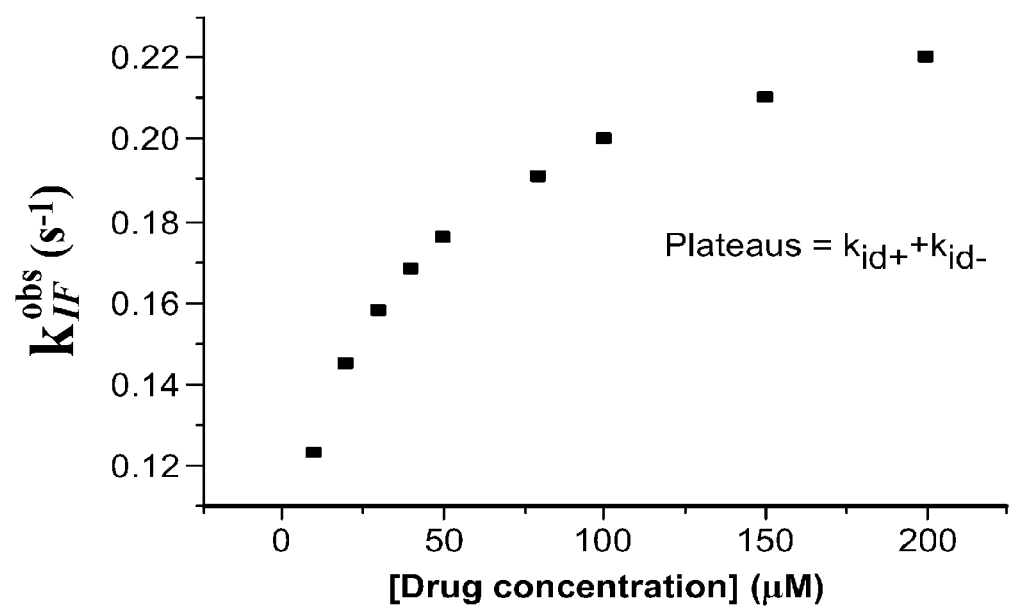

| | Aurora A PIF pocket residues important for TPX2 binding | | | | | |
|---|---|---|---|---|---|---|
| | 206 | 201 | 199 | 169 | 178 | 182 |
| Aur<sub>ANC1</sub> | V | H | H | L | V | — |
| Aur<sub>ANC2</sub> | V | H | H | L | V | — |
| Aur<sub>ANC3</sub> | V | H | Y | L | L | — |
| Aur<sub>ANC4</sub> | V | H | Y | L | L | — |
| AurAmodern | V | H | Y | L | L | V |

FIG. 33B cont.
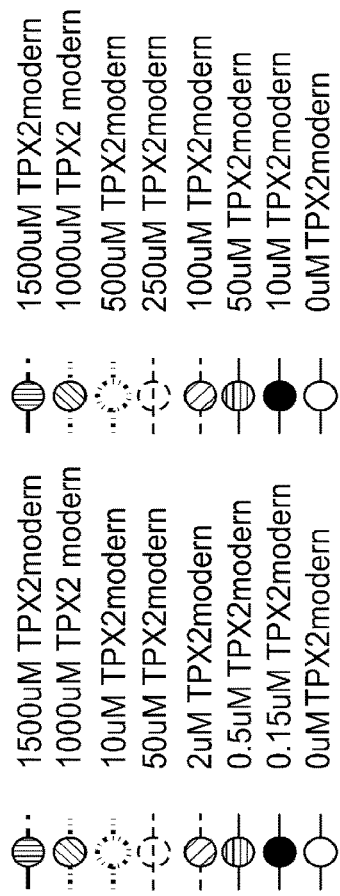
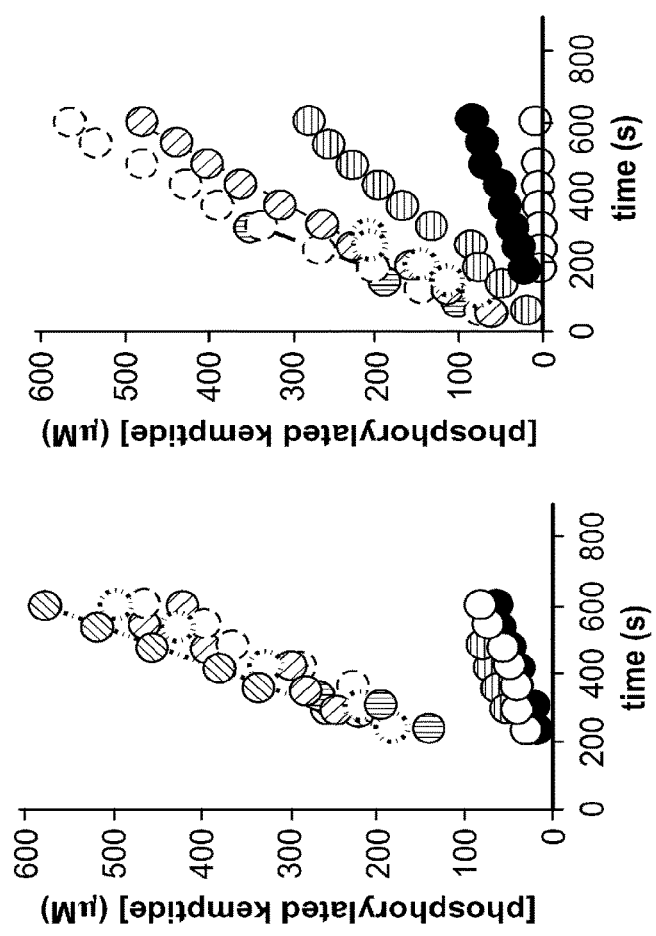

FIG. 33C cont.
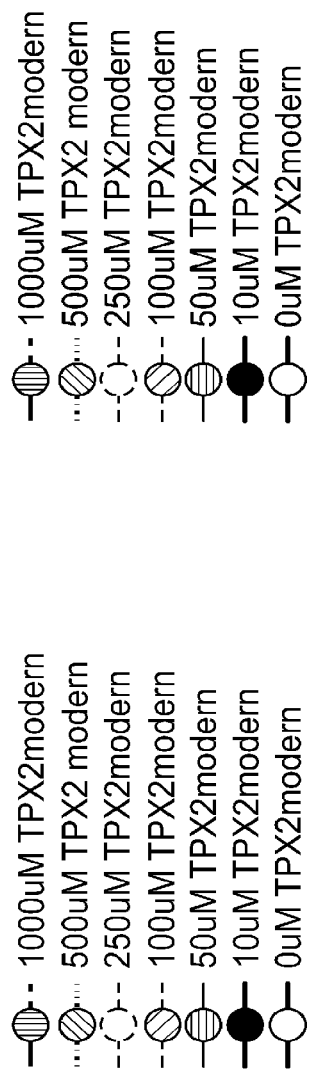
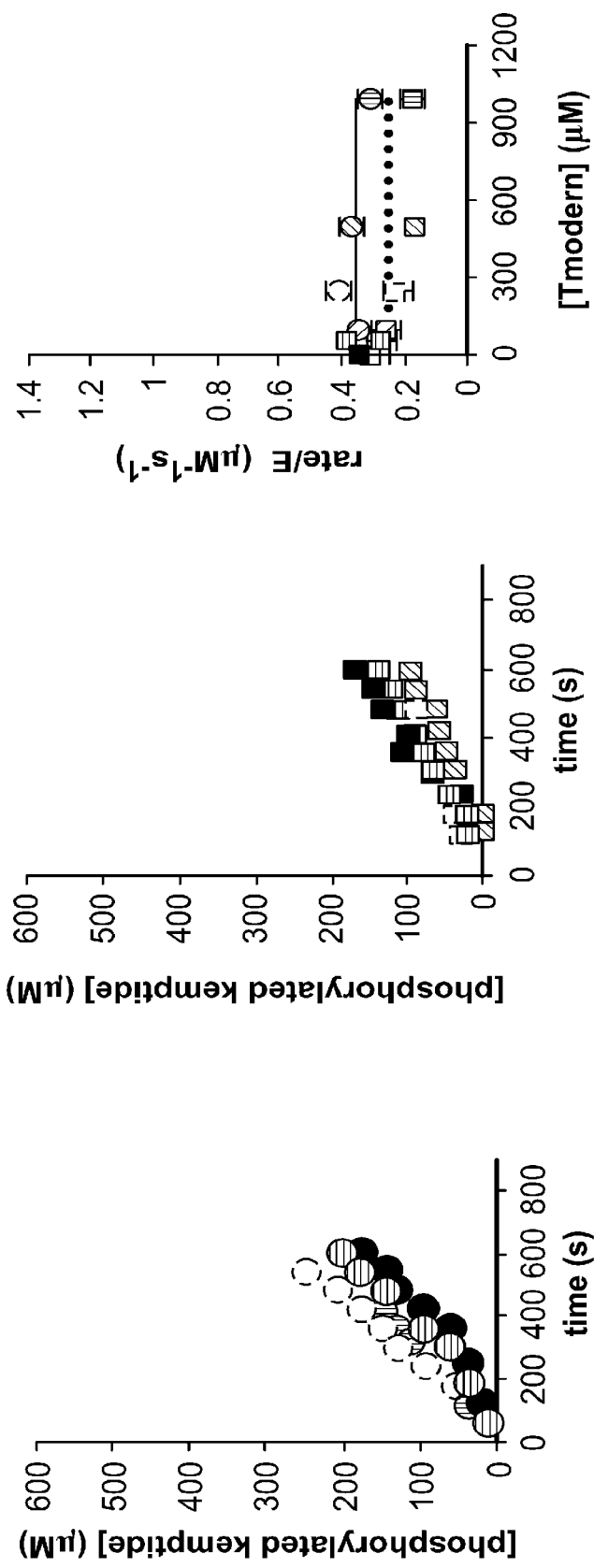

Clusters of highly correlated residues

Active                                          Inactive

Mutual Information is General Correlation $$MI(X,Y) = \sum_{x \in X}\sum_{y \in Y} p(x,y) \log\left(\frac{p(x,y)}{p(x)p(y)}\right)$$

FIG. 37 cont.
Clusters of highly correlated residues
Active　　　　　　　　　　　Inactive
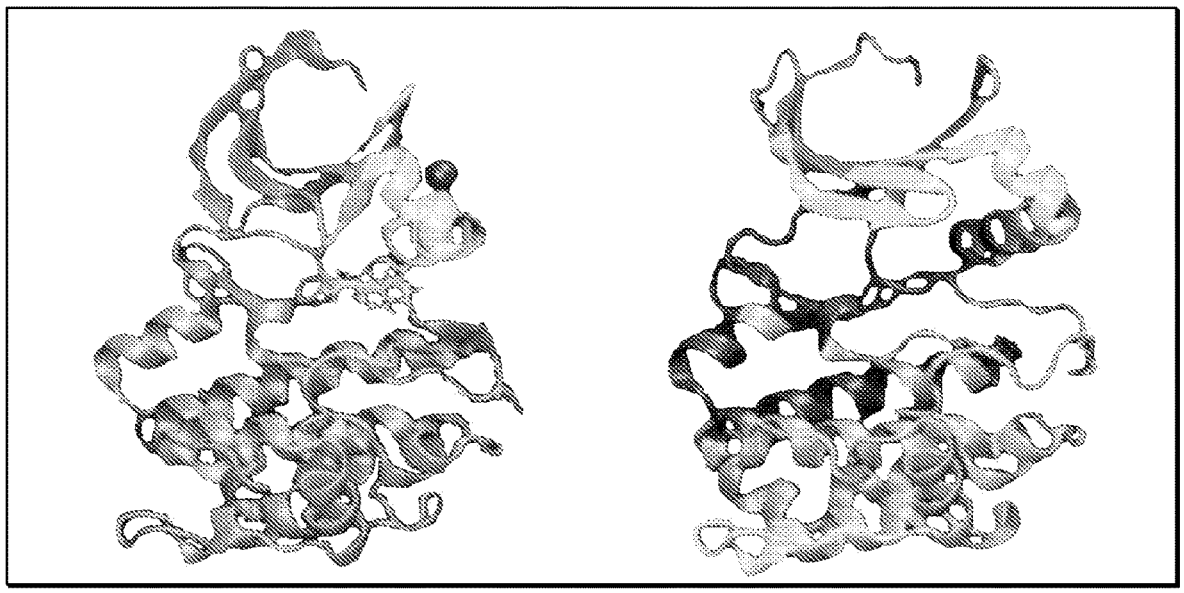
Different colors identify regions with highly correlated motions
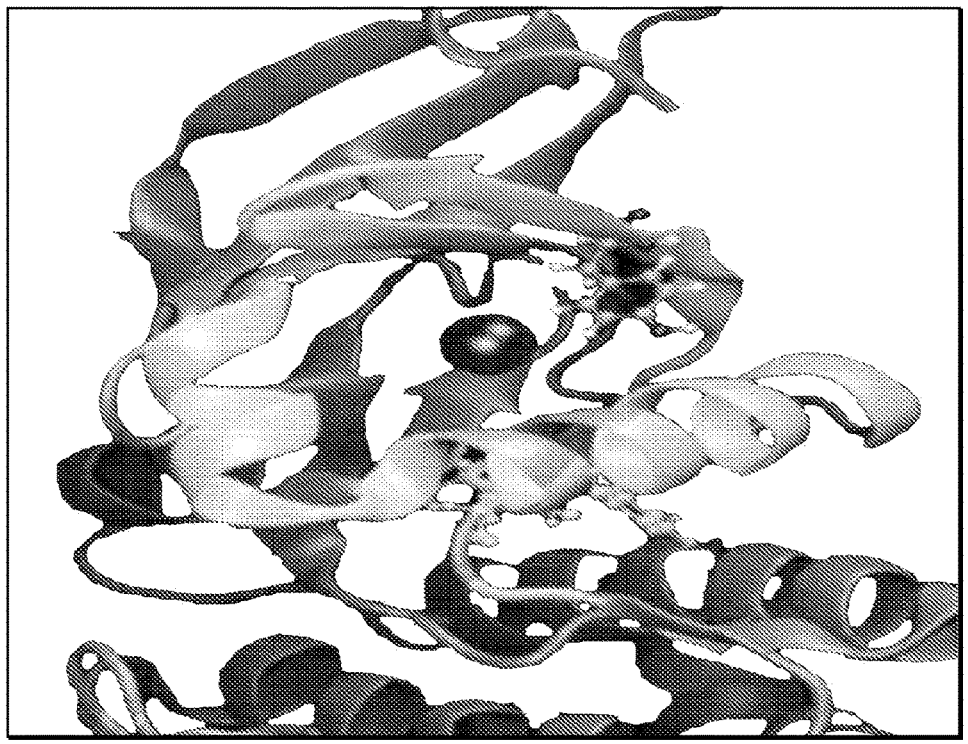

FIG. 38

Mechanisms and Kinetics of Aurora A

Kinase conformational state on inhibitor potency and selectivity is important but poorly understood.

☐ Understanding the mechanism of Aur A by using *small molecule inhibitors*

| Conformational Selection | Binding | Induced Fit |

$$AAK_{in} \rightleftharpoons AAK_{out} \rightleftharpoons AAK_{out}{:}D \rightleftharpoons AAK'_{out}{:}D$$

Active State      Inactive State
$(DFG_{IN})$           $(DFG_{OUT})$

*Small molecule inhibitors*

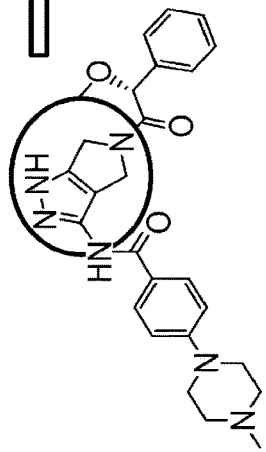

Danusertib (type I inhibitor) binds to inactive state ($DFG_{OUT}$) ⇒ Mimics ATP

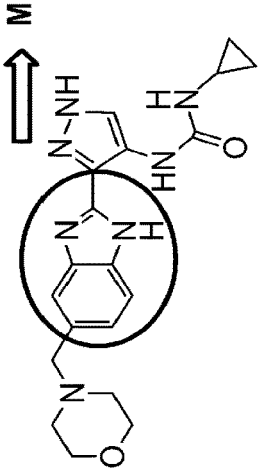

AT9283 (type I inhibitor) binds to active state ($DFG_{IN}$) ⇒ Mimics ATP

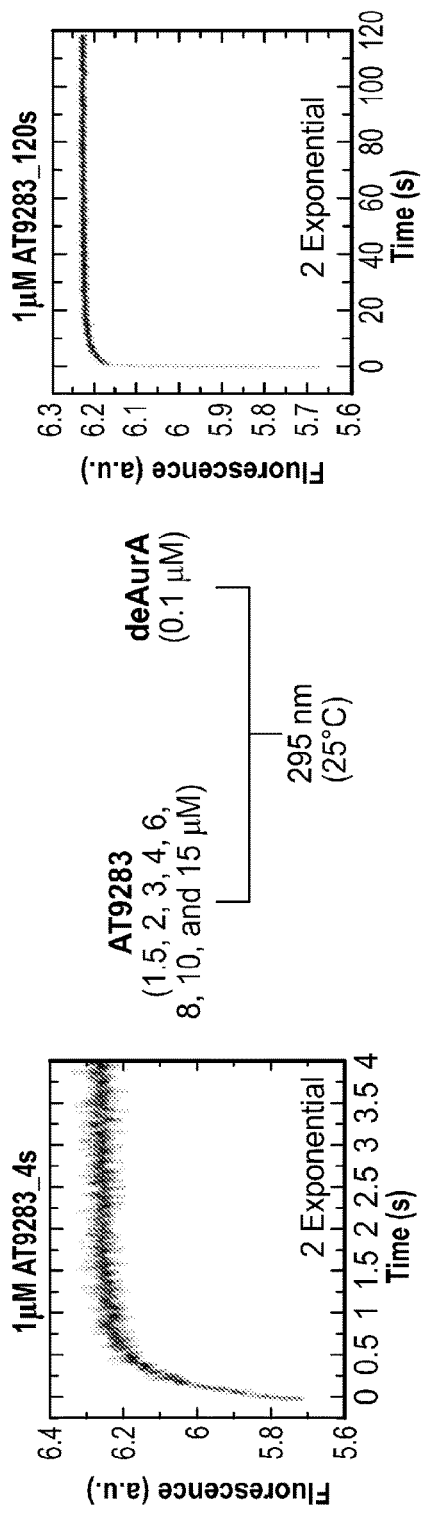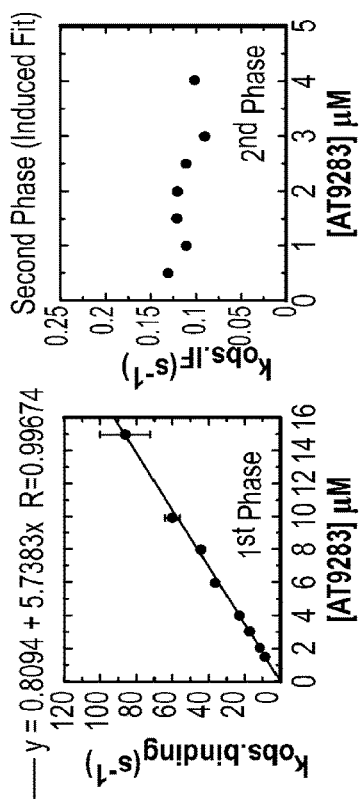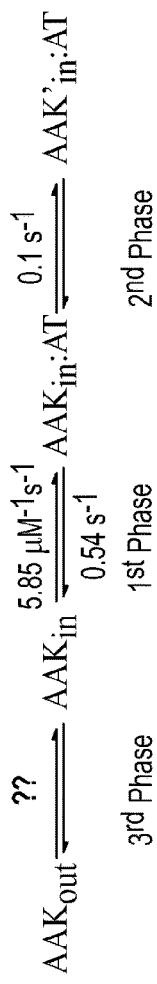
FIG. 43A
AT9283: DFG$_{IN}$ Position
Pre-Steady-State Kinetic at 25°C

FIG. 43B
AT9283: DFG$_{IN}$ Position
Pre-Steady-State Kinetic at 35°C
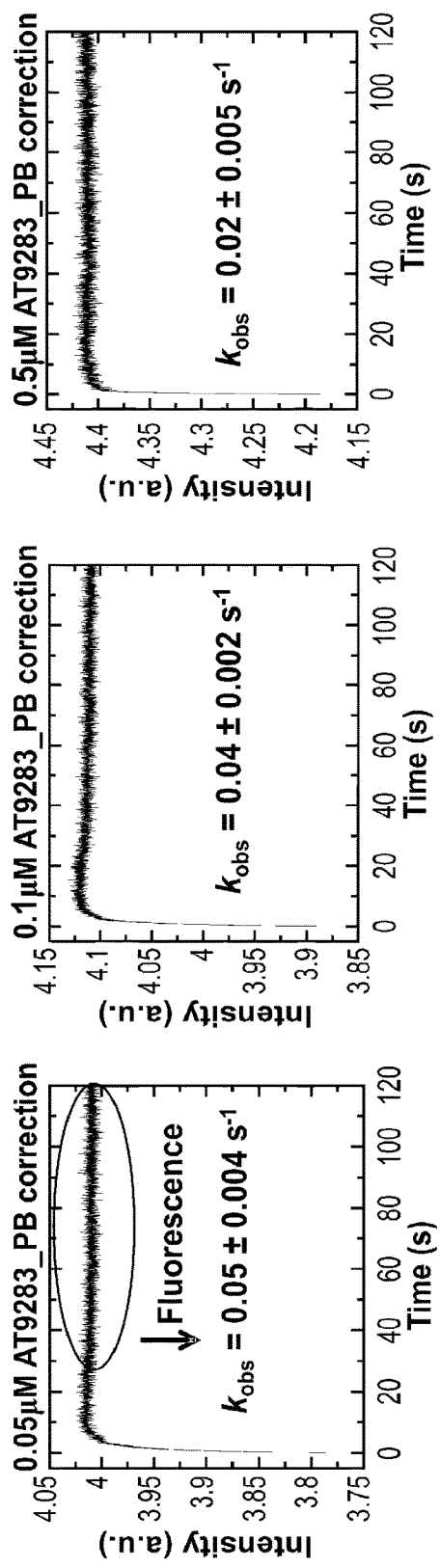
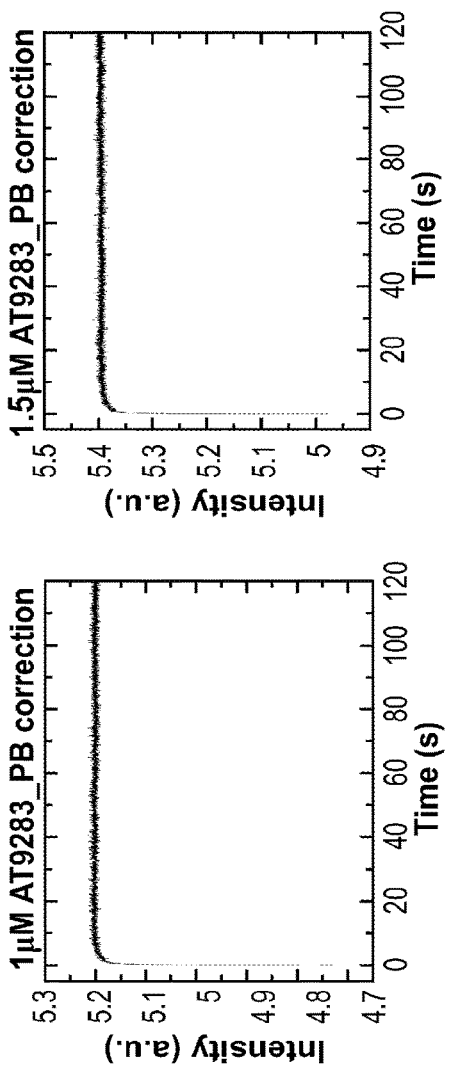

FIG. 43C

AT9283: DFG$_{IN}$ Position

Pre-Steady-State Kinetic of low [AT9283] at 25°C

Buffer: 50mM HEPES, 50mM NaCl, 20mM MgCl$_2$, 5mM TCEP, 5% DMSO, pH 7.30

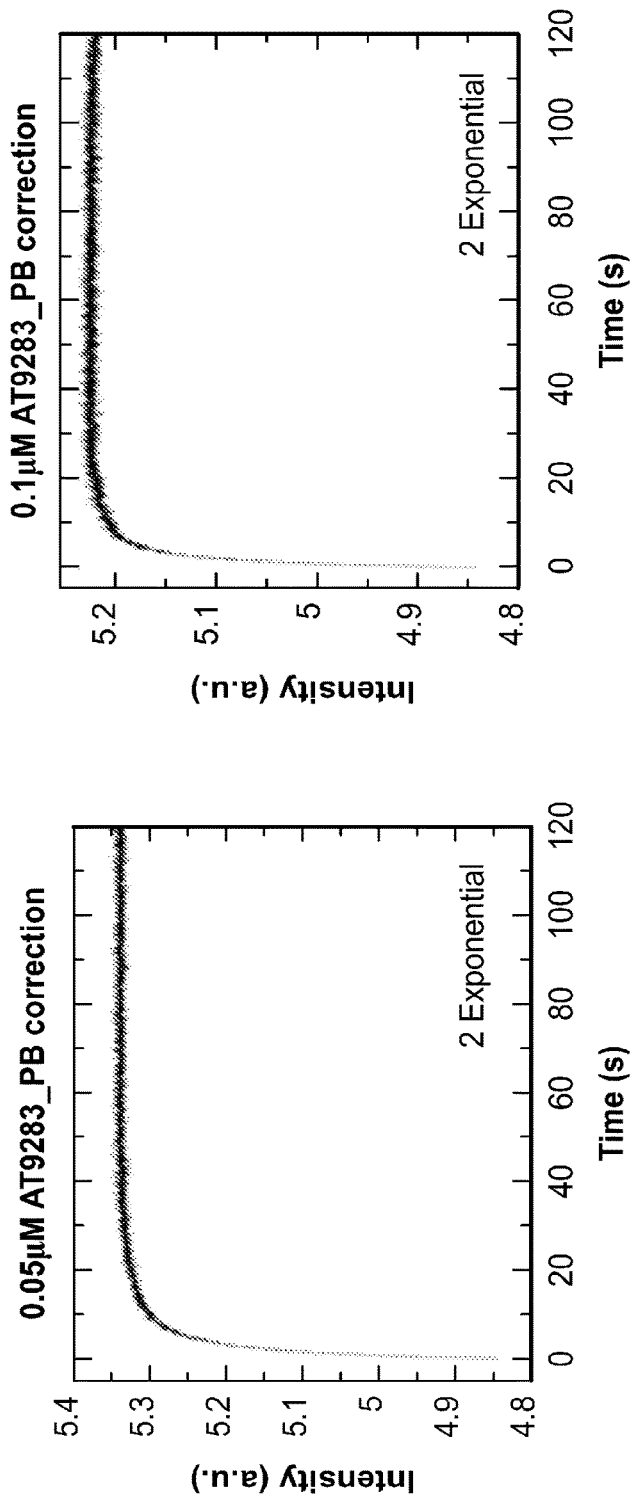

3$^{rd}$ Phase is not observed at low [AT9283] 25°C $$AAK_{out} \underset{\leq 0.05 \, s^{-1}}{\rightarrow} AAK_{in} \underset{0.54 \, s^{-1}}{\overset{5.85 \, \mu M^{-1} s^{-1}}{\rightleftarrows}} AAK_{in}:AT \underset{}{\overset{0.1 \, s^{-1}}{\rightleftarrows}} AAK'_{in}:AT$$

3$^{rd}$ Phase    1$^{st}$ Phase    2$^{nd}$ Phase

Two-step mechanism of the Uni-Bi Branched Type

FIG. 44B
Macroscopic $K_D$ of Danusertib
Overall Reaction of Danusertib at 25°C
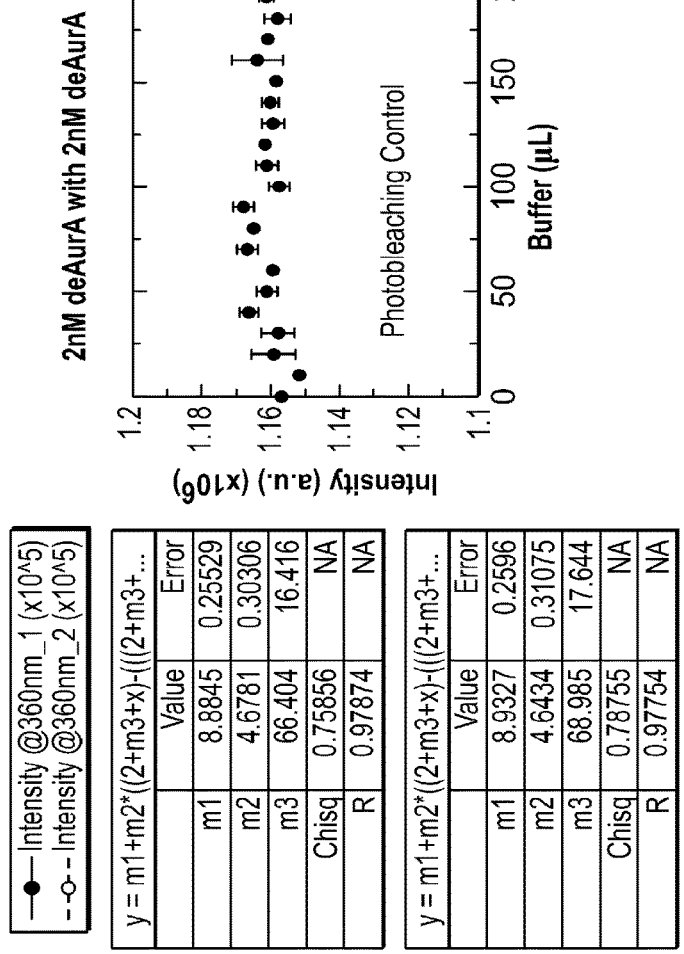
$$AAK_{in} \xrightarrow{0.09\ s^{-1}}_{\leq 0.05\ s^{-1}} AAK_{out} \xrightarrow{0.59\ \mu M^{-1} s^{-1}}_{0.62\ s^{-1}} AAK_{out}:D \xrightarrow{5.43\ s^{-1}}_{0.0009\ s^{-1}} AAK'_{out}:D$$
$$K_1 = \sim 0.56 \qquad K_2 = 1.05\ \mu M \qquad K_3 = 1.66 \times 10^{-4}$$
$$K_D = 0.27\ nM$$
$$K_D = \frac{(K_1 + 1) \times K_2 \times K_3}{(1 + K_3)}$$
☐ Single Point Auto-Titration with Danusertib Stock 10 nM
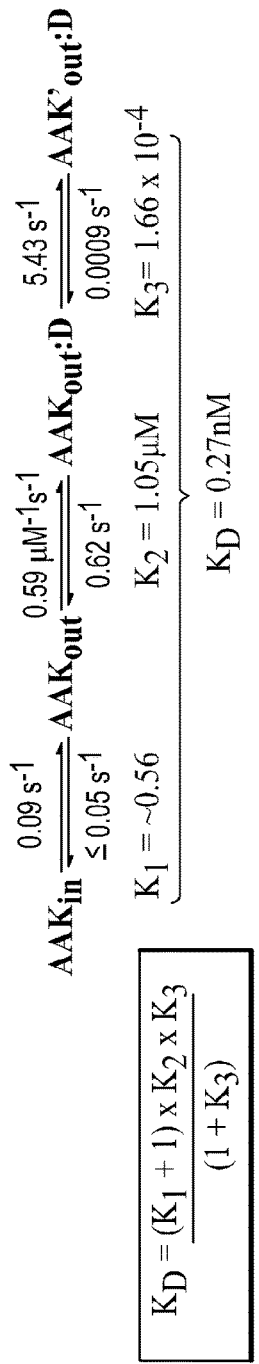
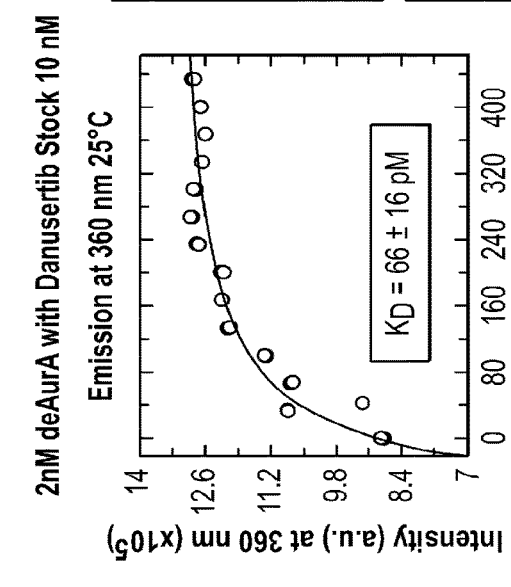

BIOPHYSICAL PLATFORM FOR DRUG DEVELOPMENT BASED ON ENERGY LANDSCAPE

CROSS REFERENCE TO RELATED APPLICATIONS

This application is the U.S. national phase application, pursuant to 35 U.S.C. § 371, of PCT International Application No.: PCT/US2015/059086, filed Nov. 4, 2015, designating the United States and published in English, which claims benefit of U.S. Provisional Application Ser. No. 62/075,043, filed on Nov. 4, 2014, the contents of which are incorporated herein by reference in their entirety.

STATEMENT OF RIGHTS TO INVENTIONS MADE UNDER FEDERALLY SPONSORED RESEARCH

This invention was made with government support under Grant No. DE-FG02-05ER15699 awarded by the U.S. Department of Energy and Grant No. GM100966-01 awarded by the National Institutes of Health. The government has certain rights in the invention.

BACKGROUND OF THE INVENTION

The fundamental importance of protein kinases is indisputable. Their central role in essential physiological processes has provoked extensive studies and has resulted in a wealth of knowledge from biological signaling cascades to atomistic structural details. Kinases are attractive therapeutic drug targets because different signaling cascades can be selectively regulated by inhibiting individual kinases. However, all kinases share a great degree of similarity, thus making it difficult to design inhibitors that are specific for a particular kinase. This complication has hampered progress in drug development and highlights the need for a deeper understanding of the biophysical principles that govern kinase-drug interactions.

The evolution of more than 500 human protein kinases from a few protein kinases in unicellular organisms allowed for the development of complexity via differential regulation. Such regulation can be achieved by autophosphorylation or interactions with other domains or binding partners. While many of the signaling cascades and their in vivo biological effectors have been well characterized, and a wealth of structural information is available, the molecular mechanism whereby kinase activity is modulated is a topic of controversial debate.

Accordingly, new methods of identifying potential protein kinase inhibitors or potential inhibitors of other proteins using an energy landscape providing tight affinity through an induced fit and binding plasticity through a conformational-selection mechanism are urgently required.

SUMMARY OF THE INVENTION

The present invention features methods of selecting or identifying an agent that inhibits a target protein having an active site. The methods comprise measuring or predicting stability of an induced fit conformation (E*-I) of a candidate agent contacted to the active site of the protein.

In one aspect, the invention provides a method of selecting or identifying an agent that inhibits a target protein having an active site, the method comprising measuring or predicting stability of an induced fit conformation (E*-I) of a candidate agent contacted to the active site of the protein, wherein the candidate agent is selected or identified as an inhibitor of the protein if the measured or predicted stability of the induced fit conformation (E*-I) of the candidate agent contacted to the active site is increased relative to a reference stability.

In another aspect, the invention provides a method of selecting or identifying an agent that inhibits a target protein having an active site, the method comprising measuring or predicting a rate of conversion between a primary bound conformation (E-I) and an induced fit conformation (E*-I) of a candidate agent contacted to an active site of the protein, wherein a candidate agent is selected or identified as an inhibitor of the protein if a measured or predicted rate of conversion from the primary bound conformation (E-I) to the induced fit conformation (E*-I) is increased and/or a measured or predicted rate of conversion from the induced fit conformation (E*-I) to the primary bound conformation (E-I) is decreased relative to a reference rate.

In yet another aspect, the invention provides a method of selecting an agent that inhibits a target protein having an active site, the method comprising measuring a structure of an induced fit conformation (E*-I) of a candidate agent contacted to an active site of the kinase, wherein the stability of the induced fit conformation (E*-I) of the candidate agent contacted to the active site of the protein is pre-identified as increased relative to a reference stability.

In various embodiments of any one of the aspects delineated herein, the reference stability is the stability of an induced fit conformation (E*-I) of a pre-selected lead agent, a natural substrate of the protein, or a natural ligand of the protein or an analog thereof contacted to the active site of the protein. In various embodiments, the reference rate is a rate of conversion to or from a primary bound conformation (E-I) to or from an induced fit conformation (E*-I) of a pre-selected lead agent, a natural substrate of the protein, or a natural ligand of the protein or an analog thereof contacted to the active site of the protein.

In another aspect, the invention provides a method of selecting an agent that inhibits a target protein having an active site for further optimization, the method comprising measuring an induced fit step when a first candidate agent is contacted with the protein, wherein the first candidate agent is selected for further optimization if an induced fit step is detected. In various embodiments, the induced fit step is measured by measuring stability of an induced fit conformation (E*-I) of the candidate agent contacted to the active site of the protein relative to a reference stability, by measuring a rate of conversion to or from a primary bound conformation (E-I) to or from the induced fit conformation (E*-I) of the candidate agent contacted to the active site of the protein relative to a reference rate, or by measuring a structure of an induced fit conformation (E*-I) of the candidate agent contacted to an active site of the protein.

In still another aspect, the invention provides a method of selecting an agent that inhibits a target protein having an active site for further optimization, the method comprising measuring stability of an induced fit conformation (E*-I) of a candidate agent contacted to an active site of the protein, wherein the candidate agent is selected for further optimization if the stability of the induced fit conformation (E*-I) is increased relative to a first reference stability. In various embodiments, the further optimization comprises identifying a modified form of the candidate agent having an increased stability of an induced fit conformation of the modified form of candidate agent contacted to the active site of the protein relative to a second reference stability.

In another aspect, the invention provides a method for selecting an agent that inhibits a target protein having an active site, the method comprising (a) measuring stability of an induced fit conformation (E*-I) of a candidate agent contacted to an active site of the protein; (b) measuring a structure of the induced fit conformation (E*-I) if the stability of the induced fit conformation in step (a) is increased relative to a first reference stability; and (c) predicting stability of an induced fit conformation (E*-I) of a modified form of the candidate agent contacted to an active site of the kinase using the structure measured in step (b), wherein the modified form of the candidate agent is selected if the predicted stability is increased relative to a second reference stability.

In various embodiments of any one of the aspects delineated herein, the first reference stability is the stability of an induced fit conformation (E*-I) of a pre-selected lead agent, a natural substrate, or a natural ligand or an analog thereof contacted to an active site of the protein. In various embodiments, the second reference stability is the stability of the induced fit conformation (E*-I) of the modified form of the candidate agent contacted to the active site of the protein. In some embodiments, the modified form of the candidate agent is an analog of the candidate agent. In various embodiments of any one of the aspects delineated herein, the method further comprises measuring a stability of or a rate of conversion to or from any one of a kinetically distinct state selected from the group consisting of a binding incompetent state, binding competent state, a primary bound conformation (E-I), and an induced fit conformation (E*-I).

In various embodiments of any one of the aspects delineated herein, the stability of the induced fit conformation (E*-I) is characterized by measuring a $K_{eq}$ of the equilibrium between the primary bound conformation (E-I) and induced fit conformation (E*-I) or by measuring a rate of conversion from a primary bound conformation (E-I) to the induced fit conformation (E*-I) is increased and/or a rate of conversion from the induced fit conformation (E-I*) to the primary bound conformation (E-I). In various embodiments, the selected agent has an increased affinity for the protein. In particular embodiments, the selected agent has an increased residence time on the protein. In some embodiments, the agent induces a conformation change in the protein during the induced fit step subsequent to the primary binding of the agent to the protein.

In some other embodiments, contacting the protein with the agent results in an equilibrium that is far-shifted to the induced fit step or induced fit conformation. In still other embodiments, the affinity of the selected agent to the protein is increased by at least about 1 kcal/mol, 2 kcal/mol, at least about 3 kcal/mol, at least about 4 kcal/mol, at least about 5 kcal/mol, at least about 6 kcal/mol, at least about 7 kcal/mol, at least about 8 kcal/mol, at least about 9 kcal/mol, or at least about 10 kcal/mol. In other embodiments, the equilibrium is shifted to the induced fit conformation (E*-I) by at least about 1000 fold or at least about 10000 fold.

In various embodiments of any one of the aspects delineated herein, the measuring involves X-ray crystallography, NMR spectroscopy, and/or fast fluorescence binding kinetics, enzyme kinetics, surface plasmon resonance, and molecular dynamics simulation. In some embodiments, the measuring of the structure of the induced fit conformation (E*-I) involves NMR spectroscopy and/or X-ray crystallography. In some other embodiments, the predicting stability of an induced fit conformation (E*-I) of a candidate agent contacted to an active site of the protein involves in silico simulation. In still other embodiments, wherein the induced fit step or induced fit conformation (E*-I) is identified by detecting a rate having a non-linear dependence on agent concentration.

In various embodiments of any one of the aspects delineated herein, the pre-selected lead agent is selected from a conventional screen of a library of agents or from an in silico simulation.

In various embodiments, the agent is a small molecule, polypeptide, peptide, or peptide mimetic.

In some embodiments, the protein is a kinase. In other embodiments, the active site is an ATP binding site. In some other embodiments, the natural ligand is ATP.

In another aspect, the invention provides a method of identifying a functional residue on a target protein, the method comprising (a) identifying a protein related to the target protein by ancestral reconstruction; (b) measuring stability of a conformation of the related protein contacted with the agent; and (c) correlating a sequence of the target protein and/or a sequence of the related protein with the stability of a conformation of the target protein and/or the related protein contacted with the agent to determine a residue that alters stability when the residue is modified, thereby identifying a functional residue on the target protein.

In still another aspect, the invention provides a method of identifying an agent that selectively modulates a kinase, the method comprising (a) identifying on the kinase a functional residue outside of the active site by ancestral reconstruction; (b) detecting or predicting binding of a candidate agent to the functional residue, and (c) detecting kinase activity of the kinase in the presence of the agent; wherein the candidate agent is identified as binding to the functional residue and modulating the kinase function. In various embodiments, the functional residue is not on an active site of the protein. In some embodiments, the agent is a small molecule.

In some other embodiments, the protein is a kinase. In still other embodiments, the active site is an ATP binding site.

In still another aspect, the invention provides a tangible, non-transitory computer readable medium comprising: computer program instructions for implementing a method of identifying or selecting an agent that inhibits a protein comprising predicting stability of an induced fit conformation (E*-I) of a candidate agent contacted to the active site of the protein, wherein the candidate agent is selected or identified as an inhibitor of the protein if the measured or predicted stability of the induced fit conformation (E*-I) of the candidate agent contacted to the active site is increased relative to a reference stability.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, "activity" or "biological activity" of a polypeptide refers to any biological function or any biological interaction of a polypeptide. Activity of a polypeptide may refer to the polypeptide's enzymatic or catalytic activity (e.g., kinase activity). For example, "kinase activity" of Aurora A kinase refers to Aurora A kinase's phosphorylation of a serine or threonine residue on a substrate polypeptide.

By "active site" is meant an area or portion on a protein where a substrate of the protein binds. For example, if the protein is a kinase, an active site of the kinase is an ATP binding site. A protein may have multiple substrates. Thus, an active site of a kinase may also bind other substrates. For example, another substrate of a kinase is a residue on a polypeptide to which the kinase transfers a phosphate group (i.e., phosphorylates), so an active site on a kinase may be a site on the kinase that binds a residue that the kinase phosphorylates.

By "agent" is meant any small molecule chemical compound, antibody, nucleic acid molecule, peptide, peptide mimetic, polypeptide, or fragments thereof.

By "ameliorate" is meant decrease, suppress, attenuate, diminish, arrest, or stabilize the development or progression of a disease.

By "alteration" is meant a change (increase or decrease) in the binding affinity, expression levels or activity of a gene or polypeptide (e.g., kinase activity) as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The terms "binding," "bind," "bound" refer to an interaction between two molecules. The interaction may include a covalent or non-covalent bond. The interaction may also be reversible or irreversible depending on the type of interaction, such as covalent bond formation.

"Detect" refers to identifying the presence, absence or amount of the analyte to be detected.

By "detectable label" or "detectable tag" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include cancer.

By "effective amount" is meant the amount of a required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "induced fit conformation (E*-I)" is meant a conformation formed by a protein-agent complex only after an agent (e.g., a small molecule) is bound to the protein (e.g., after an agent binds to a site, such as an active site, of the protein). The conformational change of the protein-agent (e.g., enzyme-inhibitor) complex happens after initial binding. The induced fit conformation does not exist in a free protein (i.e., a protein not bound or contacted with the agent).

In some embodiments, the induced fit conformation is formed after a "primary bound conformation (E-I)" (i.e., a conformation corresponding to the initial binding or contact of the agent with the site on the protein). The "induce fit step" corresponds to step of transitioning or converting from the primary bound conformation (E-I) to the induced fit conformation (E*-I) Formation of an induced fit conformation is after the binding of an agent to a site (e.g., active site) on the protein generally results in increased affinity of the agent and/or increased residence time of the agent on the protein.

In particular embodiments, the agent is an inhibitor of the protein (e.g., the agent inhibits an activity, such as catalytic or enzymatic activity, of the protein). The agent may inhibit the protein by binding to the active site of the protein (i.e., by competitive binding of the agent to the active site, where the natural substrate binds). Generally, an induced fit conformation may form when a substrate, particularly a natural substrate, is bound to the active site of a protein. However, because a natural substrate must be turned over, the induced fit conformation formed by the natural substrate-protein complex is not extremely stable. An inhibitor of a protein is effective if the inhibitor forms a very stable induced fit conformation, resulting in a highly increased affinity and increased residence time of the inhibitor to the active site of the protein.

In some embodiments, the free energy of binding of an agent at the initial binding step (or primary binding step) is at least about 2 kcal/mol, at least about 3 kcal/mol, at least about 4 kcal/mol, or at least about 5 kcal/mol. In particular embodiments, the induced fit step adds at least about 2 kcal/mol, at least about 3 kcal/mol, at least about 4 kcal/mol, or at least about 5 kcal/mol to the free energy of binding to the energy of binding of the initial binding step. In other embodiments, the overall free energy of binding of the agent to a protein (or to an active site on a protein) is at least about 2 kcal/mol, at least about 3 kcal/mol, at least about 4 kcal/mol, at least about 5 kcal/mol, at least about 6 kcal/mol, at least about 7 kcal/mol, at least about 8 kcal/mol, at least about 9 kcal/mol, or at least about 10 kcal/mol.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence. "Polynucleotide" and "nucleic acid molecule" are used interchangeably herein.

Unless otherwise specified, a "polynucleotide encoding an amino acid sequence," a "polynucleotide encoding a polypeptide," or a "nucleotide sequence encoding an amino acid sequence," includes all nucleotide sequences that are degenerate versions of each other and that encode the same amino acid sequence. The phrase nucleotide sequence that encodes a polypeptide or an RNA may also include introns to the extent that the nucleotide sequence encoding the polypeptide may in some version contain an intron(s).

By an "isolated polypeptide" is meant a polypeptide of the invention that has been separated from components that naturally accompany it. The terms "polypeptide" and "protein" are used interchangeably herein. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "kinase" is meant a protein that catalyzes a phosphorylation reaction, i.e., the transfer of a phosphate group from a phosphate-donor molecule (e.g., ATP) to another agent (e.g, a substrate such as a protein residue). In some embodiments, the protein is a kinase. In some embodiments, the active site of the kinase is an ATP binding site.

By "lead agent" or "pre-selected lead agent" is meant an agent (e.g., a small molecule) that has been identified, detected, or predicted to bind a protein (e.g., a target protein). For example, the lead agent may be an initial "hit" from a conventional screen of a library of agents (e.g., a library of compounds). The lead agent may also be an agent predicted to bind the target protein via in silico simulation methods that calculate predicted binding free energy of the agent to the protein based on atoms or residues on the agent and/or protein. In some embodiments, the agent or lead agent is a macrocycle. In some embodiments, the lead agent is selected from a screen of a library of macrocycles. In particular embodiments, the macrocycle or library of macrocycles is synthesized by DNA encoded synthesis. In other embodiments, the macrocycle is based on a peptide bond.

By "marker" is meant any protein or polynucleotide having an alteration in expression level or activity that is associated with a disease or disorder.

By "modulate" is meant increase or decrease a measured parameter. In one embodiment, the parameter is kinase activity, binding affinity or equilibrium. For example, an increase in affinity is by at least about 1 kcal/mol, 2 kcal/mol, at least about 3 kcal/mol, at least about 4 kcal/mol, at least about 5 kcal/mol, at least about 6 kcal/mol, at least about 7 kcal/mol, at least about 8 kcal/mol, at least about 9 kcal/mol, or at least about 10 kcal/mol.

As used herein, "obtaining" as in "obtaining an agent" includes synthesizing, purchasing, or otherwise acquiring the agent.

As used herein, a "peptide mimetic" or "peptidomimetic" is a small, peptide-like molecule having a structure and/or molecular properties that mimic a peptide.

By "phosphorylation rate" or "rate of phosphorylation" is meant the kinetic rate of a phosphorylation reaction catalyzed by a kinase. An exemplary measure of the rate is the value of a rate constant, k. The rate constant may be determined by plotting the concentrations of phosphorylated substrate against time, and fitting a curve or line to the concentration vs. time data. In some embodiments, the rate constant is determined by determining the slope of a line fit to concentrations of phosphorylated kemptide (substrate of Aurora A kinase) or another substrate of Aurora A kinase over time.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

A "reference stability" is a pre-determined or pre-measured stability used as a basis for stability comparison. For example, without limitation, a reference stability may be the stability of a conformation of a protein (or active site of a protein) contacted with a natural ligand or a natural substrate of the protein. In some embodiments, the conformation is an induced fit conformation (E*-I) of an active site of a protein contacted with a natural ligand or a natural substrate of the protein. The natural ligand of the protein may be ATP, for example, if the protein is a kinase. A reference stability may also be the stability of a conformation of a protein (or active site of a protein) contacted with a pre-selected lead agent. For example, the pre-selected lead agent may be a small molecule that binds the active site of the protein with weak or moderate affinity.

The "stability" of a conformation or a state of a protein (or, a protein in contact with an agent) may be characterized by the ratio of rates of conversion or transition between the conformation to another conformation (e.g., rate of conversion to or from a primary bound conformation E-I to an induced fit conformation E*-I). Stability of a particular conformation is increased when the rate of conversion from another conformation to the particular conformation (i.e., "forward rate") is increased and/or the rate of conversion from the conformation (i.e., "reverse rate") is decreased. In particular embodiments, the stability of an induced fit conformation (E*-I) is increased by decreasing a rate of conversion from the induced fit conformation (E*-I) to another conformation. Stability of a particular conformation may also be characterized by the fraction (or concentration) of the particular conformation relative to other conformations at equilibrium. A particular conformation has high stability if the fraction or concentration of that conformation is high relative to the fraction or concentration of other conformations at equilibrium. Conversely, a particular conformation has low stability if the fraction or concentration of that conformation is low relative to the fraction or concentration of other conformations at equilibrium. Concentrations of such conformations at equilibrium may be characterized by measuring an equilibrium constant (Keq). In some embodiments, stability of the induced fit conformation (E*-I) is characterized by measuring a $K_{eq}$ of the equilibrium between the primary bound conformation (E-I) and induced fit conformation (E*-I) or by measuring a rate of conversion from a primary bound conformation (E-I) to the induced fit conformation (E*-I) is increased and/or a rate of conversion from the induced fit conformation (E-I*) to the primary bound conformation (E-I).

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 g/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "specifically binds" is meant an agent (e.g., a small molecule) that recognizes and binds a polypeptide (or an active site thereof) of the invention, but which does not substantially recognize and bind other molecules in a sample, for example, a biological sample, which naturally includes a polypeptide of the invention. An agent may also "specifically bind" to a particular site on a polypeptide, and not bind to other sites of the polypeptide. In some embodiments, a small molecule (e.g., Gleevec or Danusertib) binds an active site of a protein (e.g., a kinase).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1C are diagrams and plots showing reconstructing of ancestors of the cytosolic tyrosine kinase family to probe the energy landscape of Gleevec selectivity. FIG. 1A depicts structures of Abl (blue/dark grey) and Src (red/light grey) kinases bound to Gleevec (stick representation). FIG. 1B shows a phylogenetic tree constructed with Bali-Phy (31) with the reconstructed nodes marked with a star, name, and color used throughout the manuscript. For the full tree including reconstruction posteriors, see FIGS. 6A-6B. FIG. 1C shows all ancestors are fully active as measured using a continuous fluorescent-based assay (Antibody Beacon) for phosphorylation of the tyrosine in the target peptide (SEQ ID NO: 1)
(EAIYAAPFAKKK).

FIG. 2A shows inhibition constants (Ki) determined from a decrease in activity with increasing Gleevec concentrations at 25° C. FIG. 2B shows dissociation constants (Kd) for Gleevec at 5° C. measured by fluorescence quenching (Kd values for the weak binders Src and ANC-S1 could not be well determined because of inner-filter effects at high Gleevec concentrations). FIG. 2C shows a proposed Gleevec binding scheme to human Src and Abl (6) and the ancestors. E and E.I correspond to free and inhibitor-bound kinase; E*.I corresponds to inhibitor-bound kinase in a distinct conformational state, DFG-in and DFG-out subscripts specify the conformation of the DFG loop. FIG. 2D shows kinetics of Gleevec binding as was measured by stopped-flow fluorescence at 5° C. Mixing 50 nM kinase with 1-150 µM Gleevec (see also FIG. 8) displayed double exponential kinetics with the fast phase reporting on the binding step (FIG. 2F) and the slow step monitoring the induced fit (FIG. 2G). FIG. 2E shows kinetics of Gleevec binding as was measured by stopped-flow fluorescence at 5° C. dissociation was measured by stopped-flow fluorescence at 5° C. Rate of dissociation was measured by 11-fold dilution of equimolar kinase/Gleevec complex is dominated by E*.I to E.I interconversion, while koff is much faster (intercept in FIG. 2F).

FIGS. 3A-3E are plots showing the evolution of the free energy landscape in tyrosine kinases. FIG. 3A shows the evolution of the DFG-in/DFG-out equilibrium. FIG. 3B shows the Gleevec binding step and FIG. 3C shows the induced fit step. In FIG. 3A, the gradual population shift between DFG-out (blue/dark grey, 4CSV) and DFG-in (pink/light grey, 4CDS, top) is reflected in the differences in amplitude of the fast phase (bottom). In FIG. 3B, the $k_{on}^{obs}$, the product of the true $k_{on}$ and the population of DFG-out, increases from ANC-AS to Abl in parallel with the increase in the DFG-out population seen in FIG. 3A. This suggests very similar true $k_{on}$ values for all proteins, and the measured $k_{off}$'s for Gleevec are also equivalent within experimental error. In FIG. 3C, for the induced fit step, a gradual decrease in the forward rate constant (kconf+, C top) and a drastic increase in the reverse rate constant (kconf−, C bottom) from the tight binder Abl via the common ancestor to the weak binder ANC-S1 and Src is apparent. FIG. 3D shows free energy contributions of conformational selection plus binding to the overall binding energy. The resulting free energy differences for the first two steps between the proteins are small, while the gradual shift in the induced-fit equilibrium from the tight to weak binders results in a large difference in Gleevec affinity (up to 5 kcal/mol). FIG. 3E shows free energy contributions of conformational selection plus and binding and the induced fit step to the overall binding energy.

FIGS. 4A-4H are diagrams and plots show the atomistic mechanism for Gleevec selectivity. In FIG. 4A a multiple sequence alignment of Src, Abl, and reconstructed ancestral sequences is shown. Mutations between ANC-AS and AS(+15) responsible for changing Gleevec affinity to levels comparable to Abl are marked in bold blue (light grey in non-shaded columns) and mapped on the ANC-AS structure bound to Gleevec (pdb id: 4CSV) as black spheres (FIG. 4B). FIG. 4C shows inhibition constants (Ki) determined from a decrease in activity with increasing Gleevec concentrations at 25° C. and FIG. 4D shows dissociation constants (Kd) for Gleevec at 5° C. measured by fluorescence quenching. FIG. 4E shows a structural comparison of Src (pdb id: 2OIQ), ANC-AS (pdb id: 4CSV) and Abl (pdb id: 1OPJ) bound to Gleevec (Van der Waals representation) highlighting the different P-loop conformations (shown as dark ribbon). As shown in FIG. 4F, the 10 residues out of the 15 identified mutations visible in all three x-ray structures are listed and shown in the structures (FIG. 4G) of Src, ANC-AS and Abl bound to Gleevec, showing how mutations introduced into the AS(+15) construct disrupt the hydrogen bond network (dotted lines) present in weak binders Src and ANC-AS. FIG. 4H shows an Abl.Gleevec structure close-up showing the additional stabilizing interactions between the P-loop and D-helix that only become possible in the absence of the identified hydrogen bonding network.

FIGS. 5A-5F are plots showing a mechanism of Gleevec evolved resistance in Abl(T315I). FIGS. 5A-5B show kinetics of Gleevec binding and dissociation. Kinetics of Gleevec binding in (FIG. 5A) and dissociation (FIG. 5B) was measured by stopped-flow fluorescence at 5° C. In FIGS. 5A, 5C, and 5D, mixing 50 nM kinase with 1-150 µM Gleevec (see also FIGS. 2A-2E) displayed double exponential kinetics with the fast phase reporting on the binding step (FIG. 5C) and the slow step monitoring the induced fit (FIG. 5D). In FIG. 5B, the rate of dissociation measured by rapid dilution of kinase/Gleevec complex is dominated by E*.I to E.I conversion and is much faster in Abl(T315I). In FIG. 5E, the site of mutation T315I is plotted onto the x-ray structure of Abl bound to Gleevec (PDB id: 1OPJ). FIG. 5F shows individual rate constants for binding and induced fit step demonstrate that the binding is almost unaltered in T315I but the induced fit step is drastically weakened (FIG. 5G) by both a decrease of the forward and increase in the reverse rate.

FIG. 10A shows a 2.9 Å x-ray structure of the last common ancestor ANC-AS bound to AMPPCP (4CDS, gold/light grey) is superimposed with active conformations of Src (2BDF, red/medium grey) (18) and Abl (2G2I, blue/dark grey) (19). ANC-AS is very similar in structure to the modern day kinases with an overall RMSD of 1 Å to Abl and 0.89 Å to Src. Zoom into the DFG loop and active site highlights that nonphosphorylated ANC-AS (gold/light grey) crystallized in the active state with DFG-in (blue/dark is Abl active state and red/light is Src active state) (FIG. 10B), and there is a poor superposition with the corresponding inactive structures of Abl (light blue/dark, 2G2F) and Src (orange/medium grey, 2SRC) (FIG. 10C).

FIG. 10D shows a 2.1 Å x-ray structure of the last common ancestor ANC-AS bound to Gleevec (4CDS, light grey/gold) superimposed with the Gleevec-bound structures of Src (2OIQ, red/medium grey) (17) and Abl (1OPJ, blue/dark grey) (20). FIG. 10E shows a comparison of the corresponding Gleevec binding pockets show that they are nearly identical. Gleevec is shown in ball-and stick representation.

10A-10E). X-ray structures are superimposed using SuperPose (21) and the corresponding C—C distance maps are shown below. C atoms that are moving closer in distance relative to each C atom in the other structure are indicated in blue (dark), and atoms that move further away are colored in yellow/red (light/medium). The activation loop is not included in the difference maps (grey) because of too weak electron density. FIG. 11A shows the C RMSD between ANC-AS.Gleevec and Src.Gleevec structures is 1.35 Å with the major differences in 2-3 loop, 4-5 loop and D-helix. FIG. 11B shows the C RMSD between ANC-AS.Gleevec and Abl.Gleevec is 1.90 Å illustrating that ANC-AS.Gleevec aligns better to Src compared to Abl. The major differences between ANC-AS.Gleevec and Abl.Gleevec are in the P-loop, the D-helix and 3-C-Helix loop. FIG. 11C shows the C RMSD between Abl.Gleevec and Src.Gleevec structures is 2.02 Å with the major changes as reported before (17). FIGS. 11A-11C are a grey scale version of color figures. A copy of the original color heat maps is available upon request.

In FIG. 12A, sequence differences between ANC-AS (weak binder) and ANC-A2 (tight binder) are plotted onto the ANC-AS.Gleevec structure as spheres. These residues where separated into two sets, N-lobe (blue) and C-lobe (red) mutations and then further split into buried residues (light red, light blue) and solvent exposed residues (dark red and dark blue) (see FIG. 12B). Such crude divide-and-conquer approach was motivated by the simple scientific intuition that solvent exposed residues are less likely be important for binding of a hydrophobic compound to the interior of the protein or intramolecular interactions. Dividing by N-terminal and C-terminal lobe was aimed at figuring out whether long-range interactions all the way into the C-terminal domain could play a role, which is not the case as revealed by the results.

FIG. 12B shows a biochemical characterization of the constructs carrying different combinations of mutations. Solubility, activity and inhibition constants for Gleevec for each of the constructs, ANC-AS and Abl are added for comparison. All constructs with mutational sets involving the C-lobe were either insoluble, or had severely compromised activity. Importantly, N-lobe buried mutations were sufficient to switch affinity for Gleevec to levels corresponding to tight binders.

FIG. 13A-13C are plots showing a comparison of the kinetic properties between ANC-AS, AS(+15) and Abl. In FIGS. 13A-13B, kinetic of binding (left) was measured by stopped-flow fluorescence at 5° C. 50-100 nM of kinase was mixed with 1-100 M of Gleevec. The fast phase (FIG. 13A) corresponds to the binding step and the slow step (FIG. 13B) corresponds to the induced fit step, (see scheme in FIG. 2C). Values for each of the observed rate are shown on the right. Shown in FIG. 13C is Gleevec dissociation initiated by 11-fold dilution of equimolar kinase/Gleevec complex (experimental conditions are the same as in FIG. 2). The rate of fluorescent change is determined by E*.I to E.I interconversion ($k_{conf-}$), while koff is much faster (interceptin A).

As shown in FIG. 14A, in Abl bound to AMPPCP, the P-loop electron density is too weak to reliably place it. In ANC-AS (FIG. 14B) and Src (FIG. 14C) the P-loop has increased B-factors relative to the rest of the fold but still enough electron density to place the P-loop.

FIG. 15A shows a X-ray structure of unphosphorylated Aurora A (122-403)+AMPPCP (AMPPCP in black stick and the magnesium in yellow sphere) in inactive (in cyan/light grey, PDB code 4C3R) and active state (in orange/dark grey, PDB code: 4UTE). In FIGS. 15B-15C, a detailed view of structural elements is shown: the nucleotide binding region (K162, D274, E181), the R-spine (L196, Q185, F275, H254, D311) and the activation loop region pinned at its N- and C-terminal anchor points (D256, K258, T292), the phosphorylated Aurora A (PDB code=1OL7) is in red. FIG. 15D shows a superposition of the DFG(W) motif in the three states. FIGS. 15E-15F show a view zoomed in in the activation loop motif. FIGS. 15G-15I show monitoring the conformational selection in Aurora A with atomic resolution. FIG. 15G shows a X-ray structure of Aurora A bound to AMPPCP (PDB code=4C3R). The four tryptophans are represented in green sticks except Trp277, which is in red. FIGS. 15H-15I show a $^{19}$F NMR spectra of Aurora A wild-type (FIG. 15H) and Aurora A W277L apo (FIG. 15I), dephosphorylated bound to AMPPCP and phosphorylated in blue/dark grey, red/medium grey and green/light grey respectively.

FIGS. 16A-16K are schematics and plots showing the kinetics of Danusertib (labeled D) binding to unphosphorylated Aurora A at 25° C. Trp277 fluorescence changed after mixing with 10 µM Danusertib (the curve is fitted with a mono-, double- and triple exponential in green/medium grey, cyan/light grey and pink/dark grey respectively). Aurora A Danusertib kinetic's is triple exponential: one binding rate $k_{obs}$ binding (FIG. 16B) and two observed rate constants that plateaus around 6 s$^{-1}$ and 0.13 s$^{-1}$ (FIG. 16C and FIG. 16D for $k_{obs}$ CS and $k_{obs}$ IF respectively) in agreement with the proposed binding scheme in FIG. 16G.

FIG. 16E shows dissociation kinetics of Aurora A/Danusertib measured by tryptophan fluorescence after a 30-fold dilution of the complex. FIG. 16F shows a dissociation constant of Aurora A-Danusertib measured by Trp fluorescence.

In FIG. 16G, a binding scheme highlighting a three-step binding mechanism combining a conformational selection and an induced fit is shown. Kinetics of Gleevec (labeled G) binding to unphosphorylated Aurora A at 10° C. FIG. 16H shows a Trp277 fluorescence change after mixing of 0.5 µM unphosphorylated Aurora A with 40 µM Gleevec. The curve is fitted with a monoexponential that corresponds to the $k_{obs}$ binding of the drug (FIG. 16I). FIG. 16J shows dissociation kinetics of Aurora A/Gleevec complex measured after a 10-fold dilution of the complex by stopped-flow fluorescence. FIG. 16K shows a binding scheme that highlights a two-step binding mechanism.

FIG. 17A shows raw data of Trp fluorescence change after mixing of 0.1 µM of Abl T315I with 2 µM Gleevec. The curve is fitted with a mono-, double- and triple exponential in green/medium grey, cyan/light grey and pink/dark grey respectively. Abl T315I/Gleevec kinetics is a triple exponential. FIG. 17B shows dissociation kinetics of Abl T315I/Gleevec complex measured by tryptophan fluorescence after a 150-fold dilution. FIG. 17C shows a binding scheme highlighting a three-step binding mechanism. The Abl T315I mutant shows a conformational selection step (not observed in the wild-type protein). Shown in FIG. 17D is a binding scheme of Abl to Gleevec that highlights a two-step binding mechanism.

FIG. 18A shows raw data of Trp fluorescence change after mixing of 0.1 µM of Abl with 2 µM Danusertib. The curve is fitted with a mono- and a double-in green/medium gray and cyan/light gray respectively. Abl/Danusertib kinetic's is double exponential: one binding rate $k_{obs}$ binding (FIG. 18B) and another observed rate constant that plateaus around 3 $s^{-1}$ (FIG. 18C). FIG. 18D shows dissociation kinetics of Abl/Danusertib complex measured by tryptophan fluorescence after a 30-fold dilution. FIG. 18E shows a binding scheme highlighting a two-step binding mechanism. The same procedure has been applied to Abl T315I/Danusertib complex. Abl T315I/Danusertib kinetic's is a triple exponential (FIG. 18G). FIG. 18H shows dissociation kinetics of Abl T315I/Danusertib complex binding scheme highlighting a three-step binding mechanism. FIG. 18I shows a X-ray structure of Abl T315I bound to Danusertib (PDB=2V7A) superimposed with the X-ray structure of Abl wild-type bound to Gleevec (PDB=1OPJ). The gatekeeper residue T315 mutated in Ile is shown in blue/medium gray sticks, Danusertib in green/light grey sticks and Gleevec in black sticks.

FIG. 19A shows raw data of Trp277 fluorescence change after mixing with 30 µM MantATP (the curve is fitted with a mono- and a double exponential in green and cyan respectively. Trp277 fluorescence change after mixing of 0.5 M of Aurora A with increasing amounts of MantATP. Aurora A/MantATP kinetic's is a double exponential: one binding rate $k_{obs}$ binding (FIG. 19B) and the other observed rate constant that plateaus around 20 $s^{-1}$ (FIG. 19C) in agreement with the proposed binding scheme in FIG. 19F. FIG. 19D shows dissociation kinetics of Aurora A/MantATP measured by Trp fluorescence after a 10-fold dilution. FIG. 19E shows a dissociation constant of Aurora A-MantATP measured by Trp fluorescence. FIG. 19F shows a binding scheme highlighting a two-step binding mechanism including an induced fit step.

FIGS. 20A-20C are a table and plots showing data on unphosphorylated Aurora A (122-403) apo and bound to AMPPCP both in the DFG-in active state. FIG. 20A is a table showing data collection and refinement statistics (Molecular Replacement) of unphosphorylated Aurora A (122-403) apo and bound to AMPPCP both in the DFG-in active state FIG. 20B shows superposition of unphosphorylated Aurora A in active conformation DFG-in state bound to AMPPCP (PDB=4UTD in orange) and apo (PDB=4UTE, in wheat). FIG. 20C shows [$^1$H-$^{15}$N] HSQC spectra of dephosphorylated apo, AMPPCP bound and $^{15}$N tryptophans specific labeling apo in blue/medium grey, red/dark grey and green/light grey respectively. Three tryptophans side chains were detected instead of the four expected.

FIG. 21B shows raw data of Trp fluorescence change after mixing with 50 µM Danusertib (the curve is fitted with a double exponential in cyan/light grey). The amplitude of the fluorescence change is 5 to 10 times smaller than in the wild-type protein. FIG. 21C shows a dissociation constant of W277L Aurora A mutant/Danusertib complex measured by Trp fluorescence at 25° C. is identical to the wild-type within an experimental error.

FIGS. 23A-23B are plots showing the effect of changing the population of DFG-in and DFG-out of Aurora A in the global fit analysis. Datasets at 10, 30 and 90 µM of Danusertib at two timescales 1 s and 30 s. $K_{off}$ is the release of the drug experiment. Global simulations were done using Kintek software. FIG. 23A shows a global fit using the scheme in FIG. 16G with the two conformational selection rates forward and backward identical and equal to 6 $s^{-1}$ (chi2/DOF=3.8). FIG. 23B shows a global fit using the scheme in FIG. 16G with the two conformational selection rates forward and backward equal to 6 $s^{-1}$ and 0.05 $s^{-1}$ respectively (chi2/DOF=4). Based on the global fit, the population of DFG-in has to be higher than 3% and lower than 40% approximately.

FIG. 24A shows an alternative scheme proposed to fit the kinetics data. In this scheme, Danusertib can binds to DFG-in and DFG-out states without any induced fit step. FIG. 24B shows datasets at 10, 30 and 90 µM of Danusertib at two timescales 1 s and 30 s. $K_{off}$ is the release of the drug experiment. Global simulations were done using Kintek software (chi2/DOF=3.7). With such a scheme, 2 $K_D$ should be measured $K_{D1}$=4.4 µM and $K_{D2}$=0.2 nM. FIG. 24C shows an alternative scheme proposed to fit the kinetics data. In this scheme, Danusertib can binds to one state of the kinase but this state can experiences two induced fit steps. FIG. 24D shows datasets at 10, 30 and 90 µM of Danusertib at two timescales 1 s and 30 s. $K_{off}$ is the release of the drug experiment. Global simulations were done using Kintek software (chi2/DOF=2.5). With such a scheme, 2 $K_D$ should be measured $K_{D1}$=0.2 nM and $K_{D2}$=0.8 µM.

FIGS. 25A-25C are plots showing kinetics of Danusertib binding to phosphorylated Aurora A at 25° C. FIG. 25A shows a dissociation constant of phosphorylated Aurora A (122-403)/Danusertib measured by Isothermal calorimetry at 25° C. Aurora A/Danusertib titration was carried out using Nano ITC (TA instruments) and analyzed via the NanoAnalyze software using an independent fit model. Injectant was added in 1 l volume, every 180 s, with a constant stirring speed at 350 rpm and at 25° C. Prior to ITC titration, the protein was dialyzed 50 mM HEPES (pH=7.3), 50 mM NaCl, 20 mM MgCl$_2$, 5 mM TCEP, 3% DMSO. The concentrations used were: 55 M phosphorylated Aurora A and 600 M Danusertib. FIG. 25B shows a kinase assay of phosphorylated Aurora A (122-403) in the presence of 2M TMAO. Ap. The rates of Ap phosphorylation of Aurora A are 1.0±0.2 $s^{-1}$ and 1.2±0.2 $s^{-1}$ without and with TMAO respectively. The presence of 2 M TMAO does not change $k_{cat}$. FIG. 25C shows kinetics of Danusertib binding to unphosphorylated Aurora A at 25° C. with 2M TMAO (50 mM HEPES (pH=7.3), 50 mM NaCl, 20 mM MgCl$_2$, 5 mM TCEP, 2 M TMAO). Trp277 fluorescence change after mixing with 40 µM Danusertib (the curve is fitted with a mono-, double and triple exponential in green/medium grey, cyan/light grey and pink/dark grey respectively). Aurora A Danusertib kinetic's is triple exponential. The presence of 2 M TMAO does not affect any step of the drug binding.

FIGS. 26A-26D are plots showing kinetics of Gleevec binding to 0.5 µM of unphosphorylated Aurora A at 10° C. (50 mM HEPES (pH=7.3), 50 mM NaCl, 20 mM $MgCl_2$, 5 mM TCEP). Trp277 fluorescence change after mixing with different concentrations of Danusertib 1 µM (FIG. 26A), 2 µM (FIG. 26B), 5 µM (FIG. 26C) (the curve is fitted with a monoexponential). At 1 µM Danusertib, the fluorescence increases due to the conformational exchange step. At 2 µM Danusertib, the fluorescence decreases due to the binding of Danusertib and increases due to the conformational exchange step (bigger amplitude for the conformational exchange step compared to the binding step.) At 5 µM and higher Danusertib, the fluorescence decreases due to the binding of Danusertib and increases due to the conformational exchange step (bigger amplitude for the binding step compared to the conformational exchange step). FIG. 26D shows a dissociation constant of Aurora A/Gleevec measured by Isothermal calorimetry at 25° C. Titration was carried out using the same condition than in FIGS. 25A-25C. Prior to ITC titration, the protein was dialyzed in 50 mM HEPES (pH=7.3), 50 mM NaCl, 20 mM $MgCl_2$, 5 mM TCEP, 3% DMSO. The concentrations used were: 160 M deP A (122-403) and 2 mM Gleevec.

FIGS. 27A-27C are plots showing kinetics of Danusertib binding to Tyrosine kinases at 25° C. FIG. 27A shows a dissociation constant of Abl gatekeeper T315I/Gleevec measured by Isothermal calorimetry at 25° C. Titration was carried out using the same condition than in FIGS. 25A-25C. Prior to ITC titration, the protein was dialyzed in 20 mM Tris, NaCl 500 mM, 1 mM $MgCl_2$, 1 mM TCEP, pH 8.0, 3% DMSO. The concentrations used were: 25 M Abl T315I and 340 M Gleevec. FIGS. 27B-27C show dissociation constant of Abl T315I.Danusertib (FIG. 27B) and Abl wild-type.Danusertib (FIG. 27C) measured by Trp fluorescence.

FIG. 28A shows a binding scheme for a three-step binding mechanism combining a conformational selection step first ($k_{in}$ and $k_{out}$), a pure binding step ($k_{on}$ and $k_{off}$) followed by an induced fit process ($k_{id+}$ and $k_{id-}$). FIG. 28B is a table showing a comparison of the $K_D$ calculated from the kinetics parameters and the macroscopic ones measured by tryptophan fluorescence titration. The $K_D$ calculated from the kinetics parameters and the macroscopic ones are in agreement within experimental error. Association and dissociation of drugs with Aurora A, Abl and Abl T315I (when both binding and conformational transitions could be clearly resolved) were also simulated and fitted globally using a numerical algorithms with KinTek explorer program (44). In these simulations the same set of kinetic rate constants was used to fit all datasets corresponding to different drugs concentrations.

FIGS. 29A-29C are plots showing analysis of kinetic data. The following naming convention is used below. Different states of enzyme with or without bound inhibitor are called $E_{in}$, $E_{out}$, $E_{out}.I$ and $E'_{out}.I$. $E_{in}$=kinase in a DFG-in state $E_{out}$=kinase in a DFG-out state $E_{out}.I$=kinase in a DFG-out state bound to the drug $E'_{out}.I$=kinase in a DFG-out state bound to the drug after the induced fit step. Rates describing the time dependence of experimentally observed changes in fluorescence are called "observed rates". $k_{on}$, $k_{off}$, $k_{in}$, $k_{out}$, $k_{id+}$, $k_{id-}$ are called "rate constants" and correspond to individual microscopic steps in chemical schemes. F denotes the amplitude of the observed fluorescent signal generated by combined fluorescence form all enzyme species.

FIG. 29A shows a one step binding scheme (pseudo-first order reaction). In the case of simple pseudo-first-order reaction, the time-dependence of fluorescent changes is mono-exponential. Binding and dissociation ($k_{on}$ and $k_{off}$ respectively) rate constants can be found from the plot of observed rate as a function of inhibitor concentration, where slope of the line is equal to $k_{on}$ and the intercept is equal to $k_{off}$. FIG. 29A further shows simulation of one-step binding scheme. All simulations are done with Kintek Explorer software concentration of enzyme was 0.5 M, rate constants were set to $k_{on}$=0.9 $s^{-1}$ $M^{-1}$, $k_{off}$=0.7 $s^{-1}$ (a) Time dependence of fluorescent signal changes. All curves are mono-exponential and the observed rate of the processes ($k_{obs}$) increases with inhibitor concentration; (b) Dependence of the observed rate on inhibitor concentration. The dependence is linear as expected for pseudo-first-order binding. Slope and intercept of the curve determines binding and dissociation rate constants $k_{on}$ and $k_{off}$.

FIG. 29B shows analysis of kinetic data of a two-step binding scheme. In a more complicated case of a two-step reaction, a double exponential process is observed. If the rates corresponding to these steps are significantly different, each step can be treated separately, and two observed rates (the sum $k_{id+}+k_{id-}$ and $k_{on}$) can be extracted from the fits of Fluorescence vs. Time graph. FIG. 29B further shows simulation of a two-step binding scheme. All simulations are done with Kintek Explorer software, concentration of enzyme was 0.5 M, rate constants were set to $k_{on}$=0.9 $s^{-1}$ $M^{-1}$, $k_{off}$=0.7 $s^{-1}$, $k_{id+}$=0.14 $s^{-1}$, $k_{id-}$=0.00007 $s^{-1}$ (a) Time dependence of fluorescent signal changes. All curves are double exponential with observed rates $k_{id+}+k_{id-}$ and $k_{on}$. (c) Dependence of the observed rate on inhibitor concentration. The dependence of $k_{on}$ is linear and can be used to extract $k_{on}$ and $k_{off}$ rate constant, the dependence of $k_{id}$ on inhibitor concentration is non-linear and plateaus at the value corresponding to the sum $k_{id+}+k_{id-}$.

FIG. 29C shows analysis of kinetic data in a three-step binding scheme. If the rates corresponding to these steps are significantly different, each step can be treated separately, and three observed rates (the sum $k_{id+}+k_{id-}$, $k_{on}$ and the rate that forms the competent state $k_{in}$) can be extracted from the fits of Fluorescence vs. Time graph. FIG. 29C further shows simulation of a three-step binding scheme. All simulations are done with Kintek Explorer software, concentration of enzyme was 0.5 M, rate constants were set to $k_{in}$=6 $s^{-1}$, $k_{out}$=1.4 $s^{-1}$, $k_{on}$=0.9 $s^{-1}$ $M^{-1}$, $k_{off}$=0.7 $s^{-1}$, $k_{id+}$=0.14 $s^{-1}$, $k_{id-}$=0.00007 $s^{-1}$ (a) Time dependence of fluorescent signal changes. All curves are triple exponential (in yellow, the orange fit is a mono-exponential) with observed rates corresponding to the sum $k_{id+}+k_{id-}$, $k_{in}$ and $k_{on}$. The dependence of $k_{on}$ is linear and can be used to extract $k_{on}$ and $k_{off}$ rate constants, the dependence of two conformational exchange before and after binding on inhibitor concentration is non-linear and plateaus at the value corresponding to $k_{in}$ and the sum of $k_{id+}+k_{id-}$ for the first and last equilibrium respectively.

FIG. 30A shows the Aurora kinase family as placed in the context of the Manning tree. FIG. 30B shows reconstruction of Aurora kinase ancestors. FIG. 30C shows activity of phosphorylated and dephosphorylated-like (T288V mutant) of Aurora A kinase.

Reactions were carried in the presence of 1 M protein, 5 mM ATP and 1 mM kemptide in assay buffer (20 mM TrisHCl, 200 mM NaCl, 20 mM MgCl2, 10% (v/v) glycerol, 1 mM TCEP, pH 7.50) at 25° C. Phosphorylated peptide production was monitored by Reverse Phase High Performance Liquid Chromatography (RP-HPLC).

Figure 31:
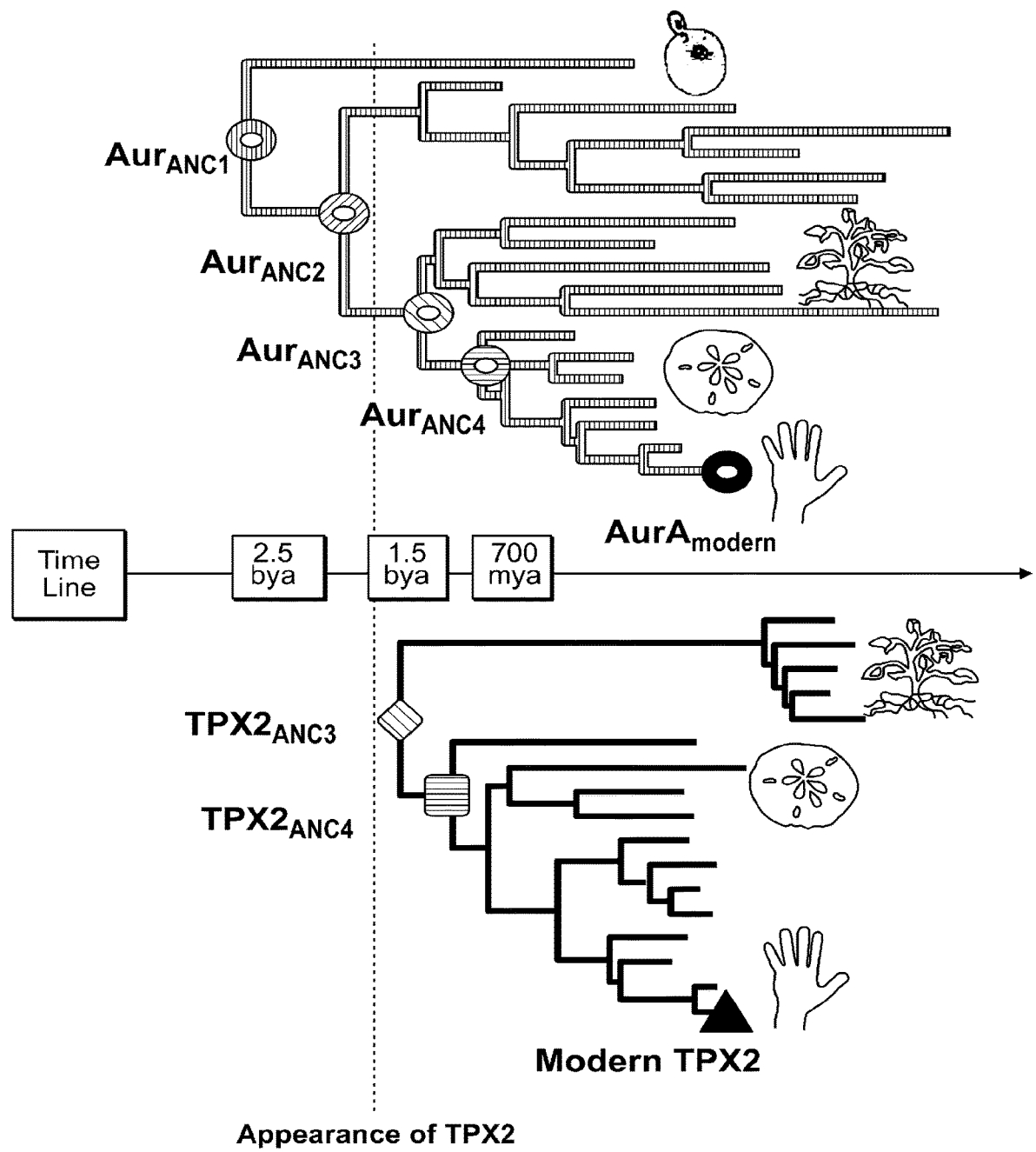

FIG. 31 is a diagram showing reconstructed Aurora kinases and TPX2s. Notice the absence of a canonical TPX2 sequence circa 1-1.8 billion years ago, although ancestral Aurora kinase was present then.

Figure 32A:
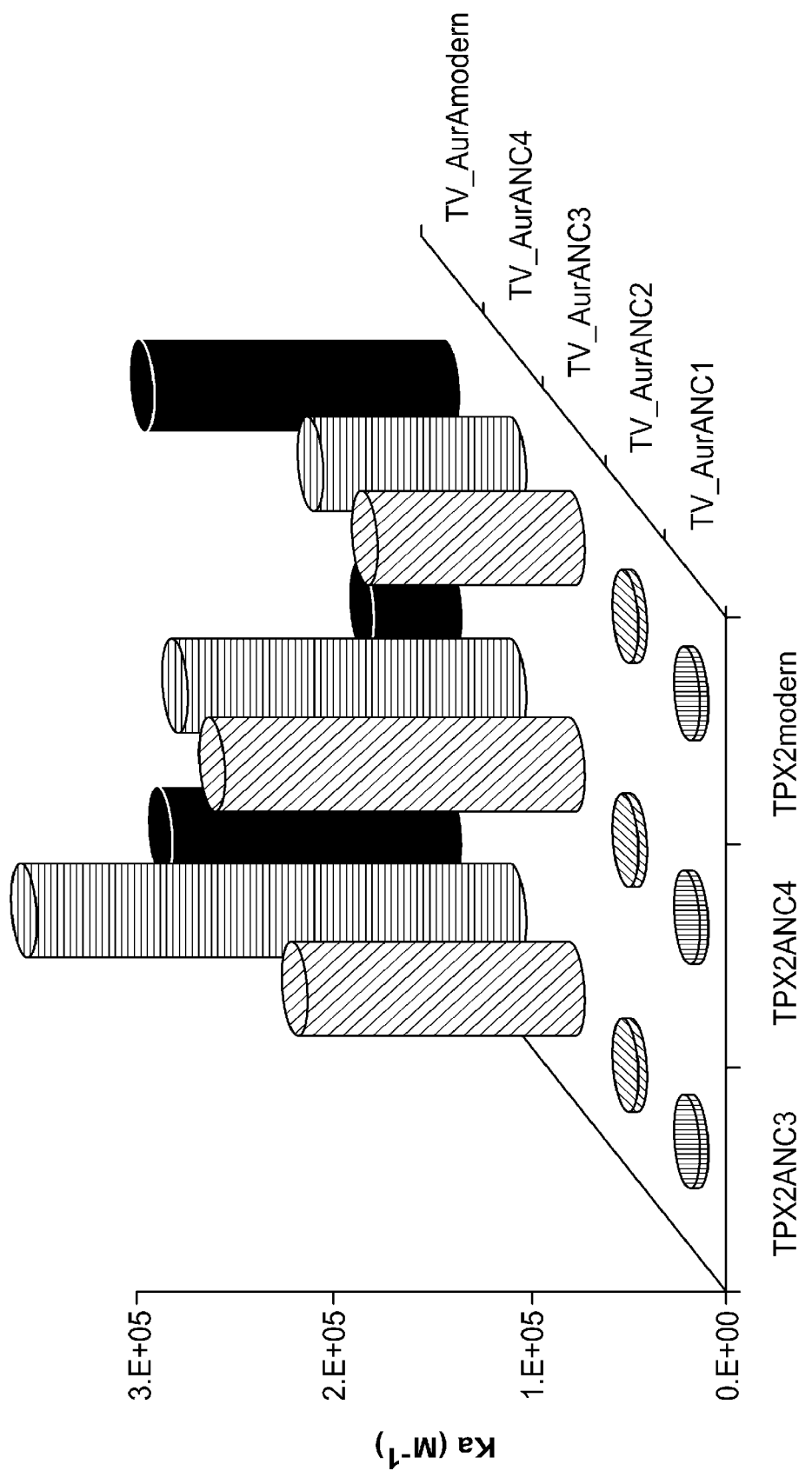
Figure 32B:
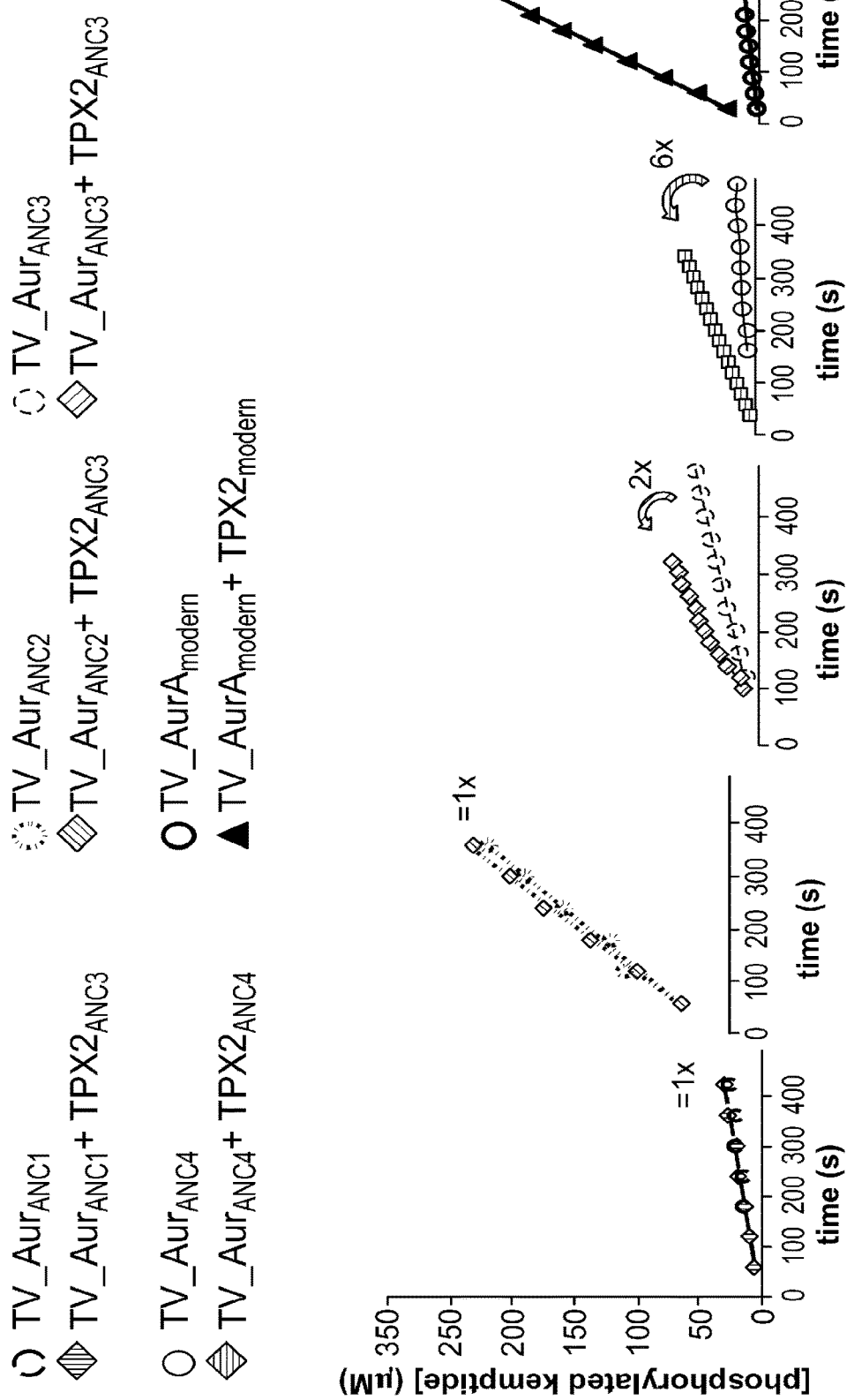
Figure 32C:
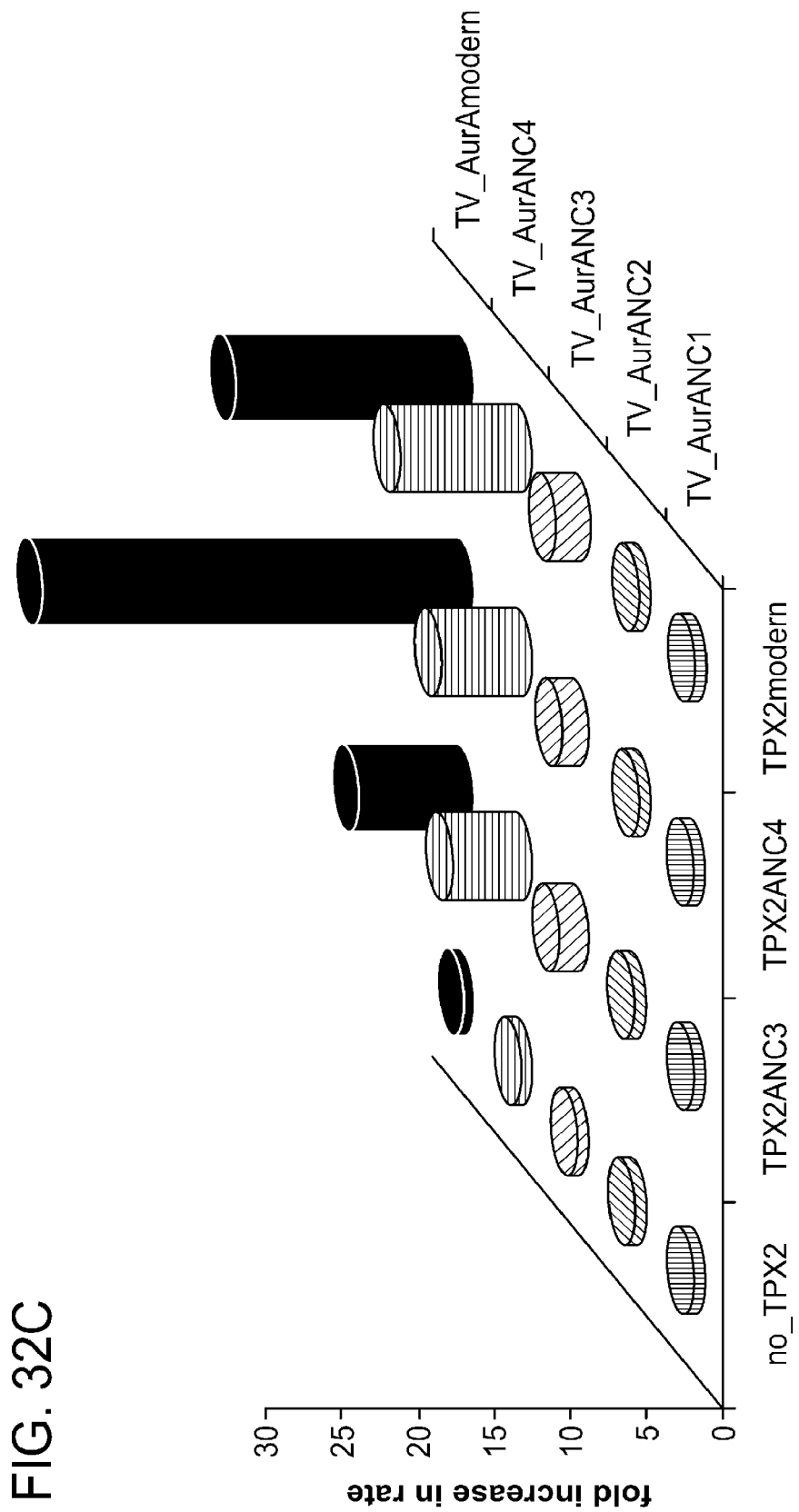

FIGS. 32A-32C are plots showing ancestral TPX2s activate ancestral Aurora kinases (present circa 1-1.8 bya (billion years ago) onwards), with chronologically younger kinases responding the most to the allosteric effect of TPX2. In FIG. 32A, Isothermal Titration calorimetry (ITC) show that ancestral TPX2s bind with similar affinity to ancestral Aurora kinases ($Aur_{ANC3}$/$Aur_{ANC4}$/$AurA_{modern}$) that are present once the canonical ancestral TPX2s appeared. In contrast, older ancestral Aurora kinases ($Aur_{ANC1}$/$Aur_{ANC2}$) only exhibit weak binding to TPX2 which was not possible to quantify by ITC. ITC runs were conducted using the nanoITC at 25° C., 350 rpm stirring speed, 1 1 titrant injection and 180 s delay between injections. Proteins were in assay buffer (20 mM TrisHCl, 200 mM NaCl, 20 mM MgCl2, 10% (v/v) glycerol, 1 mM TCEP, pH 7.50). See FIGS. 35A-35CF for the raw data. FIG. 32B shows that whereas TPX2 cannot activate older ancestral Aurora kinases ($Aur_{ANC1}$/$Aur_{ANC2}$), it can increase the activity of younger Aurora kinases ($Aur_{ANC3}$/$Aur_{ANC4}$/$AurA_{modern}$), with the most recent Auroras feeling the greatest effect of TPX2. Reactions were carried in the presence of 1 M protein, +/−400 M TPX2, 5 mM ATP and 1 mM kemptide in assay buffer at 25° C. Phosphorylated peptide production was monitored by Reverse Phase High Performance Liquid Chromatography (RP-HPLC). FIG. 32C shows an increase in the overall rate of Aurora kinase activation by matched or mismatched TPX2 partners. See FIG. 36 for the raw data.

Figure 33A:
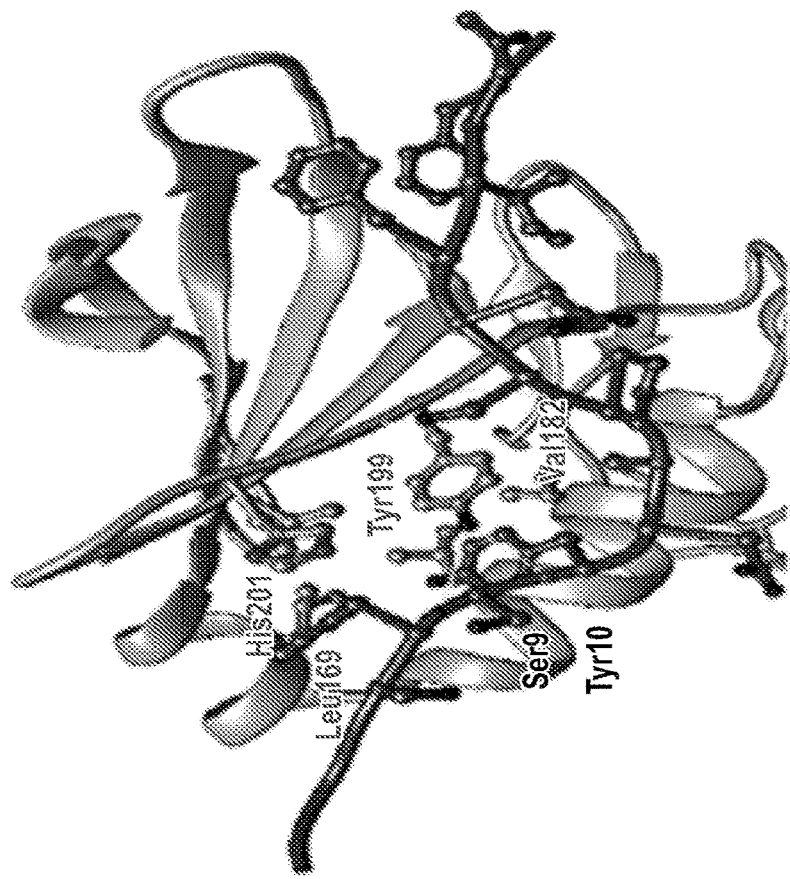
Figure 33B:
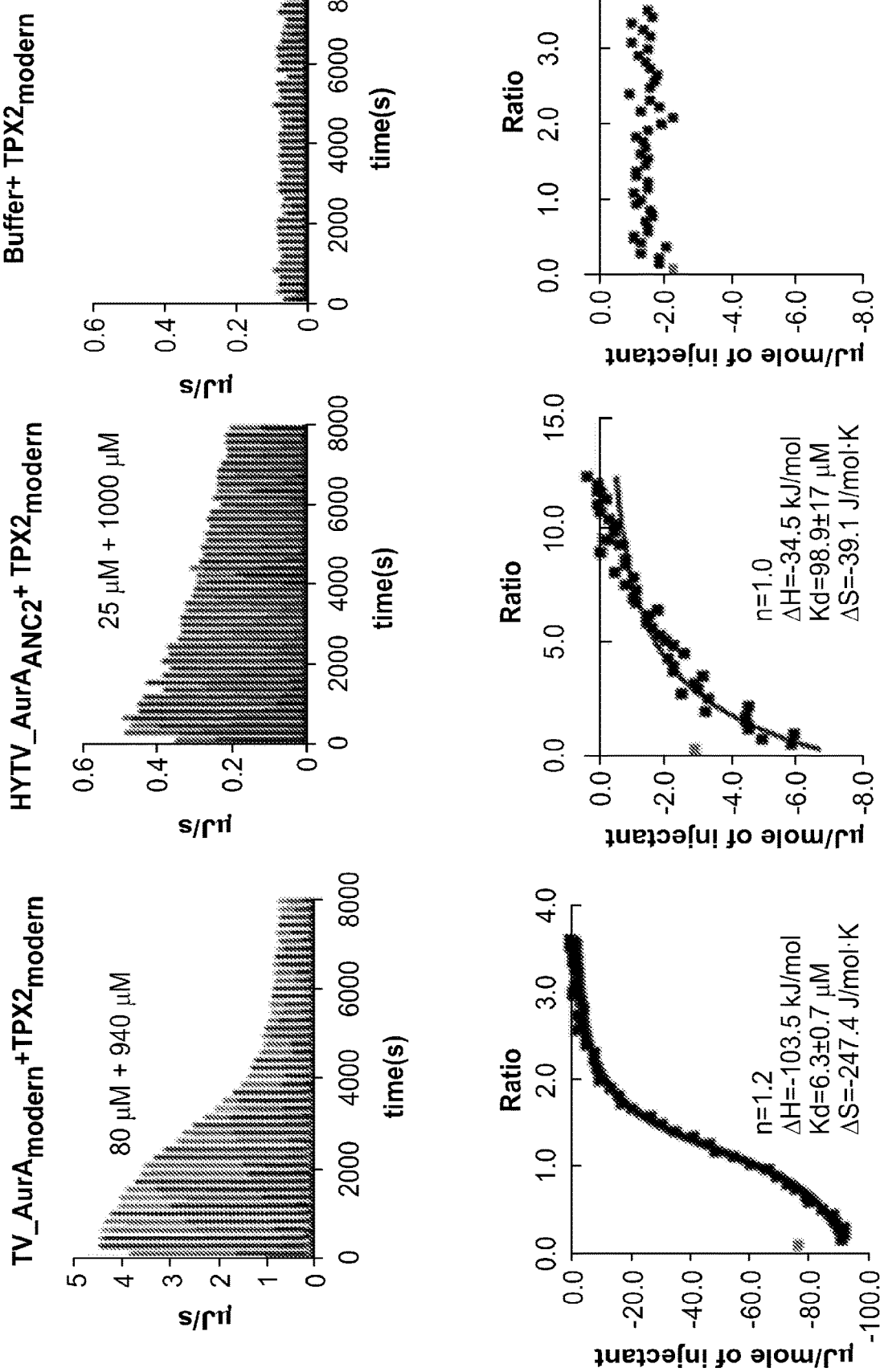
Figure 33C:
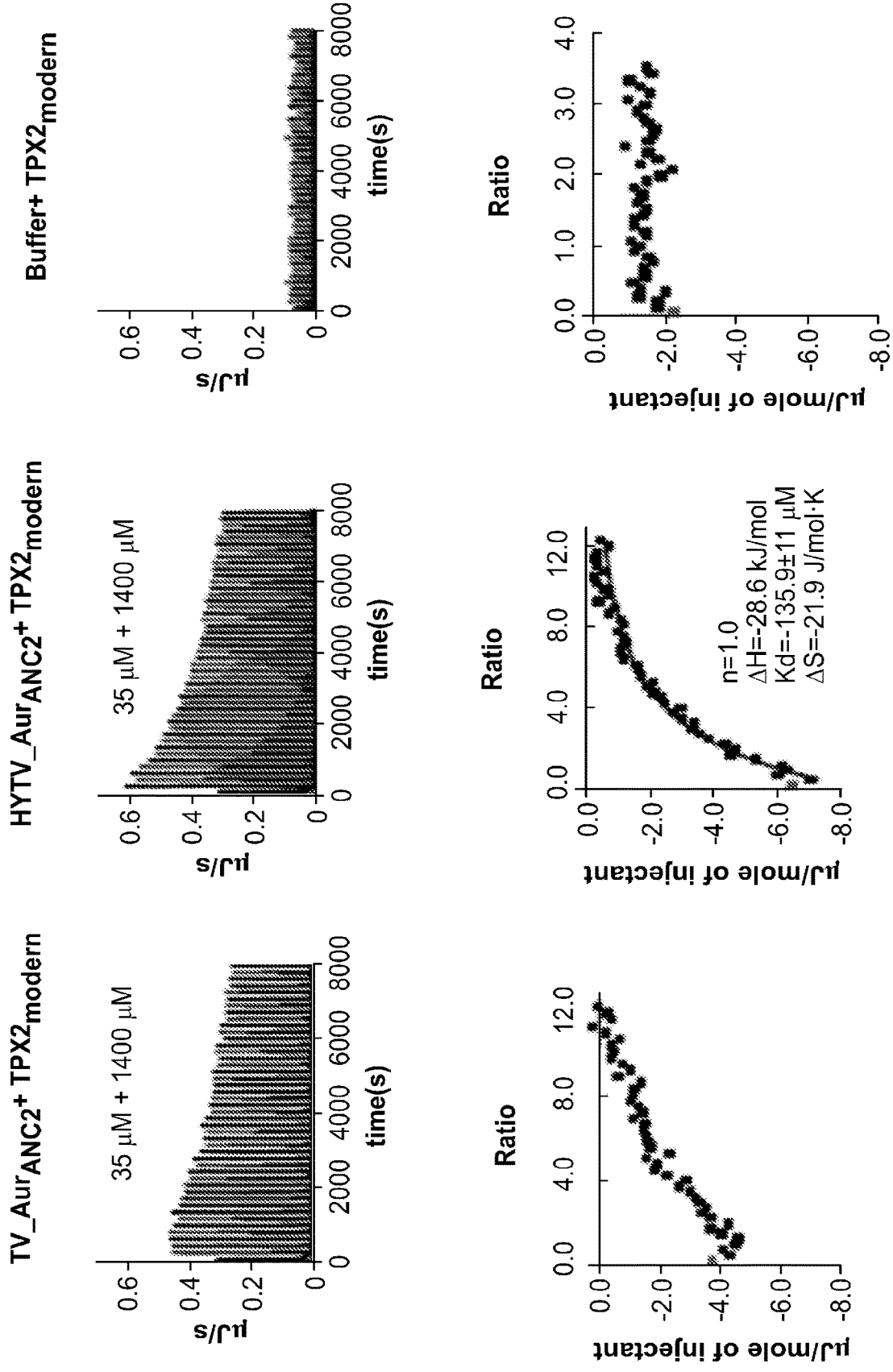

FIGS. 33A-33C are plots and schematics showing Y199 is an Aurora A hotspot important in TPX2 binding. Y199H Aurora A (FIG. 33A) shows severely impaired binding to modern TPX2, Tmodern. However, as shown in FIG. 33B, once above $K_d$, Tmodern can activate Aurora A to the same extent it can activate the wild type kinase. FIG. 33C shows the analogous (H to Y mutation) in $Aur_{ANC2}$ that existed before the appearance of a canonical TPX2 motif, significantly increases the binding of $Aur_{ANC2}$ towards $TPX2_{modern}$. However, despite enhanced binding, activation by TPX2 is not achieved in $Aur_{ANC2}$ thus suggesting that evolutionary adaptation of Aurora A kinase is what governs full allosteric activation by TPX2.

Figure 34:
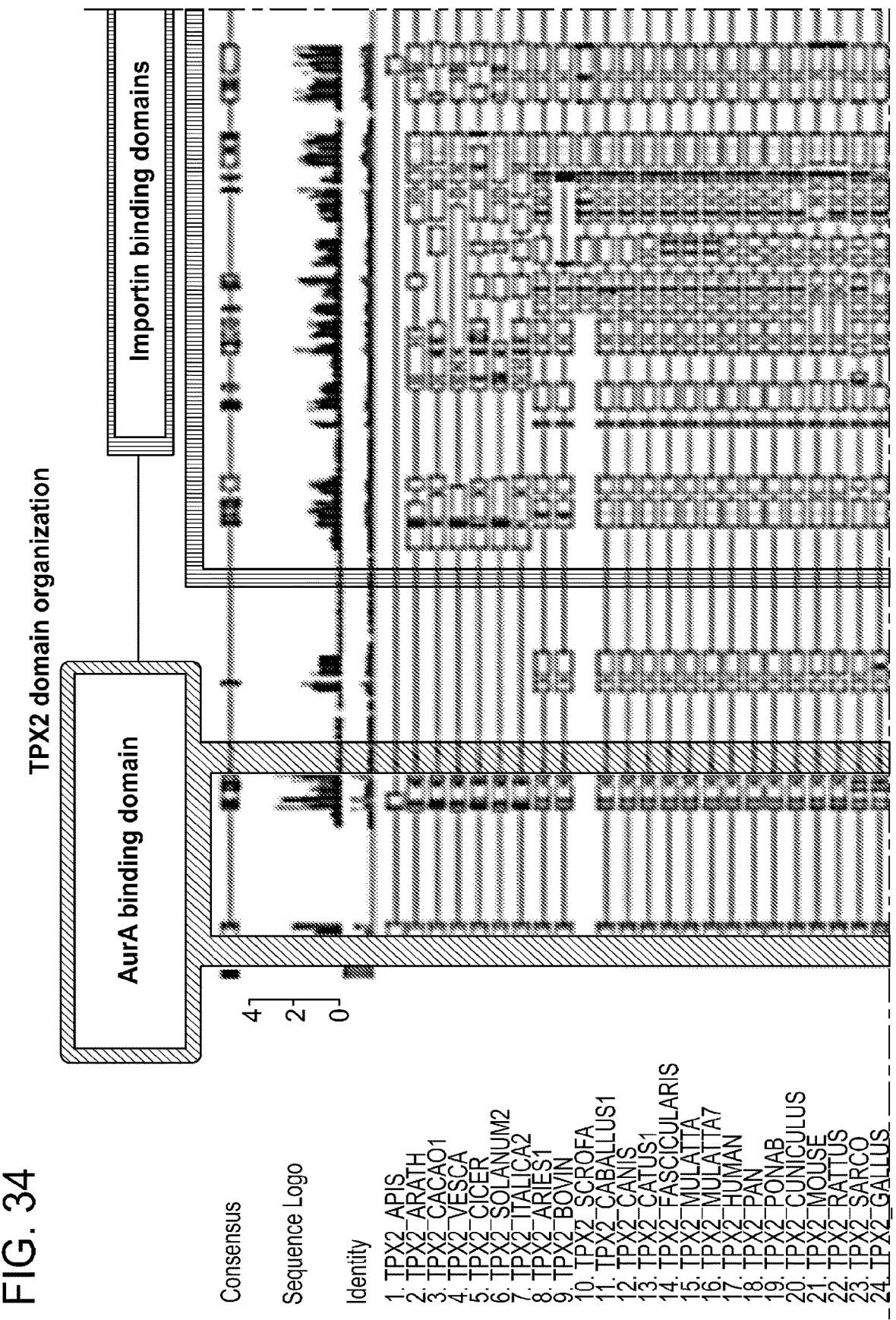
Figure 34:
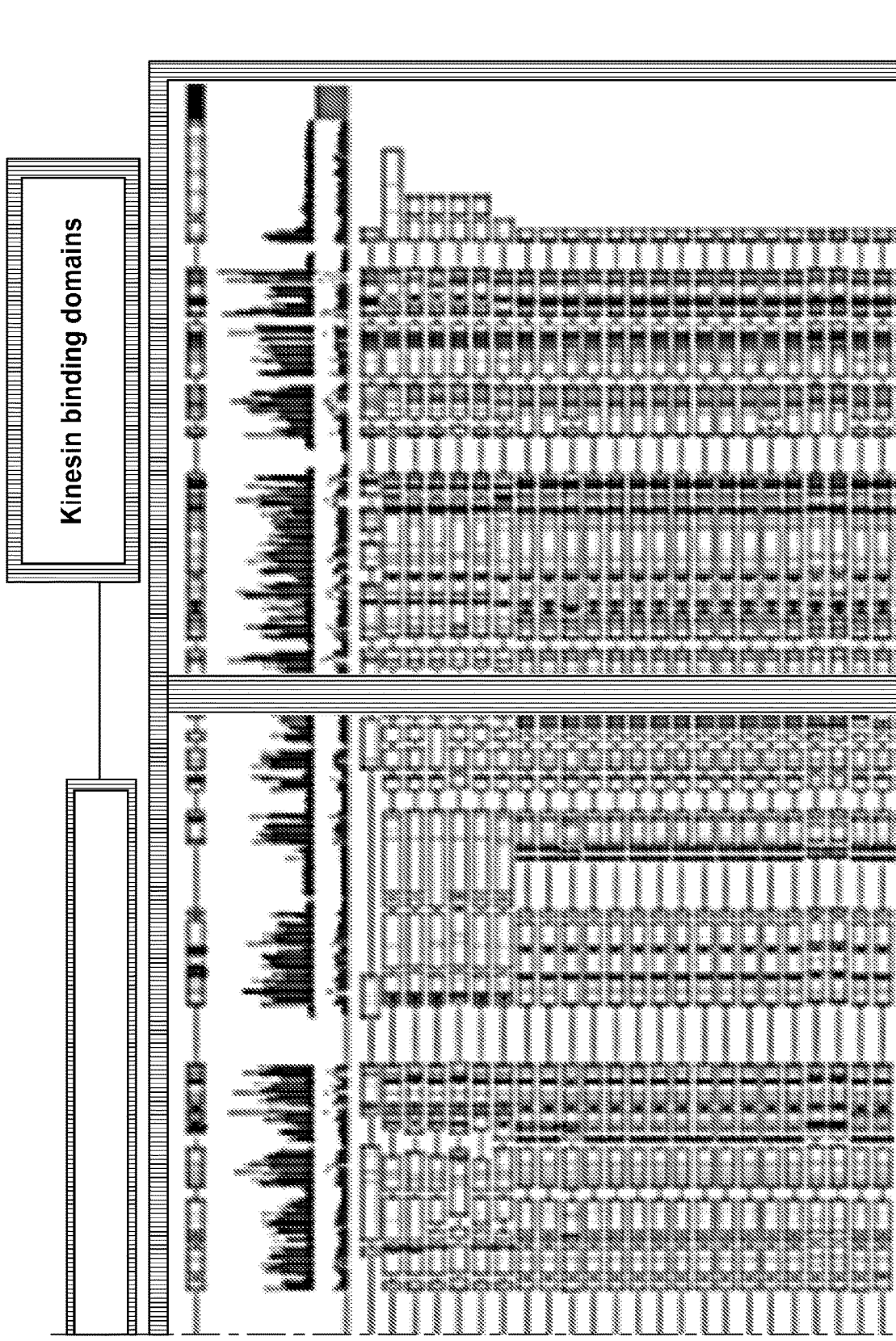
Figure 34:
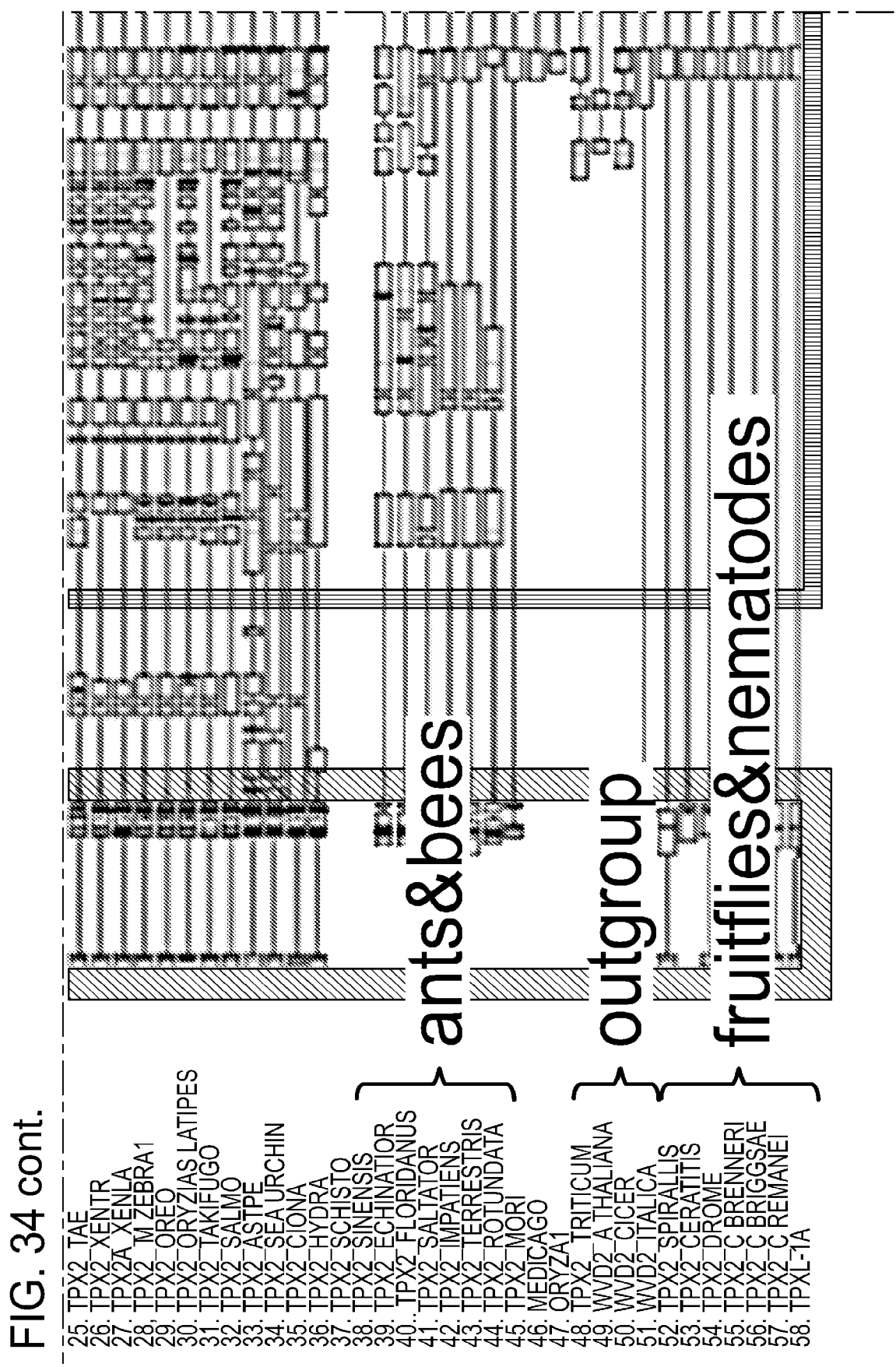
Figure 34:
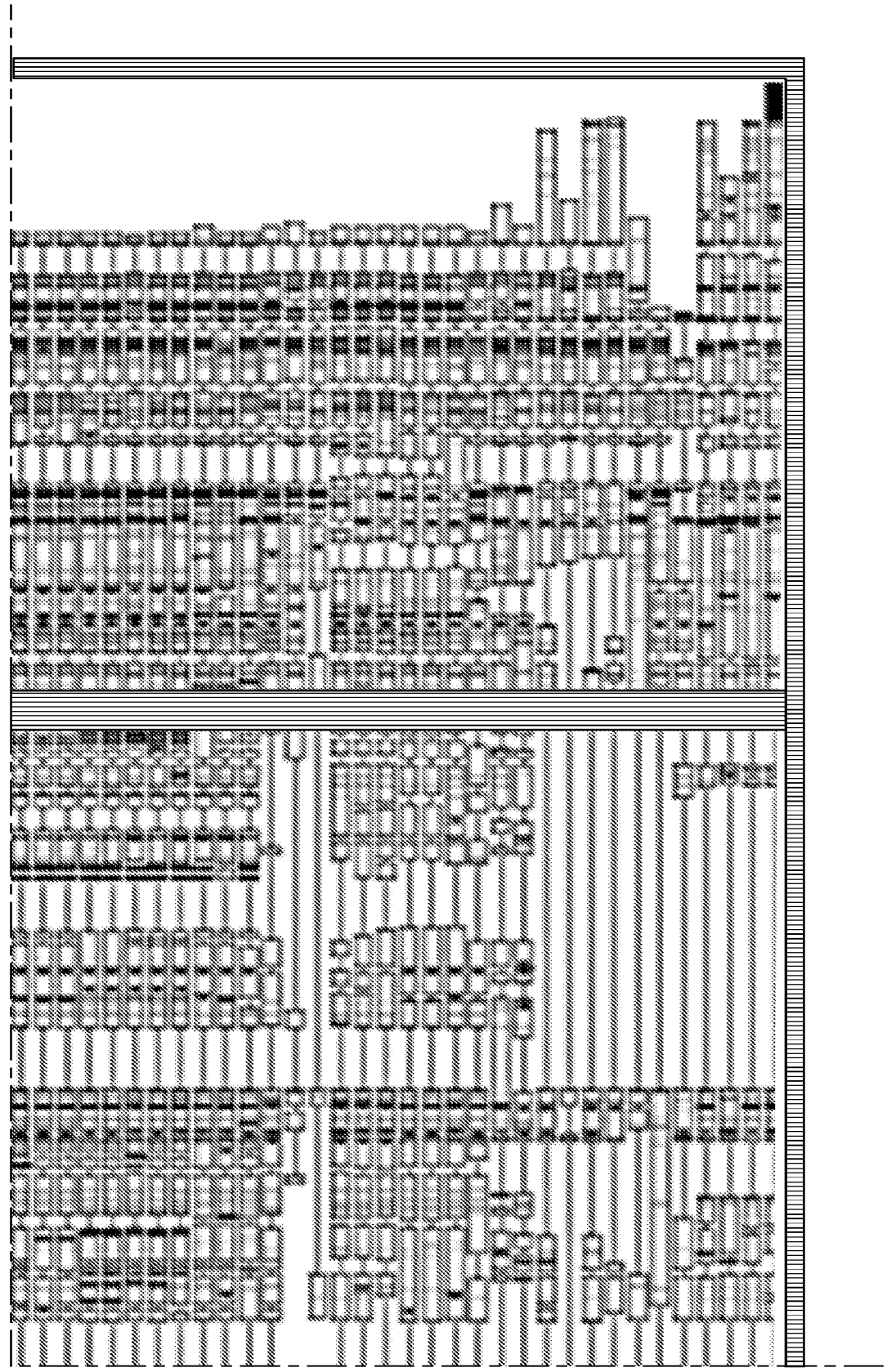
Figure 34:
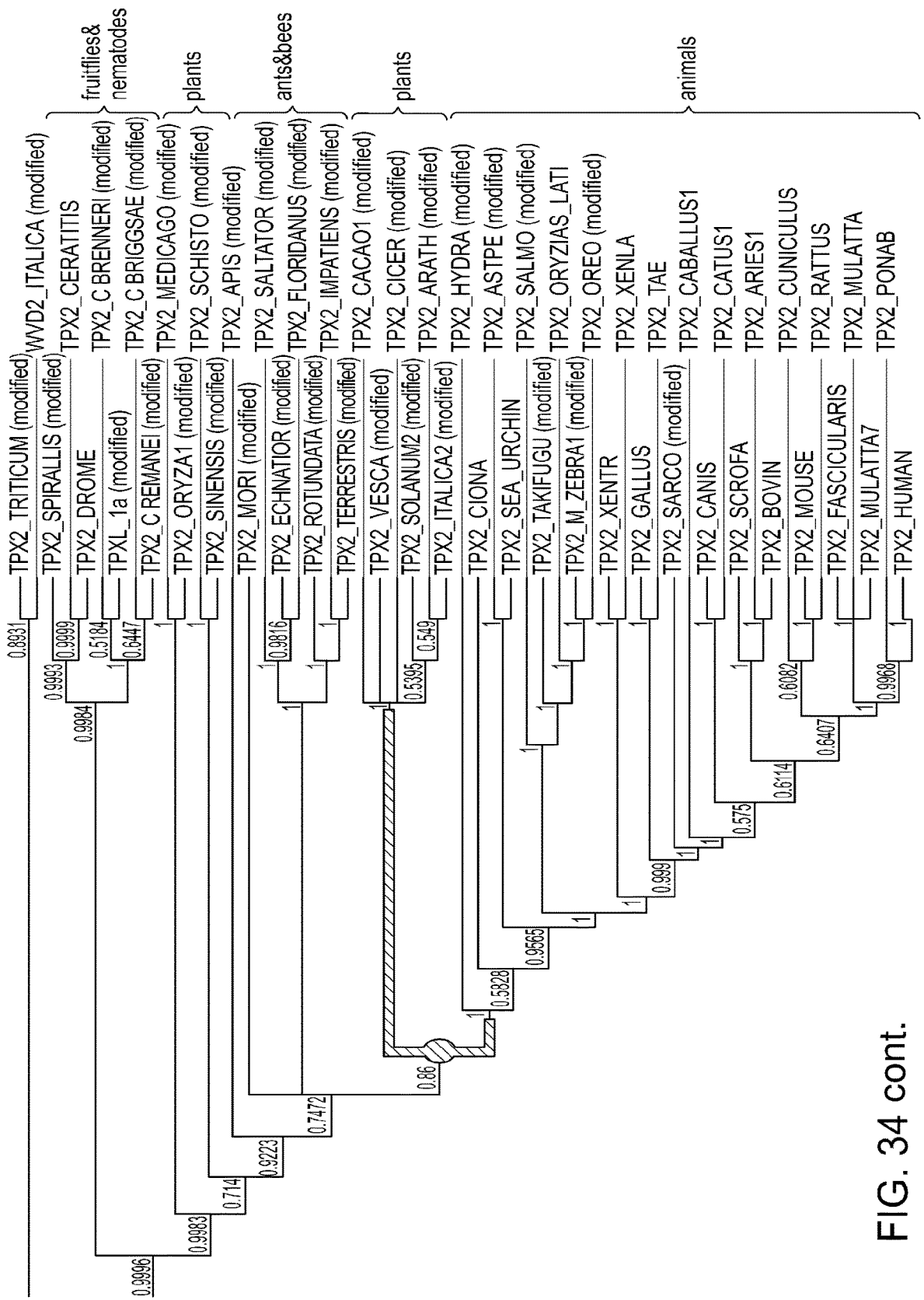

FIG. 34 is a schematic showing a full TPX2 tree.

Figure 35A:
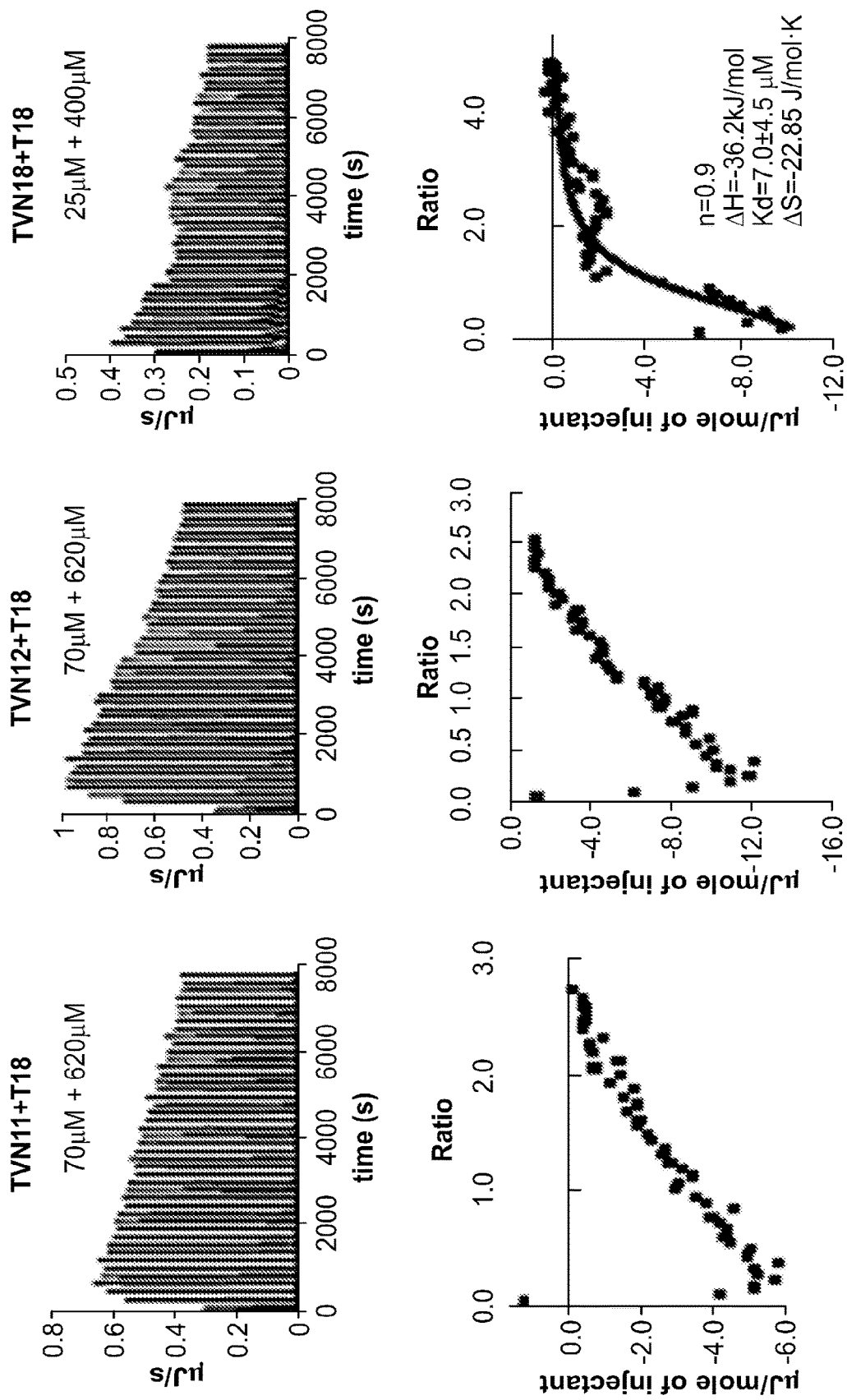
Figure 35A:
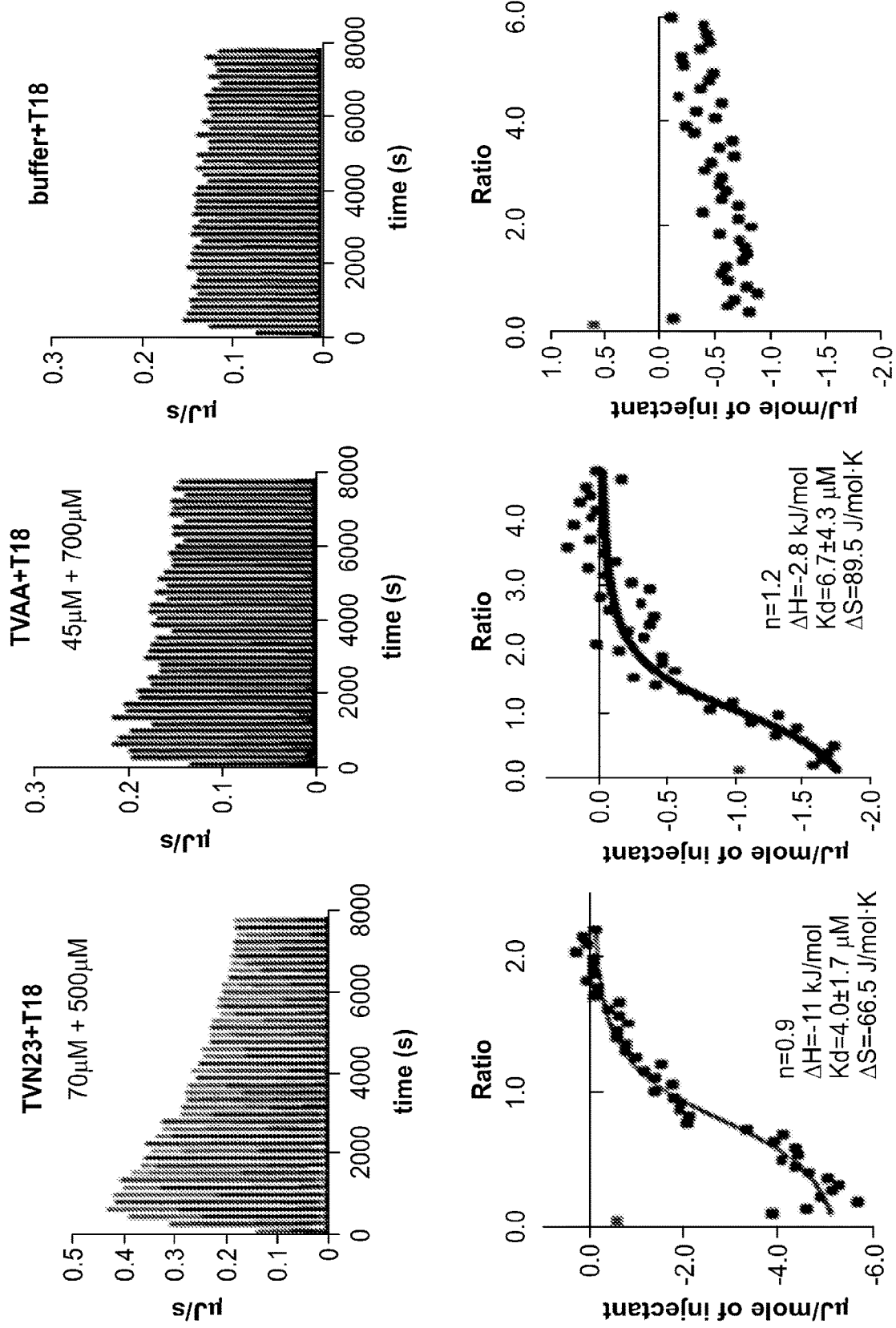
Figure 35B:
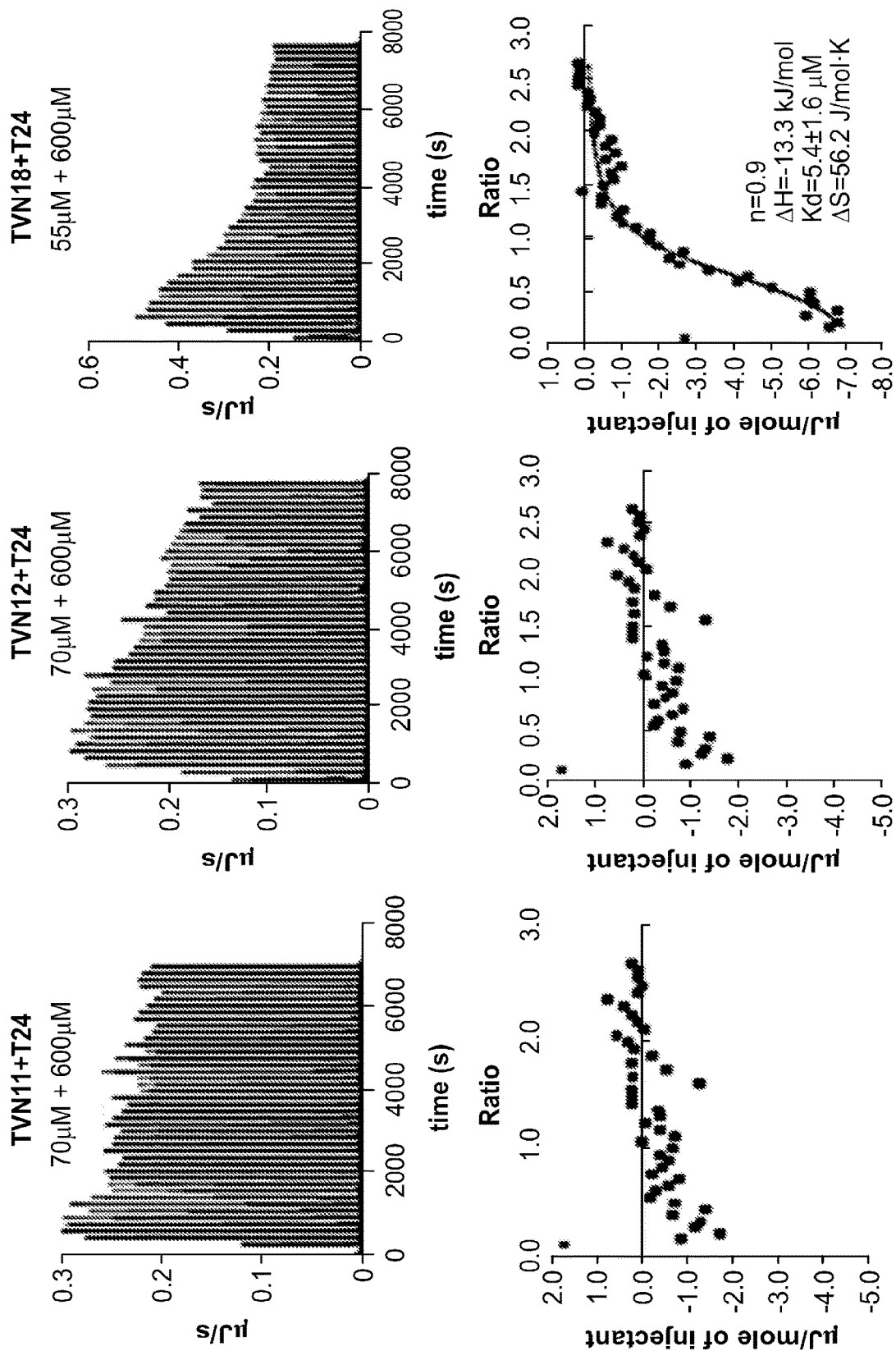
Figure 35B:
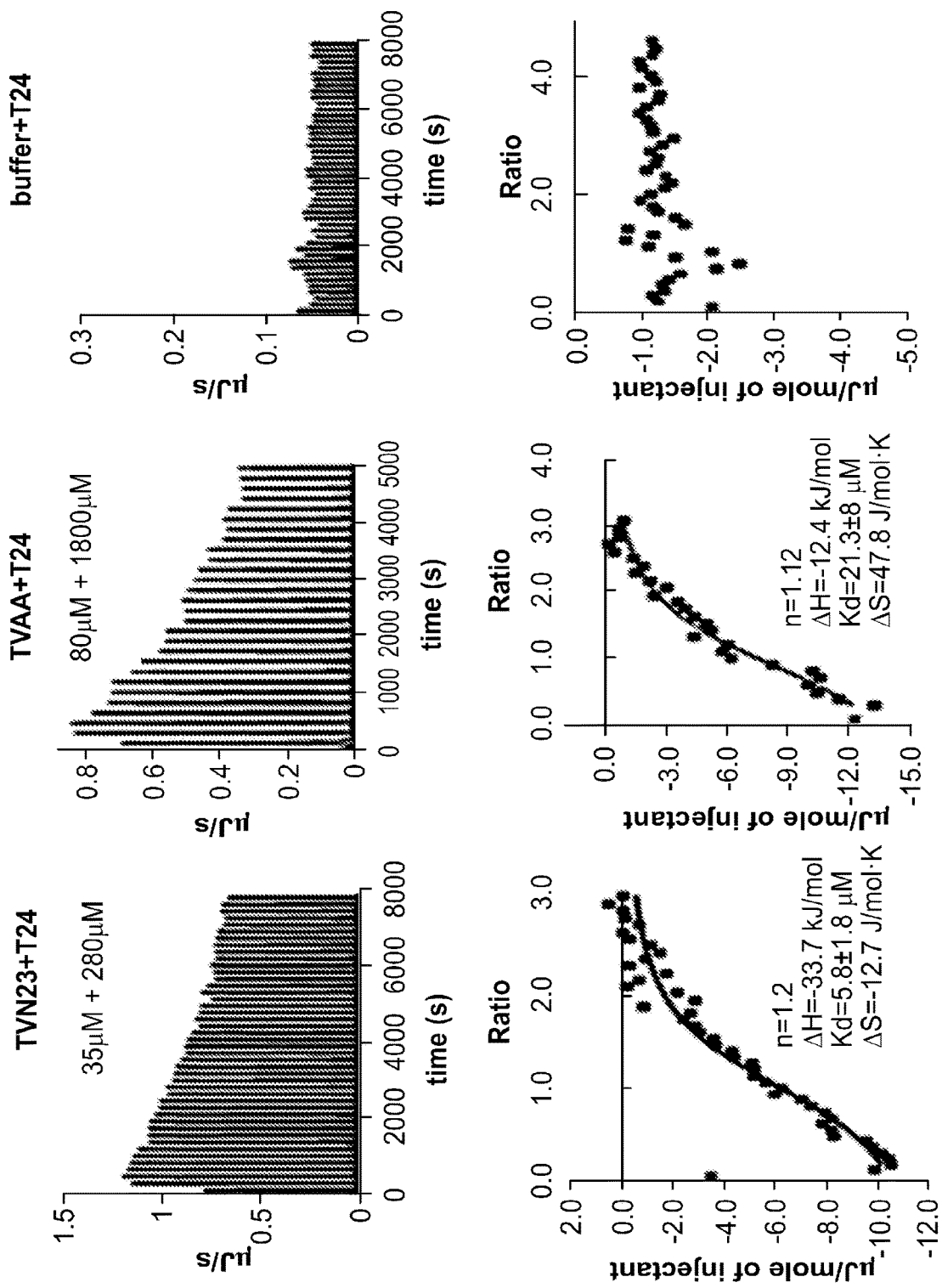
Figure 35C:
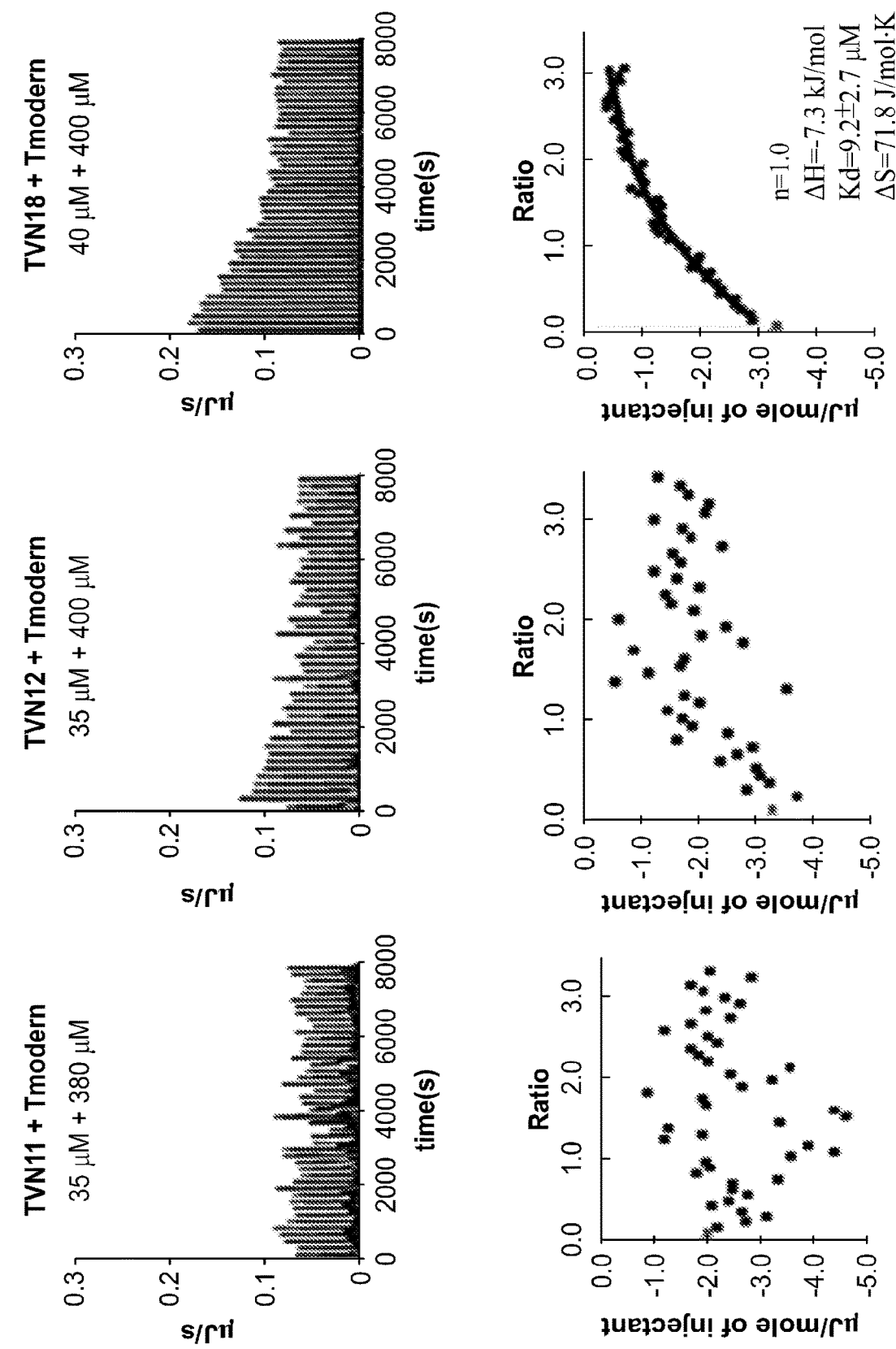
Figure 35C:
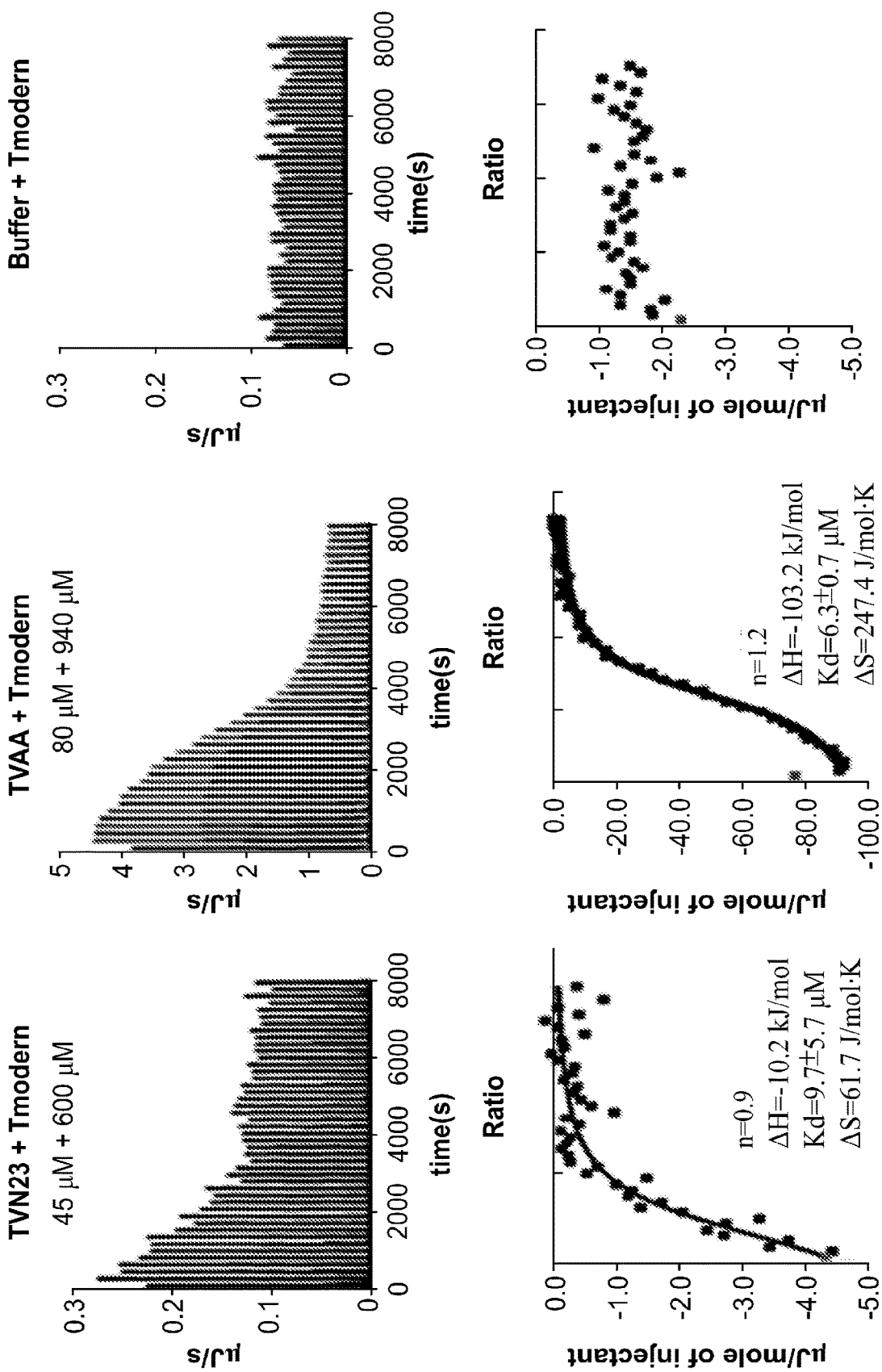

FIGS. 35A-35C are plots showing ITC runs. In FIG. 35A, ITC runs were conducted using the nanoITC at 25° C., 350 rpm stirring speed, 1 1 titrant injection and 180 s delay between injections. Proteins were in assay buffer (20 mM TrisHCl, 200 mM NaCl, 20 mM MgCl2, 10% (v/v) glycerol, 1 mM TCEP, pH7.50). In FIG. 35B, ITC runs were conducted using the nanoITC at 25° C., 350 rpm stirring speed, 1 1 titrant injection and 180 s delay between injections. Proteins were in assay buffer (20 mM TrisHCl, 200 mM NaCl, 20 mM MgCl2, 10% (v/v) glycerol, 1 mM TCEP, pH 7.50). In FIG. 35C, ITC runs were conducted using the nanoITC at 25° C., 350 rpm stirring speed, 1 1 titrant injection and 180 s delay between injections. Proteins were in assay buffer (20 mM TrisHCl, 200 mM NaCl, 20 mM MgCl2, 10% (v/v) glycerol, 1 mM TCEP, pH7.50).

Figure 36:
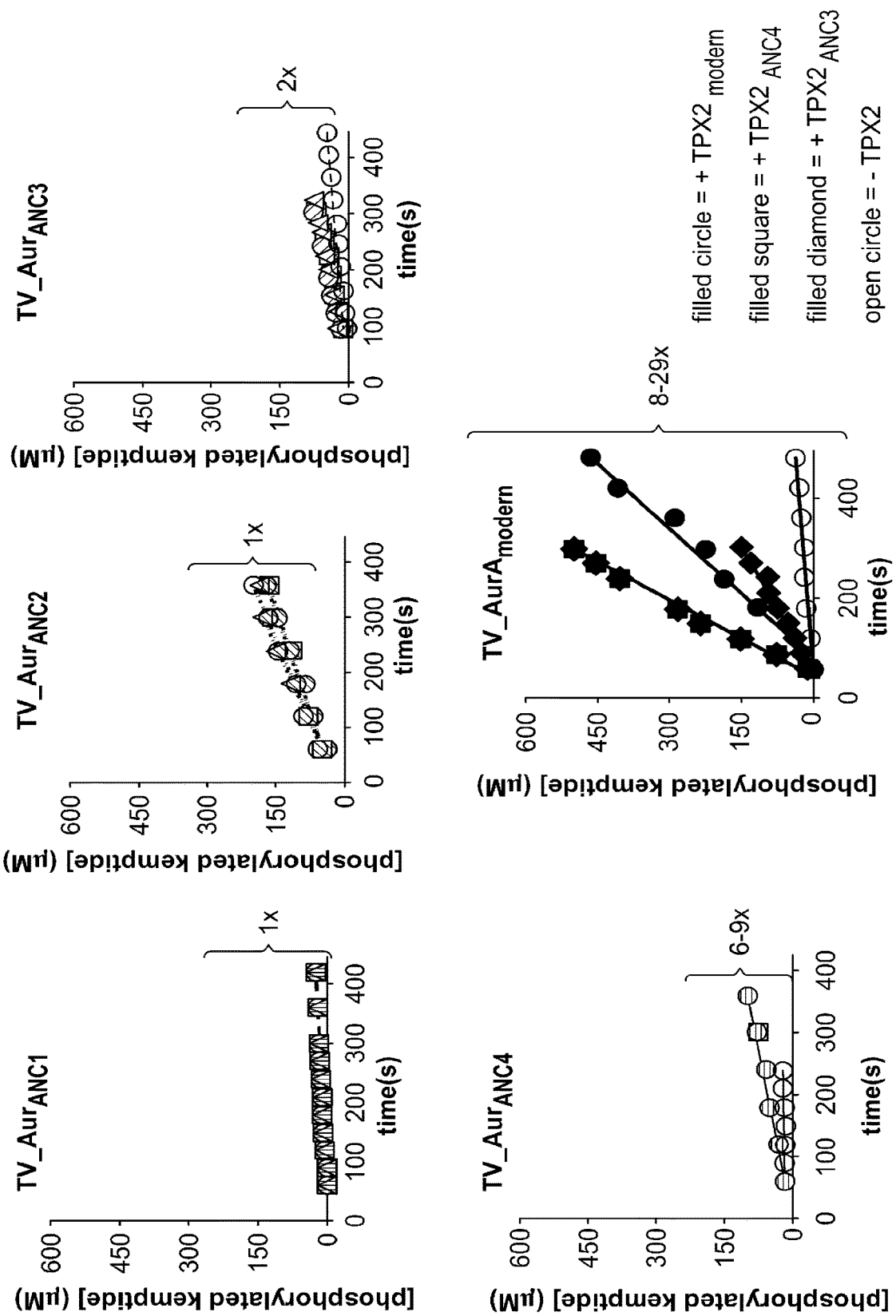

FIG. 36 is a series of plots showing data on activation of ancestral Aurora kinase by TPX2s from different time periods, shows that the younger the Aurora kinase, the greater the fold increase in Aurora activity.

Figure 37:
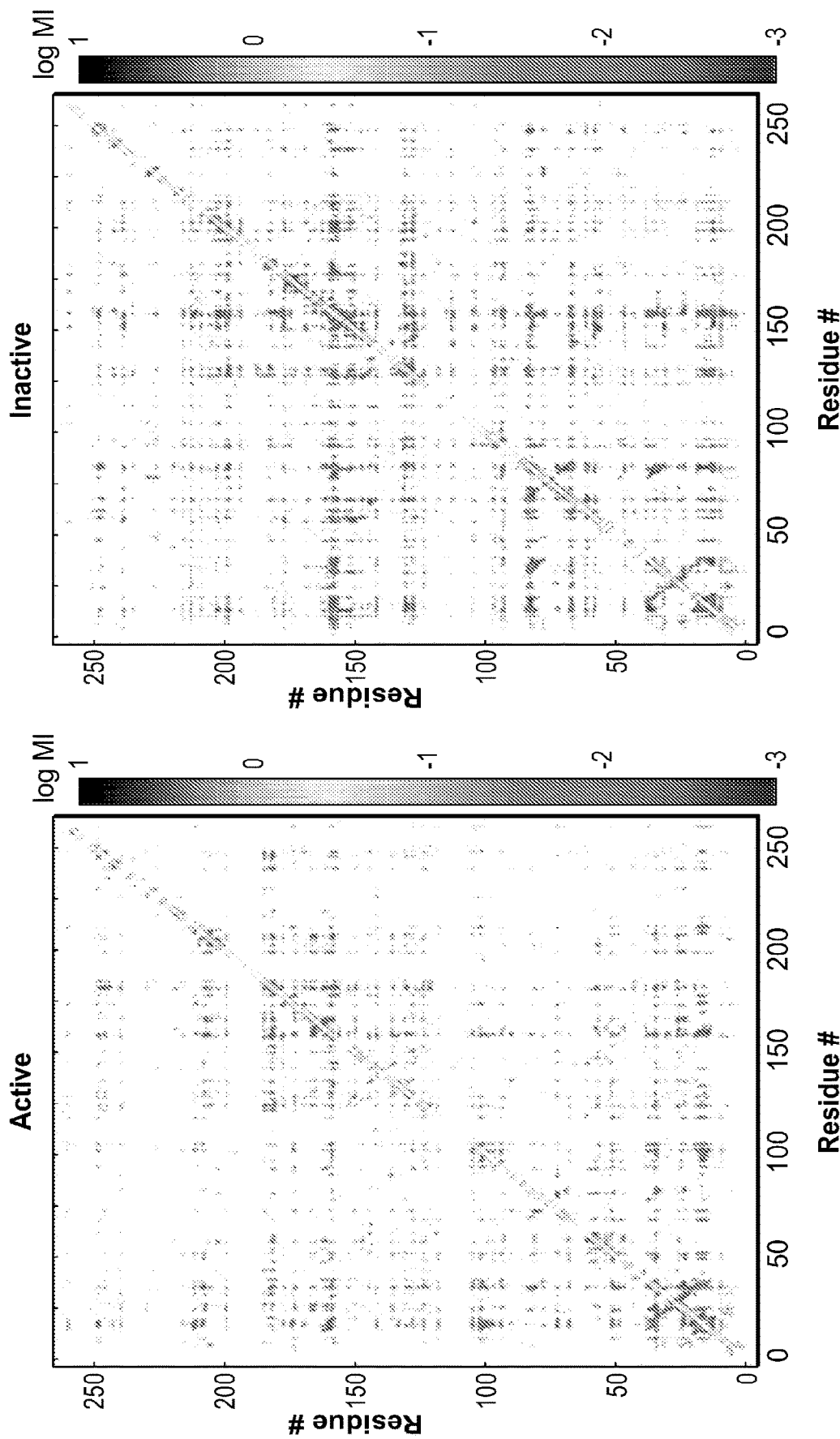
Figure 37:
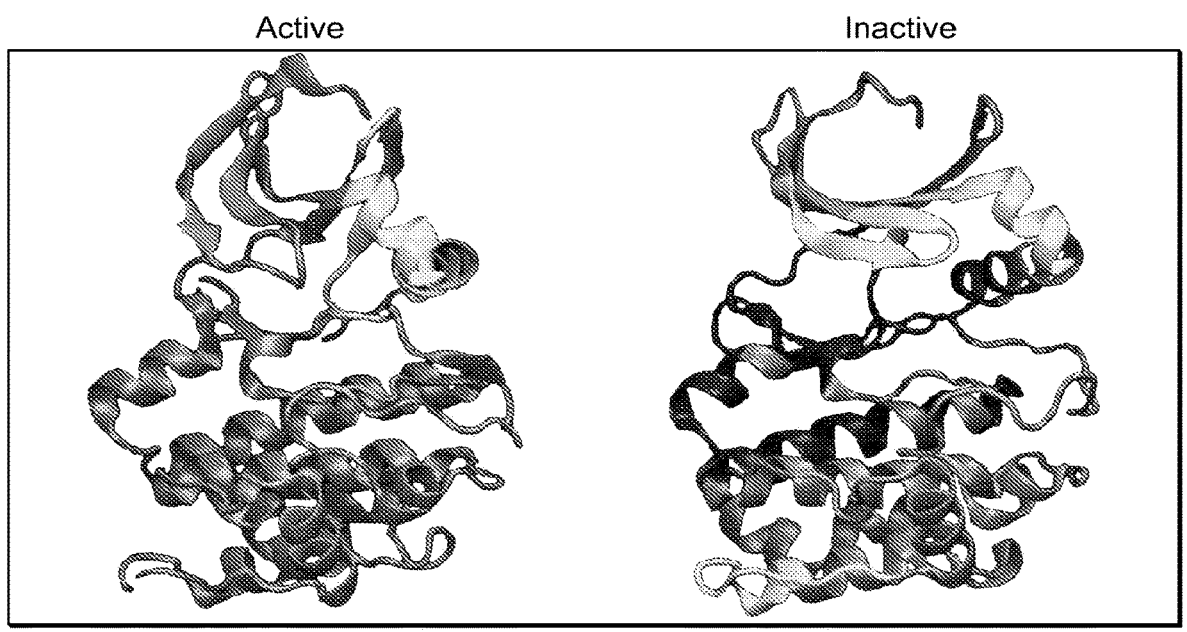

FIG. 37 is a series of plots and schematics showing calculations of mutual information metrics for backbone and side chains from MD simulations (picosecond to microsecond dynamics). Such correlation has been successfully identified for Aurora A kinase. Calculating mutual information metrics for backbone and side chains for Aurora A in its inactive and active state revealed a different set of residues with correlated motions.

FIG. 38 is a schematic depicting a mechanism and kinetics of Aurora A binding to small molecular inhibitors Danusertib.

Figure 39:
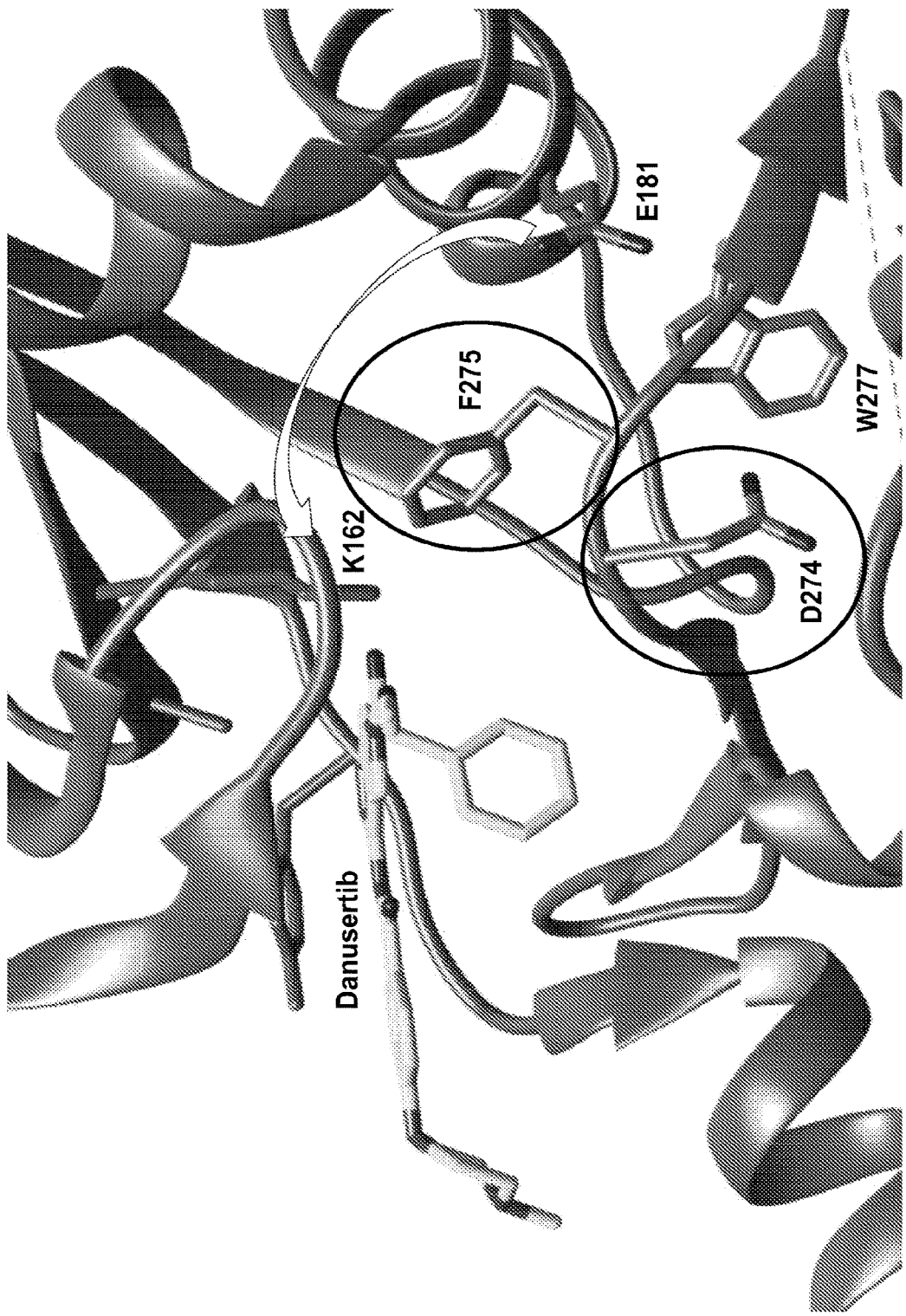

FIG. 39 is a schematic representation showing a crystallography structure of Danusertib bound to the DFGout position.

Figure 40:
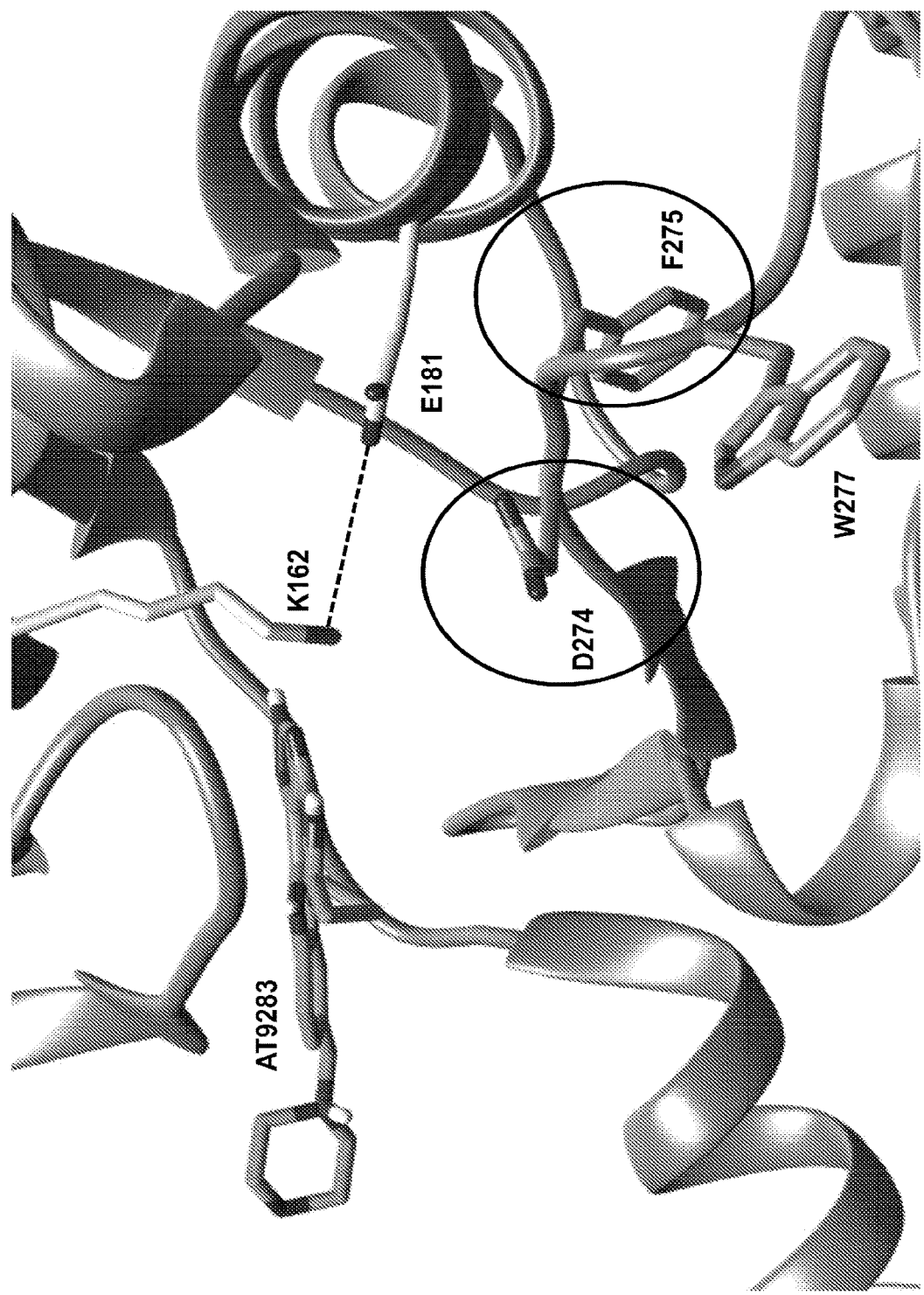

FIG. 40 is a schematic representation showing a crystallography structure of AT9283 bound to the DFGin position.

Figure 41:
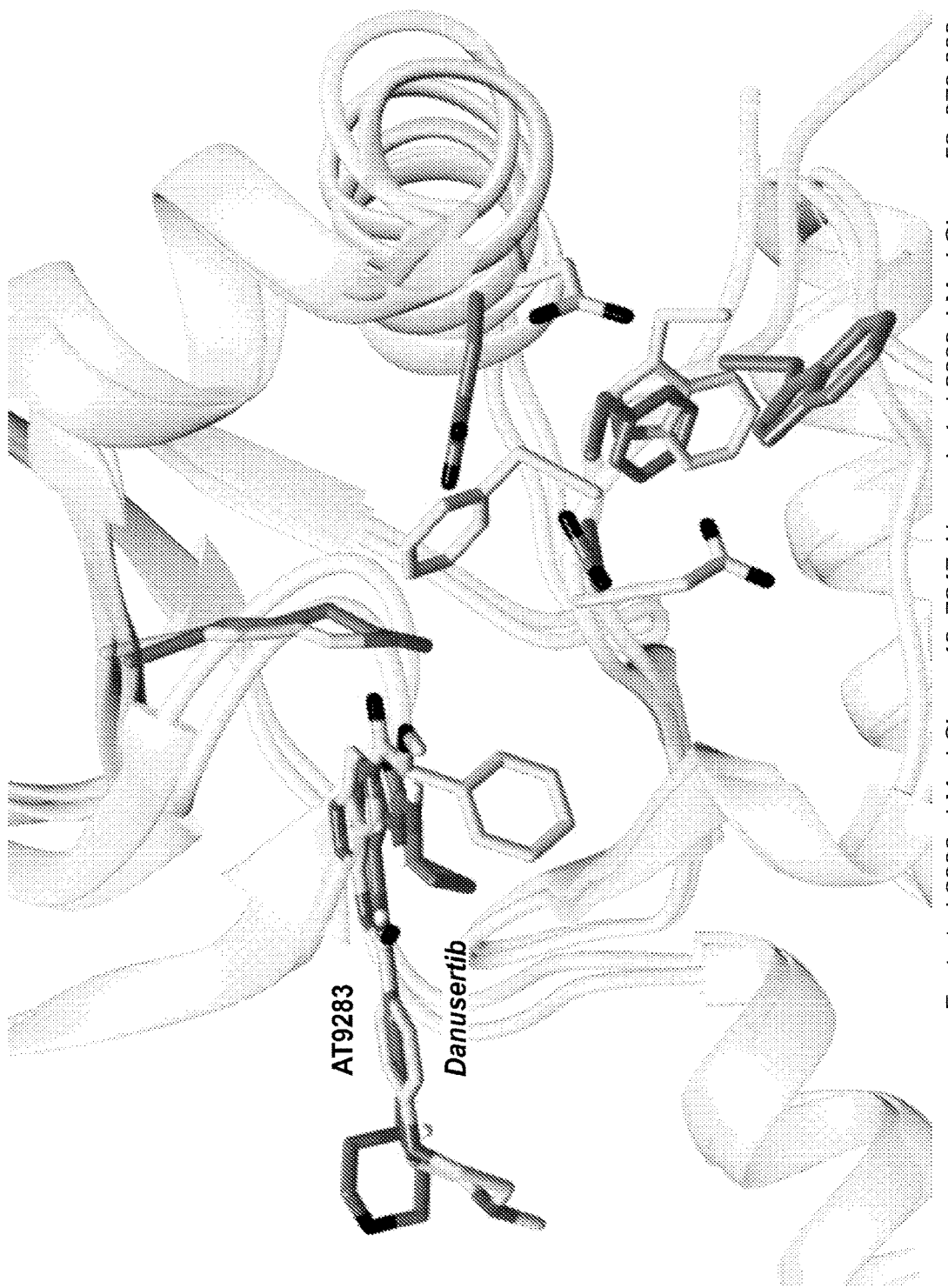

FIG. 41 is a schematic representation showing an alignment of the structures of Danusertib bound to the DFGout position and AT9283 bound to DFGin position.

Figure 42:
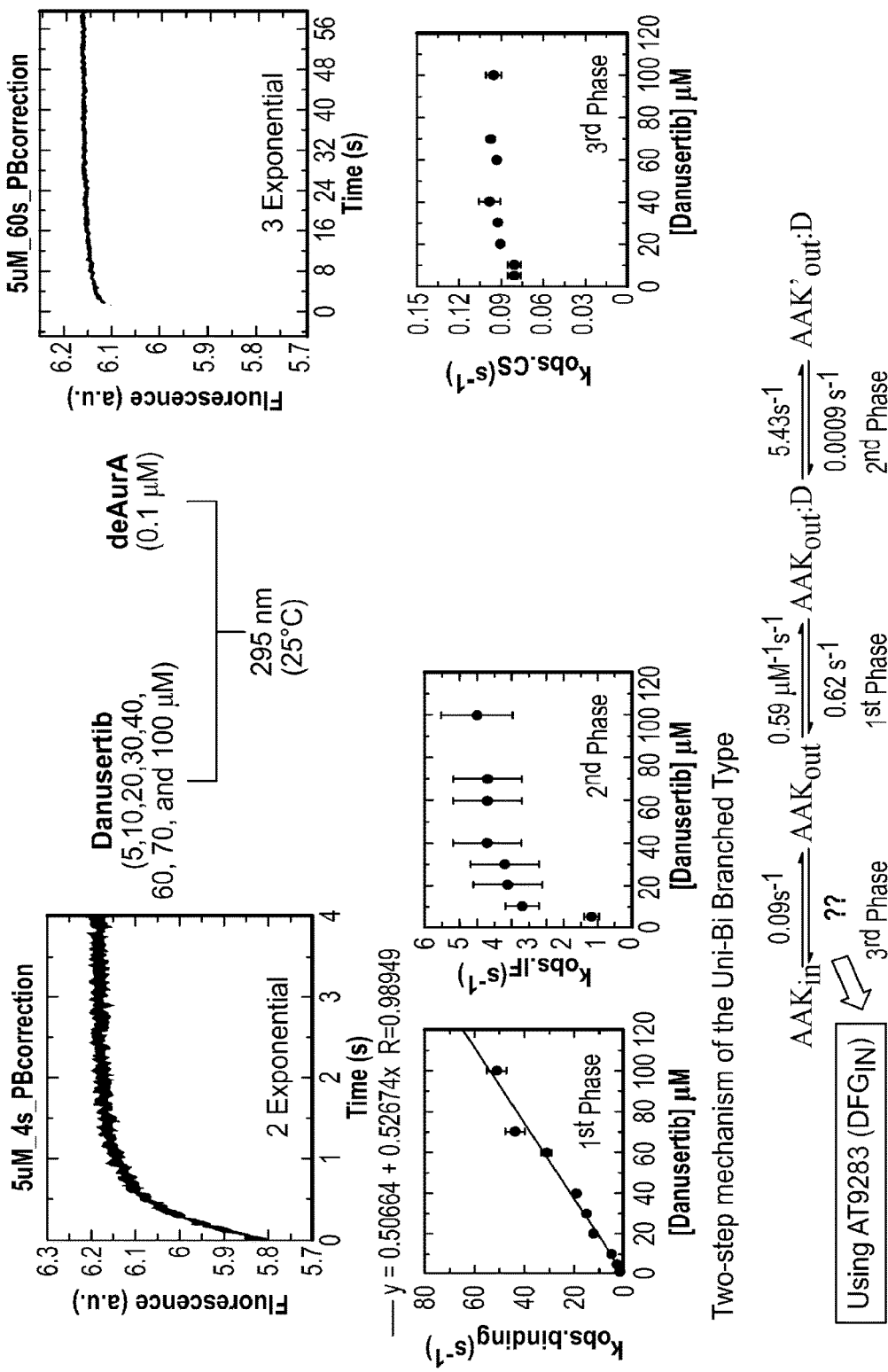

FIG. 42 is a set of plots and schematics showing characterization of Danusertib binding to Aurora A kinase.

FIGS. 43A-43C are plots and schematics showing characterization of AT9283 binding to Aurora A kinase. FIG. 43A shows kinetics of binding at 25° C.; FIG. 43B shows kinetics of binding at 35° C.; FIG. 43C shows kinetics of binding at a low AT9283 concentration at 25° C.

Figure 44A:
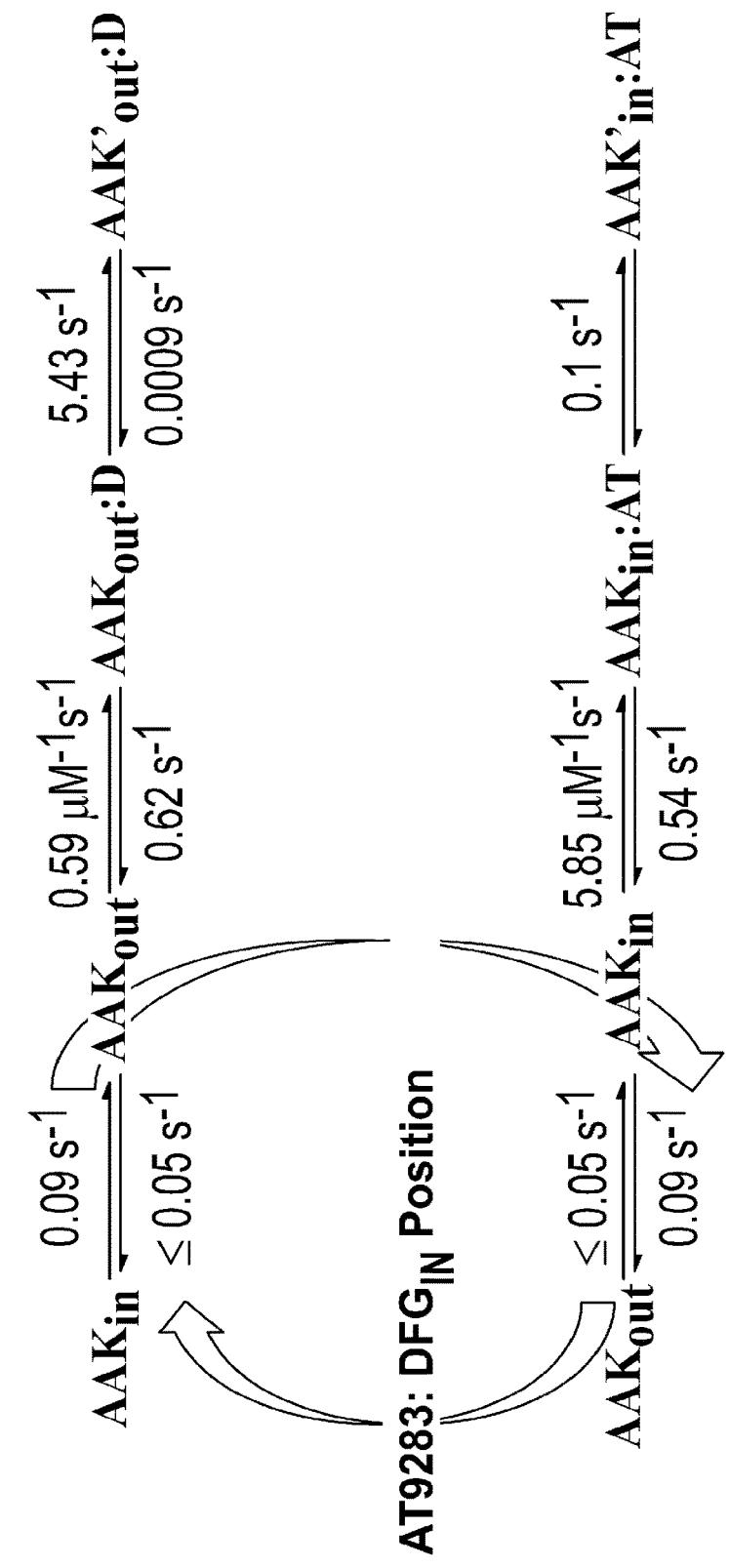

FIGS. 44A-44B are schematics and plots showing a binding scheme and kinetics of the overall binding reaction of Danusertib and AT9283 binding to Aurora A kinase. FIG. 44A shows binding scheme and kinetics of Danusertib and AT9283 at 25° C. FIG. 44B shows a macroscopic dissociation constant ($K_D$) of Danusertib.

Figure 45:
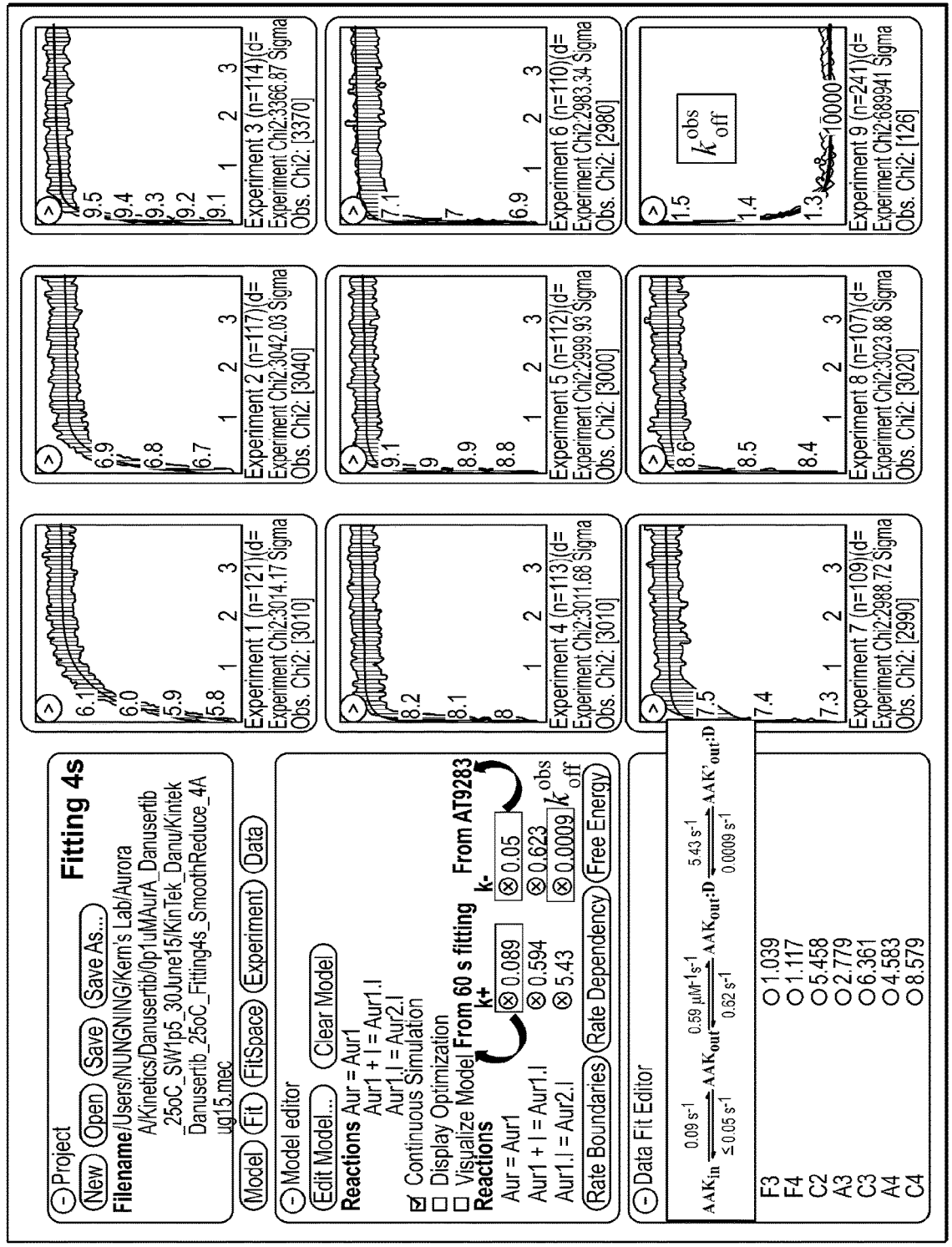
Figure 45:
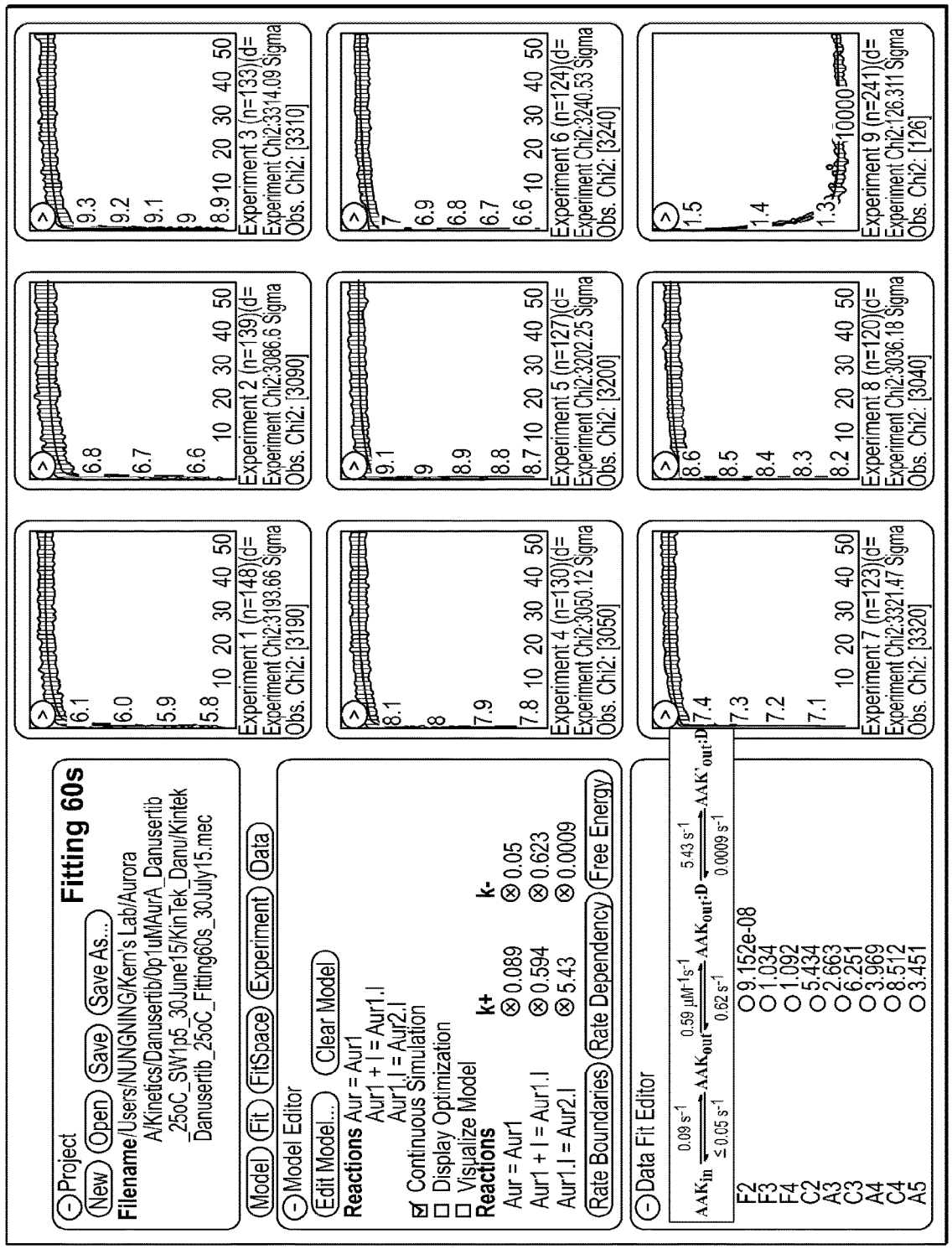

FIG. 45 is a set of images illustrating exemplary fitting of kinetic rates to fast fluorescence kinetic binding data.

DETAILED DESCRIPTION OF THE INVENTION

The invention features methods of selecting or identifying an agent that inhibits a target protein having an active site. The methods comprise measuring or predicting stability of an induced fit conformation (E*-I) of a candidate agent contacted to the active site of the protein. The invention is based, at least in part, on the discovery that agents (e.g., small molecules or drugs) that increased stability of an induced fit conformation (E*-I) (as opposed to stability of other conformations, e.g., primary bound conformation (E-I)) was key to having a high affinity and/or a long residence time of the drug on the protein.

Drug Design Platform

In some aspects, the present invention provides an integrated platform combining NMR, fast kinetics experiments, x-ray structures, MD simulations and ancestral reconstruction to identify the energy landscapes of targets and their optimal use for drug design. Current drug design is primarily based on just considering static structures. It is proposed herein that the conformational dynamics of the targets are the crucial part for high affinity and specificity for inhibitors, and described herein is a novel approach to characterize the dynamic ensemble of targets in the pre-bound states and after the initial binding of the drug with the goal to use this plasticity of the protein for drug binding.

Present technology is based on single static structures. Accordingly, the present invention identifies that the dynamics of the targets are crucial for binding, hence the need to characterize the target dynamics in different states, free and when bound to compounds. Present technology identifies "pockets" from static structures, and uses docking. Herein is provided a method to design better inhibitors by exploiting the dynamic nature of the targets. Second, current technology does not realize the power of efficient induced fit steps. The new technology is focused to deliberately target dynamic parts of the protein for engaging them in induced fit steps.

In some aspects, the current invention designs inhibitors of a target protein with high very high affinity, long life-time of the drugs on the targets and potentially very high specificity. Using this platform, the underlying atomistic mechanism for high affinity and selectivity for Abl was characterized. The mechanism for Gleevec resistance in the most commonly occurring resistance mutation in cancer patients was also solved. Other test examples are active site binders (available inhibitors) binding to Abl and Aurora A. These test data underscore the importance of the induced fit step for selectivity, high affinity, long residence time of the drug on the target, and the power of this new platform.

In one aspect, the invention provides a method of selecting or identifying an agent that inhibits a target protein having an active site, the method comprising measuring or predicting stability of an induced fit conformation (E*-I) of a candidate agent contacted to the active site of the protein, wherein the candidate agent is selected or identified as an inhibitor of the protein if the measured or predicted stability of the induced fit conformation (E*-I) of the candidate agent contacted to the active site is increased relative to a reference stability. In one embodiment, the invention comprises a method of identifying an inhibitor for a target compound, wherein the target compound is a protein, protein kinase or other inhibitable compound.

The process would start with either already known initial hits of compounds, or a first screen for compounds. Thus, in some embodiments, the reference stability is the stability of an induced fit conformation (E*-I) of a pre-selected lead agent or lead compound contacted to an active site of the protein. In other embodiments, the reference stability is the stability of an induced fit conformation (E*-I) of a natural substrate of the protein, or a natural ligand of the protein or an analog thereof contacted to the active site of the protein.

In particular embodiments, the measuring involves fast fluorescence kinetics. Next overall affinities may be measured using fluorescence, ITC or SPR methodology. Next, characterization of the binding kinetics using stopped-flow fluorescence experiments to characterize the individual steps for binding (measurement of association and dissociation kinetics) may be performed. The obtained kinetics traces may be globally fit. These experiments will yield the binding scheme for the compounds and the individual contribution of the different microscopic steps to the overall affinity. Steps include conformational selection steps and induced fit steps. If a number of compounds were found in the initial screen, the comparison between them will be informative for relating differences in compound structure to differences in the energy landscape of binding. The binding of the compounds will then be followed by NMR titrations either using 1H 15N or 1H 13 C HSQC spectra. These experiments deliver information about which parts of the protein experiencing conformational changes in which step of the binding. Accordingly, in some aspects, the invention provides method of selecting an agent that inhibits a target protein having an active site, the method comprising measuring a structure of an induced fit conformation (E*-I) of a candidate agent contacted to an active site of the kinase, wherein the stability of the induced fit conformation (E*-I) of the candidate agent contacted to the active site of the protein is pre-identified as increased relative to a reference stability.

In particular embodiments, the measuring involves X-ray crystallography and/or NMR spectroscopy. The appropriate NMR dynamics experiments may be performed on the free protein and also on the enzyme/drug complex to characterize the flexibility of the target. X-ray structures of the free protein and bound to the compounds will be solved. To successfully obtain crystals, strategies such as seeding, soaking, and ethylation of lysine side chains will be included.

These experiments together with the stopped-flow kinetics data will deliver a description of the energy landscape of the apo protein, the inhibitor binding and the protein bound to the inhibitor. The combined approach between fast kinetics and NMR is novel.

Agents that are selected or identified as binding to or inhibiting a protein may be further optimized to increase affinity and/or residence time of the agent on the protein. To increase affinity and/or residence time of the agent on the protein, a structure of the protein in the induced fit conformation (E*-I) when in contact with the agent may be measured, for example, by X-ray crystallography and/or NMR. The measured structure may then be used to design agents (e.g., small molecule) that better bind or having increased stability in the induced fit conformation (E*-I). Such "optimized" agents may be design by predicting stability in the induced fit conformation (E*-I) of the protein bound or in contact with the optimized agent. Prediction of stability may be done using molecular docking techniques or simulations. Such techniques are well-known in the art. Such techniques typically involve calculations of energies of binding and/or interaction of the agent with the target protein (or active site of the protein) using relevant atoms or residues in the target protein and/or agent and their spacing or distances from each other.

In other aspects, molecular dynamic (MD) simulations in explicit water on the apo protein will deliver information on flexibility on the picosecond to microsecond time scale. Dynamic NMR experiments will reveal motions on this faster time scale, but additionally on the millisecond and slower time scale as well. The combination of NMR and MD characterization will allow identification of the flexible regions in the apo, and the goal is to exploit this plasticity for the drug binding.

In use, the same experiments may be performed in the inhibitor-bound state to exploit conformational flexibility after inhibitor binding that can be exploited for further optimization of the inhibitor via an induced-fit step. Induced fit steps for lead optimization will result in higher affinity and better specificity, because an induced fit step has at least two major advantageous effects for drug development; i) it strengthens the binding and ii) it increases the residence time of the drug on the target. Therefore the detailed characterization of the dynamics of the target when bound to initial hits is a major focus.

For targets where high specificity is a major agenda, such as protein kinases, calculating ancestral sequences using either maximum likelihood methods or Bayesian phylogenetic analysis, and interpreting evolution of amino acid changes may be a powerful additional method to be employed. The characterization of the differences in inhibitor binding between the ancestral nodes will allow to identify the crucial residues for specificity. In analogy, determining differences in dynamics, particularly correlated motions along the different evolutionary trees will narrow down the amino acids differences that can be exploited for specificity. MD simulations as described above can be repeated quite quickly on ancestors and the results be interpreted in respect to differences in energetics. This approach has been successful for (i) the discovery of the residues responsible for Gleevec specificity for Abl vests Src, and (ii) for identifying the allosteric network between the TPX2 biding site and the active site in Aurora A.

For identifying new allosteric sites, correlated motions will be identified by calculating mutual information metrics for backbone and side chains from MD simulations (picosecond to microsecond dynamics) (FIG. 37). Such correlation has been successfully identified for Aurora A kinase. Calculating mutual information metrics for backbone and side chains for Aurora A i its inactive and active state revealed a different set of residues with correlated motions.

Implementation in Hardware and/or Software

The methods described herein can be implemented on general-purpose or specially programmed hardware or software. For example, the methods can be implemented by a computer readable medium. Accordingly, the present invention also provides a software and/or a computer program product configured to perform the algorithms and/or methods according to any embodiment of the present invention. It is well-known to a skilled person in the art how to configure software which can perform the algorithms and/or methods provided in the present invention. The computer-readable medium can be non-transitory and/or tangible. For example, the computer readable medium can be volatile memory (e.g., random access memory and the like) or non-volatile memory (e.g., read-only memory, hard disks, floppy discs, magnetic tape, optical discs, paper table, punch cards, and the like). The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001).

The present invention may also make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.) Additionally, the present invention may have preferred embodiments that include methods for providing genetic information over networks such as the Internet as shown in U.S. Ser. Nos. 10/197,621, 10/063,559 (US Pub No 20020183936), Ser. Nos. 10/065,856, 10/065,868, 10/328,818, 10/328,872, 10/423,403, and 60/482,389.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Using Ancient Protein Kinases to Unravel a Modern Cancer Drug's Mechanism

Results of studies described in this example show that macromolecular function is rooted in energy landscapes, where sequence determines not a single structure but an ensemble of conformations. Hence, evolution can modify a protein's function by altering its energy landscape. Here the evolutionary pathway between two modern human oncogenes, Src and Abl, was recreated by reconstructing their common ancestors and characterizing the respective ancestral energy landscapes. The evolutionary reconstruction revealed a detailed molecular mechanism for the selectivity of the successful cancer drug Gleevec. While Gleevec had a 3000-fold preference for modern Abl versus Src, their common ancestor had an intermediate affinity for Gleevec. Affinity for Gleevec was gained during the evolutionary trajectory towards Abl and lost towards Src, primarily by shifting an induced-fit equilibrium. The subset of atomic interactions underlying this difference in Gleevec specificity was identified using mutations, guided by X-ray crystal structures of the common ancestor bound to Gleevec. It is further shown that Gleevec resistance in the clinically relevant T315I mutation is caused by disruption of the induced-fit step, and not by steric hindrance of drug binding. This work simultaneously sheds light on the mechanism of Gleevec specificity at atomic resolution while offering insights into how energy landscapes evolve.

Figure 1C:
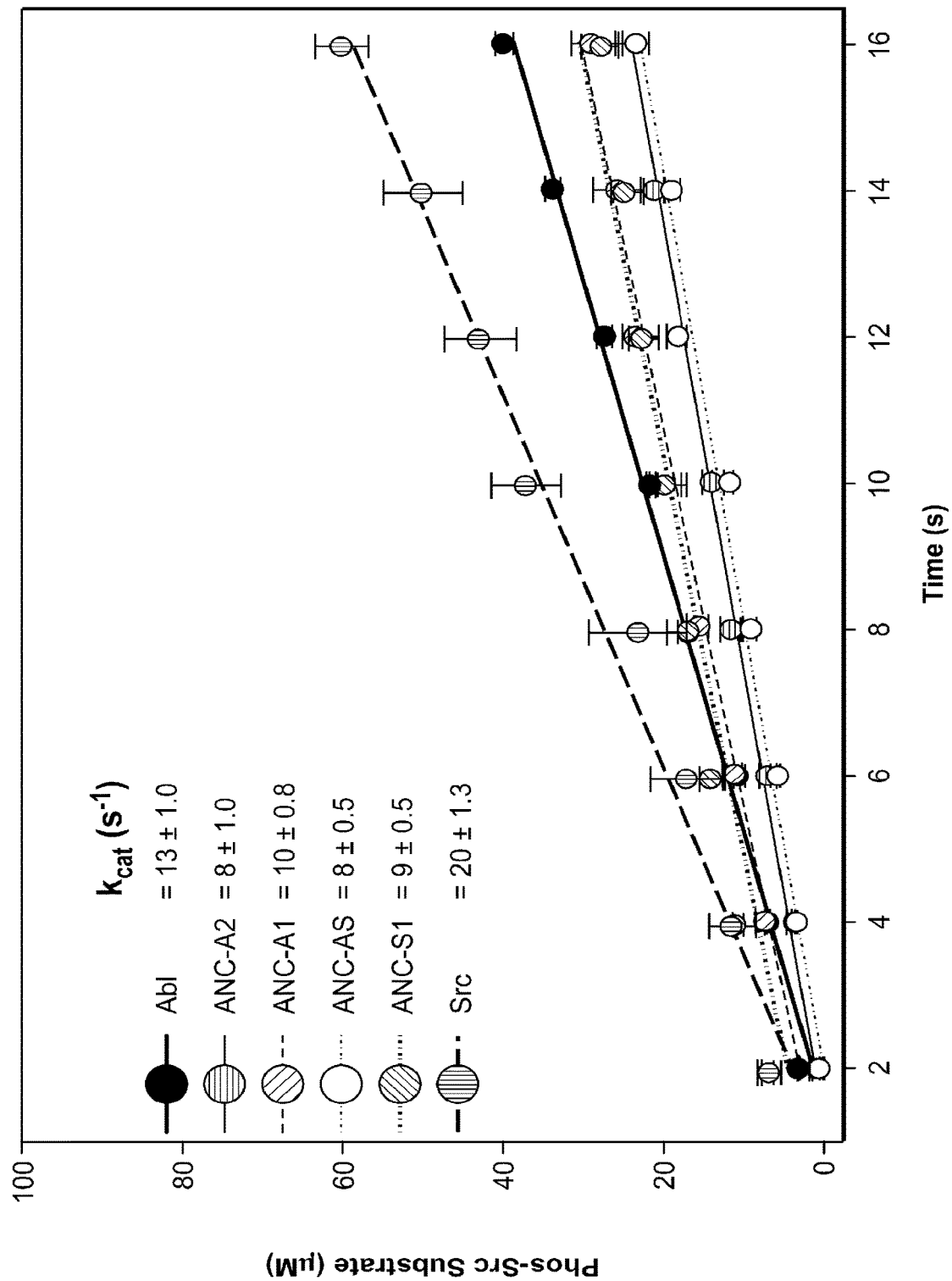

The evolution of protein kinases is a key event in the origin of multicellularity (1). This enabled the development of more complex signaling cascades essential for the evolution of higher organisms. The central role of protein kinases in the cell cycle has placed them at the center of cancer drug research. Despite an explosion in diversity in the kinome (2), the catalytic kinase domains have maintained nearly identical structures (2-5). It is therefore surprising that the clinically successful cancer drug Gleevec has such strong selectivity towards Abl versus other tyrosine kinases, including the closely related Src. This is puzzling because the structures of Abl and Src bound to Gleevec are nearly identical, including the N- and C-terminal lobes and the 3000-fold difference in affinity for these two kinases (6). The atomistic determinants of this selectivity, however, are still an open question, and sequence swaps between human Abl and Src ascertained from the x-ray structures (FIG. 1A) have failed to answer this question for the past 20 years (3, 7). The differences between Src, Abl and other homologous kinases have evolved over a billion years from their common ancestor—not via amino acid swaps from one modern kinase to another. Sequence swap experiments using modern enzymes have a fundamental shortcoming by neglecting epistasis (the effect of the surrounding amino acid background). However, evolution has already navigated the complex epistatic protein space by producing functional proteins at each stage despite large numbers of accumulated mutations. It was therefore reasoned that it may be essential to exploit current knowledge of the evolution of Src and Abl along its phylogentic branches using ancestral reconstruction to determine the atomistic mechanism of Gleevec selectivity.

Ancestral reconstruction has recently provided a novel way to achieve mechanistic insight into protein function (8-13). Studies described herein elucidate the basis of modern specificity towards Gleevec with atomic resolution by recapitulating the evolution of the Src and Abl catalytic domain from their last common ancestor. Analysis of the ancestral kinases allowed tracking of the evolution of the protein energy landscape (14, 15). The term "energy landscape" is defined herein as a set of free energy and kinetic parameters linking kinetically distinct states that are relevant to biological processes.

Figure 6A:
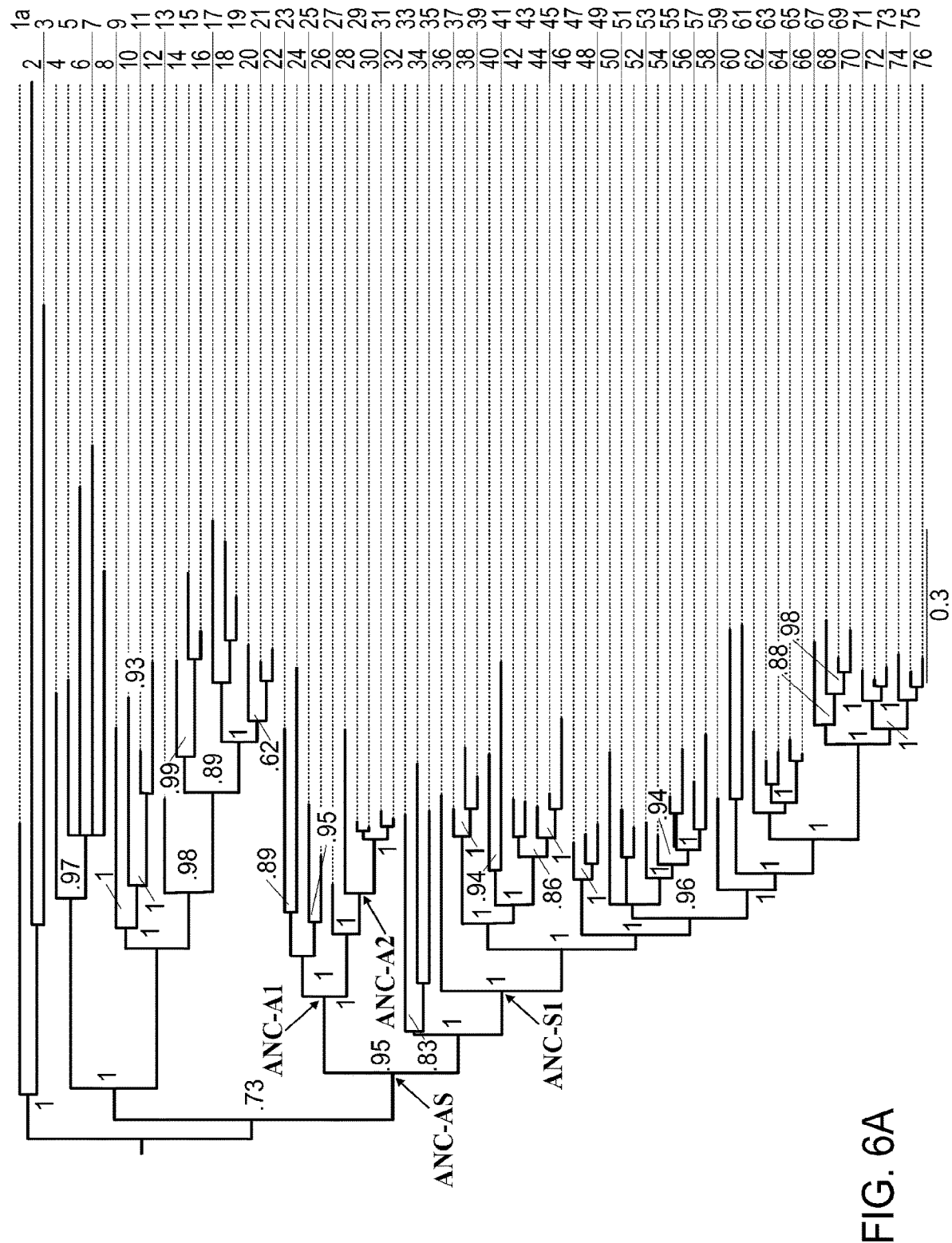
FIGS. 6A-6B are diagrams showing a full phylogenetic tree of the Src/Abl/Tec tyrosine kinases and binned probabilities of ancestral state reconstruction at each residue. Shown in FIG. 6A is a phylogenetic tree of Src/Abl/Tec tyrosine kinases. Posterior probabilities>0.50 for each node are shown. Resurrected nodes are labeled and colored using the color scheme presented in the manuscript. Shown in FIG. 6B are histograms of the posterior probabilities of each site.
Figure 6B:
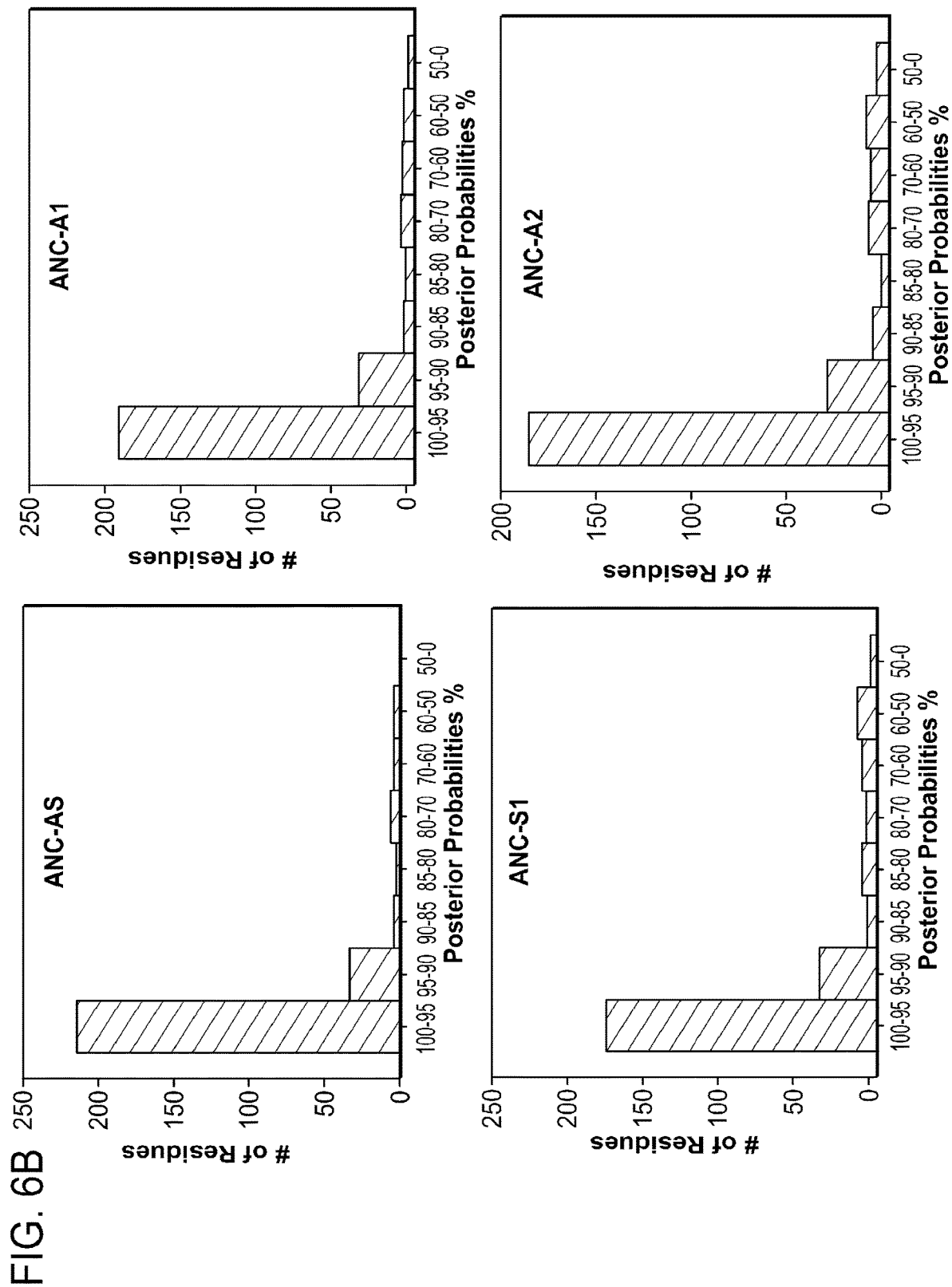

Seventy-six modern day sequences spanning the cytosolic tyrosine kinase family (Src/Abl/Tec families) were used in a Bayesian phylogenetic analysis with receptor tyrosine kinases as the out-group (FIG. 1B). Since the quality of the ancestral reconstruction strongly depends on the alignment, the tree and alignments were estimated simultaneously. The most probable sequences were inferred for four key ancestral proteins between modern Src and Abl and their last common ancestor (FIG. 1B; FIG. 4A; FIG. 4B; FIGS. 6A-6B), and their corresponding proteins were expressed, purified, and characterized. It is noted that although ancestral reconstruction is a well-established method (8, 16) it is still a developing field.

Figure 2A:
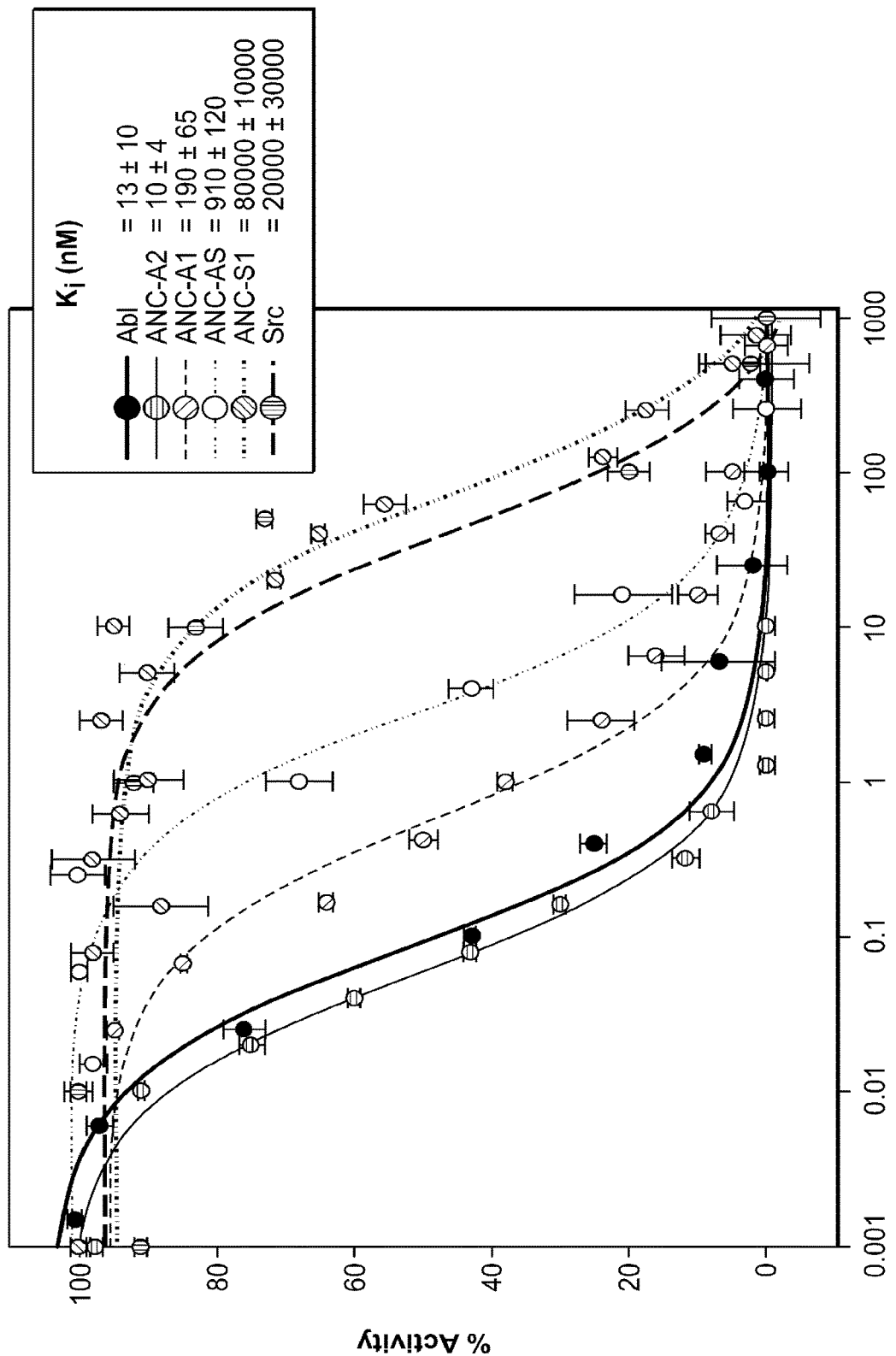
FIGS. 2A-2G are plots showing comparison of Gleevec affinity and binding kinetics between modern and ancestral tyrosine kinases.
Figure 2B:
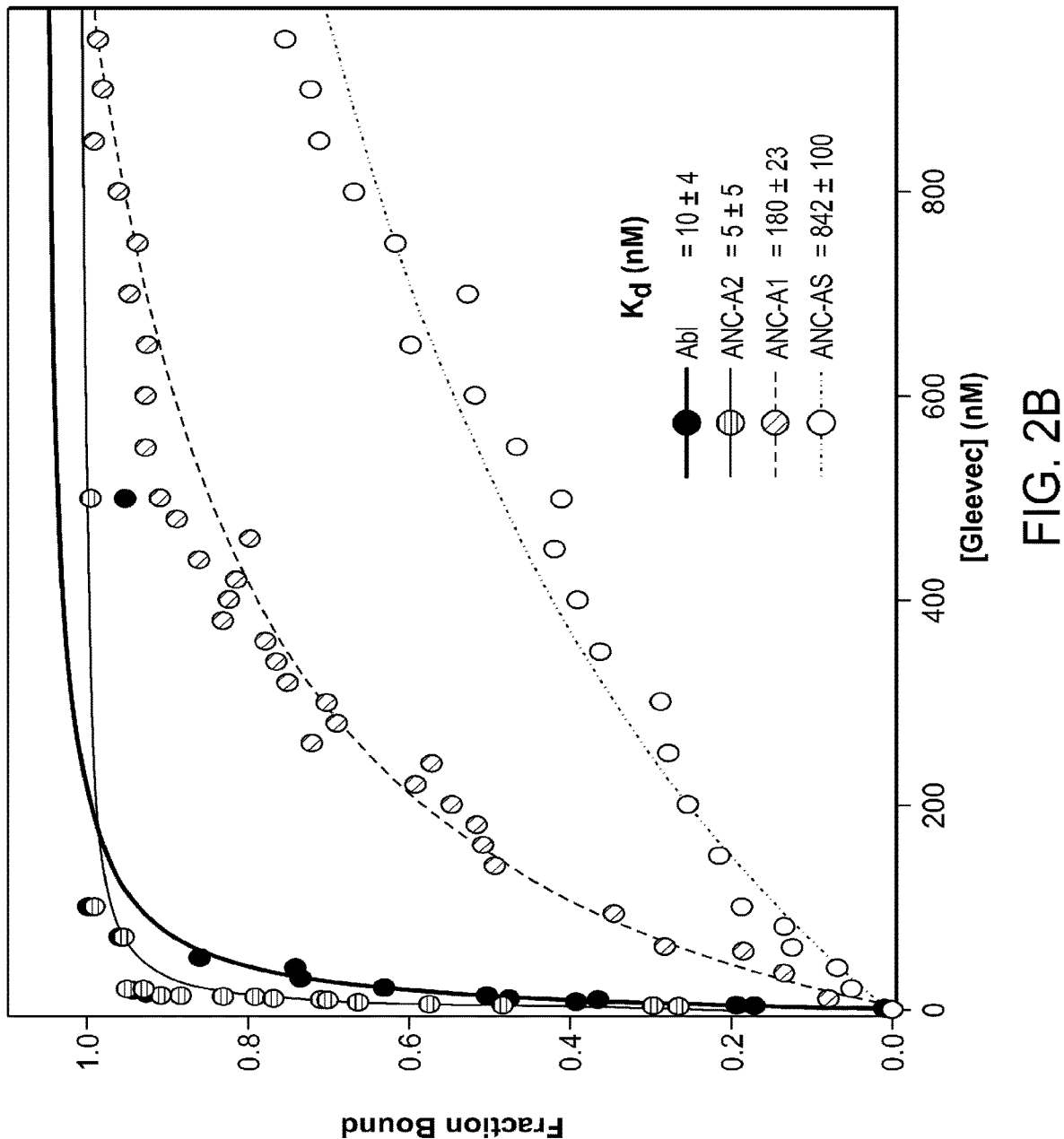
Figure 7:
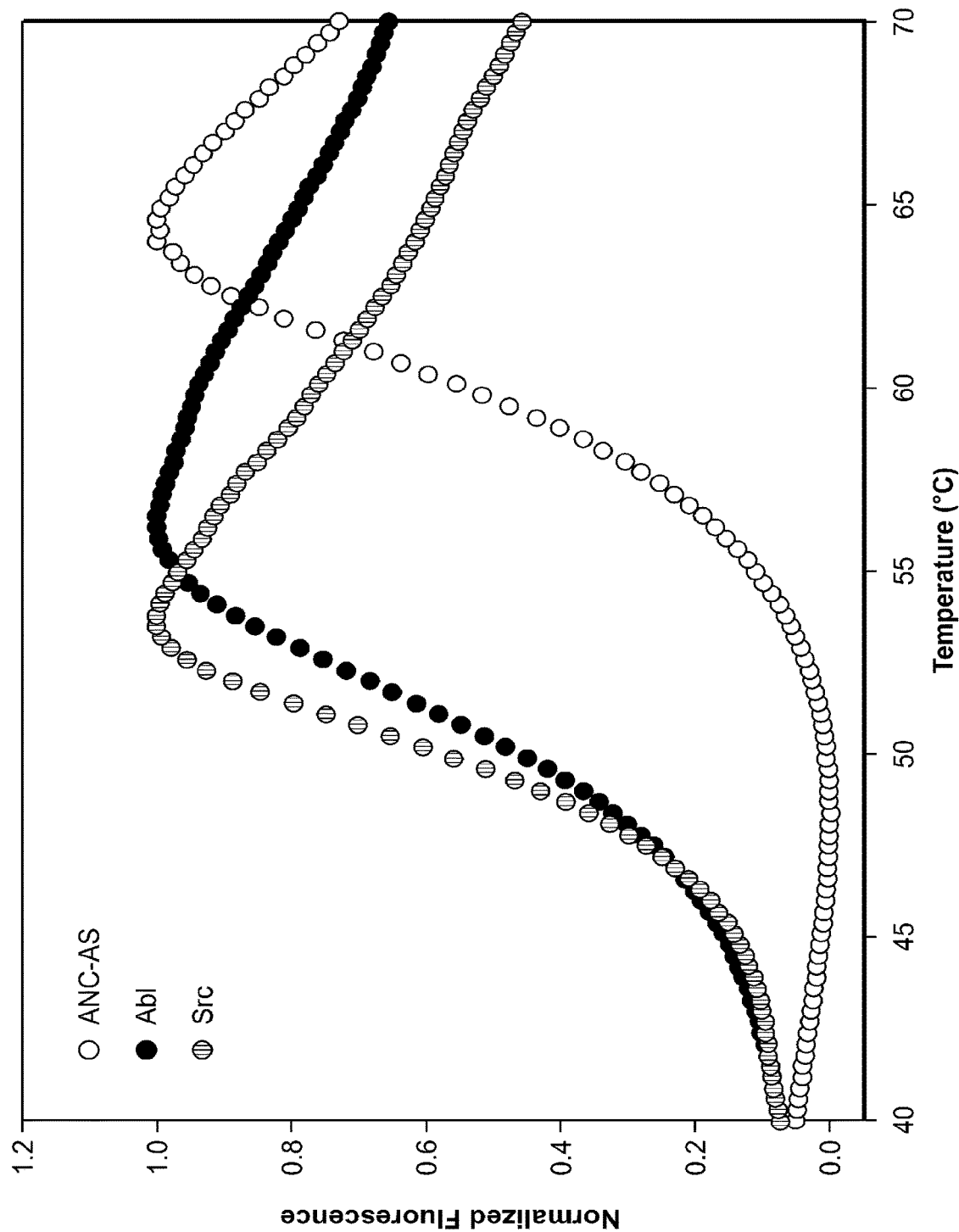
FIG. 7 is a plot showing ANC-AS has a higher melting temperature then Src and Abl. The ThermoFluor assay (16) was used to measure the melting temperatures of Src, Abl and ANC-AS. The dye Sypro Orange is similar in structure to ANS (1-anilinonaphthalene-8-sulfonate), and when bound to hydrophobic patches that are exposed in denatured proteins, is fluorescent. Utilizing a RT-PCR machine the temperature was gradually changed between 20 and 100° C. and the increase in fluorescence was monitored. ANC-AS melts at a temperature 11 degrees higher than modern Src and Abl suggesting an increase in thermal stability. This is in accordance with other resurrections in which ancestral proteins show higher melting temperatures than their modern day counter parts.
Figure 8:
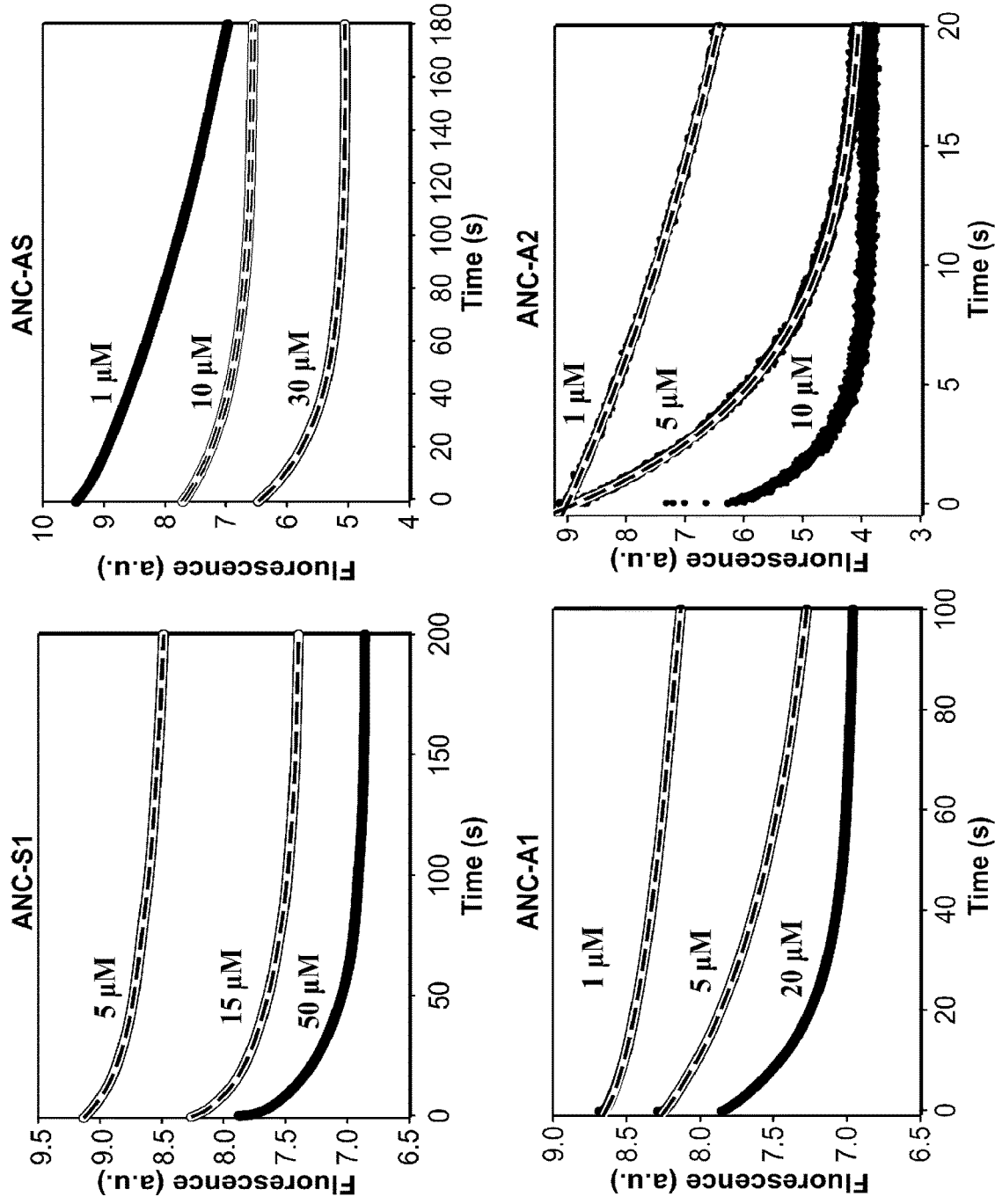
FIG. 8 is a panel of plots showing kinetics of Gleevec binding to all ancestors at 5° C. Representative time traces of quench of tryptophan fluorescence at different Gleevec concentrations, measured by stopped-flow fluorescence, are shown in black. 50 nM kinase was mixed with varying Gleevec concentrations and fit to double-exponentials (red/light grey). Complete results are shown in FIGS. 2E-2F.

The reconstructed protein corresponding to the last common ancestor of Src and Abl is denoted as ANC-AS. Similarly, on the lineage leading from ANC-AS to the modern Abl, ANC-A1 represents the common ancestor between humans and colonial choanoflagellates, while ANC-A2 corresponds to the common ancestor between humans and *C. elegans*. On the lineage leading to modern Src, ANC-S1 is the last common ancestor between humans and colonial choanoflagellates/sponges. Despite the fact that the oldest ancestor (ANC-AS) differs by 96 amino acid residues from any modern cytosolic tyrosine kinase, all ancestral kinases reconstructed herein were fully active and thermostable (FIG. 1C; FIG. 7; FIG. 8). Using the activity assay, the specificity of Gleevec towards the ancestral kinases was evaluated by measuring inhibition constants. The last common ancestor's (ANC-AS) inhibition was intermediate between modern Src and Abl. Gleevec affinity increased gradually towards Abl along the evolutionary pathway, while it drastically decreased towards Src (FIG. 2A). Direct measurement of Gleevec binding affinity by fluorescence quenching corroborated these results (FIG. 2B).

Figure 2C:
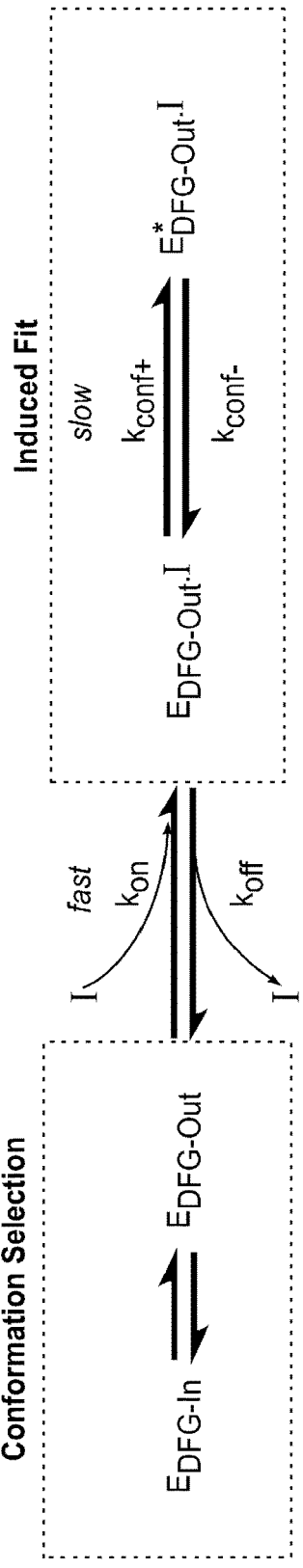
Figure 2E:
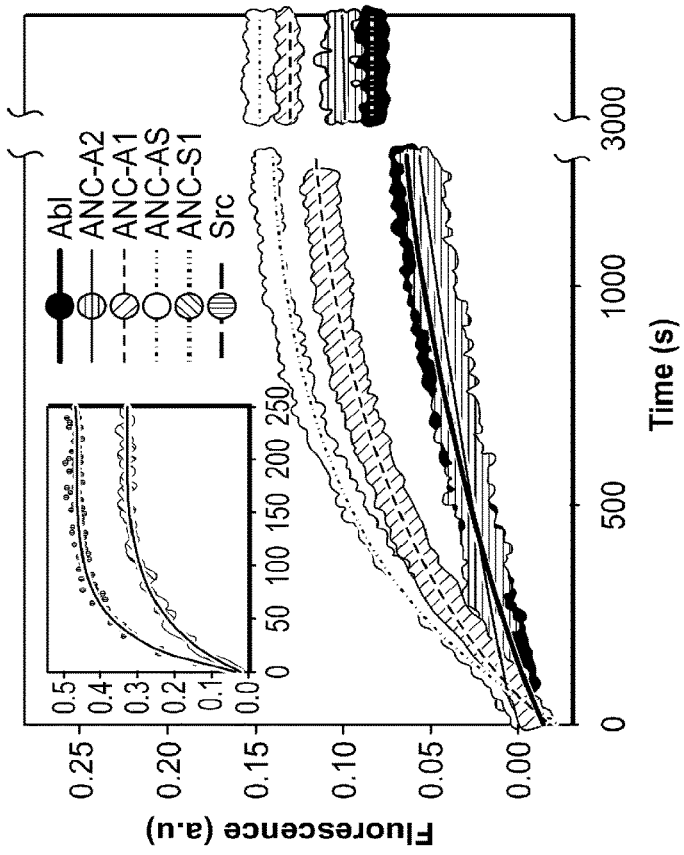
Figure 2D:
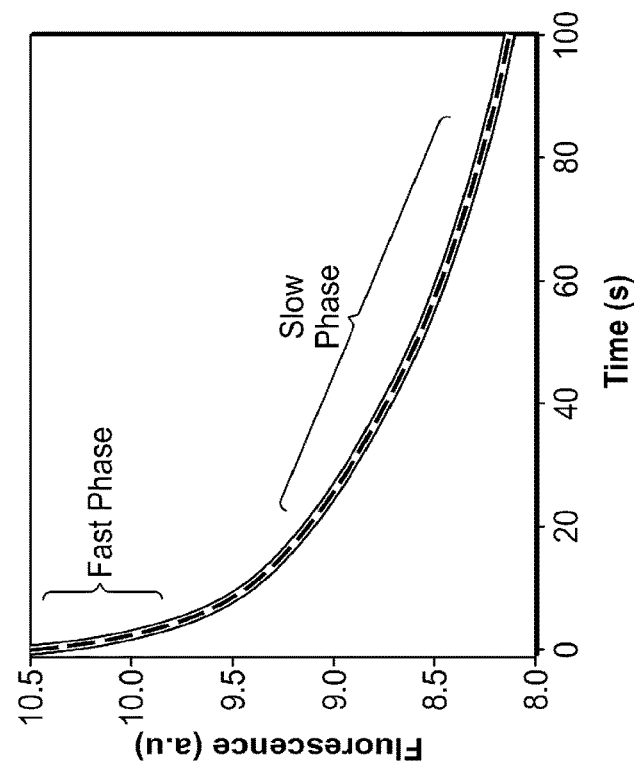
Figure 2F:
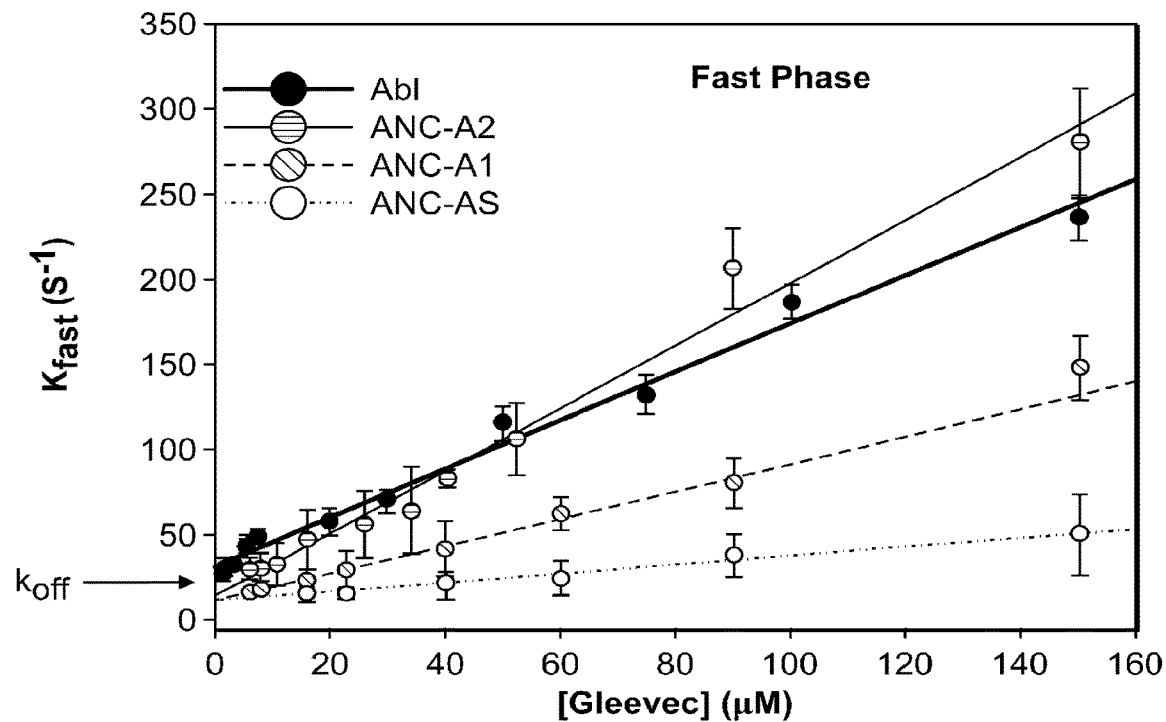
Figure 2G:
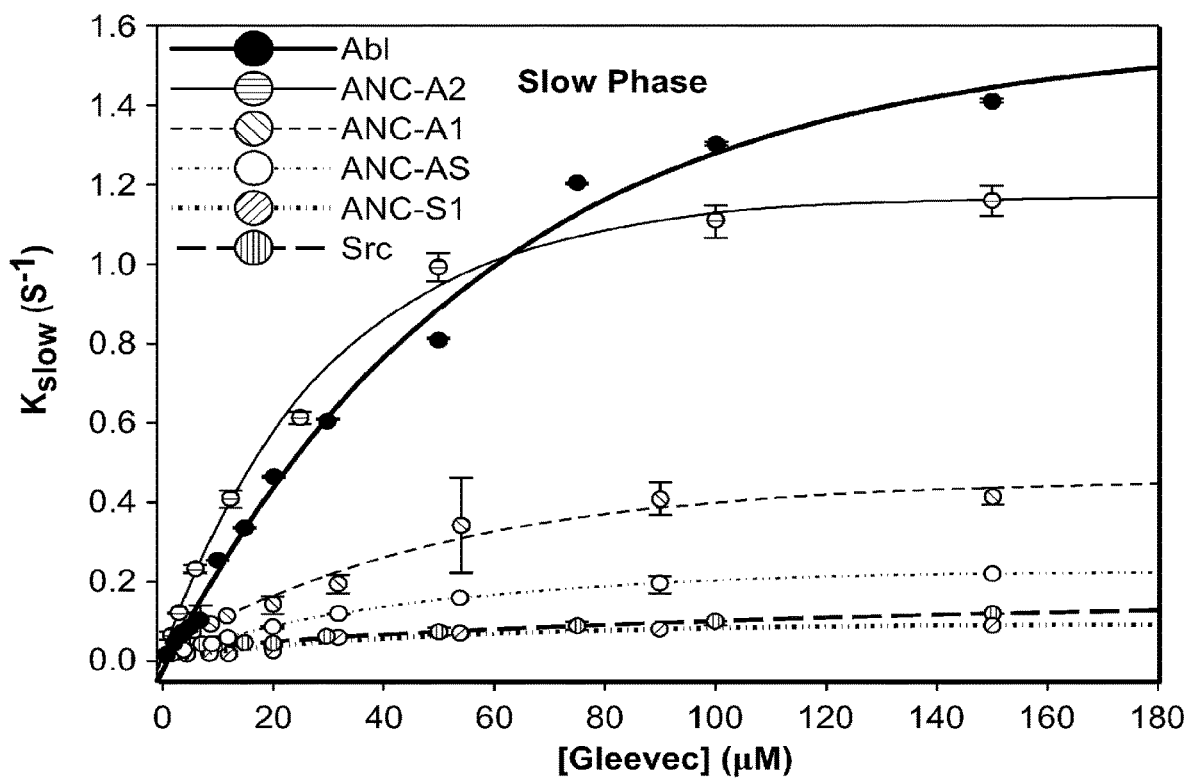
Figure 3D:
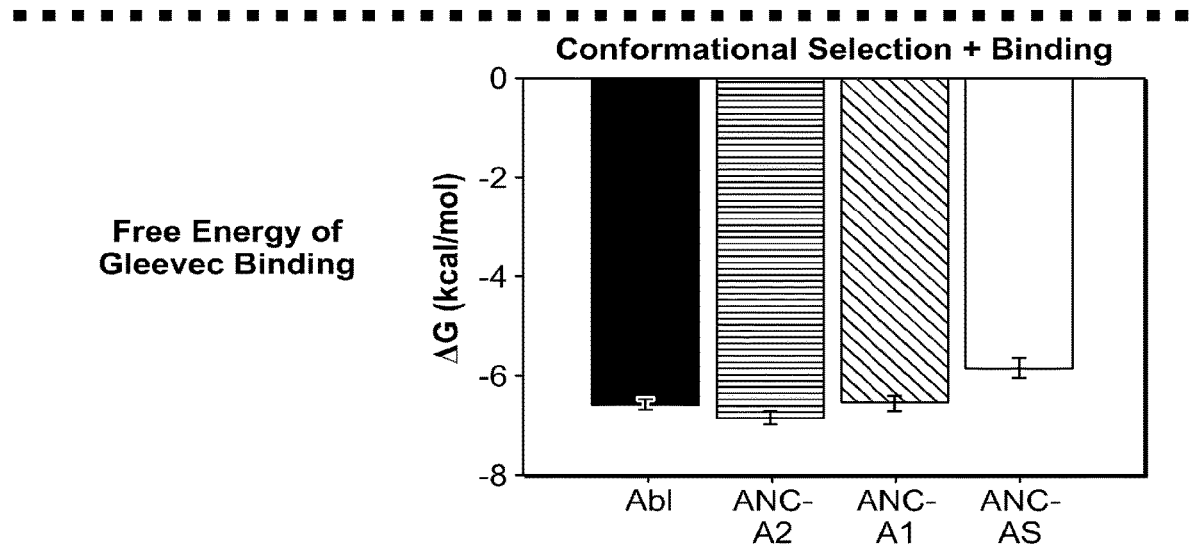
Figure 3E:
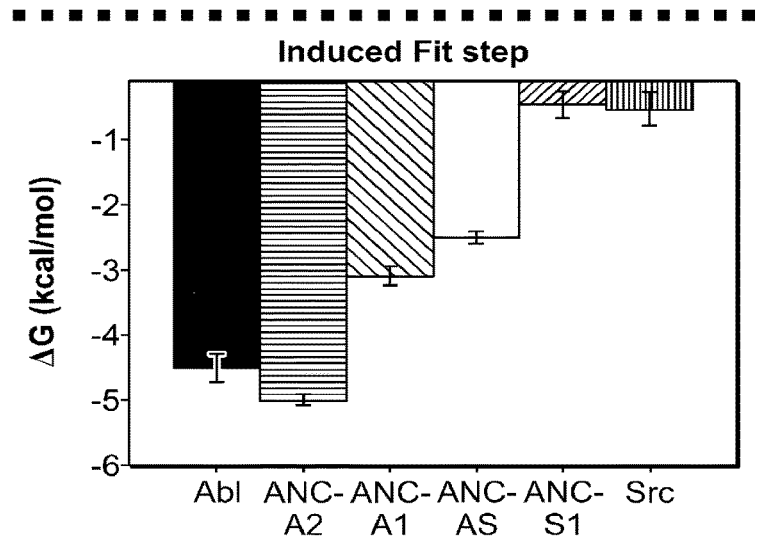

Recently, it has been proposed that Gleevec binding is controlled by and induced-fit step, a protein conformational changes after binding (6). However, Src and Abl differ by 146 amino acids and experiments with the modern kinases could not identify the subset of residues responsible for the changes in dynamics (6). Because the reconstructed kinase ancestors had intermediate Gleevec affinities, the evolution of energy landscapes could be explored. To this end, the changes in the energy landscape from the oldest ancestor (ANC-AS) to modern Src and Abl were characterized by comparing the kinetics of Gleevec binding. All ancestors followed the same kinetic scheme as modern Src and Abl (FIG. 2C), but with differences in individual conformational steps. The double exponential binding kinetics (FIG. 2D) reflected the physical binding step (identified by the linear dependence of the observed rate on Gleevec concentration, (FIG. 2F), followed by the induced fit step with the observed rate approaching a maximum at Gleevec saturation (FIG. 2G). The gradual change in these kinetic parameters (kfast and kslow) from the weak binders to the tight binders was clearly visible, while the physical off rates (koff), identified by the intercept in FIG. 2F remained similarly fast. The process reversal to binding, namely dissociation of the inhibitor-enzyme complex, was extremely slow for ancestors ANC-AS, ANC-A1 and ANC-A2, and much faster for ANC-S1 (FIG. 2E). However these observed rate constants for dissociation were still much smaller than the physical off-rate, revealing that the rate-limiting step in Gleevec release for all ancestors was a conformational change before dissociation (E*.I→E.I) (FIG. 2E) (see methods for details of the kinetic analysis). Strikingly, a systematic shift in the conformational equilibrium from E*.I to E.I when traversing the evolutionary tree from Abl to Src was detected, caused by a gradual decrease in the forward rate (kconf+) (FIG. 2G; FIG. 3C) and a more dramatic increase in the reverse rate ($k_{conf-}$) (FIG. 2E; FIG. 3C; FIG. 3E). This conformational step, independently validated previously by a direct visualization of the E.I and E*.I conformers by NMR on the enzyme-drug complex (6), accounted for the major difference in binding energy between the different ancestors and modern Src and Abl, while changes in the drug's binding/dissociation step were nearly negligible (FIGS. 3A-3E).

A frequently cited but controversial model for Gleevec selectivity posits a pre-existing equilibrium between two alternative conformations of the fully conserved segment of the activation loop, the DFG-motif (for Asp-Phe-Gly) (3, 6, 7, 17-21). A number of x-ray structures have revealed the sampling of a Gleevec-binding-competent DFG-out position and a binding-incompetent DFG-in position (FIG. 3A) (3, 7, 19, 20). Quantification of the equilibrium between these two alternative states has proven elusive, despite direct observation of both states in crystal structures (3) The analysis of the evolutionary trajectory of Src and Abl described herein provides experimental estimates of the relative populations of the in- and out-conformations of the DFG loop and illustrates that this equilibrium plays only a minor role in Gleevec affinity (FIG. 3A; FIG. 3D).

This unexpected opportunity arises from the time-resolved detection of the binding step. The relative amplitude of the fast binding step reflects the propensity to populate the DFG-out conformation (pDFG-out). As apparent from FIG. 3A, one can indeed "watch" this flip in population from mainly being in DFG-in state for modern Src and ANC-S1 to increasing DFG-out populations in ANC-AS as an intermediate, and to even higher DFG-out populations for ANC-A1, ANC-A2 and Abl (large amplitudes). The DFG-out population is also an intrinsic component of the observed rate $k_{on}^{obs}$ ($k_{on}^{obs}=k_{on} \times p_{DFG\text{-}out}$). Notably, the increase in pDFG-outmeasured from the amplitudes (FIG. 3A) was mirrored in the gradual increase in $k_{on}^{obs}$ (FIG. 3B), implying that the true $k_{on}$ rate constants were very similar. The populations of DFG-out in ANC-S1 and Src were too small to allow a quantitative analysis of the fast binding step (FIG. 3A). The "thermodynamic Kd" (FIG. 2B) agreed well with the Kd calculated from all microscopic rate constants (FIG. 9, see discussion of methods herein and (6)), which corroborated the kinetic scheme and the accuracy of the fitted values.

During the evolution of the energy landscape from the last common ancestor (ANC-AS) to the modern tight-binding Abl and the weak-binding Src, the major contribution to increased affinity arose from an induced-fit mechanism (FIG. 3E) with a minor but significant contribution from the pre-existing DFG-in/out flip in the free enzymes (FIG. 3D). The actual binding/unbinding step, which is commonly used in structure-guided rational drug design (e.g., docking analyses), was very similar between the weak and strong binders.

The sequence differences responsible for the two major changes in the energy landscape, the DFG loop equilibrium and the E.I E*.I equilibrium, were examined. The ancestral reconstruction narrowed down the regions responsible for these changes dramatically. Modern Abl and Src differ at 146 amino acids, yet only 70 differences separate ANC-AS and ANC-A2 and only 42 differences separate ANC-AS and ANC-S1. These sequence changes were distributed throughout the protein, in agreement with NMR observations from Gleevec titrations of Src and Abl (6).

Figure 4E:
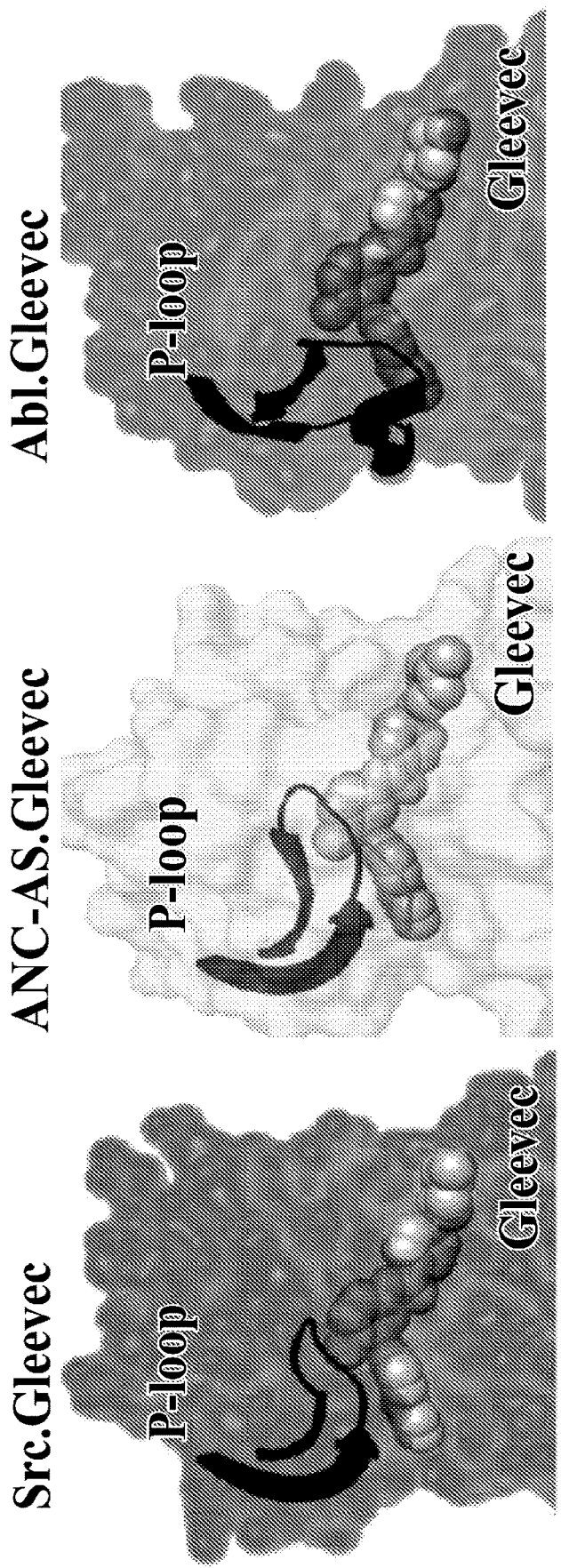
Figures 4F, 4G, 4H:
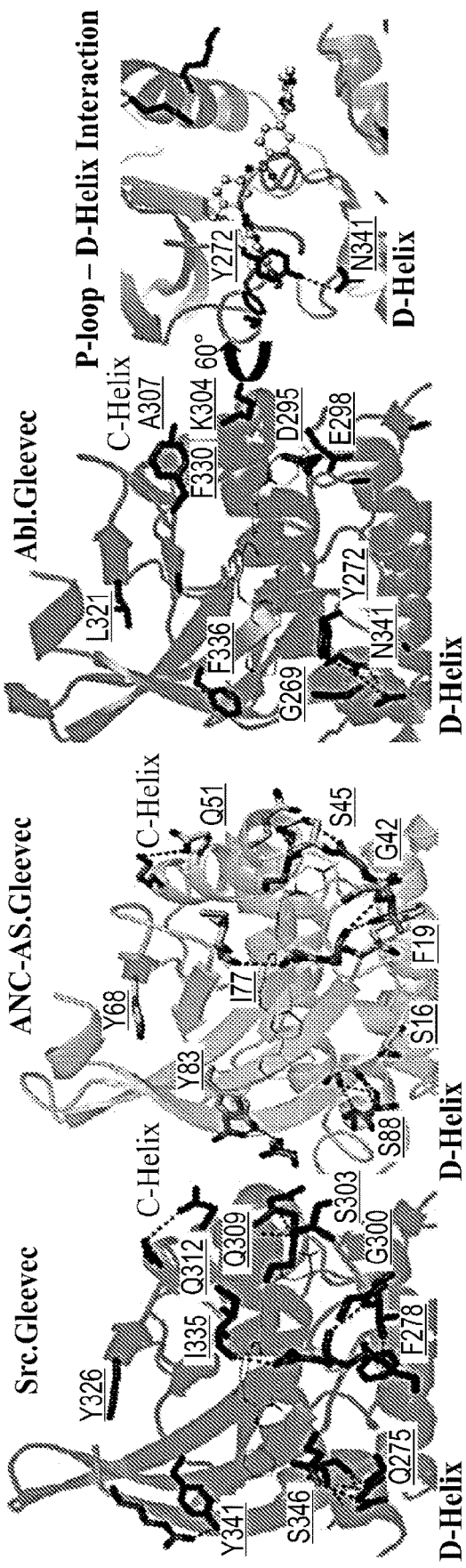
Figures 11A, 11B, 11C:
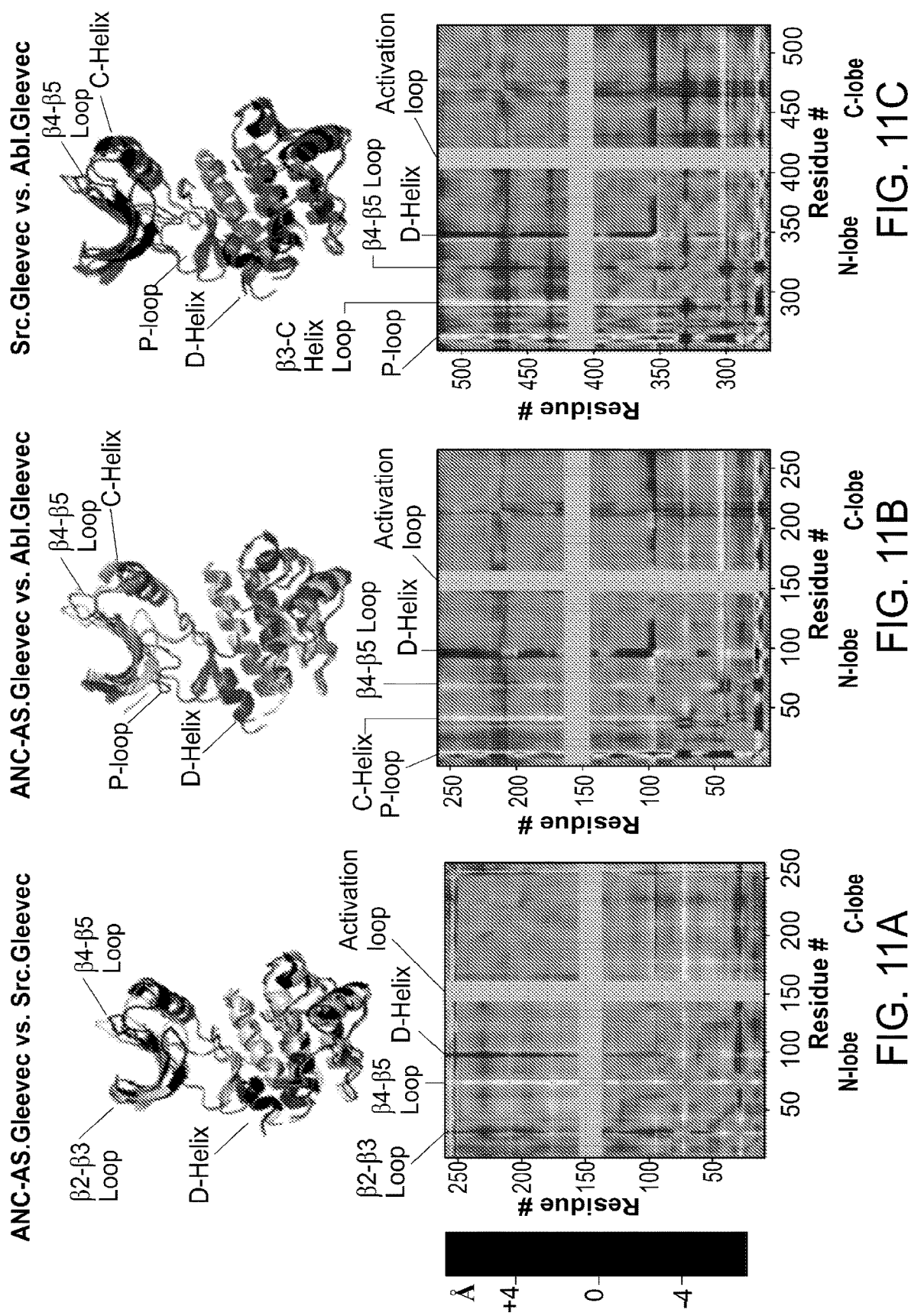
FIGS. 11A-11C are plots showing a comparison of crystal structure of the ANC-AS.Gleevec complex with structures of Src and Abl bound to Gleevec (same pdb's as in FIGS.
Figures 12A, 12B:
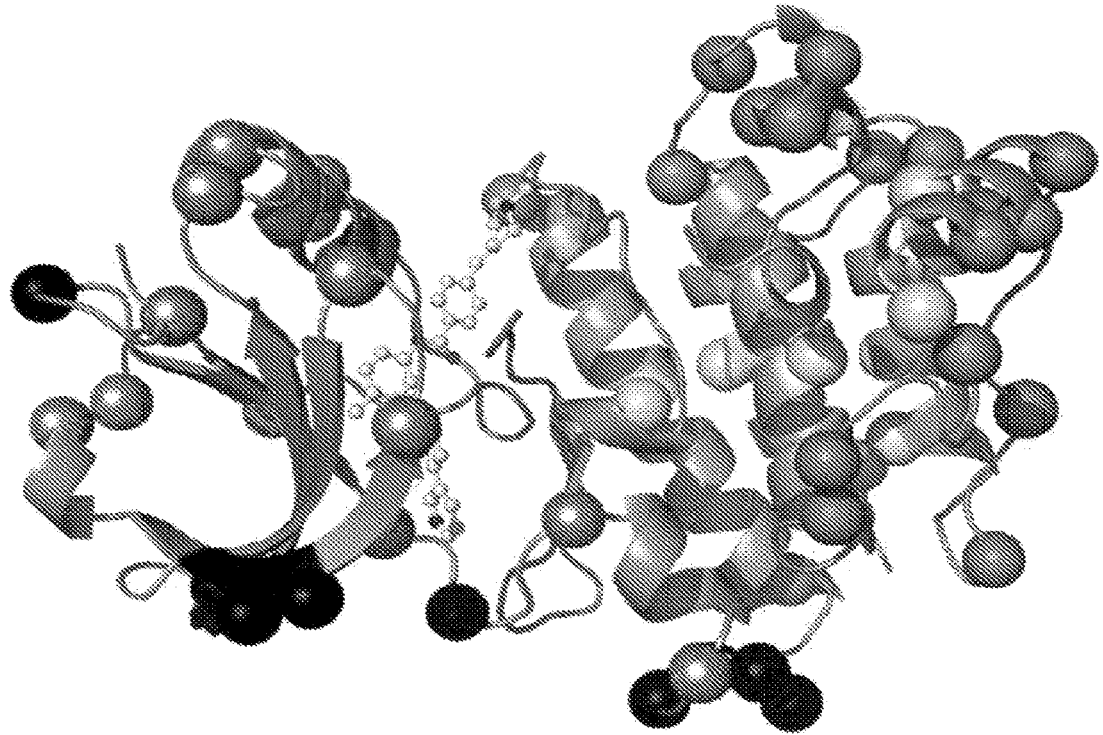
FIGS. 12A-12B are diagrams showing a mutational screen between ANC-AS and A2 identifies subsets of mutations sufficient for major increase in Gleevec affinity.

The X-ray crystal structures of ANC-AS bound to AMPPCP (FIGS. 10A-10C) and ANC-AS bound to Gleevec (FIGS. 4A-4H) illustrated the structural consequences of sequence evolution. As expected, the overall structure of ANC-AS was highly similar to modern Src and Abl with subtle differences in the P-loop, C-helix and 4-5 loop (FIG. 4E; FIG. 4G; FIGS. 10A-10E; FIGS. 11A-11C). Ancestral reconstruction identified a subset of 70 residues potentially responsible for the dramatic shift of E.I E*.I conformational equilibrium between ANC-AS and ANC-A2 (FIG. 4A), but not all of these residues were necessarily important for the observed increased affinity. To pinpoint the essential residue differences, the ANC-AS-Gleevec structure was analyzed and these 70 residues were divided into four groups using a crude divide-and-conquer approach (FIGS. 12A-12B). Constructs containing subgroups of mutations were then tested for activity and Gleevec binding (FIGS. 12A-12B). Remarkably, changing only 15 amino acids in the core of the ANC-AS N-terminal lobe to the Abl sequence (named AS(+15)) drastically increased Gleevec affinity to a level similar to Abl (FIGS. 4C-4D). This drastic increase in affinity is rooted in changes in the conformational dynamics of the induced fit step (FIGS. 13A-13C). Therefore, a small subset of residues located only in the N-terminal lobe were responsible for the majority of the change in the E.I E*.I equilibrium, which is the most important step in the Gleevec binding mechanism.

Figures 14A, 14B, 14C:
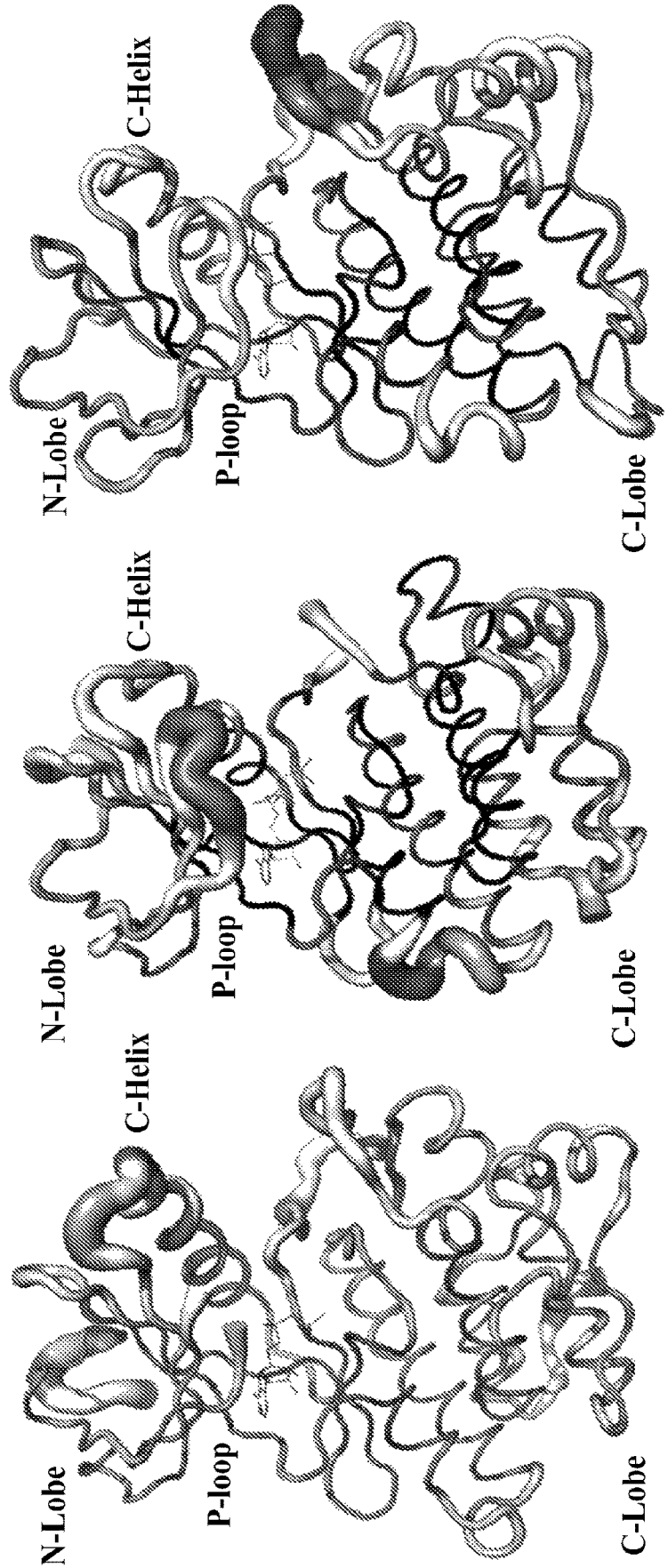
FIGS. 14A-14C are illustrations showing a comparison of B-factors of nucleotide-bound crystal structures of Abl, ANC-AS and Src indicate differences in flexibility of the P-loop. B-factors are illustrated in putty, orange/red thick lines indicate high B-factors while thin-blue lines indicate low B-factors.

With the importance of these 15 residues clearly established, rationalization of the change in the energy landscape at an atomistic level can be attempted using the ANC-AS x-ray structures. Most of these 15 amino acids were distant from the drug-binding pocket and were part of a hydrogen-bonding network in both of the AMPPCP- and Gleevec-bound conformations in ANC-AS and Src. In contrast, amino acid changes of these residues in AS(+15) and Abl prohibited such hydrogen bonding networks (FIG. 4F; FIG. 4G). Without being bound by theory, it is hypothesized that the lack of these hydrogen bonds allowed the P-loop to close over Gleevec in a kinked conformation, while in Src and ANC-AS the identified hydrogen bonds prohibited such a conformational change (FIG. 4E). A stabilizing role of the N-lobe hydrogen bond networks for the P-loop is consistent with the clear P-loop electron density in Src and ANC-AS bound to nucleotide, in contrast to the high B-factors or missing P-loop electron density in the corresponding Abl structures (FIGS. 14A-14C).

It is noted that the difference in P-loop conformation for kinase/gleevec structures has been discussed previously as the potential basis for differential affinity (21). However, a sequence swap of the two P-loop residue differences placing Abl residues into Src, F278Y and Q275G, failed to increase Src's affinity towards Gleevec (3). The data described herein suggest that the kinked P-loop seen in the Gleevec-bound Abl structure is stabilized by a hydrogen bond between Y272 in the P-loop and N341 in the D-helix (FIG. 4H), in addition to other interactions with the drug. However, this energetically favorable interaction is only possible in the absence of the restricting hydrogen bonds in the N-lobe identified above (FIG. 4G).

A long-standing problem in molecular biology is how to establish the sequence determinants for specificity within protein families. As a modern anthropogenic creation, Gleevec could not have provided evolutionary pressure for the divergence of the Src and Abl kinase families. However, the ancestral kinases delivered a deeper understanding of the molecular mechanism underlying the impressive selectivity of a modern cancer drug. Surprisingly, Gleevec takes full advantage of the evolution of "incidental" differences in the Src and Abl energy landscapes, even though the structure-based design of Gleevec did not have this in mind. In addition, Gleevec binding served as an experimental readout for the natural evolution of the DFG in/out equilibrium, which is widely considered to be a key element for differential regulation in the protein kinase kingdom, although the corresponding mechanism has been elusive (3, 4, 7, 17, 18). It was found that a gradual evolution of the DFG in/out equilibrium was governed by residues far removed from the catalytic site.

There is of course a natural evolutionary pressure in the development of Gleevec resistance. During the therapeutic use of Gleevec in chronic myelogenous leukemia patients, a number of clinically relevant resistance mutations have evolved, including the most common Abl(T315I) mutation (22) (FIGS. 5A-5G). This single amino acid mutation drastically decreased the affinity for Gleevec ($K_d$ of 12±5 µM at 25° C.). This mutation has been called the "gatekeeper" mutation because of the hypothesis that the Ile residue obstructs binding due to steric hindrance (23) (24). Surprisingly, it was found that the binding step is in fact unaltered by the T315I mutation, but that the subsequent induced fit step is severely hampered (FIGS. 5A-5G). As described before this latter step of conformational dynamics after drug binding is the key for high affinity in the wild type protein, and it is the very same step that is altered under the evolutionary pressure in cancer cells treated with Gleevec.

Previous ancestral reconstruction studies fall into two types: reconstruction of highly conserved protein families that remain relatively unchanged in function and sequence over a vast period of time (up to 4 billion years) (25-28), and reconstructions within metazoan lineages (within the last 600 million years) characterized by large functional divergence caused by a small number of amino acids changes (29, 30). The system differs from both categories with respect to the time period (ANC-AS is ~1 billion years old) and the number of residues involved. In addition, the implications of the ancestral reconstruction performed here are mainly focused on revealing the atomistic mechanism of a modern cancer drug for modern kinases. The results described herein on the gradual change in energy landscape from the common ancestor to modern kinases, and the data described herein for the resistance mutant that evolved under natural pressure, advocate that altering conformational dynamics—hence energy landscapes—may be a crucial driving force in evolution.

The results described herein were obtained using the following methods and materials.

Methods and Materials

Ancestral Protein Sequence Reconstruction.

Seventy-six sequences were selected from the NCBI non-redundant protein sequence database spanning the Tec, Src and Abl kinase subfamilies. Both phylogeny and alignment were co-estimated using the Bayesian BAli-Phy software package (FIGS. 6A-6B) (1). The analysis was performed using the RS07 insertion/deletion model, LG amino acid substitution matrix, estimating equilibrium amino acid frequencies, with gamma distributed rates across sites (four categories). Two independent chains were run until the ASDSF and PSRF-80% CI criteria fell below 0.01 and 1.01 respectively. Ancestral sequences were inferred using the marginal likelihood method implemented in PAML (2), with the maximum a posteriori phylogeny and expected parameters (normalized equilibrium frequencies, gamma shape parameter) from the BAli-Phy run.

It is noted that although ancestral reconstruction is a well-established method (3, 4) it is still a developing field, and the underlying assumptions should be considered (5). The reconstructed proteins are probabilistic inferences. The estimated probability of reconstructing the exact actual ancestral sequence is the product of the probabilities for each site in the protein, and hence the overall probability is vanishingly small. However, the histograms of the posterior probabilities associated with each inferred position in the ancestral proteins (FIGS. 6A-6B) show that the estimated confidence is high (PP>95%) for the great majority of ancestral residues. In fast evolving regions of the protein the majority of the ambiguous residues are expected to be selectively neutral or nearly neutral, and the sequence alternatives involve chemically conservative substitutions. These mathematical considerations also reflect the fact that, like modern proteins, the ancestral proteins existed in large populations of organisms (in this case single-celled eukaryotes), comprising a polymorphic ensemble of similar proteins that changed over time. From a practical perspective, reconstructed sequences can be viewed as representatives of groups of proteins that are likely similar to ancestral sequences in biophysically relevant ways.

Expression and Purification

Ancestral sequence cDNAs were constructed by Genscript. Ancestral and extant inserts were sub-cloned into pET-41M vector containing a His-tag and MBP-tag on the N-terminus. Vector was co-transformed with the YOPH phosphatase (6) to ensure de-phosphorylated protein and to lower toxicity of the insert into GROEL competent BL-21 cells (GROEL under Tetracycline induction). Cells were grown in TB media to an OD of 0.8 at 37° C. then switched to 18° C. for 1 hour before induction with 100 uM of IPTG. Cells were allowed to grow for 16 hours at 18° C. Cells were lysed in the presence of Benzonase by sonication. After purification via a Talon and MBP column the tags were cleaved with His-tagged TEV-protease overnight at 4° C. while dialyzing against storage buffer (25 mM Tris-HCl pH 8, 500 mM NaCl, 5% Glycerol). Cleaved sample was collected and run over Ni-NTA column to remove Histagged TEV, cleaved MBP and uncleaved His-MBP-Kinase contaminants. Flow-through was collected, concentrated to 5 ml and passed over a 16/60 S-100 gel filtration column. All columns were run at 4° C. Samples where confirmed to be unphosphorylated by western blot using a standard phosphorylated-Tyr antibody.

Activity, IC50 and Kd Measurements.

Protein activity was assayed using the Antibody Beacon™ Tyrosine Kinase Assay Kit (Molecular Probes). In addition to kit components the reaction mixture contained 10-50 nM of protein, 500 uM of standard peptide EAIYAAPFAKKK (SEQ ID NO: 1), and 1 mM Mg ATP. Phosphorylated peptides of known concentration were used for fluorescence level calibration. All reactions were performed at 25° C. Ki's for Gleevec were calculated from IC50's using the standard equation:

$$K_i = IC_{50} / \left(1 + \left(\frac{[ATP]}{K_m}\right)\right)$$

where we used a Km for ATP of 70 uM. For several samples, the resulting rates were validated by HPLC analysis of the reaction products using Agilent Infinity 1260 and C18-AR columns from ACE. Phosphorylated and unphosphorylated peptides were separated using a linear gradient between 0 and 40% of acetonitrile with 0.1% TFA as a mobile phase. The results were within experimental error with the fluorescence assays.

For dissociation constant (Kd) measurements of Gleevec to the ancestors, 10 nM of kinase was mixed with 2-1000 nM of Gleevec. Binding was monitored via changes in Trp fluorescence. Measurements were done using the FluoroMax-4 (Jobin-Yvon) fluorimeter. Tryptophanes were excited at 295 nm, and fluorescence was detected at 350 nm. Extracted intensities were fitted to a generalized binding equation:

$$F = F_0 + A \cdot \frac{[I] + [Et] + Kd - \sqrt{([I] + [Et] + Kd)^2 - 4 \cdot [Et] \cdot [I])}}{2 \cdot [Et]},$$

where $[E_t]$ is total enzyme concentration, [I] concentration of Gleevec, $F_0$ and A are background fluorescent and a scaling factor respectively. The dissociation constant ($K_d$) of Gleevec Abl (T315I) could not be determined by Trp fluorescence because of too weak binding and severe inner filter effects of the drug at the high concentrations. Only ITC at 25° C. gave a reliable data for the Gleevec affinity to Abl (T315I). Titrations were carried out on a Nano ITC (TA instruments) and analyzed with the NanoAnalyze software. Injectant was added in 1 L volume, every 180 s. The concentrations used were 25 M Abl (T315I) and 340 M Gleevec.

X-Ray Crystallography.

Hexagonal crystals of ancestor ANC-AS with bound AMPPCP (with dimensions h=50-100 μm, a=20 μm) were grown for three days and were flash frozen in liquid nitrogen. 6.3 mg/ml of lysine modified (ethylated) protein was crystallized at 18° C. using the hanging drop method in 50 mM TRIS, pH 8.0, 500 mM NaCl, 5% Glycerol, 20 mM MgCl₂, 2 mM Imidazole, 1 mM AMPPCP, mixed 1:1 with 2.2 M Ammonium Sulfate. The data were indexed, integrated and scaled using programs from the CCP4 suite (XIA2) (7). Molecular replacement was performed with CCP4 MOLREP (8) using a human ABL kinase structure (pdb code 2HYY) as an initial search model. Model refinement was performed using PHENIX (9) and CCP4 REFMAC (10). Models were built using COOT and WINCOOT (11). Molecular replacement and the first refinement cycles were done without the nucleotide and the magnesium ion in the model. Later, AMPPCP was placed into the positive peak of the difference electron density map. No density could be confidently determined for the magnesium ion. In an effort to minimize model bias, simulated annealing (both Cartesian and torsion angles) was performed with PHENIX using default parameters for several rounds. Table 1 and 2 summarize the data collection/processing statistics and the refinement statistics. Model validation was done with MOL-PROBITY (12).

Two-dimensional plates of ANC-AS with bound Gleevec (with dimensions 300 μm×300 μm) grew within one week on dust particles using the sitting drop method. These crystals were later used for microseeding using the hanging drop method. Smaller but 3-dimensional plates (100 μm×100 μm×15 μm) where flash frozen in liquid nitrogen. For both steps, 10 mg/ml of lysine modified (ethylated) protein was used in 30 mM TRIS pH 8.0, 500 mM NaCl, 1 mM Gleevec, mixed 1:1 with 200 mM Ammonium Acetate, 100 mM Sodium Acetate Trihydrate pH 4.6 and 30% PEG 4000, at 18° C. XDS (13) was used for indexing and integration while scaling was done with AIMLESS (14) (CCP4). Further processing and model building was done as described for protein in the presence of AMPPCP.

ThermoFluor Experiments.

Solutions of 10 ul of 225X Sypro Orange, 15 ul of storage buffer (50 mM HEPES pH 8, 500 mM NaCl, 5% Glycerol and 10 mM TCEP) and 5 ul of 100 uM protein was added to a 96-well PCR plate. A control containing the storage buffer+Sypro Orange was added. The plates were sealed with optical sealing tap and heated in a Applied Biosystems 9600 real-time PCR machine from 20 to 100 degrees with increments of 0.2 degrees Celsius. Fluorescence of the Sypro orange dye was measured by exciting at 490 nm and measuring at 575 nm.

Stopped-Flow Kinetics Experiments and Data Analysis.

All stopped-flow experiments were performed with the Applied Photophysics SX-20 instrument at 5° C. or 25° C. as specified in the text. Binding was monitored via changes in tryptophan fluorescence, samples were excited at 295 nm (9 nm bandwidth) and emission was detected using a longpass 320 nm cut-off filter. After mixing the concentration of kinase was 0.1 M, and the concentration of Gleevec was varied. To study dissociation kinetics, protein (at 0.1-1 M) was pre-incubated with 0.1-100 M of Gleevec (depending on the $K_d$ of the kinase) for 10 minutes, placed into the 0.5 mL syringe and then diluted 11-fold. All experiments were performed in a buffer containing 50 mM TRIS, 500 mM NaCl, 1 mM MgCl$_2$, 1 mM TCEP and 5% DMSO (pH 8.0). Data were analyzed using Applied Photophysics software. Kinetic fluorescence traces were fitted to a single or multi-exponential function. To account for photobleaching, an additional exponential term was included into the fitting function. This rate was fixed to the value determined in control experiments where protein was mixed with buffer in the absence of Gleevec.

Analysis of Kinetic Data.

The following naming convention is used throughout the text. Different states of the enzyme without or with bound inhibitor are called E, E.I and E*I, respectively. The conformation of the DFG-loop is specified with "DFG-in" or "DFG-out" subscripts. Rates describing the time dependence of experimentally observed changes in fluorescence are called observed rates. F denotes the amplitude of the observed fluorescent signal and is generated by combined fluorescence from all enzyme species. $k_{on}$, $k_{off}$, $k_{conf+}$ and $k_{conf-}$ are rate constants and correspond to individual microscopic steps in the reaction schemes.

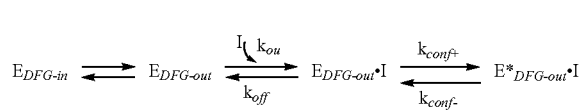

In this scheme the first step (conformational selection), $E_{DFG-in}$ $E_{DFG-out}$, is fast and not directly observed in the kinetic experiment. However the equilibrium between these two states affects the population of the binding competent state ($E_{DFG-out}$) and hence is reflected in the amplitude of the next step in the scheme (the binding step). This phenomenon allowed qualitative tracking of the evolutionary change in the DFG-in/DFG-out equilibrium along the phylogenetic tree (FIG. 3A).

Figure 5D:
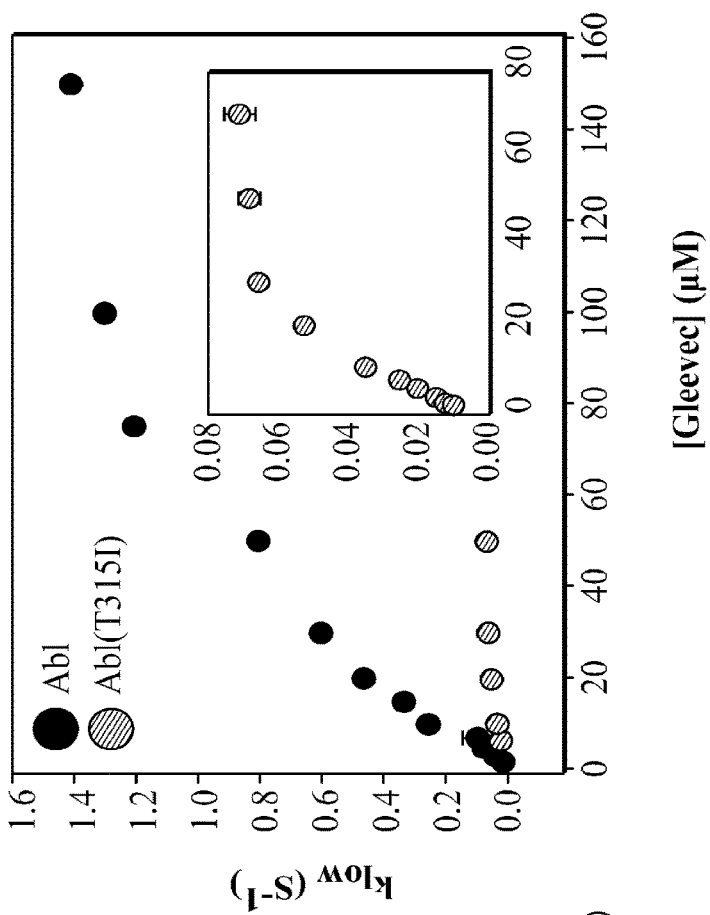
Figure 5C:
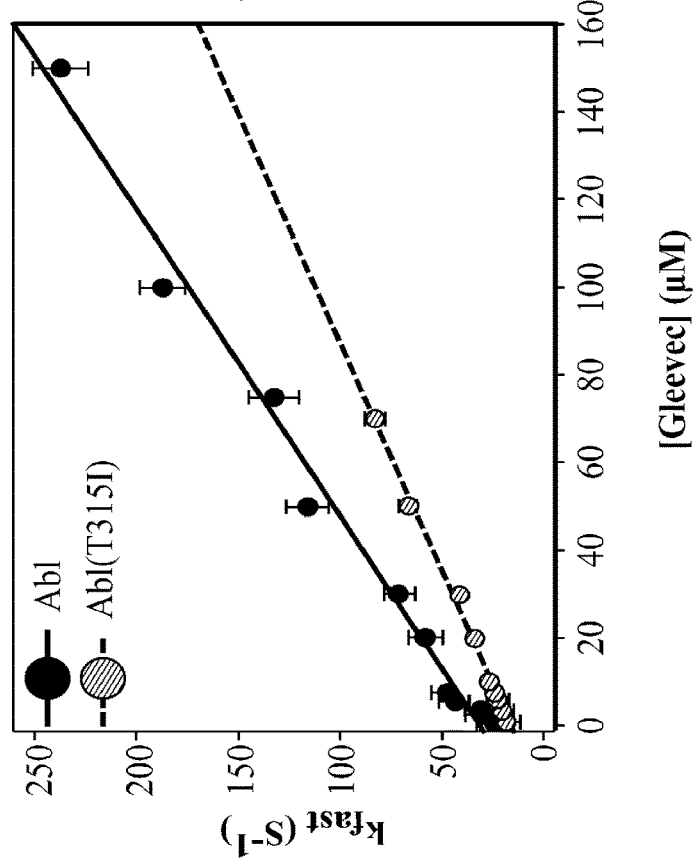

In all of the binding kinetic experiments, the concentration of the inhibitor was much greater than concentration of the enzyme ([I]>>[E]). Under such conditions the binding is a pseudo-first-order reaction ($E_{DFG-out}$+I $E_{DFG-out}$.I) and thus characterized by a linear dependence of the observed binding rate ($k_{fast}$) on inhibitor concentration (FIG. 2F; FIG. 5D; FIG. 13A). This linear dependence is the feature that allows clear identification of the phase corresponding to binding in the multi-exponential kinetic traces. In contrast, the observed rate that characterizes the conformational change after binding (the induced fit step, $k_{slow}$) has a non-linear dependence on inhibitor concentration, since the transient concentration of the $E_{DFG-out}$.I depends on inhibitor concentration (FIG. 2G; FIG. 5E; FIG. 13B) (15). These plots of $k_{fast}$, $k_{slow}$ as a function of inhibitor concentration can be used to extract the microscopic rate constants for different steps of the binding scheme. From the linear plot of $k_{slow}$ vs. [I] one can extract the $k_{on}^{obs}$ (which is equal to the slope of the line) and the $k_{off}$ (which is equal to the intercept). It is noted that $k_{on}^{obs}$ is not a microscopic rate constant $k_{on}$, but rather is a product of $k_{on}$ and the fractional population of the kinase in the binding capable state $P_{DFG-out}$: $k_{on}^{obs}=k_{on} \times P_{DFG-out}$. As a consequence, $k_{on}^{obs}$ reflects both the $E_{DFG-in}$ $E_{DFG-out}$ equilibrium and the rate of the physical binding step simultaneously.

The Gleevec dissociation experiment was used to determine the $k_{conf-}$ rate constant. Since the fluorescent change observed in this experiment was mono-exponential and much slower than the $k_{off}$ (determined as described above), the rate constant characterizing the dissociation must be attributed to the conformational change $k_{conf-}$. In addition, the value of the plateau on the $k_{slow}$ vs [I] graph (FIG. 2G; FIG. 5E; FIG. 13B) determines the sum $k_{conf+}+k_{conf-}$, which allows calculating the value of $k_{conf+}$. Thereby the system is fully determined (15).

Figure 9:
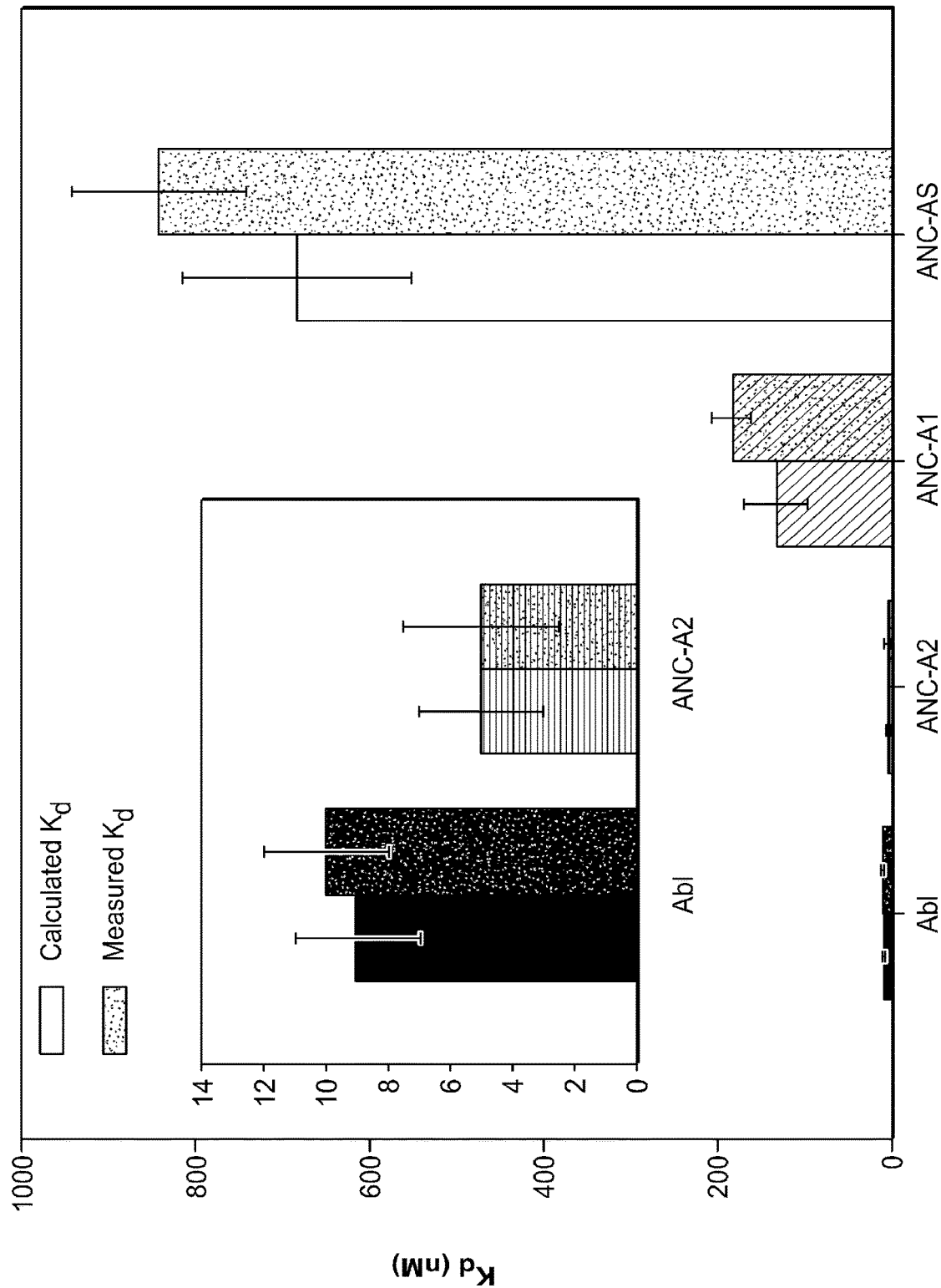
FIG. 9 is a plot showing a stringent test for validity of kinetic scheme and measured rate constants for Abl and several ancestors. Measured $K_d$'s (FIG. 2B) are within experimental error to $K_d$'s calculated from all microscopic rate constants (FIG. 3). For the very weak Gleevec binders Src and ANC-S1, the $K_d$ is too weak to measure accurately (17) and also the $K_d$'s cannot be calculated from the kinetic rate constants because the amplitude of the fast phase is too small (FIG. 3A).
Figure 10A:
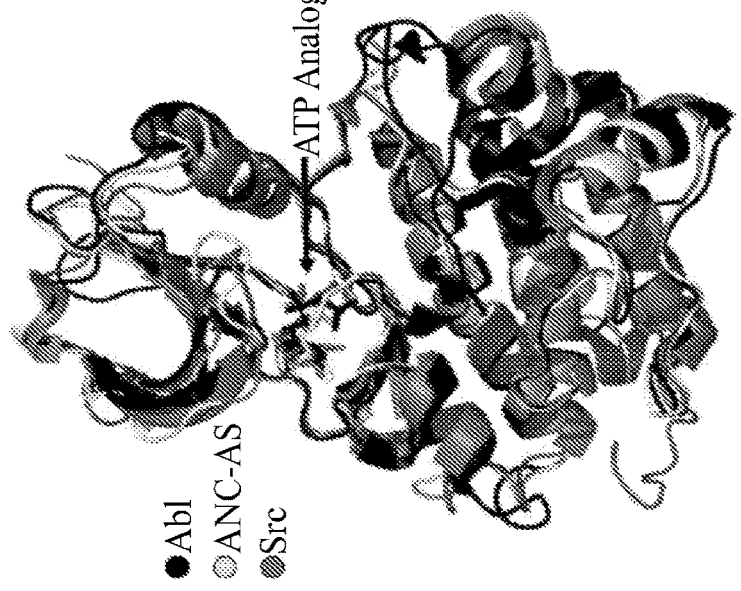
FIGS. 10A-10E are plots and diagrams showing a comparison of ANC-AS bound to AMPPCP with active and inactive Src and Abl, and inactive ANC-AS bound to Gleevec with the corresponding Abl and Src structures. ANC-AS samples a fully active state without phosphorylation of Tyr 159 in the activation loop.
Figure 10B:
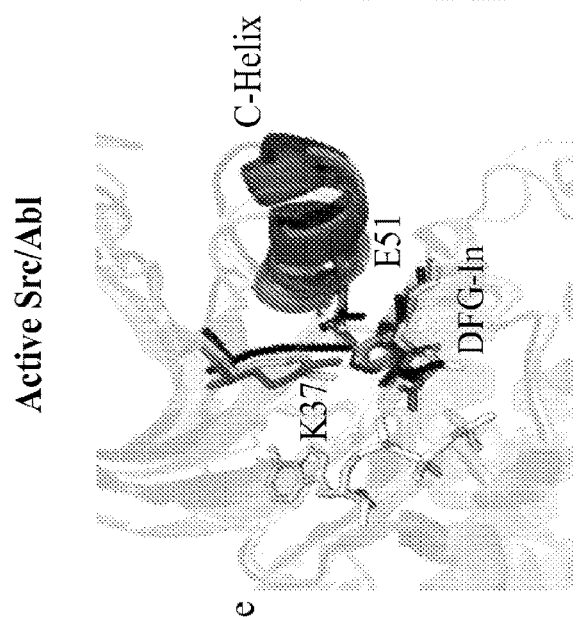
Figure 10C:
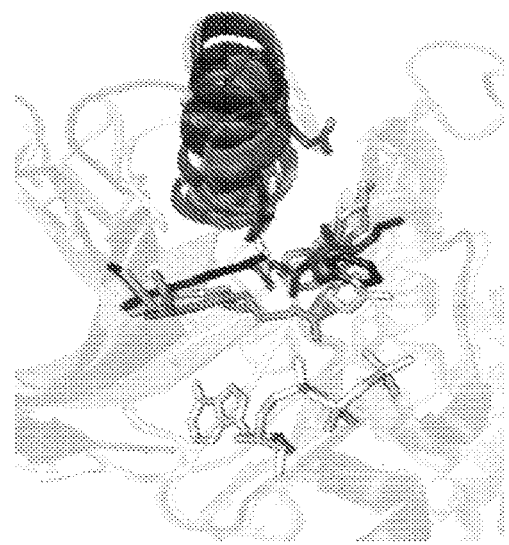
Figures 10D, 10E:
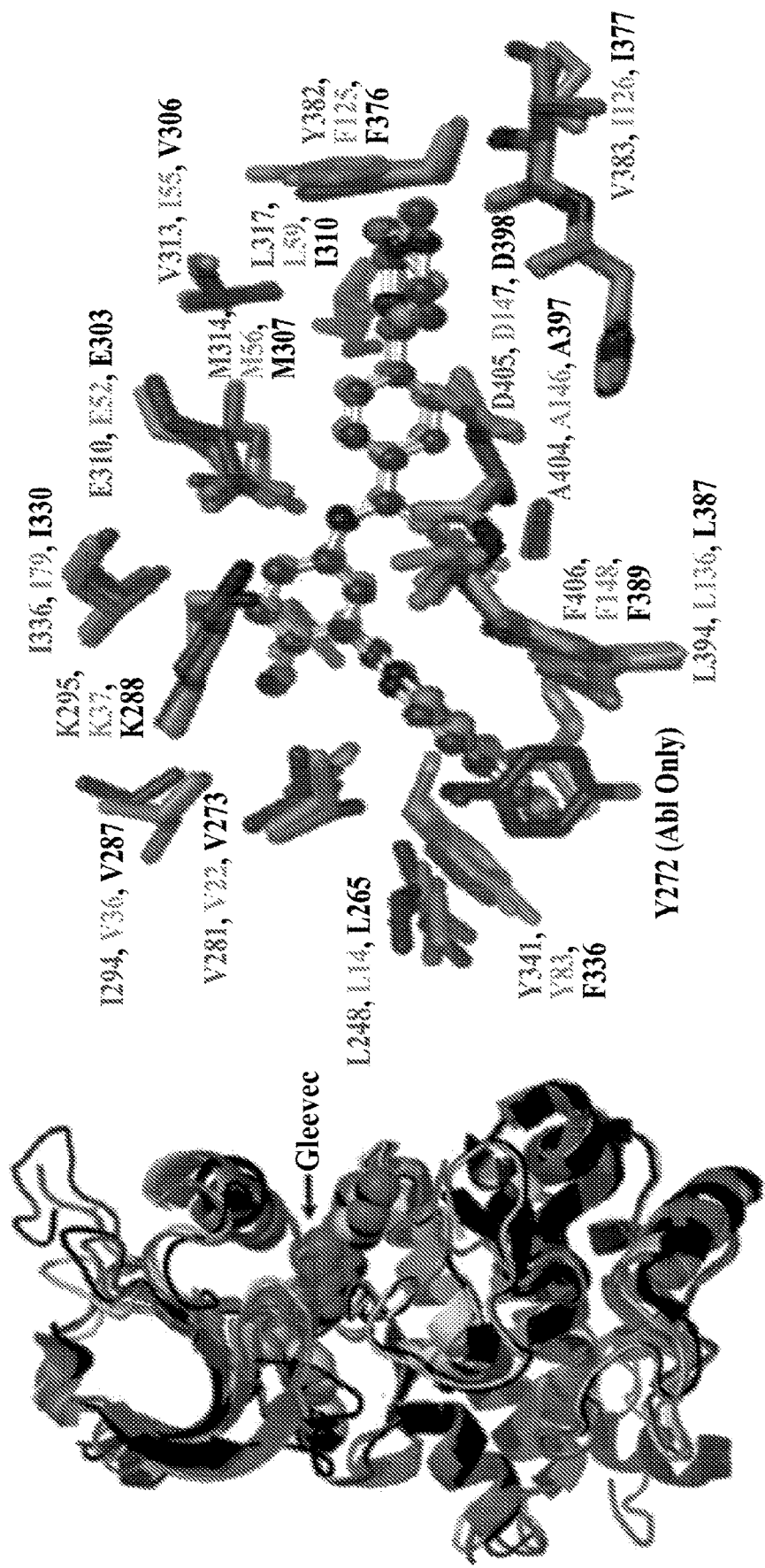

Knowledge of the individual microscopic constants enables calculation of the overall $K_d^{calc}$:

$$K_d^{calc} = \frac{K_{bind}^{obs} \cdot K_{IF}}{(1 + K_{IF})}$$

Where $K_d^{calc}$ is the overall dissociation constant, $K_{bind}^{obs}$ and $K_{IF}$ correspond to the observed dissociation constant for binding and equilibrium constant for the induced fit step respectively. This calculated $K_d^{calc}$ can be compared with the value of $K_d^{measured}$ (FIG. 9), which was determined in an independent thermodynamic experiment (FIG. 2B; FIG. 9). Such a comparison serves as an independent verification of the model and the determined parameters.

TABLE 1

X-ray data collection and processing statistics. Values in parentheses correspond to the highest-resolution shell.

|  | ANC-AS bound to AMPPCP (pdb id: 4CDS) | ANC-AS bound to Gleevec (pdb id: 4CSV) |
| --- | --- | --- |
| Beamline | BL8.2.2. ALS | BL8.2.2. ALS |
| Detector | Quantum 315 ADSC Area Detector | Quantum 315 ADSC Area Detector |
| Wavelength (Å) | 0.999995 | 0.999956 |
| Temperature (K) | 100 | 100 |
| Crystal-detector distance (mm) | 375 | 285 |
| Rotation range per image (°) | 0.5 | 0.5 |
| Total rotation range (°) | 180 | 122 |
| Space group | $P6_2$ | I2 |
| Unit cell parameter (Å, °) | 127.92 × 127.92 × 52.46, 90 × 90 × 120 | 71.03 × 56.87 × 76.12, 90 × 116.62 × 90 |
| Mosaicity | 1.094 | 0.320 |
| Resolution limits (Å) | 110.778 – 2.91 (3.03 – 2.91) | 42.36 – 2.048 (2.11 – 2.048) |
| Total number of reflection | 106756 | 40153 |
| Unique reflections | 10551 | 15954 |
| Redundancy | 10.1 | 2.5 |
| I/(I) | 7.2 (2.0) | 10.1 (2.0) |
| Completeness (%) | 100 (100) | 93.1 (96.8) |
| $R_{merge}$ (%) | 18.3 (94.9) | 4.3 (41.0) |
| $R_{meas}$ (%) | 19.2 (99.8) | 6.1 (57.8) |
| $R_{p.i.m.}$ (%) | 6.0 (30.6) | 4.3 (40.7) |
| Overall B-factor from Wilson plot (Å$^2$) | 78.5 | 50.3 |
| Optical resolution (Å) | 2.17 | 1.72 |

TABLE 2

Refinement statistics. Values in parentheses correspond to the highest-resolution shell

| Resolution range (Å) | 63.97 – 2.91 (3.04 – 2.91) | 62.43 – 2.049 (2.102 – 2.049) |
| --- | --- | --- |
| Total number of atoms (nonhydrogen) | 2095 | 2061 |
| Number of protein atoms | 2064 | 1968 |
| $R_{cryst}$ (%) | 21.9 (31.2) | 18.7 (30.5) |
| $R_{free}$ (%) | 26.2 (31.1) | 24.2 (37.3) |
| RMSD from ideality; bonds (Å), angles (°) | 0.0097, 0.653 | 0.0100, 1.420 |
| Ramachandran plot, favored regions, outliers | 94.0, 0.4 | 98.3, 0.0 |
| Rotamer outliers (%) | 0.5 | 3.3 |
| C-beta outliers | 0 | 0 |
| Molprobity clashscore | 3.66 | 3.78 |
| Molprobity overall score | 1.56 | 1.67 |
| Average B-factor (Å$^2$) | 71.4 | 59.5 |

The structures of the catalytic domain of ANC-AS in its active and inhibited state were solved at 2.91 Å and 2.05 Å, respectively. One monomeric kinase molecule can be found in the asymmetric unit cell of both crystal structures. The activation loop and the C-terminal residues in both models, and the residues 97-100 (inhibited state model only) could not be traced into the electron density map. The P-loop (residues 17-24) and the loop between the D- and E-helix (residues 95-100) of the active state model have high B-factors (two times of the average B-factor). However, there is enough main chain density to model these amino acids.

Mutational Screen to Pinpoint Essential Residues for Gleevec Selectivity.

There is a large difference in Gleevec affinity between ANC-AS and ANC-A2, and 70 mutations separate ANC-AS from ANC-A2. Many of these mutations are likely unnecessary to shift Gleevec affinity and may simply be neutral substitutions. Identifying the functional residues is challenging, as there are still quite a few differences between the two nodes. A conquer-and-divide strategy was used, whereby the mutational set between ANC-AS and ANC-A2 into the N-lobe set and the C-lobe sets were partitioned (see red/medium grey and blue/dark grey dots FIGS. 12A-12B). These two sets where further split into solvent-exposed residues and core residues (light and dark dots in FIGS. 12A-12B). Constructs were made containing combinations of these sets of mutations. Proteins were expressed using the same protocol as ancestral proteins (see methods described herein). Constructs containing only N-lobe mutations expressed normally (see FIGS. 12A-12B). Surprisingly, constructs that contained the C-lobe mutations did not express, with the exception of C-lobe mutations of only the core residues. All of the N-lobe mutations showed reduced activity relative to the extant or ancestral constructs (FIGS. 12A-12B), ranging from 6-fold to 1200-fold less activity when compared to Abl. These results highlight the remarkable ability of ancestral sequence reconstruction, as opposed to rational design, to produce enzymes with high levels of activity that are comparable to modern day enzymes.

References—Example 1

1. D. J. Richter, N. King, The Genomic and Cellular Foundations of Animal Origins. Annual Review of Genetics, Vol 47 47, 509-537 (2013).
2. G. Manning, G. D. Plowman, T. Hunter, S. Sudarsanam, Evolution of protein kinase signaling from yeast to man. Trends Biochem Sci 27, 514-520 (2002).
3. M. A. Seeliger et al., c-Src binds to the cancer drug imatinib with an inactive Abl/c-Kit conformation and a distributed thermodynamic penalty. Structure 15, 299-311 (2007).
4. S. S. Taylor, A. P. Kornev, Protein kinases: evolution of dynamic regulatory proteins. Trends Biochem Sci 36, 65-77 (2011).
5. A. P. Kornev, S. S. Taylor, Defining the conserved internal architecture of a protein kinase. Biochim Biophys Acta 1804, 440-444 (2010).
6. R. V. Agafonov, C. Wilson, R. Otten, V. Buosi, D. Kern, Energetic dissection of Gleevec's selectivity toward human tyrosine kinases. Nat Struct Mol Biol 21, 848-853 (2014).
7. Y. M. Yen-Lin Lin, Wei Jiang, and Benoît Roux, Explaining why Gleevec is a specific and potent inhibitor of Abl kinase. PNAS 10, (2013).
8. M. J. Harms, J. W. Thornton, Evolutionary biochemistry: revealing the historical and physical causes of protein properties. Nat Rev Genet 14, 559-571 (2013).

9. Pauling L., Z. E., Chemical Paleogenetics Molecular "Restoration Studies" of Extinct Forms of Lifer. Acta Chemica Scandinavica 17 (1963).
10. A. M. Dean, J. W. Thornton, Mechanistic approaches to the study of evolution: the functional synthesis. Nat Rev Genet 8, 675-688 (2007).
11. D. A. Liberles, Ancestral Sequence Reconstruction (Oxford University Press Oxford, 2007).
12. P. D. Williams, D. D. Pollock, B. P. Blackburne, R. A. Goldstein, Assessing the accuracy of ancestral protein reconstruction methods. PLoS Comput Biol 2, e69 (2006).
13. N. M. Krishnan, H. Seligmann, C. B. Stewart, A. P. De Koning, D. D. Pollock, Ancestral sequence reconstruction in primate mitochondrial DNA: compositional bias and effect on functional inference. Mol Biol Evol 21, 1871-1883 (2004).
14. T. Hunter, Tyrosine phosphorylation: thirty years and counting. Curr Opin Cell Biol 21, 140-146 (2009).
15. W. Eckhart, M. A. Hutchinson, T. Hunter, An activity phosphorylating tyrosine in polyoma T antigen immunoprecipitates. Cell 18, 925-933 (1979).
16. S. J. Gould, Dollo on Dollo's law: irreversibility and the status of evolutionary laws. J Hist Biol 3, 189-212 (1970).
17. A. Aleksandrov, T. Simonson, Molecular Dynamics Simulations Show That Conformational Selection Governs the Binding Preferences of Imatinib for Several Tyrosine Kinases. Journal of Biological Chemistry 285, 13807-13815 (2010).
18. S. Lovera et al., The different flexibility of c-Src and c-Abl kinases regulates the accessibility of a druggable inactive conformation. J Am Chem Soc 134, 2496-2499 (2012).
19. S. W. Cowan-Jacob et al., The crystal structure of a c-Src complex in an active conformation suggests possible steps in c-Src activation. Structure 13, 861-871 (2005).
20. A. C. Dar, K. M. Shokat, The evolution of protein kinase inhibitors from antagonists to agonists of cellular signaling. Annu Rev Biochem 80, 769-795 (2011).
21. Y. B. Shan et al., A conserved protonation-dependent switch controls drug binding in the Abl kinase. Proc Natl Acad Sci USA 106, 139-144 (2009).
22. M. E. Gorre et al., Clinical resistance to STI-571 cancer therapy caused by BCR-ABL gene mutation or amplification. Science 293, 876-880 (2001).
23. M. Modugno et al., Crystal structure of the T315I Abl mutant in complex with the aurora kinases inhibitor PHA-739358. Cancer Res 67, 7987-7990 (2007).
24. H. Daub, K. Specht, A. Ullrich, Strategies to overcome resistance to targeted protein kinase inhibitors. Nat Rev Drug Discov 3, 1001-1010 (2004).
25. A. Ingles-Prieto et al., Conservation of Protein Structure over Four Billion Years. Structure 21, 1690-1697 (2013).
26. R. Perez-Jimenez et al., Single-molecule paleoenzymology probes the chemistry of resurrected enzymes. Nat Struct Mol Biol 18, 592-596 (2011).
27. E. A. Gaucher, S. Govindarajan, O. K. Ganesh, Palaeotemperature trend for Precambrian life inferred from resurrected proteins. Nature 451, 704-U702 (2008).
28. E. A. Gaucher, J. M. Thomson, M. F. Burgan, S. A. Benner, Inferring the palaeoenvironment of ancient bacteria on the basis of resurrected proteins. Nature 425, 285-288 (2003).
29. M. J. Harms, J. W. Thornton, Analyzing protein structure and function using ancestral gene reconstruction. Current Opinion in Structural Biology 20, 360-366 (2010).
30. S. F. Field, M. V. Matz, Retracing Evolution of Red Fluorescence in GFP-Like Proteins from Faviina Corals. Molecular Biology and Evolution 27, 225-233 (2010).
31. B. D. Redelings, M. A. Suchard, Joint Bayesian estimation of alignment and phylogeny.
Syst Biol 54, 401-418 (2005).

References—Example 1—Methods And Materials

1. B. D. Redelings, M. A. Suchard, Joint Bayesian estimation of alignment and phylogeny. Syst Biol 54, 401-418 (2005).
2. Z. Yang, PAML 4: phylogenetic analysis by maximum likelihood. Mol Biol Evol 24, 1586-1591 (2007).
3. D. A. Liberles, Ancestral Sequence Reconstruction (Oxford University Press Oxford, 2007).
4. M. J. Harms, J. W. Thornton, Evolutionary biochemistry: revealing the historical and physical causes of protein properties. Nat Rev Genet 14, 559-571 (2013).
5. P. D. Williams, D. D. Pollock, B. P. Blackburne, R. A. Goldstein, Assessing the accuracy of ancestral protein reconstruction methods. PLoS Comput Biol 2, e69 (2006).
6. M. A. Seeliger et al., High yield bacterial expression of active c-Abl and c-Src tyrosine kinases. Protein Sci 14, 3135-3139 (2005).7. C. C. P. N. 4, CCP4 Suite: programs for protein crystallography. Acta crystallogr 50, 760-763 (1994).
8. A. Vagin, A. Teplyakov, MOLREP: an automated program for molecular replacement. Journal of Applied Crystallography 30, 1022-1025 (1997).
9. P. D. Adams et al., PHENIX: a comprehensive Python-based system for macromolecular structure solution. Acta Crystallogr D Biol Crystallogr 66, 213-221 (2010).
10. A. A. Vagin et al., REFMAC5 dictionary: organization of prior chemical knowledge and guidelines for its use. Acta Crystallographica Section D-Biological Crystallography 60, 2184-2195 (2004).
11. G. Winter, xia2: an expert system for macromolecular crystallography data reduction. Journal of Applied Crystallography 43, 186-190 (2010).
12. V. B. Chen et al., MolProbity: all-atom structure validation for macromolecular crystallography. Acta Crystallogr D Biol Crystallogr 66, 12-21 (2010).
13. W. Kabsch, Xds. Acta Crystallogr D Biol Crystallogr 66, 125-132 (2010).
14. P. Evans, Scaling and assessment of data quality. Acta Crystallogr D Biol Crystallogr 62, 72-82 (2006).
15. R. V. Agafonov, C. Wilson, R. Otten, V. Buosi, D. Kern, Energetic dissection of Gleevec's selectivity toward human tyrosine kinases. Nat Struct Mol Biol 21, 848-853 (2014).
16. U. B. Ericsson, B. M. Hallberg, G. T. DeTitta, N. Dekker, P. Nordlund, Thermofluor-based high-throughput stability optimization of proteins for structural studies. Analytical Biochemistry 357, 289-298 (2006).
17. M. A. Seeliger et al., c-Src binds to the cancer drug imatinib with an inactive Abl/c-Kit conformation and a distributed thermodynamic penalty. Structure 15, 299-311 (2007).

18. D. Dalgarno et al., Structural basis of Src tyrosine kinase inhibition with a new class of potent and selective trisubstituted purine-based compounds. Chem Biol Drug Des 67, 46-57 (2006).
19. O. K. Nicholas M. Levinson, Kui Shen, Matthew A. Young, Michael Koldobskiy, Martin Karplus, Philip A. Cole, John Kuriyan, A Src-Like Inactive Conformation in the Abl Tyrosine Kinase Domain. PLos Biology 4, (2006).
20. B. Nagar et al., Structural basis for the autoinhibition of c-Abl tyrosine kinase. Cell 112, 859-871 (2003).
21. R. Maiti, G. H. Van Domselaar, H. Zhang, D. S. Wishart, SuperPose: a simple server for sophisticated structural superposition. Nucleic Acids Res 32, W590-594 (2004).

Example 2

Dynamics of Human Protein Kinases Linked to Drug Selectivity

Protein kinases are promising cancer drug targets due to their overexpression and deregulation in cancer. Both Aurora A, a Serine/Threonine kinase, and Abl, a Tyrosine kinase have become attractive targets for the development of new anticancer therapies. In particular, the Asp-Phe-Gly (DFG) motif, in the activation loop of kinases has been intensely explored in the past decade as a hot-spot for designing compounds capable of keeping the kinase in an inactive conformation. Using a combination of fast fluorescence kinetics, X-ray crystallography and fluorine NMR experiments, a universal drug binding mechanism that rationalizes selectivity, affinity and drug resistance in Ser/Thr and Tyr kinases is proposed.

Both the Ser/Thr kinase Aurora A, and the Tyr kinase Abl are important targets for the development of new anticancer therapies. A longstanding question is how to inhibit specifically and effectively those kinases. For this aim, understanding of the inhibition mechanism of Aurora A and Abl by different drugs is essential. The binding kinetics of two distinct kinase drugs, Danusertib and Gleevec, to Aurora A, Abl, and the Gleevec resistant mutant T315I Abl were characterized. Results herein show that inhibitors affinities do not rely exclusively on the recognition of a specific conformation of the Asp-Phe-Gly loop of the kinase. Quantitative binding kinetics described herein put forward an opposing mechanism in which a slow conformational change after drug binding (i.e., induced fit) dictates drug affinity.

Introduction

Due to its central role in cellular processes and involvement in various types of cancers (1-3), protein kinases have become the number one drug target of the 21$^{th}$ century (4; 5). Despite their large therapeutic relevance, the development of specific kinase inhibitors proved to be extremely challenging because they must discriminate between the very similar structures of a large number of kinases in human cells. One of the biggest success stories is the specific Abl kinase inhibitor Gleevec for the treatment of chronic myelogenous leukemia (CML) (6) highlighting the therapeutic benefit of a drug that targets specifically one kinase in terms of cancer treatment efficiency and minimizes side effects. While being a multi-billion cancer drug, the mechanism responsible for the impressive specificity has been elusive until recently. For Gleevec and other kinase inhibitors it has been proposed that the conformational state of the fully conserved DFG (for Asp-Phe-Gly) loop (7) dictates drug specificity (8). Strikingly, recent quantitative binding kinetics put forward an opposing mechanism in which an induced fit step after drug binding is responsible for Gleevec specificity.

Here the question of whether such a fundamentally distinct mechanism might be a more general principle for drug efficiency and specificity not only for Tyr kinases such as Abl, but also for Ser/Thr kinases, is explored. To this end, the binding kinetics of two distinct kinase drugs, Danusertib and Gleevec, to the Ser/Thr kinase Aurora A and the Tyr kinase Abl were compared. Aurora A kinase is one of the key regulators of mitotic events, including mitotic entry, centrosome maturation and spindle formation (9-11), and neuronal migration (12). Aurora A has attracted significant attention in recent years because it is overexpressed in many tumors ranging from breast and colon, to ovary, skin, and other tissues. For these reasons, Aurora A is a popular target for the development of targeted agents for cancer (1-3; 13; 14). So far, the clinical significance of Aurora A inhibition by drugs has been established, but very little is known about the binding kinetic of drugs to the kinase. High-resolution X-ray structures of Aurora A kinase bound to different inhibitors (15-18) have been solved, but the selectivity profile of the kinase inhibitors remain very difficult to explain.

Danusertib or PHA739358 (Nerviano Medical Sciences, Italy) is a small ATP competitor of all Aurora kinase members ($IC_{50}$=13, 79 and 61 nM for Aurora A, B and C respectively (19; 20). Danusertib was one of the first Aurora kinase inhibitors to enter in phase I and II clinical trials (21; 22). An X-ray structure of Aurora A kinase with Danusertib bound shows the DFG loop in the -out conformation (17) (PDB code 2J50). Interestingly, Danusertib also inhibits several receptor tyrosine kinases such as Abl ($IC_{50}$=25 nM) (23; 24). Notably, in CML, Danusertib binds with high affinity to the Abl kinase domain, including the Gleevec resistant T315I Abl mutant (25). The mutation of Thr315 to Ile is responsible for up to 25% of all clinically observed resistances in CML patients undergoing Gleevec and second-generation tyrosine kinase inhibitors therapies (26) (such as Dasatinib, Nilotinib and Bosutinib). This mutation is called "gatekeeper residue mutation" due to the hypothesis put forward that Gleevec cannot bind due to the steric hindrance imposed by the substitution of threonine by isoleucine (27).

Here it is shown that this proposed mechanism is not correct and that the resistance for Gleevec is rather caused by a severe impairment of the induced fit step. Importantly, Danusertib can efficiently bind to wild-type and T315I Abl kinase because of the preservation of the induced fit step that is of different nature for this drug. Consequently, Danusertib promises to be an attractive candidate for anti-tumor therapy for patients with this mutation (Clinical trial number NCT number=NTC00766324).

Combining X-ray crystallography, NMR spectroscopy and fast kinetics, a novel view of the underlying mechanism for kinase inhibitor affinity and selectivity including insight into drug resistance mechanism is proposed. Differential drug binding is rooted in the dynamic personality of each individual kinase that evolved for its natural substrates.

The results described herein were obtained using the following methods and materials.

Aurora A, Abl and Abl T315I were expressed in *E. Coli*. Protein purifications and subsequent analyses were carried out as described herein.

Cloning and Purification of Aurora A and Abl/Abl T315I

All the proteins were produced and purified as described. All the proteins used have been analyzed by mass spectrometry.

X-Ray Crystallography

Crystals of dephosphorylated A (122-403) in complex with AMPPCP were grown at 18° C. by vapor diffusion and the hanging drop method. A 2:1 ratio of protein mixture: mother liquor was obtained by combining 300 M (10 mg/ml) dephosphorylated A(122-403)+1.5 mM AMPPCP with 0.2 M lithium sulfate monohydrate, 0.1 M bisTris pH5.5, 25% PEG3350. Similarly, crystals of dephosphorylated A(122-403) apo were grown at 18° C. by vapor diffusion and the sitting drop method. A 1:1 ratio of protein mixture:mother liquor was obtained by combining 300 M (10 mg/ml) dephosphorylated A(122-403) with 0.15 M ammonium acetate, 0.1 M TrisHCl pH 7.5, 35% PEG3350 using 20% PEG400, 20% Ethylene glycol, 10% water, 50% mother liquor as a cryo solution. Diffraction data were collected at 100K at Advanced Light Source (Lawrence Berkeley National Laboratory) beamlines (8.2.1 and 8.2.2). Data were processed, scaled, phased, and refined in sequence by using iMOSFLM, Scala, Phase, and REFMAC5 in CCP4. The initial molecular replacement models were used as a search model from Aurora kinase A structure (PDB code 1MQ4).

Figure 20B:
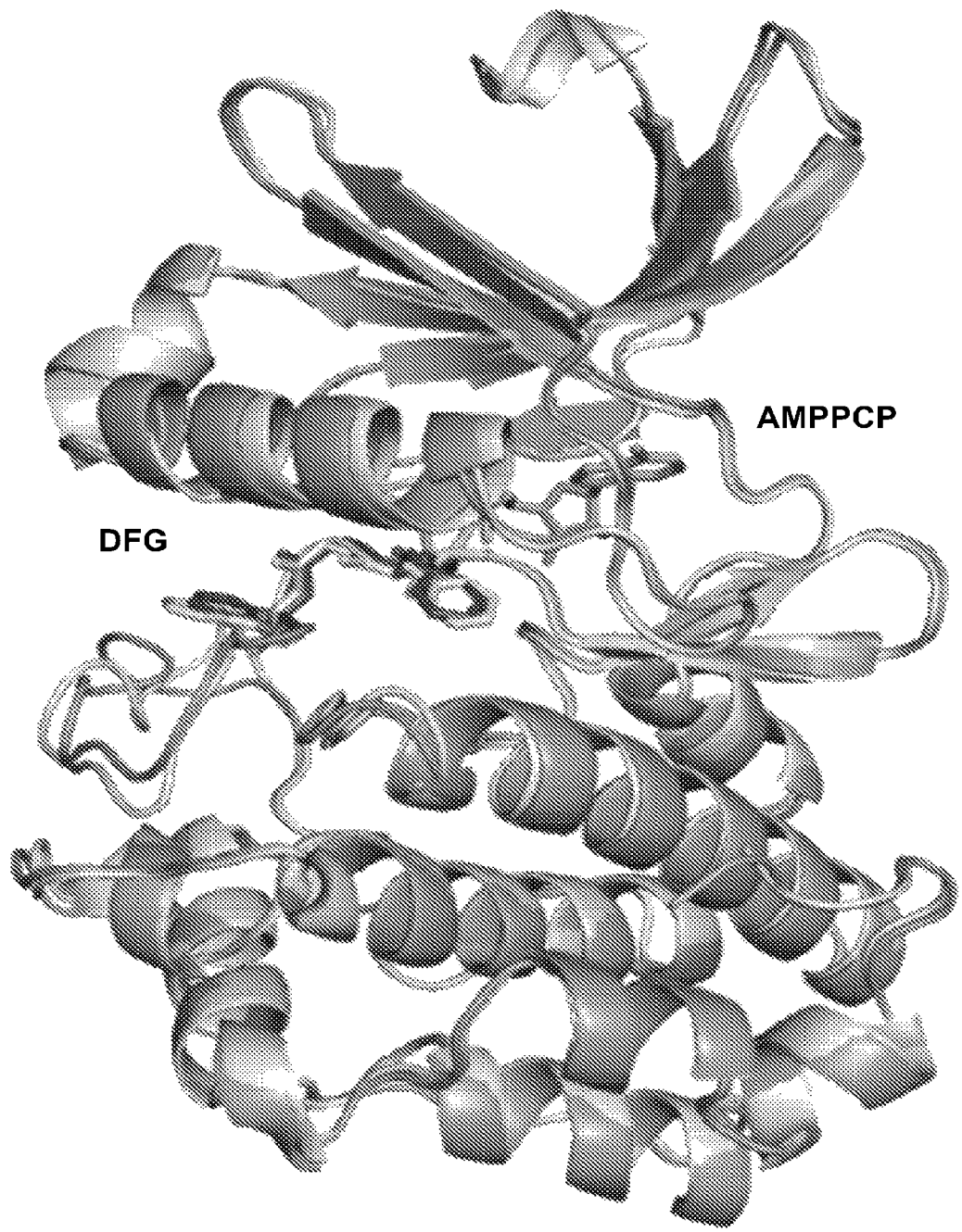
Figure 20C:
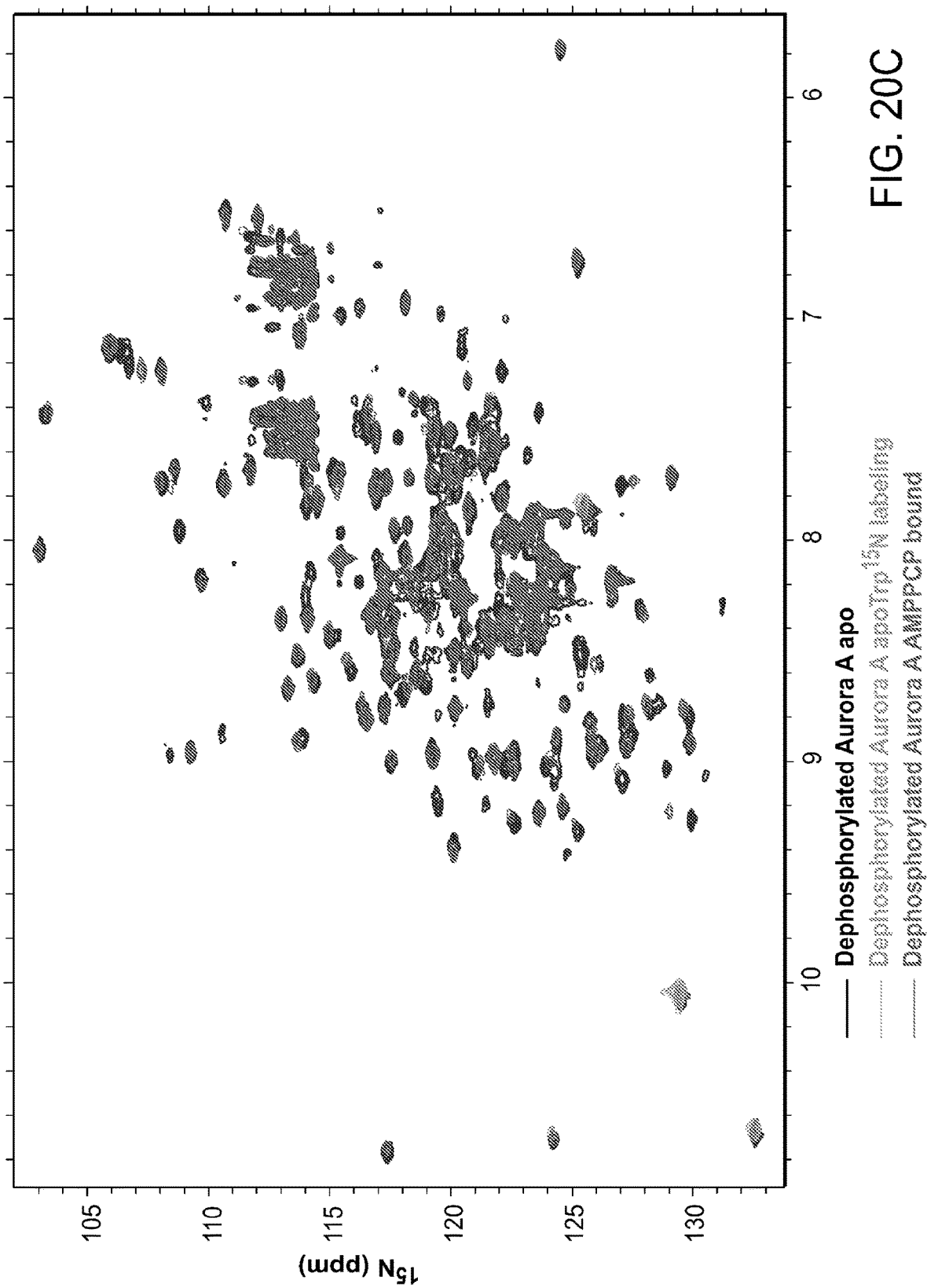

Aurora A bound to AMPPCP have the PDB code 4UTD and the PDB code is 4UTE for the apo form. First refinement was carried out, followed by manual rebuilding in Coot, and iterative further refinements were carried out using PHENIX (FIGS. 20A-20C).

NMR Samples Preparation $^{19}$F and $^{15}$N Labeled.

Wild type and W277L Aurora A labeled selectively on tryptophans were produced using classical M9 minimum media complemented with all the amino acids (0.5 g/L) except tryptophan or with $^{15}$NH$_4$Cl (for uniform $^{15}$N labeling). For tryptophans specific labeling samples, 1 hr prior induction, 30 mg of 5-$^{19}$F-L-tryptophan or $^{15}$N L-tryptophan were added to the media (43). A final buffer exchange step using a buffer that contains 50 mM HEPES (pH=7.3), 50 mM NaCl, 20 mM MgCl$_2$, 5 mM TCEP, 2 M TMAO was done prior to analysis. The samples were concentrated to 200-300 µM using a 10 KDa cut-off membrane.

$^{19}$F NMR Experiments

All NMR experiments were performed on an Agilent/Varian Unity Inova 500 MHz spectrometer, equipped with a 1H/19F switchable probe tuned to fluorine (470.23 MHz). All 1D $^{19}$F spectra were recorded with a sweep width of ~60 ppm, a 0.5 s acquisition time, 10000 transients, a 1.5 s relaxation delay time, and a 12 µs 90° pulse width, giving rise to a total acquisition time of 2.5 h per spectrum. To remove background signal from the probe and avoid baseline distortions, data acquisition was started after an ~100 µs delay (using the "delacq" macro) and appropriate shifting of the data followed by backward linear prediction was performed using NMRPipe. The data were apodized with an exponential filter (2.5 Hz line broadening) and zero-filled before Fourier transform, where applicable data sets were added together to improve the signal-to-noise ratio. $^{19}$F chemical shifts were referenced externally to trifluoroacetic acid (TFA) at −76.55 ppm.

Fluorescence Experiments

All fluorescence measurements were done at 25° C. except the Gleevec kinetics that were measured at 10° C. and 5° C. for Aurora A and Abl/Abl T315I respectively because the binding of the drug ($K_{on}$ observed) is too fast at higher temperature. 100 mM/50 mM stock solutions of Danusertib/Gleevec (purchased from selleckchem.com) dissolved in 100% DMSO were used and stored at −20° C. The stopped-flow instrument is a SX20 series from AppliedPhotophysics. The spectrofluorimeter Fluorimax-4 from Horiba Scientific is temperature controlled and equipped with an autotitrator.

Aurora A Wild-Type and W277L Mutant Binding to Danusertib or Gleevec

Figure 21A:
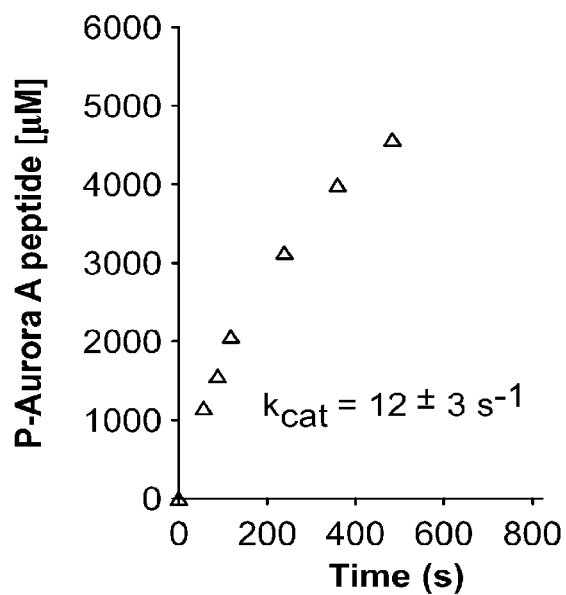
FIGS. 21A-21C are plots showing a kinase assay of phosphorylated Aurora A (122-403) W277L. The rates of Ap phosphorylation of W277L is 12±3 $s^{-1}$. Reactions are carried in the presence of 5 mM ATP and 5 mM Ap in assay buffer (50 mM HEPES (pH=7.3), 50 mM NaCl, 20 mM MgCl$_2$, 5 mM TCEP) at 25° C. Kinetics of Danusertib binding to unphosphorylated W277L mutant Aurora A at 25° C.
Figure 21B:
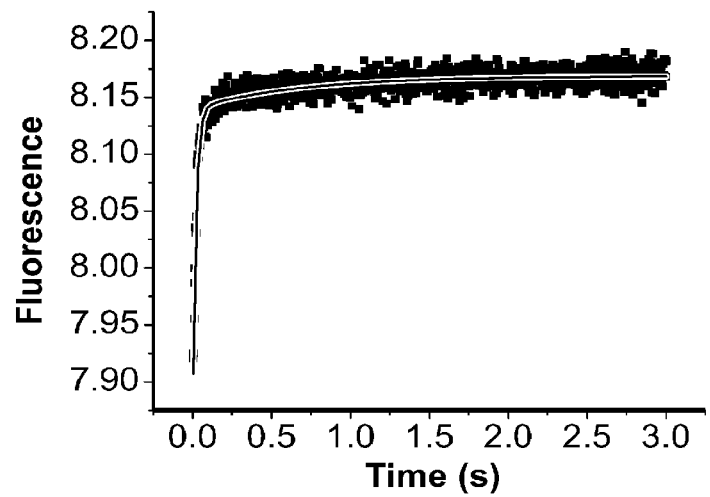
Figure 21C:
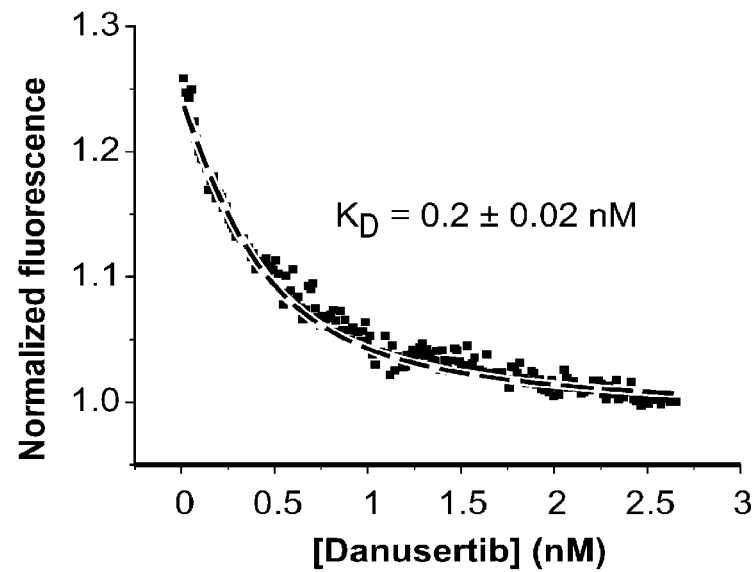

Tryptophan fluorescence spectroscopy is used to monitor drugs binding kinetics to Aurora A using W277 as a fluorescence probe. W277 contribution to the protein fluorescence is shown in FIGS. 21B-21C. In the binding experiment or $K_{on}$, increasing concentration of Danusertib/Gleevec were quickly mixed to 0.5 µM Aurora A (ratio 1:10). A significant increase (for Danusertib) and decrease (for Gleevec) in the fluorescence intensity of Aurora A (excitation at 295 nm, emission cut-off at 320 nm) can be seen due to the drug binding. Based on this signal the characteristic kinetic constant ($k_{obs}$) values were fitted using a mono-, double or a triple exponential equation. In the release of the drug experiment or $k_{off}$ 0.3 µM/0.3 µM Aurora A/Danusertib complex were diluted with buffer (ratio 1:30). A significant decrease in the fluorescence intensity of Aurora A (excitation at 295 nm, emission at 340 nm) can be seen due to the Danusertib release. The fluorescence signal was recorded every min for 1 s during 2 or 6 hrs using the Horiba fluorimeter using photobleaching minimization option. For Aurora A/Gleevec complex, the release of the drug was recorded after a 10 times dilution of the complex using the stopped-flow instrument during 1 s (excitation at 295 nm, emission cut-off at 320 nm). Based on this signal the characteristic kinetic constant ($k_{obs}$) values were fitted using a monoexponential equation. The same procedure was used for Abl and Abl T315I gatekeeper binding to Gleevec or Danusertib.

Dissociation Constant Parameter Calculated from the Kinetics

In the following equations, $K_1$, $K_2$ and $K_3$ equal to:

Conformational selection followed by inhibitor binding     Equation 1

$$K_1 = \frac{k_{-1}}{k_1}$$

$$K_2 = \frac{k_{-2}}{k_2}$$

$$K_3 = \frac{k_{-3}}{k_3}$$

$$E_{in} \underset{k_{-1}}{\overset{k_1}{\rightleftharpoons}} E_{out} + I \underset{k_{off}}{\overset{k_{on}}{\rightleftharpoons}} E_{out} \cdot I$$
$$\phantom{E_{in}\;\;} K_1 \phantom{\;\;\;\;\;\;\;\;\;} K_2$$

$$K_D = (K_1 + 1) * K_2$$

Conformational selection followed by     Equation 2
inhibitor binding by an induced fit step $$E_{in} \underset{k_{-1}}{\overset{k_1}{\rightleftharpoons}} E_{out} + I \underset{k_{off}}{\overset{k_{on}}{\rightleftharpoons}} E_{out} \cdot I \underset{k_{-3}}{\overset{k_3}{\rightleftharpoons}} E_{out} \cdot I$$
$$\phantom{E_{in}\;\;} K_1 \phantom{\;\;\;\;\;\;\;} K_2 \phantom{\;\;\;\;\;\;\;} K_3$$

$$K_D = \frac{(K_1 + 1) * K_2 * K_3}{(1 + K_3)}$$

Conformational selection followed by an induced fit step     Equation 3

$$E_{out} + I \underset{k_{off}}{\overset{k_{on}}{\rightleftharpoons}} E_{out} \cdot I \underset{k_{-3}}{\overset{k_3}{\rightleftharpoons}} E_{out} \cdot I$$
$$\phantom{E_{out}\;\;\;\;} K_2 \phantom{\;\;\;\;\;\;\;} K_3$$

$$K_D = \frac{K_2}{\left(1 + \frac{1}{K_3}\right)}$$

Error bars calculations of the dissociation constant parameter (calculated from the kinetics) are calculated using classical error propagation equations.

Aurora A Wild-Type Binding to MantATP

FRET using intrinsic tryptophan fluorescence is used to monitor MantATP binding kinetics to Aurora A at 10° C. In the binding experiment or $K_{on}$, increasing concentration of MantATP were quickly mixed to 0.5 µM Aurora A (ratio 1:10, excitation at 295 nm, emission cut-off at 395 nm). In the release of MantATP experiment or $k_{off}$, 10 µM/10 µM Aurora A/MantATP complex were diluted with buffer (ratio 1:10). A significant decrease in the fluorescence intensity of Aurora A (excitation at 295 nm, emission cut-off at 395 nm) can be seen due to the MantATP release.

Macroscopic Dissociation Constant Experiments

Fluorescence titration experiments were measured using Horiba fluorimeter. Increasing quantities of kinase-drug complex (0.2-0.5 nM kinase and 20 nM drug) or kinase-MantATP (1 µM kinase and 2 mM MantATP) were injected into the kinase solution (1 µM kinase). The excitation wavelength used is 295 nm (bandwidth=5 nm) and the emission is 340 nm (bandwidth=20 nm). In all experiments, 5 mM equilibration time was used between two injections. The dissociation constant ($K_D$) derived from the fit of the equation:

$$F = F_0 + A \cdot \frac{[I] + [Et] + Kd - \sqrt{([I] + [Et] + Kd)^2 - 4 \cdot [Et] \cdot [I])}}{2 \cdot [Et]}$$

F and $F_0$ are the fluorescence and the initial fluorescence respectively. [I] and [Et] are the total concentration of the drug or MantATP and the kinase respectively.

The results of the experiments herein are now described.

Dephosphorylated Aurora A Samples Both an Inactive and Active Structure

A large wealth of X-ray structures and functional assays led to the general notion that unphosphorylated Aurora A and, more universal, Ser/Thr kinases are in an inactive structure and that phosphorylation or activator binding induces the active structure. A comparison of many X-ray structures of "inactive" and "active" forms of Ser/Thr kinases resulted in an elegant universal proposal of the structural hallmarks for the active state by Taylor and collaborators (28): the completion of both the regulatory and catalytic spines spanning the N- and C-terminal domains in the active state.

Figure 15A:
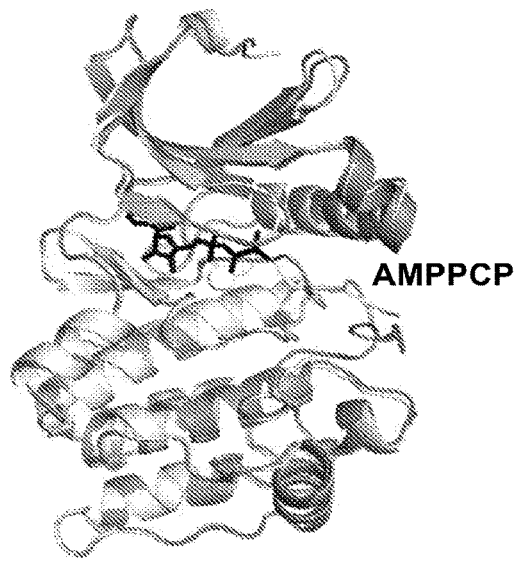
FIGS. 15A-15I are plots and diagrams showing that unphosphorylated Aurora A adopts an active conformation.
Figure 15B:
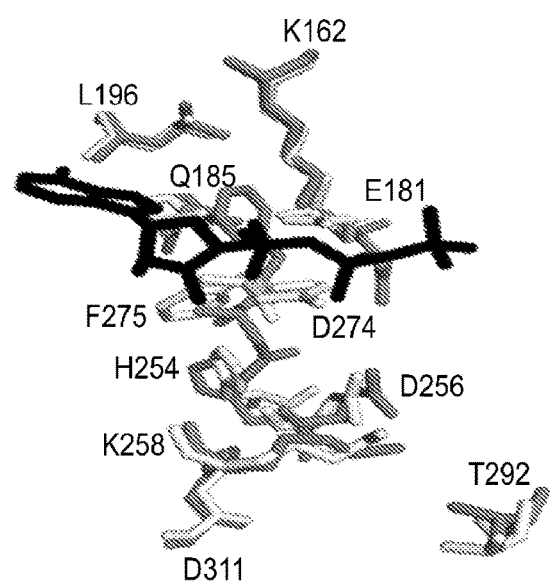
Figure 15C:
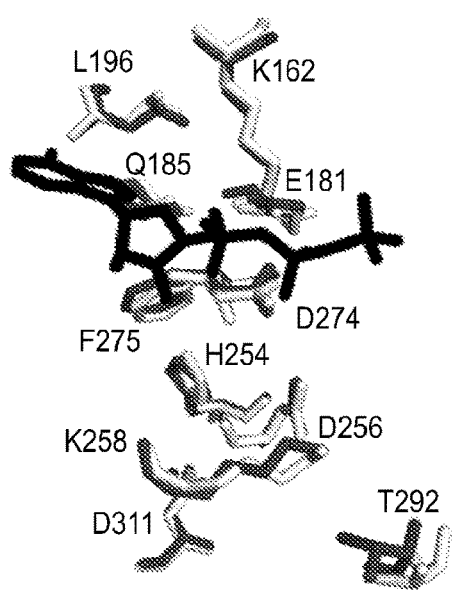
Figure 15D:
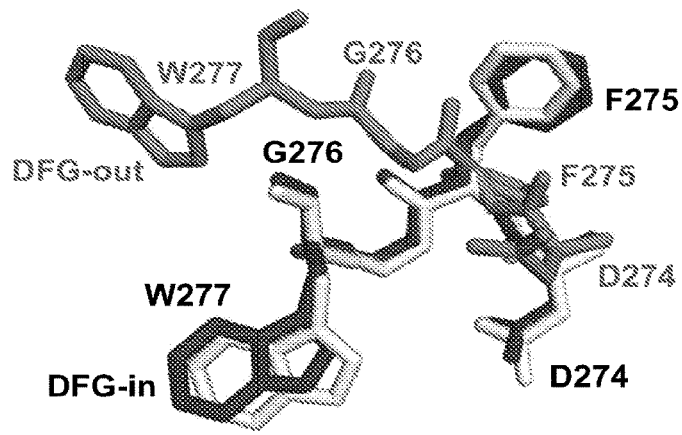
Figure 15E:
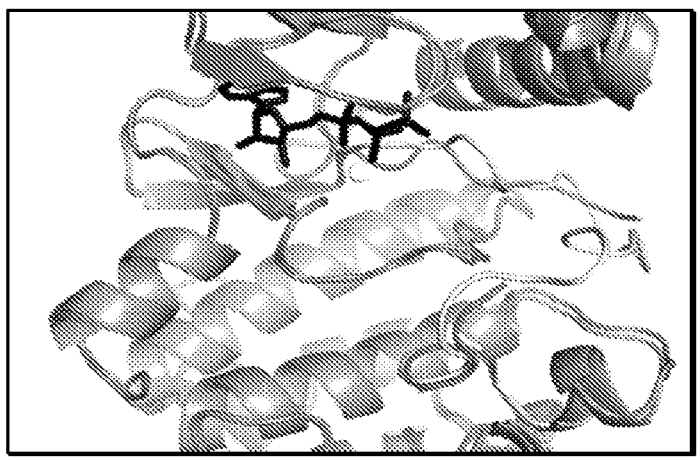
Figure 15F:
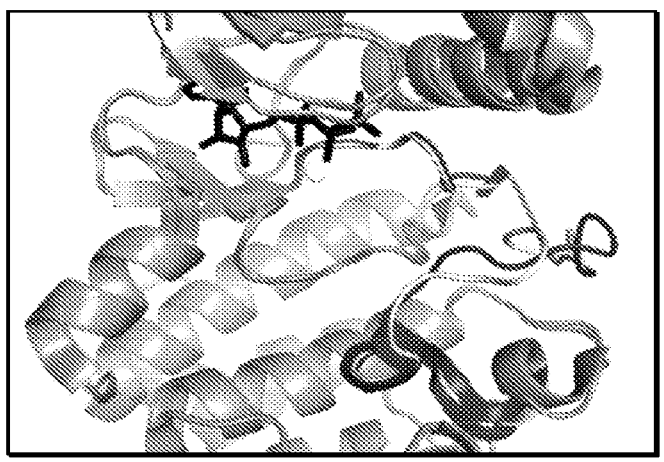

It was surprisingly found that two crystals from the same crystallization well captured the active and inactive conformation of unphosphorylated Aurora A (FIG. 15A; FIG. 15B; FIG. 15E; FIG. 20A). The inactive structure (PDB code: 4C3R) perfectly superimposes with the well-known inactive unphosphorylated Aurora A structures (PDB code: 1MUO) (29) and the activation loop is not visible as commonly observed for kinases lacking phosphorylation of the activation loop. The active structure superimposes extremely well with the previously published phosphorylated active structure (PDB code: 1OL7) (30) (FIG. 15C; FIG. 15F) and the activation loop is visible without Thr288 being phosphorylated although the B-factors are high. Every hallmark of the active state including the DFG flip into the DFG-in position essential for completing the regulatory spine is seen for the unphosphorylated protein. In contrast, the DFG loop is in the -out position for the inactive form (FIG. 15D). As a side note, in the active structure, electron density is seen for a $Mg^{2+}$ ion in the tighter $Mg^{2+}$-binding site coordinated to the -and -phosphates of AMPPCP and to D274. In the inactive structure, no electron density for $Mg^{2+}$ can be identified possibly due to the fact that D274 is rotated out (DFG-out) and therefore lost as coordination partner to the $Mg^{2+}$.

It is pointed out that in Aurora kinases a Trp, Trp277, is immediately following the DFG motif and displays drastically different orientation whether Aurora A is in an active (DFG-in) or inactive (DFG-out) conformation (FIG. 15D). This Trp is unique for the Aurora family in the Ser/Thr kinome and the nature of this residue has been suggested for tuning the substrate specificity (31). Importantly, this Trp was used as probe to monitor the DFG flip and drug binding in real time described below.

The fact that the inactive and active state is seen in the crystal implies that both are sampled, however, it does not deliver information about the relative populations or interconversion rates. Therefore, an experimental approach was next set out to attempt to monitor the conformational exchange of the DFG in/out flip in solution. Owing to the importance of the DFG flip for activity, regulation and drug design, there have been extensive efforts to characterize this conformational equilibrium in solution. NMR is a possible method for such characterization, however efforts on several Ser/Thr and Tyr kinases led to the general conclusion that the activation loop including the DFG motif and most of the active site cannot be detected due to exchange broadening, and they can only been seen after binding of drugs that stabilize conformations.

Figure 15G:
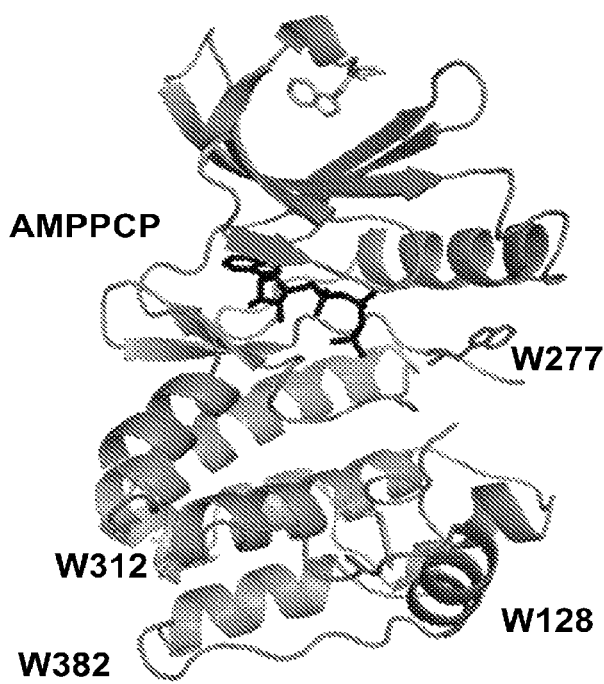
Figure 15I:
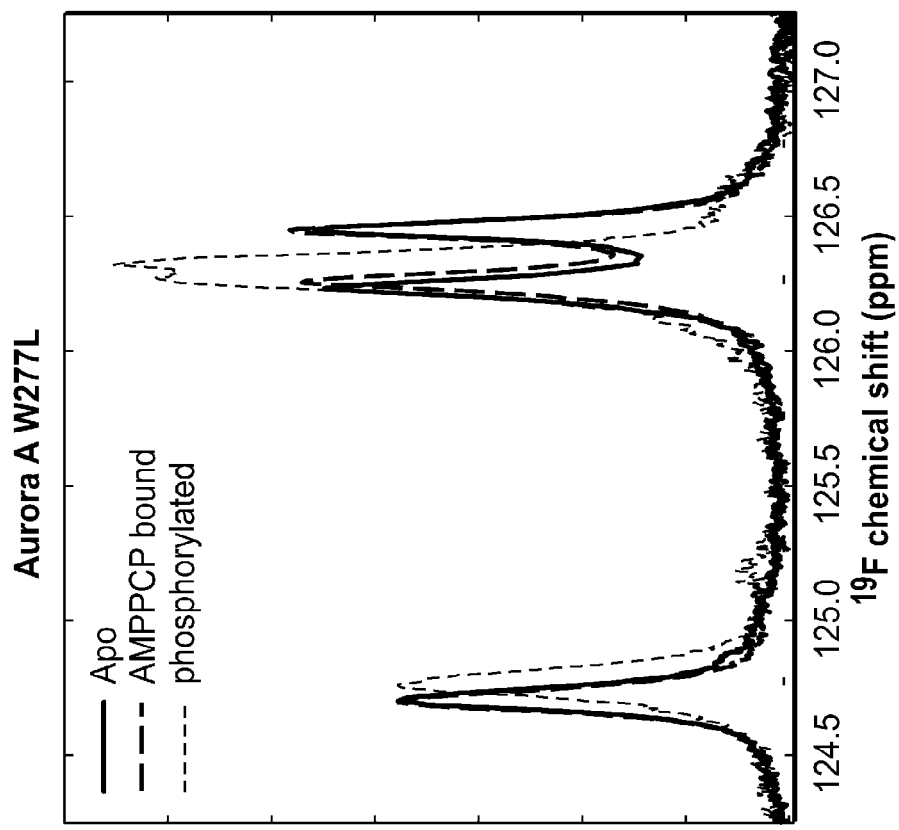
Figure 15H:
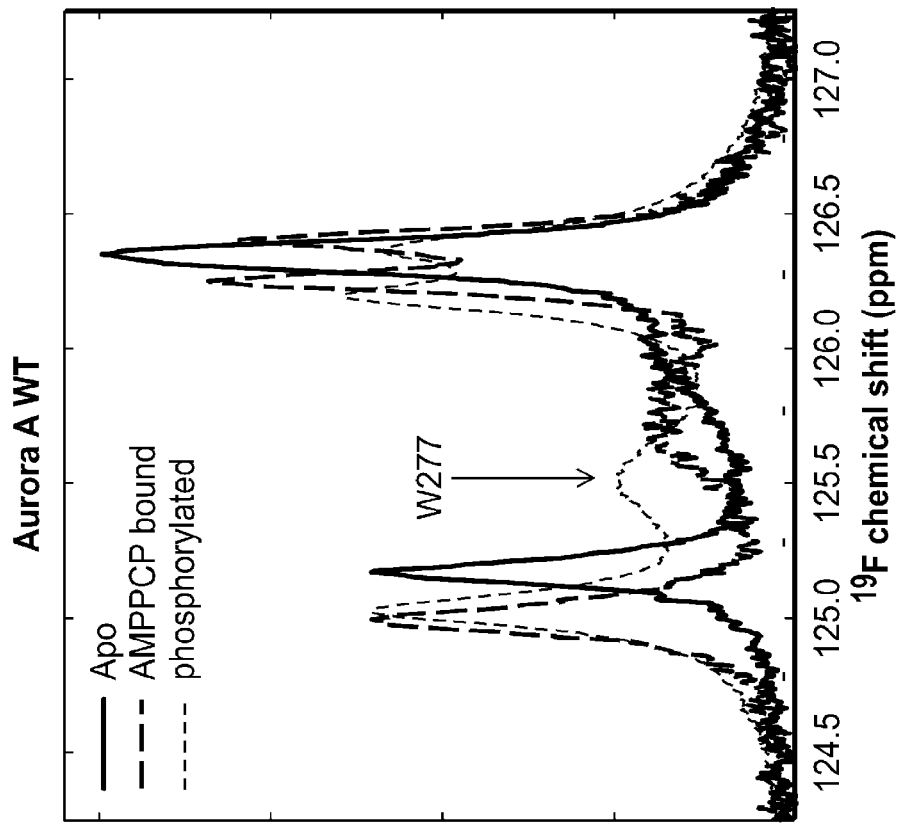

$^1H$-$^{15}N$ HSQC Experiments on Fully Labeled Samples and Tryptophans $^{15}N$ specific labeling of Aurora A proved to be no exception as many peaks are missing (FIG. 20C). Therefore, a strategy to overcome this general problem of exchange broadening, that hampers the detection of the DFG equilibrium, was sought. Aurora A was produced containing four $F^{19}$-labeled tryptophans (FIGS. 15G-15I) for one-dimensional spectra to deal with the exchange broadening while providing sensitivity close to proton NMR (32). For apo and AMPPCP-bound Aurora A, indeed four peaks were observed. One peak is very broad and is therefore a prime candidate for Trp277 adjacent to the DFG loop (FIG. 15H). A W277L mutation confirmed this assignment (FIG. 15I). This mutant is still active (FIGS. 21A-21C), most likely because this Trp is not conserved in Ser/Thr kinases with a Leu at the position for several family members. Mutating each of the other three Trp that are much more conserved resulted in insoluble proteins. From the broad lineshape for the Trp277 peak it was estimated that the DFG loop interconverted on an intermediate timescale. Determination of the relative populations of the two states and exact rate constants of interconversion was not possible with these physical constraints of the system, however this missing piece was obtained by stopped-flow kinetics of drug binding as described in the next paragraph.

Figure 16A:
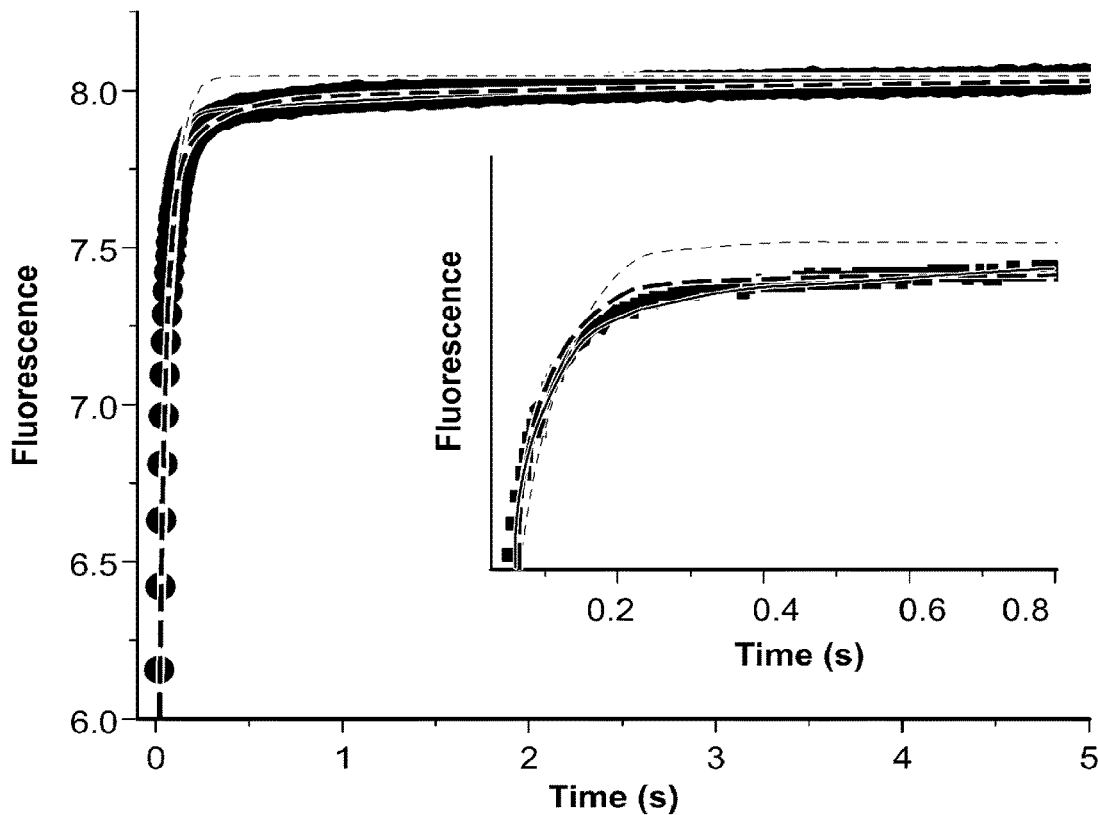
Figure 16B:
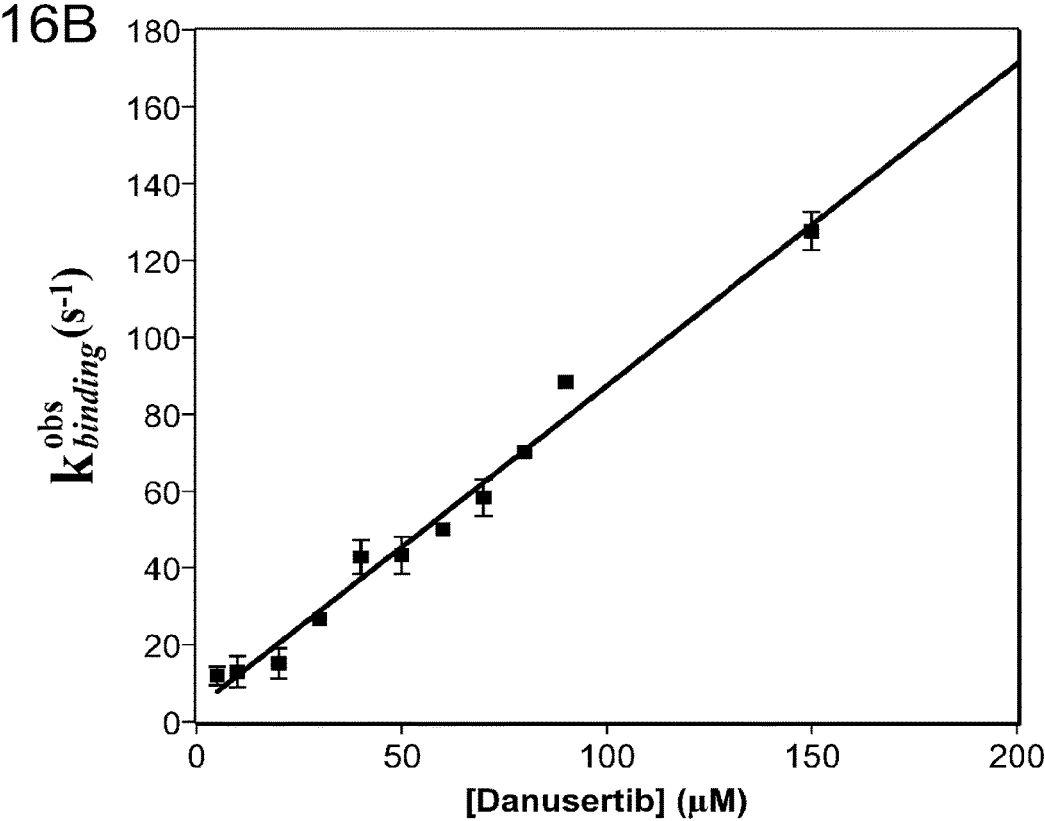
Figure 16C:
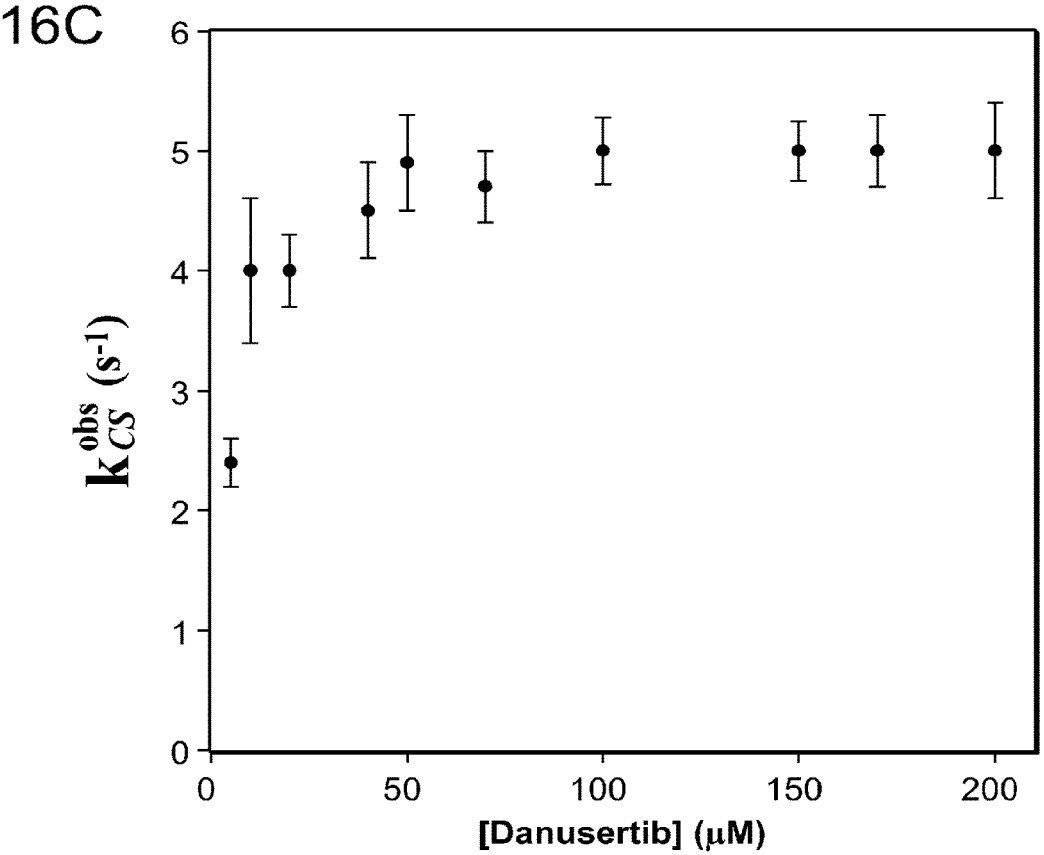
Figure 16D:
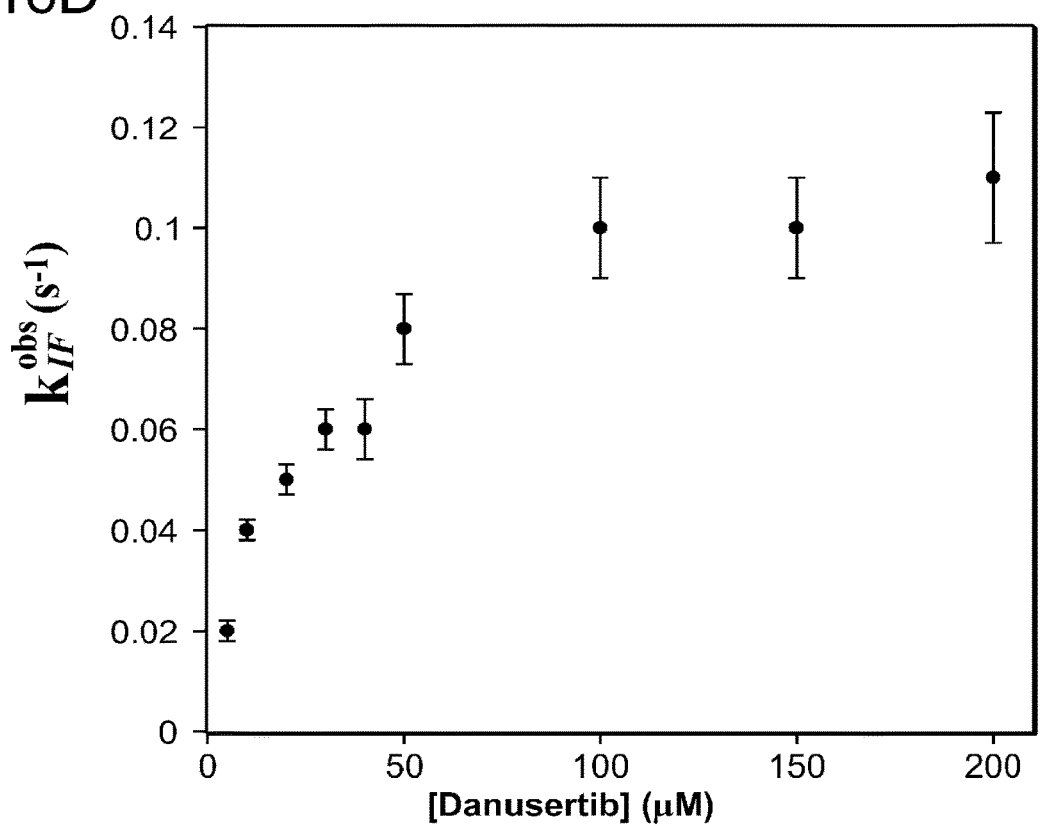

Kinetics of Danusertib Binding to Aurora A: Three-Step Kinetics That Couples a Conformational Selection and an Induced Fit Mechanism Through groundbreaking experiments on the Tyr kinases Abl and Src, the concept of drug selectivity based on the DFG conformation has received considerable attention in kinase drug discovery (27; 33). A recent report provides kinetic evidence for such conformational selection, but identifies an induced fit step after drug binding as the overwhelming contribution for Gleevec selectivity towards Abl compared to Src. The question of whether this mechanism of Gleevec binding to Abl might exemplify a more general mechanism for kinase inhibitors was explored. First, the kinetics of Danusertib binding to Aurora A directly by a series of rapid mixing experiments using intrinsic tryptophan fluorescence was measured. For inhibitor binding to Aurora A, fluorescence kinetics at all Danusertib concentrations were triple exponential at 25° C. (FIG. 16A). The dependence of the three observed rates constants on drug concentration is linear for one of these rates (FIG. 16B) and non linear for the other two with apparent plateaus reached at approximately 0.13 $s^{-1}$ and 6 $s^{-1}$ (FIG. 16C-16D).

Figure 22:
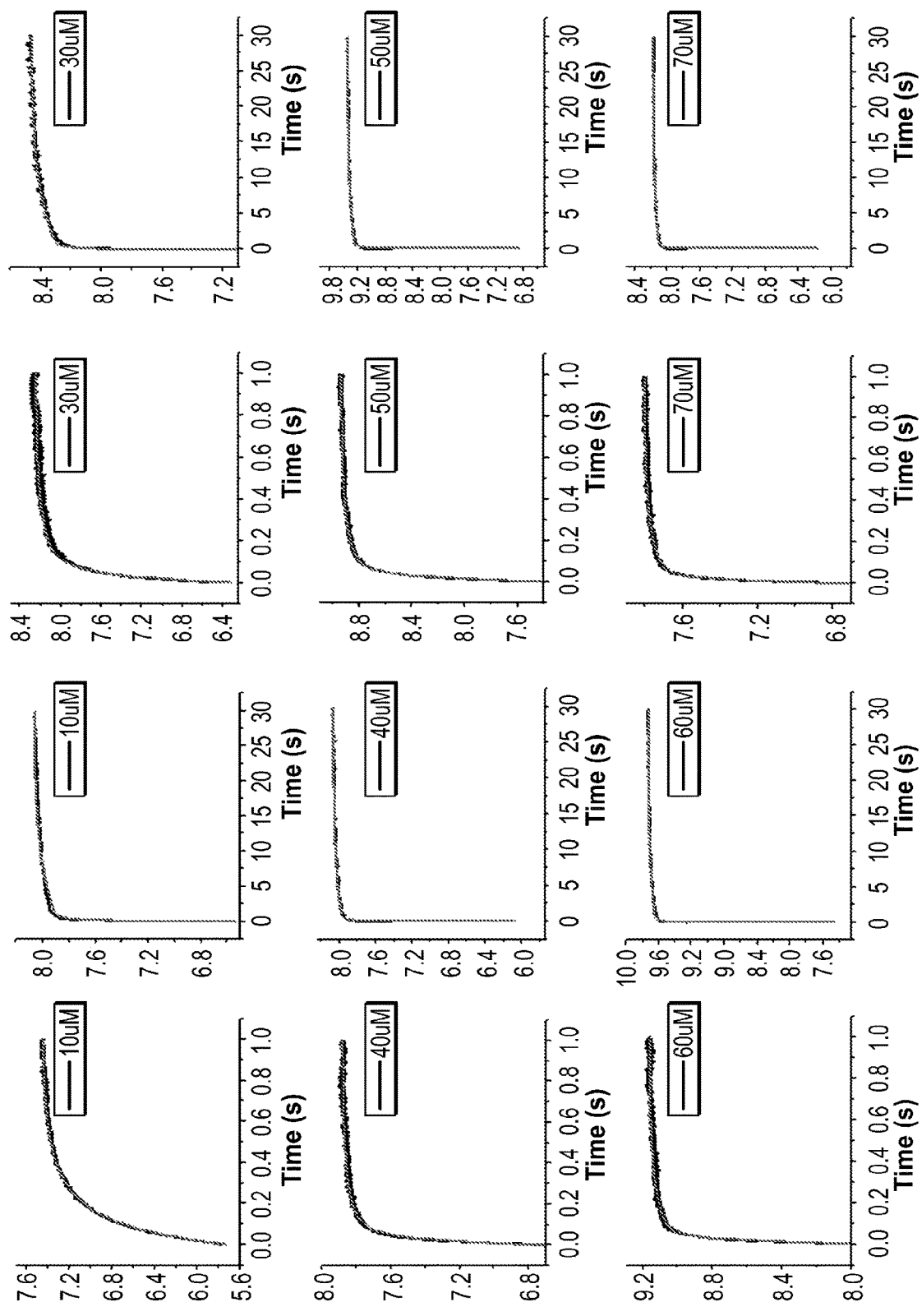
FIG. 22 shows kinetics of Danusertib binding to unphosphorylated Aurora A at 25° C. Datasets at 10, 30, 40, 50, 60, 70, 80, 80, 90, 100, 150 and 200 µM of Danusertib at two timescales 1 s and 30 s. At 100, 150 and 200 µM, the binding rate constant is too fast to be measured. $K_{off}$ is the release of the drug experiment. Global simulations were done using Kintek software using the scheme in FIG. 16G (chi2/DOF=1.8).
Figure 22:
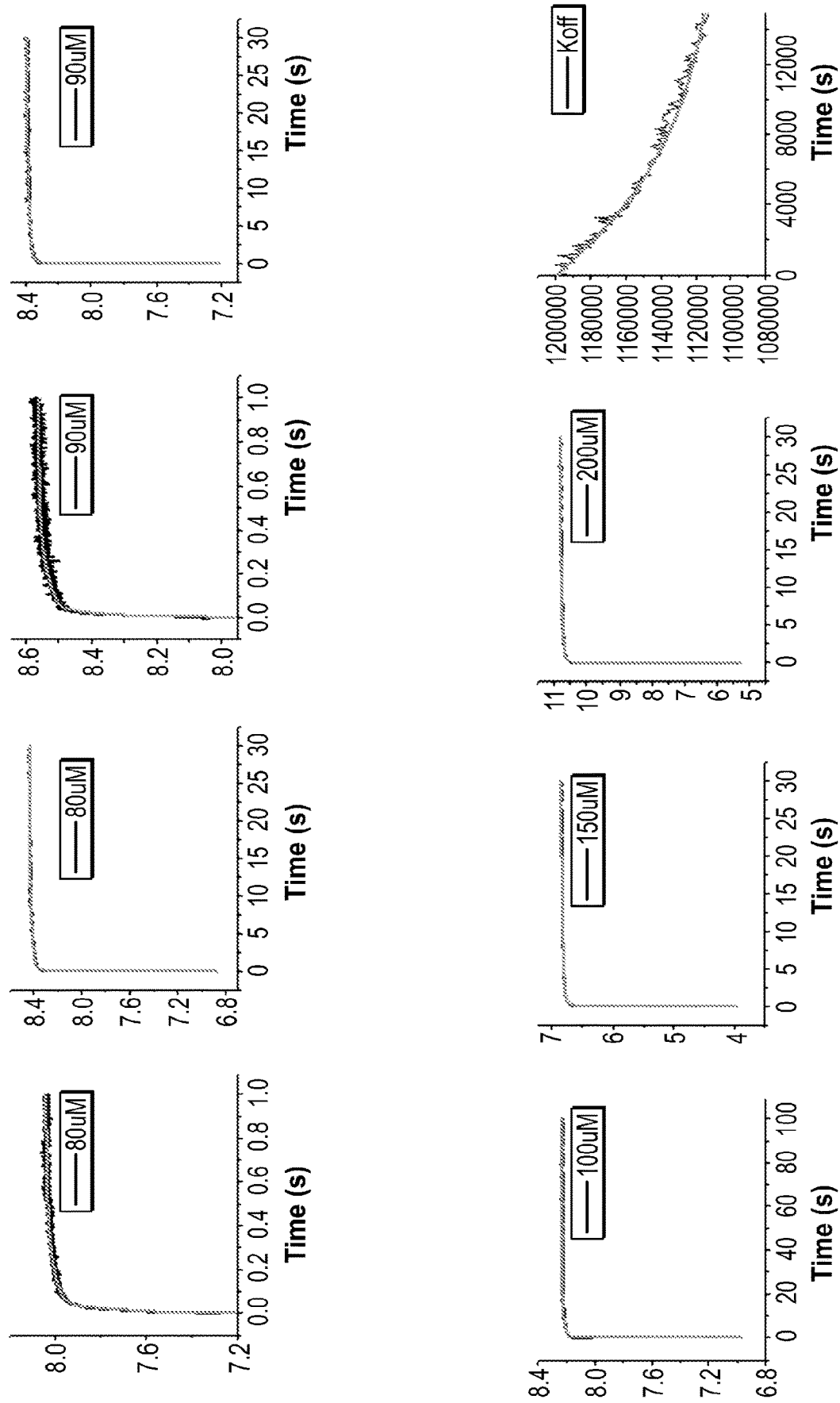
Figure 23B:
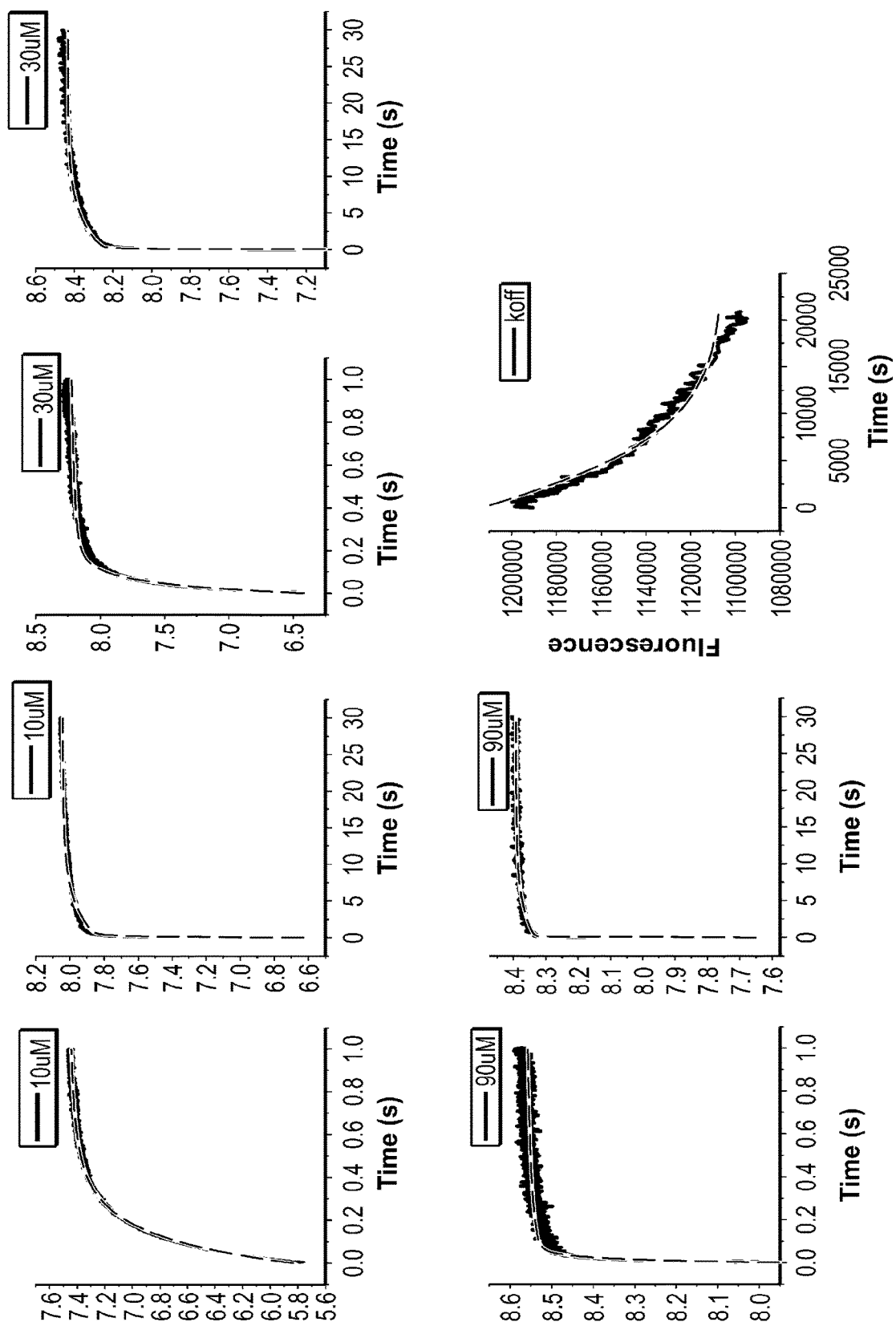
Figure 24A:
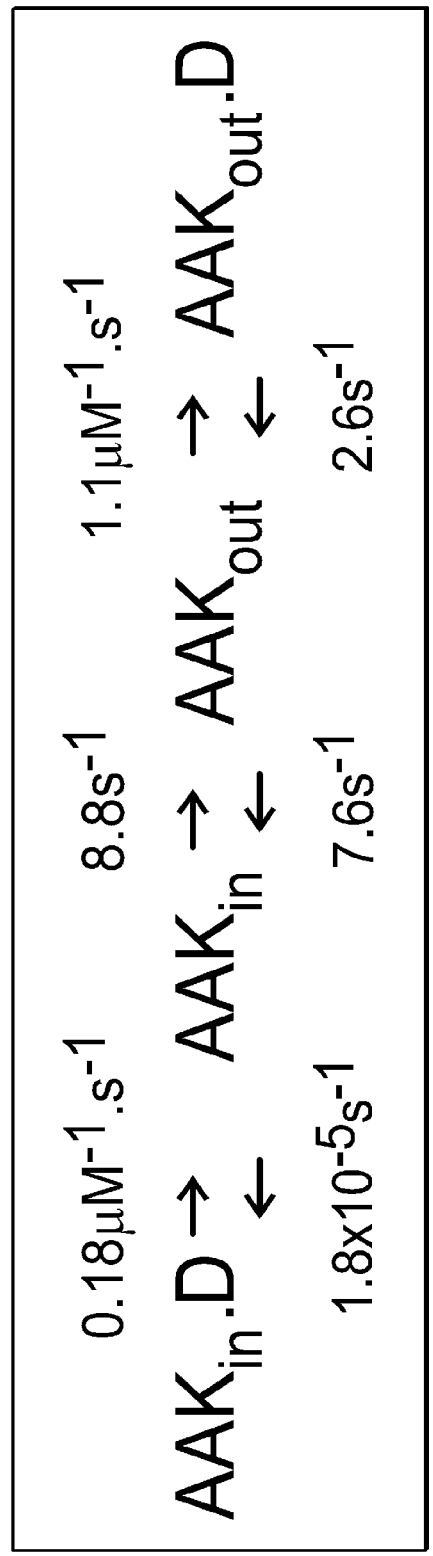
FIGS. 24A-24D are plots and schematics showing kinetics of Danusertib binding to unphosphorylated Aurora A at 25° C.
Figure 24B:
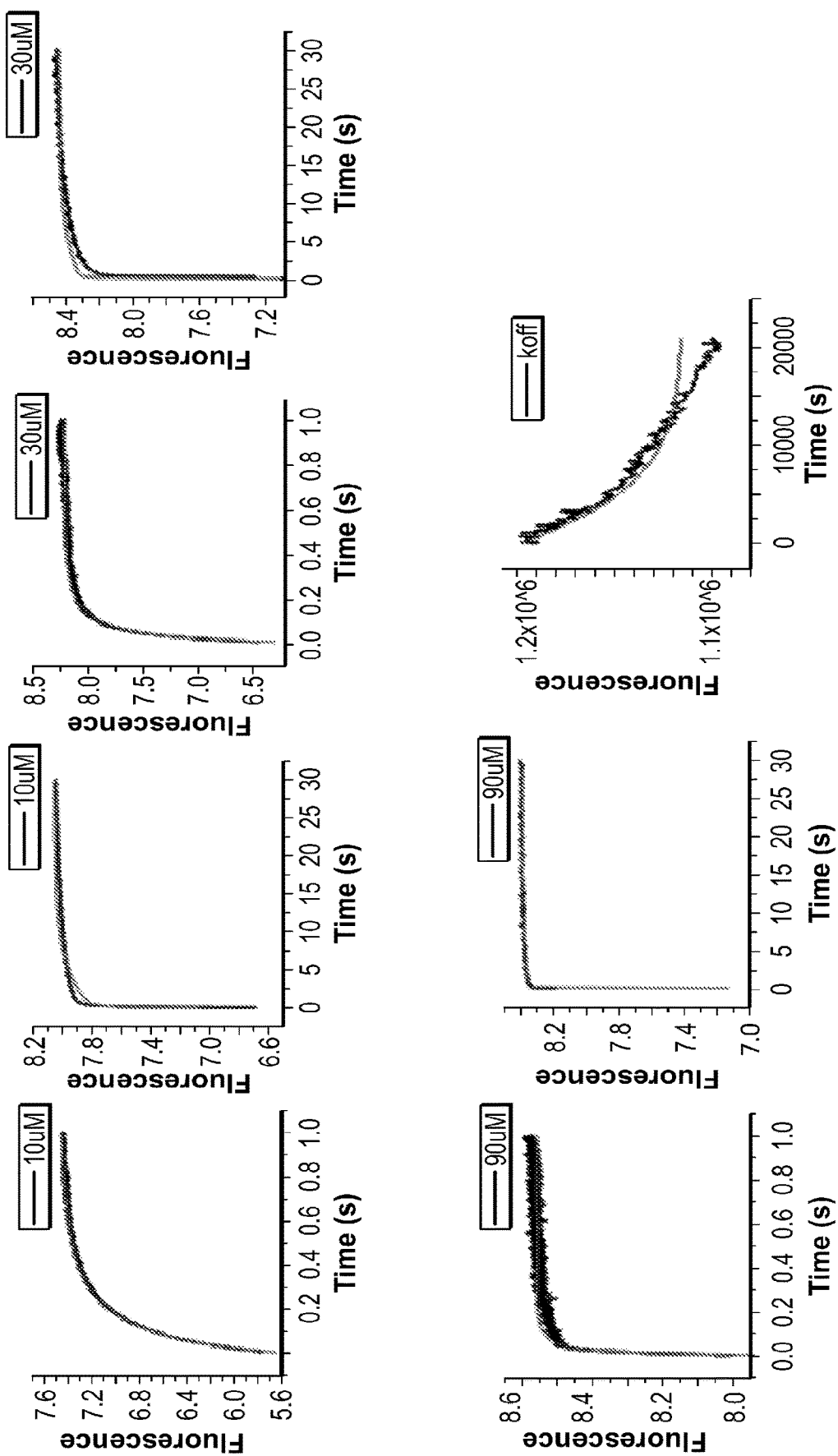
Figure 24C:
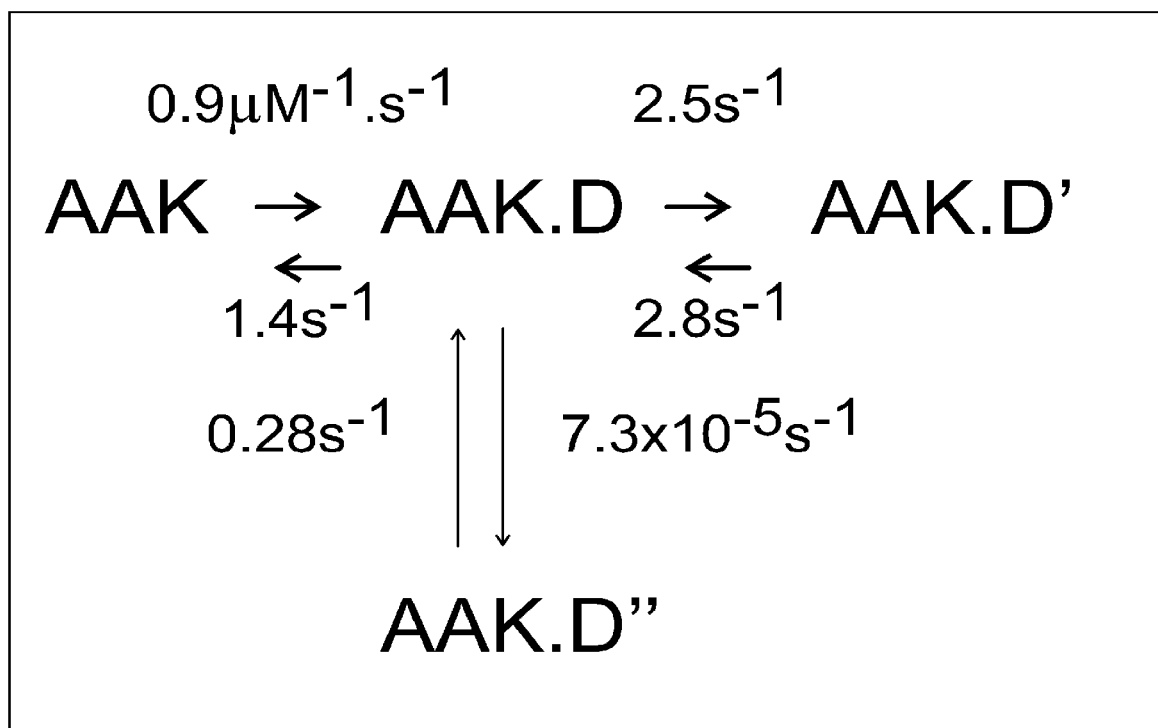
Figure 24D:
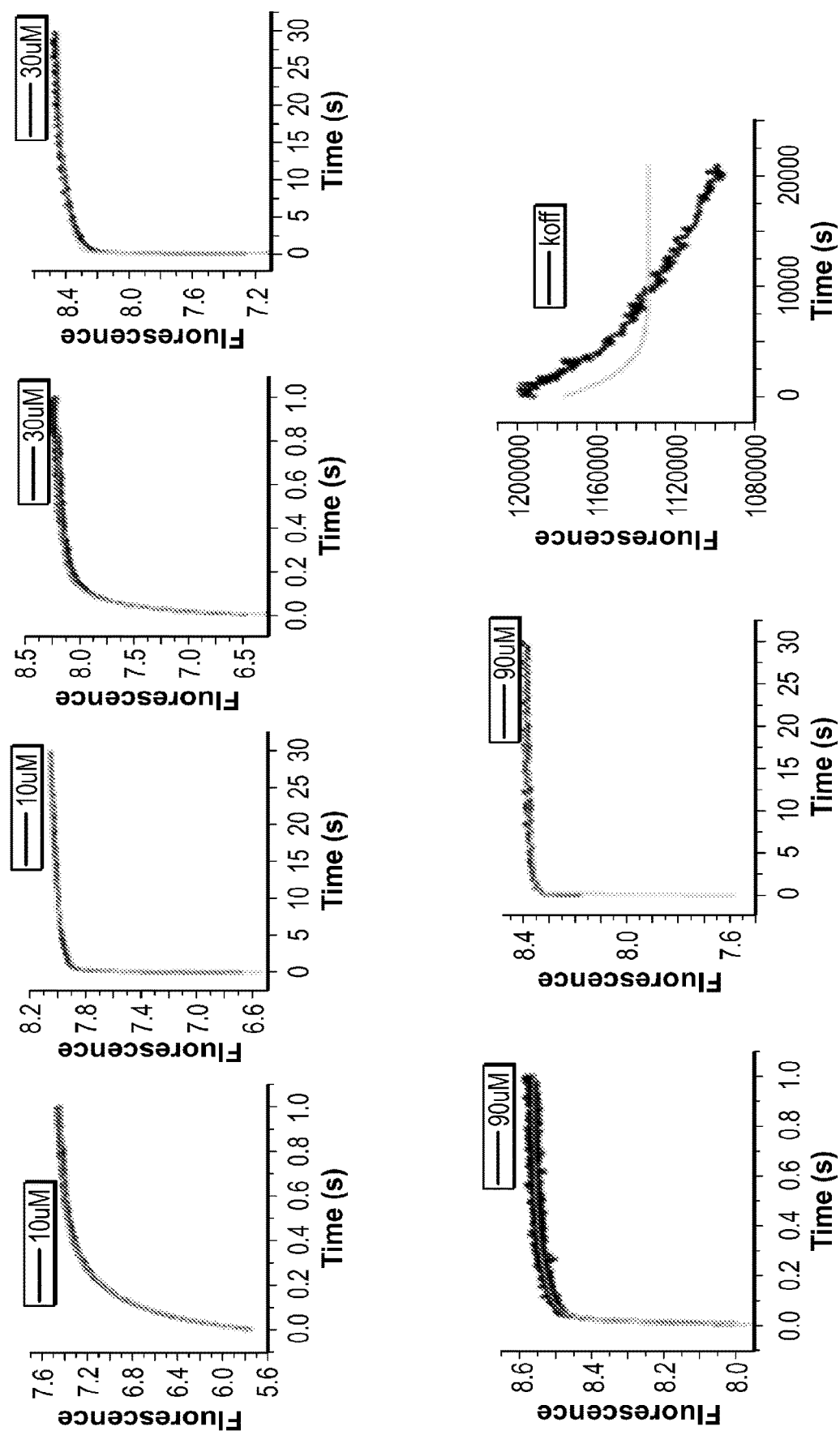

A three-step mechanism was deciphered as follows. The kinetic step with linear inhibitor concentration dependence is typical of the second-order binding step while non-linear concentration dependence rate hints at protein conformational transitions. As an important additional experiment, the dissociation kinetics for Danusertib was measured and is slow, taking hours to be released (FIG. 16E). Rationalization of such complex binding kinetics cannot be done by visual inspection and kinetic intuition any more, which can, in fact, be misleading. In order to elucidate the correct binding mechanism, all kinetic traces were globally fit assuming all possible three-step binding schemes (FIG. 22; FIGS. 23A-23B; FIGS. 24A-24D). The result was unambiguous with a conformational interconversion in the free protein as the faster of the two conformational transitions and a far-shifted induced fit step after Danusertib binding as the slower step (FIG. 16G). All "true" microscopic rate constants were obtained from the global fit (FIG. 22 and FIGS. 23A-23B) demonstrating sampling of two conformations in the free protein with an equilibrium constant of 0.23, a fast binding step that accounts for an affinity of 0.83 µM for this step, and a very far-shifted induced fit step with a $K_{eq}$ of $5 \times 10^{-4}$.

A powerful independent validation of the selected binding scheme can be obtained by comparing the macroscopically measured overall $K_D$ of for Danusertib with the calculated macroscopic $K_D$ from the kinetic scheme (FIG. 16F-16G and FIGS. 28A-28B) according to Equation 2 (described in the materials and methods of Example 2), which indeed delivered values that were within experimental error.

Figure 25B:
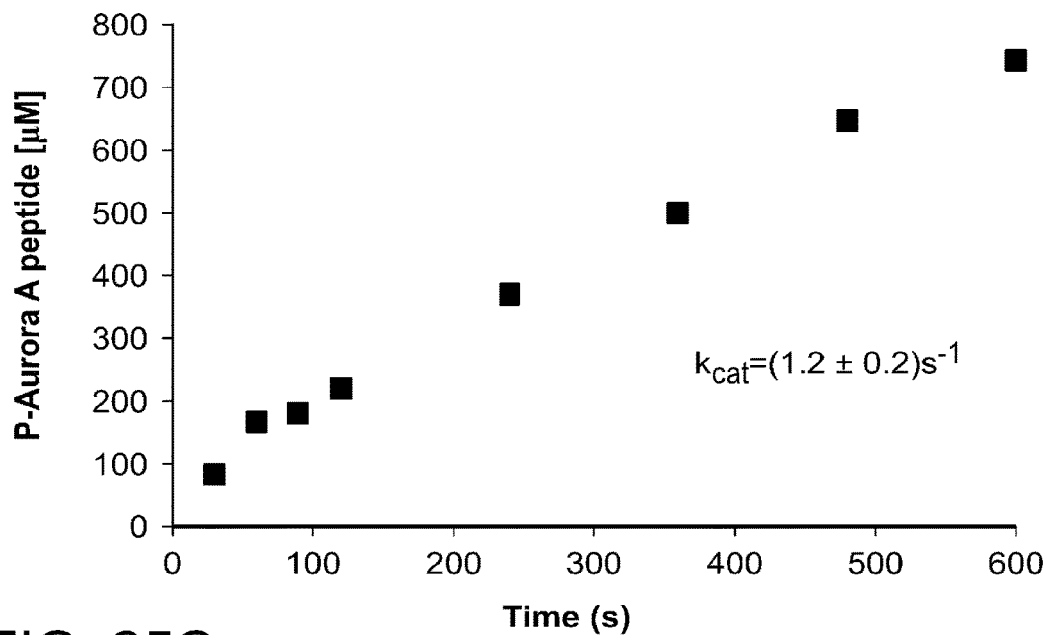
Figure 25C:
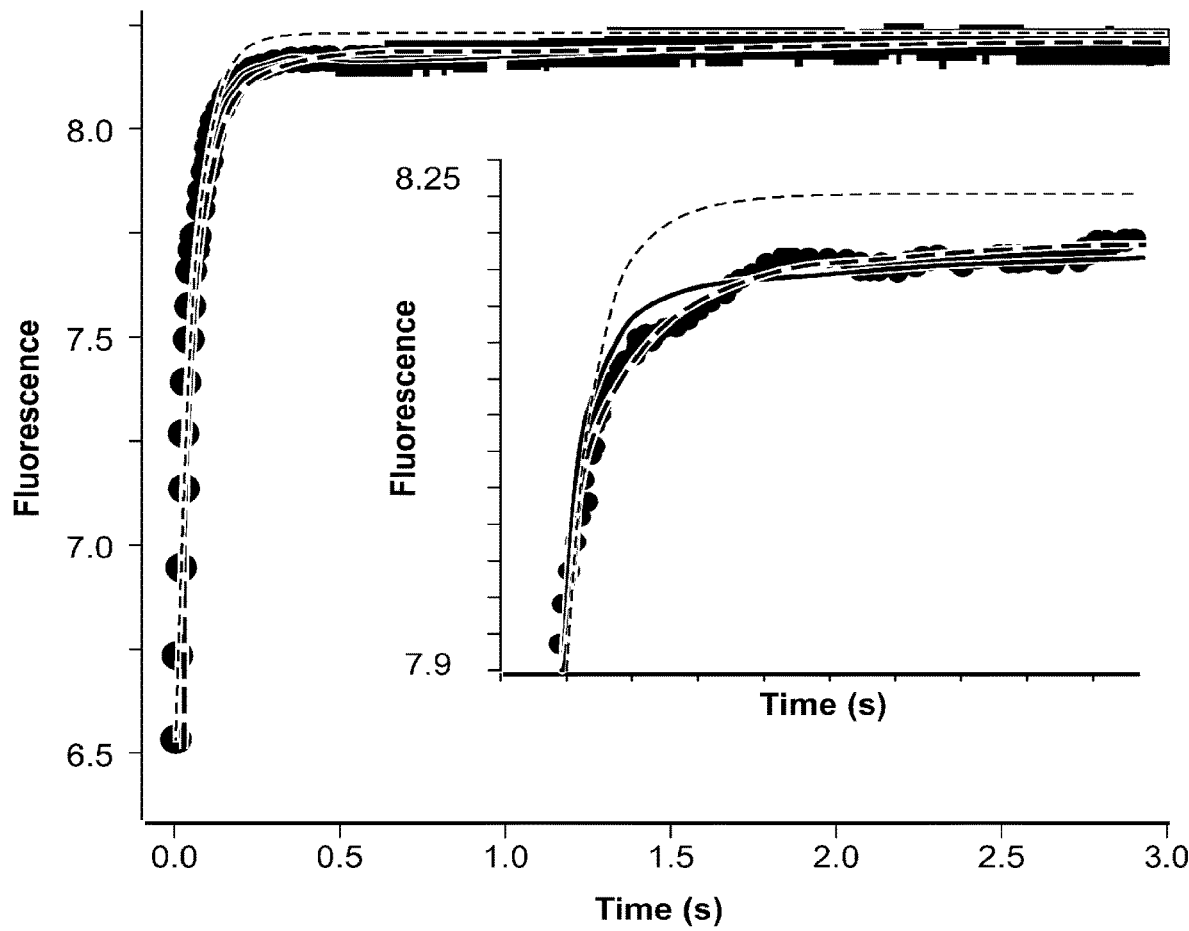

It was hypothesize that the first step in our scheme reflects the interconversion between the inactive and active structures that are correlated with the DFG-in and -out position (FIG. 15A-15I; FIGS. 25A-25C) because (i) the two X-ray structures sampled for the apo-protein show Trp277 in very different environments (FIG. 20A-20B), (ii) Danusertib has been proposed to selectively bind to the DFG-out conformation based on a co-crystal structure, (iii) the dissociation constant of Danusertib for the phosphorylated form of Aurora A (in DFG-in active state) was $10^4$ weaker than for the unphosphorylated form (FIG. 25A) and (iiii) the amount of exchange broadening for W277 in the NMR experiment was in agreement with the kinetics of interconversion in the free enzyme measured by fluorescence (FIG. 15H).

The results herein illuminate trivial but profound principles of binding affinities and lifetimes of drug/target complexes: any conformational selection step weakens the overall inhibitor affinity, while an induced fit tightens the affinity in relation to the amount of equilibrium shift in the enzyme/drug complex (Equations 1, 2 and 3). For Danusertib, the DFG-in/-out equilibrium weakens the overall affinity by only 20%, however, the conformational change after drug binding results in a three orders of magnitude tighter binding.

Gleevec Binding to Aurora A Demonstrates Role of the Induced Fit Step

Figure 16H:
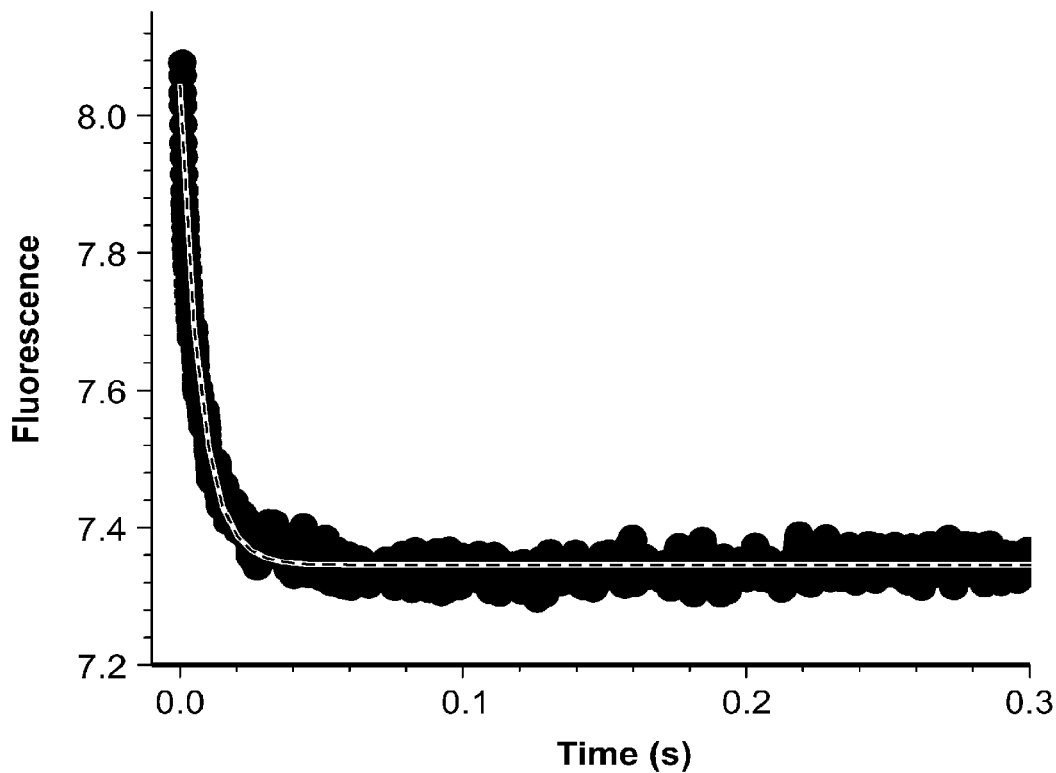
Figure 16I:
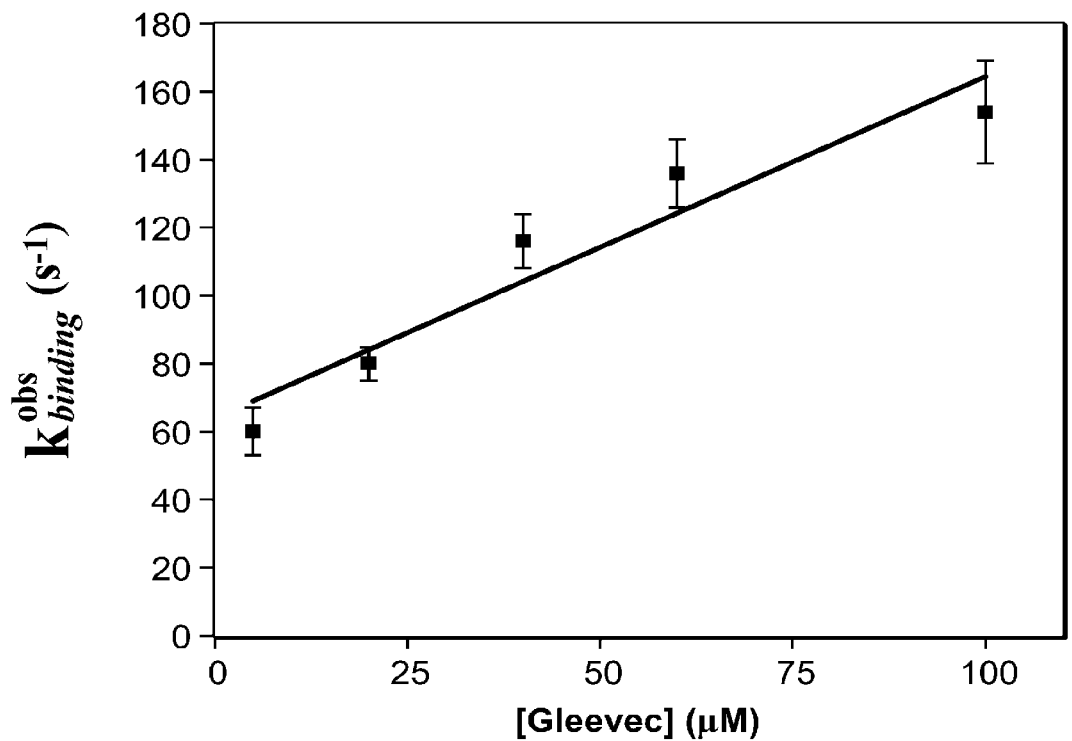
Figure 26A:
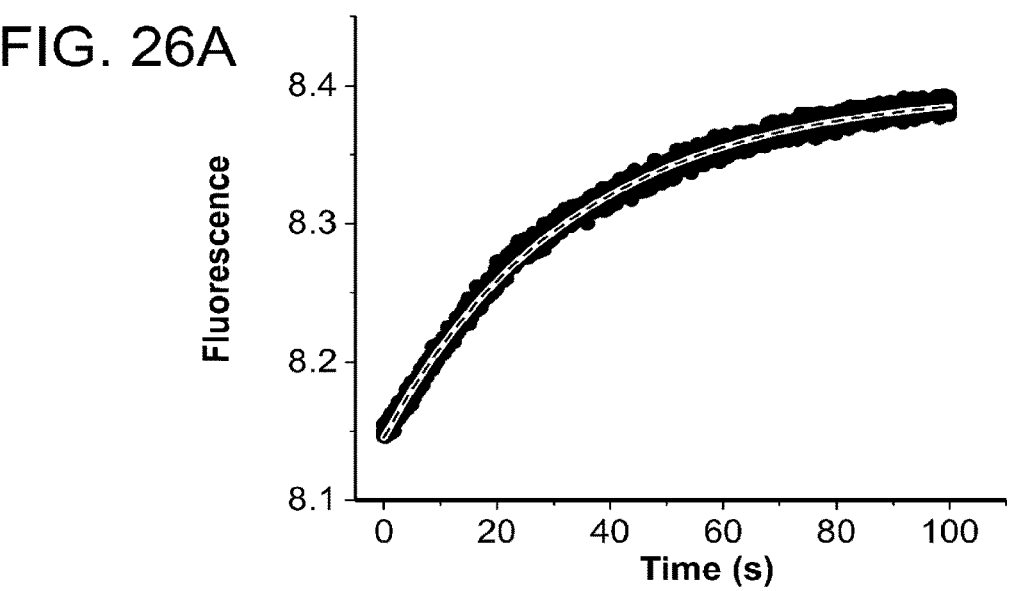
Figure 26B:
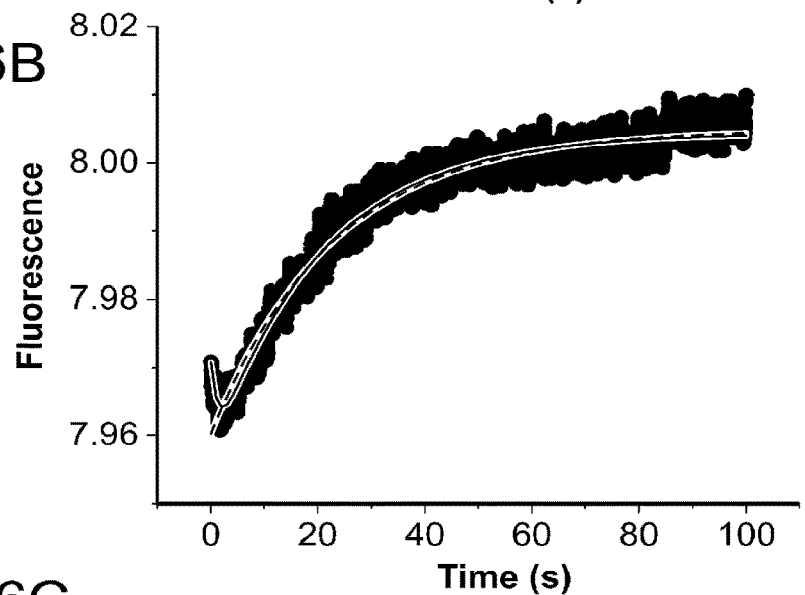
Figure 26C:
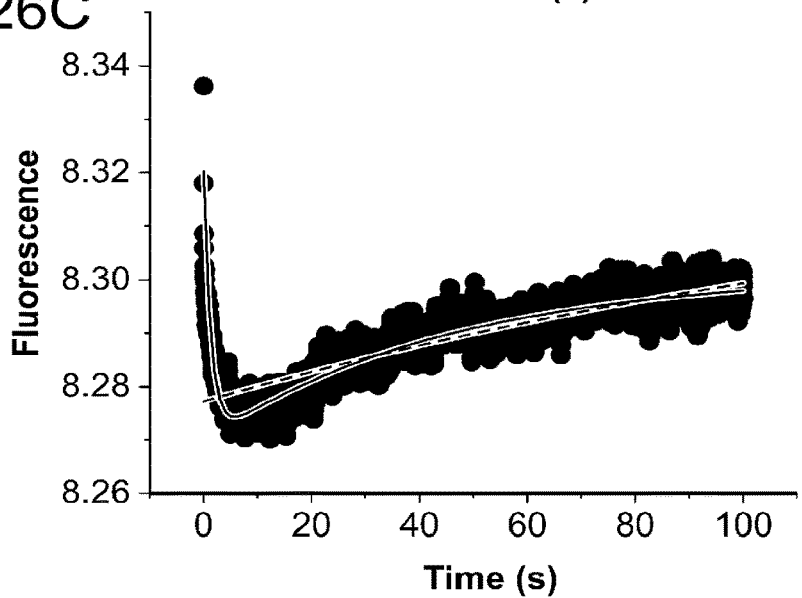
Figure 29C:
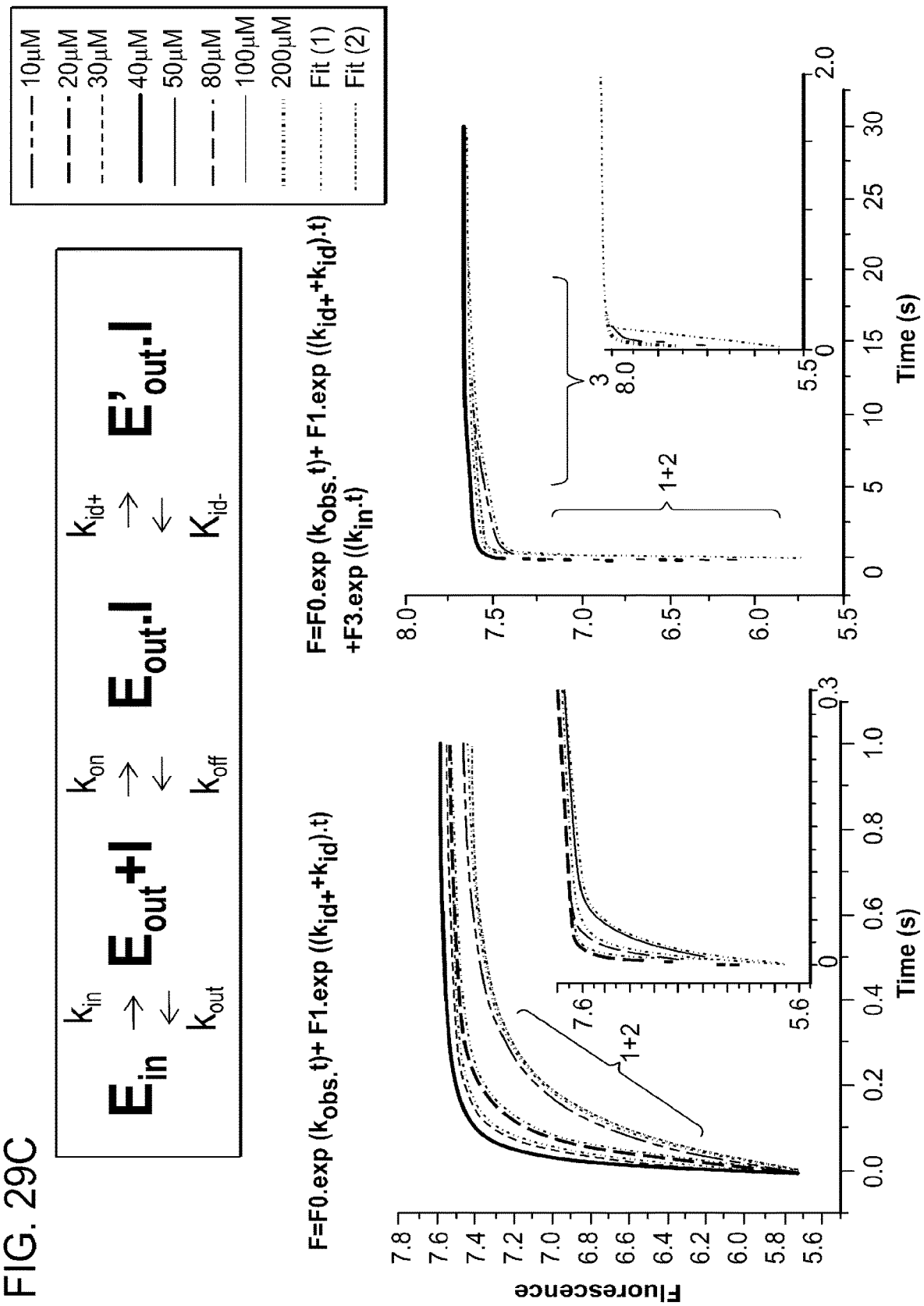
Figure 29C:
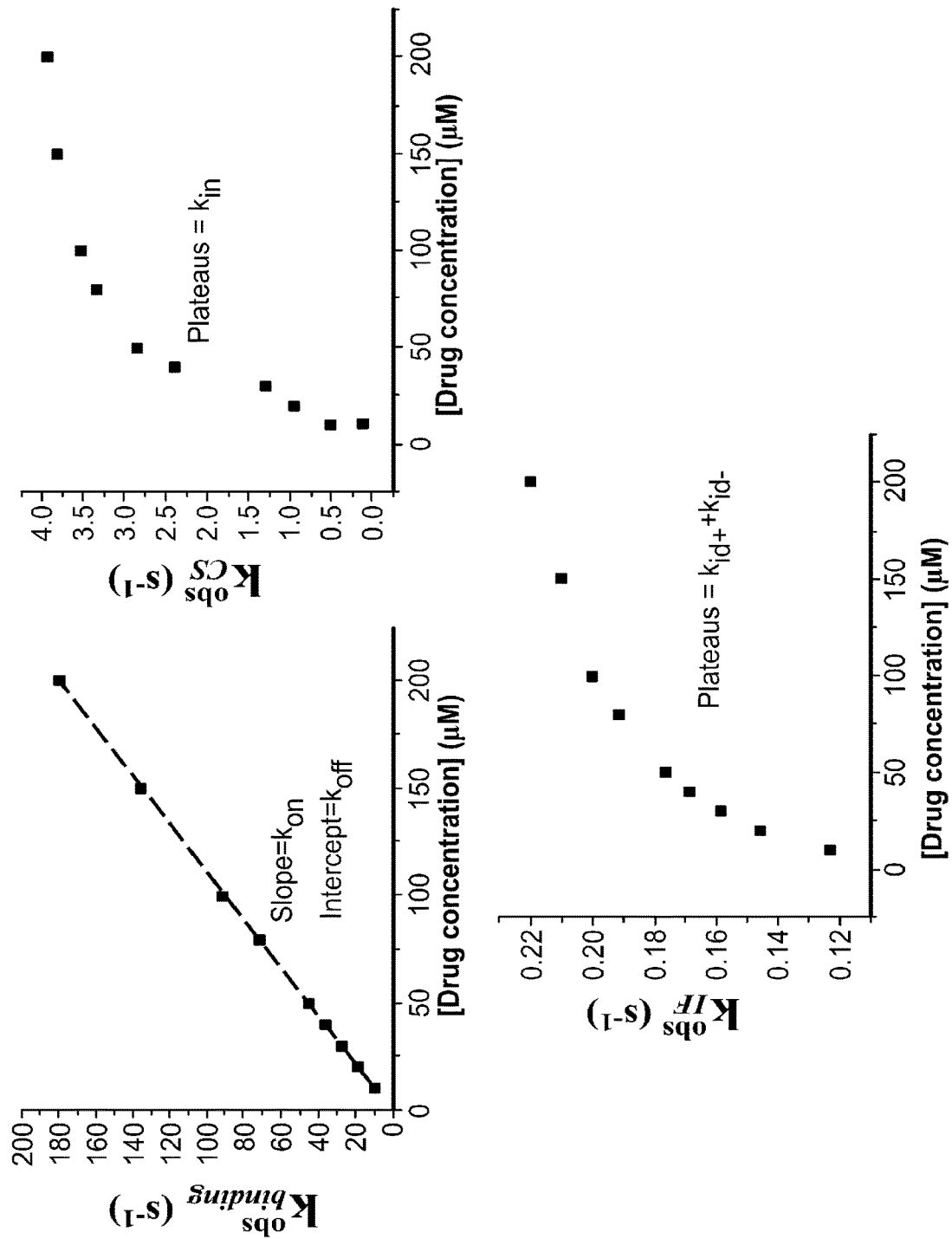

In order to assess which kinetic step(s) controls the drug affinity and selectivity, the binding kinetics for Gleevec, to Aurora A were analyzed. At 25° C., the binding of Gleevec to Aurora A was too fast to be monitored. At 10° C., the binding kinetics at Gleevec concentrations above 5 µM was monoexponential with a linear dependence on the ligand concentration providing a $k_{on}$ value of 1 µM$^{-1}$ s$^{-1}$ (FIG. 16H-16I). It was puzzling that by using a different drug, the binding kinetics changed from a triple exponential binding kinetics with two conformational exchange steps to the simplest pseudo-first order binding kinetics (see FIGS. 29A-29C for further description of orders of binding kinetics). Particularly concerning is the apparent lack of the kinetic phase previously assigned to the DFG-in to -out flip since (i) Gleevec is considered to be a DFG-out specific inhibitor and (ii) this conformational exchange happens before binding hence is independent from drug binding. It was noticed, however, that Gleevec binding to Aurora A caused a decrease in fluorescence while all three phases for Danusertib binding show fluorescence increases. The suspicion that the DFG flip (with a corresponding increase in fluorescence) was masked by the large amplitude of fluorescence decrease from the Gleevec binding step was confirmed by repeating Gleevec binding kinetics at very low drug concentrations showing the expected fluorescence increase due to the DFG-out selection (FIGS. 26A-26C). The latter result strongly supported the DFG-in/out equilibrium in Aurora A and the selective binding of both drugs to the DFG-out state. What happened to the induced fit step was then investigated.

Figure 16J:
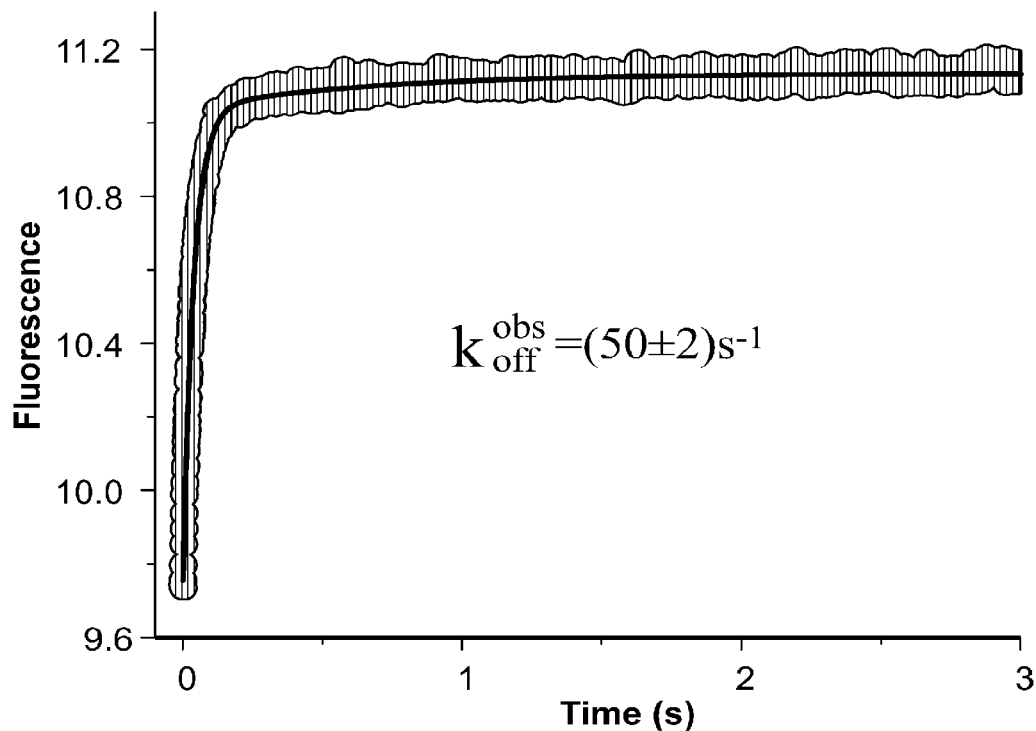
Figure 16K:
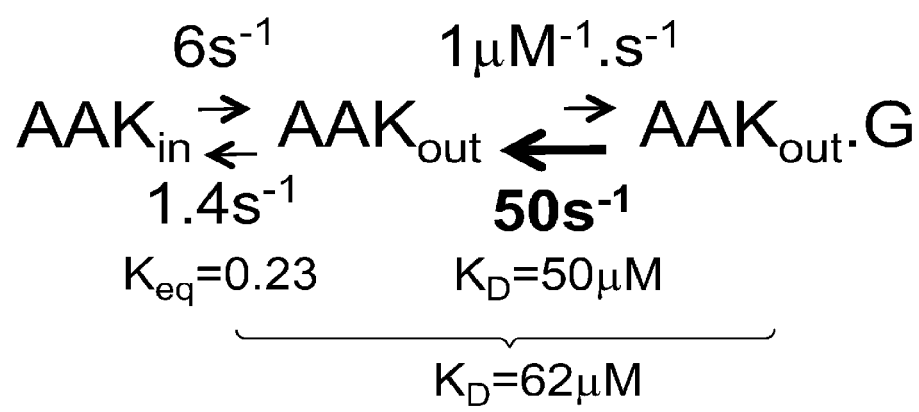

The Danusertib binding kinetics data suggest that the conformational transition after drug binding (i.e., induced fit) dramatically enhances drug affinity. If this hypothesis is correct, the absence of this additional induced fit step for Gleevec in the fluorescence kinetics should be reflected in a higher $K_D$ and a faster overall dissociation of the drug. Indeed, Gleevec bound to Aurora A with a $K_D$ of 55 µM (FIG. 26D) and dissociated with an apparent rate constant of 50 s$^{-1}$ (FIG. 16J). Two pieces of independent evidence establishes that there is indeed not an induced fit step for Gleevec binding to Aurora A: (i) the calculated $K_D$ from the kinetic scheme is in agreement with the macroscopic $K_D$ (FIG. 28B), and (ii) the observed off rate (FIG. 16J) now coincided with the physical dissociation rate (intercept of the $k_{on}$ observed, FIG. 16I) consequently being $10^6$-$10^7$ faster than the Danusertib -off rate (FIG. 16E). In summary, the lack of an induced fit step for Gleevec binding to Aurora A was the major reason for the weak binding and not the DFG loop conformation (FIG. 16K).

Figure 17A:
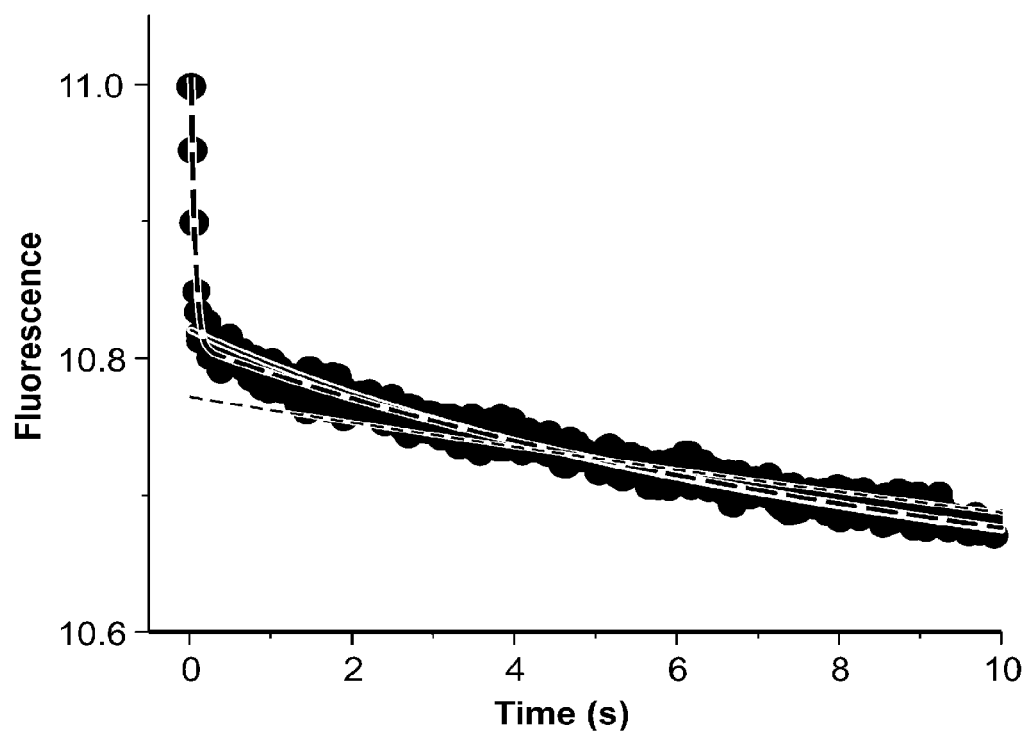
FIG. 17A-17D are schematics and plots showing kinetics and binding scheme of Gleevec (labeled G) to Abl and Abl T315I gatekeeper at 5° C.
Figure 17B:
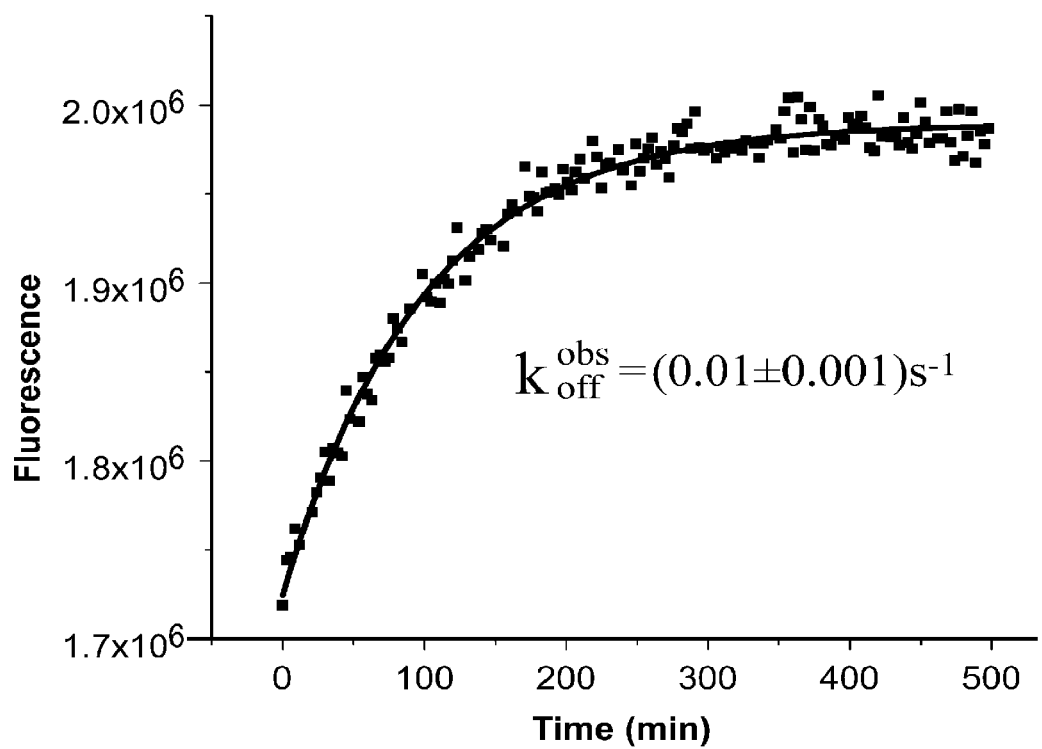
Figure 17C:
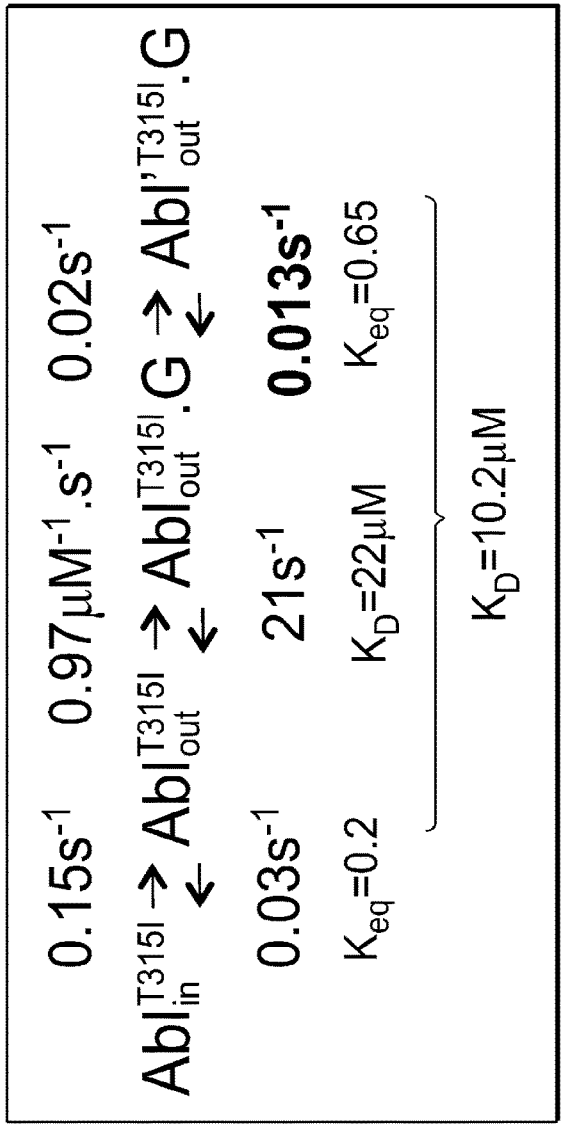
Figure 17D:
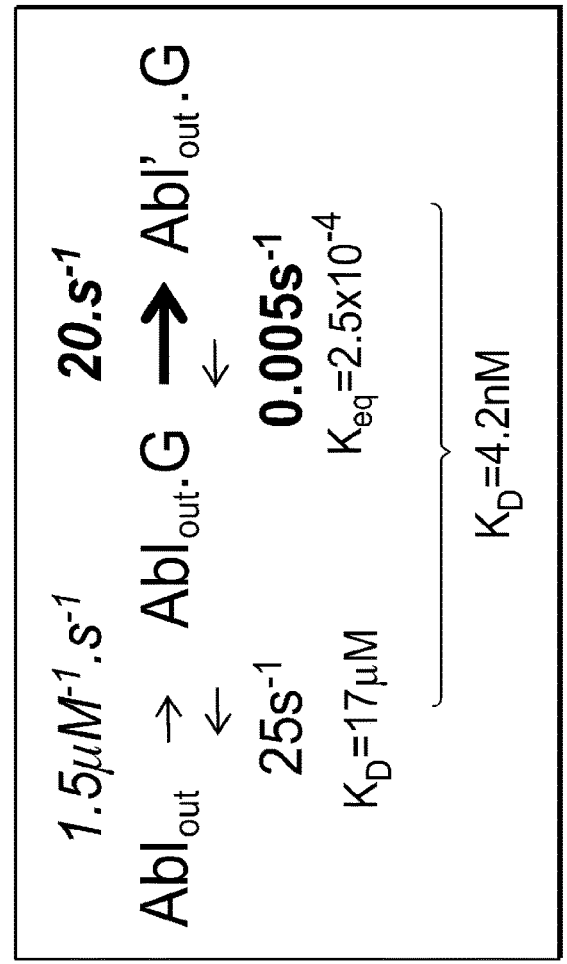
Figure 27B:
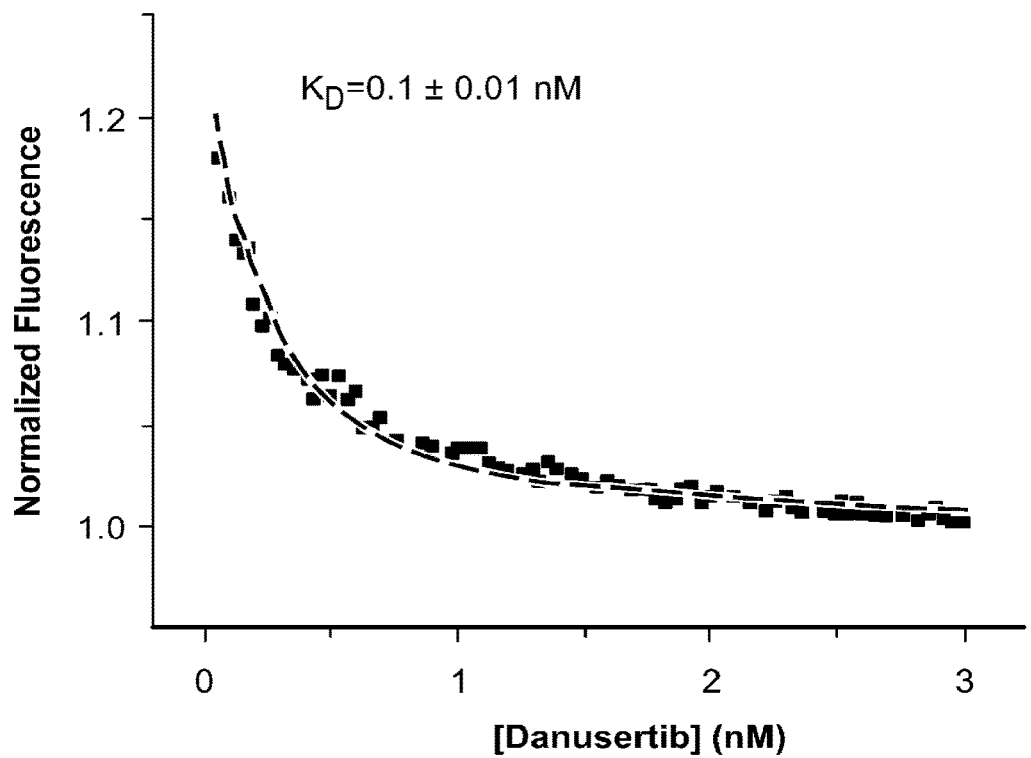
Figure 27C:
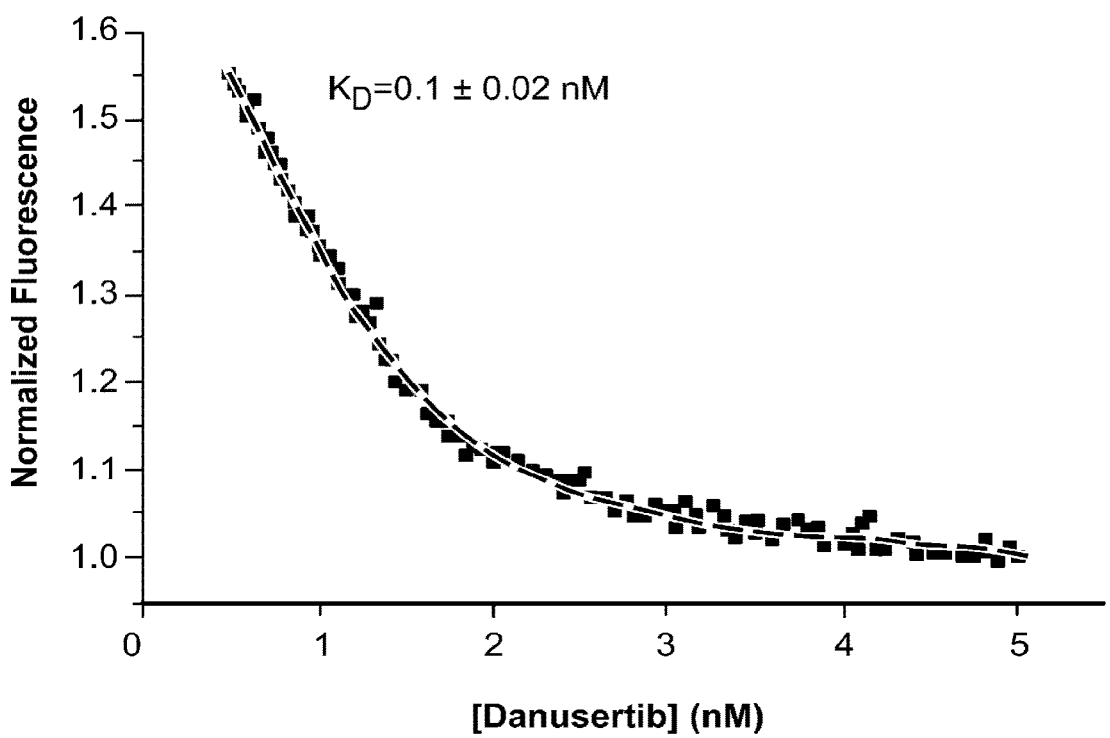
Figures 28A, 28B:
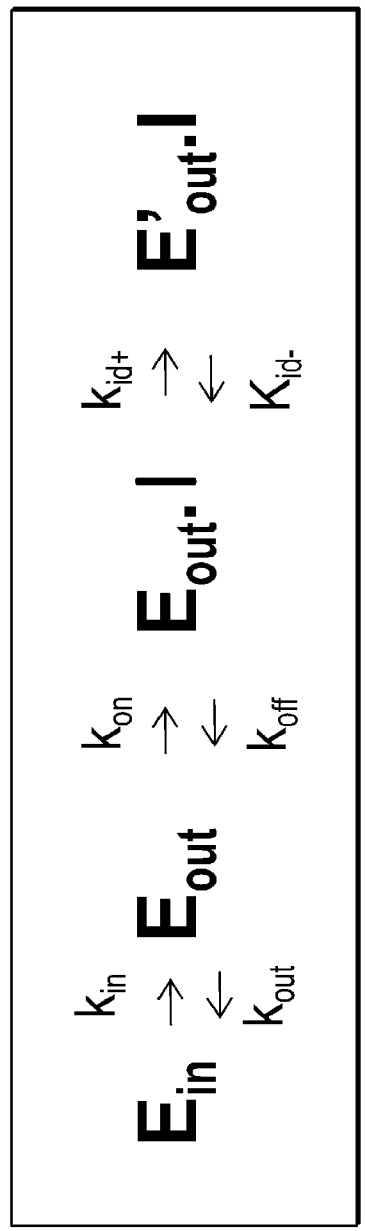
FIGS. 28A-28B are a table and a schematic showing kinetics and macroscopic parameters measured by fluorescence experiments for Aurora A/Danusertib, Aurora A/Gleevec, Abl/Danusertib, Abl T315I/Gleevec and Abl T315I/Danusertib binding.

Revealing the Mechanism of the Gleevec Resistant Gatekeeper Mutant T315I Abl and Mechanism of Inhibition Rescue Despite the enormous success of Gleevec as a highly selective drug for Bcr-Abl, a growing number of resistant mutations demand the development of second and third generation inhibitors. An understanding of the underlying mechanism responsible for the resistance may guide this mission (34) (FIGS. 17A-17D; FIGS. 27A-27C). One of the major Gleevec resistant mutations in Abl developed in patients is T315I, labeled as Gatekeeper mutation because of the proposed steric hindrance for Gleevec binding (35; 36). Surprisingly it was found that T315I "binds" Gleevec similarly to the wild-type, meaning that the physical binding step was almost identical (FIG. 17C). Strikingly, the induced fit step was severely affected resulting in a much weaker overall affinity ($K_D$=12 µM for T315I (FIG. 27A) compared to 4 nM for wild type, (FIG. 17D). It is emphasized that the Gleevec resistance by this mutation (i.e. meaning weak affinity) was solely due to alterations in the conformational change step after binding, and not due to the binding/unbinding of the drug. A second observation is the fact that this mutation also affected the conformational exchange between the binding competent and incompetent state of the free protein to the point that this DFG flip is now detectable in the stopped-flow fluorescence binding kinetics (FIG. 17A; FIG. 17C). However this DFG in/out equilibrium change has a negligible effect on the Gleevec affinity.

Figure 18A:
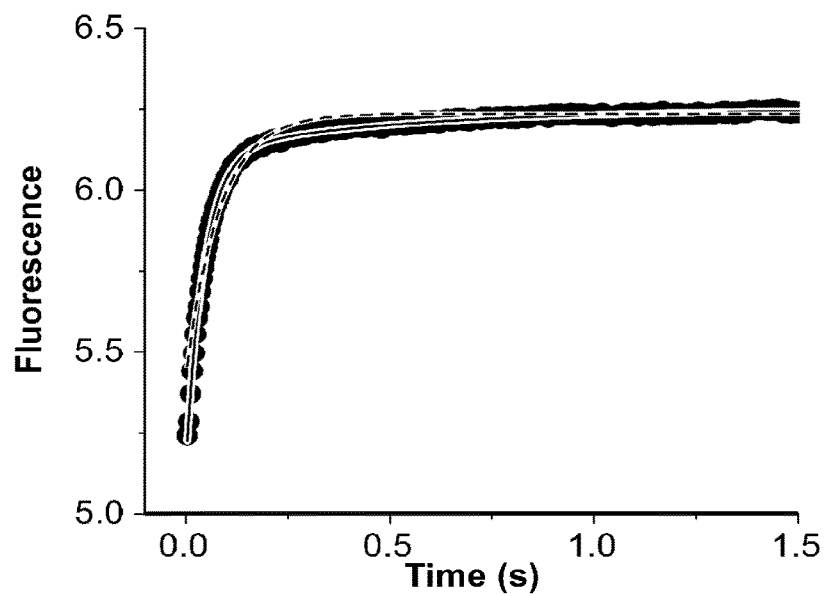
FIGS. 18A-E, and 18G-18I are plots and schematics showing kinetics and binding scheme of Danusertib (labeled D) to Abl and Abl T315I gatekeeper at 25° C.
Figure 18B:
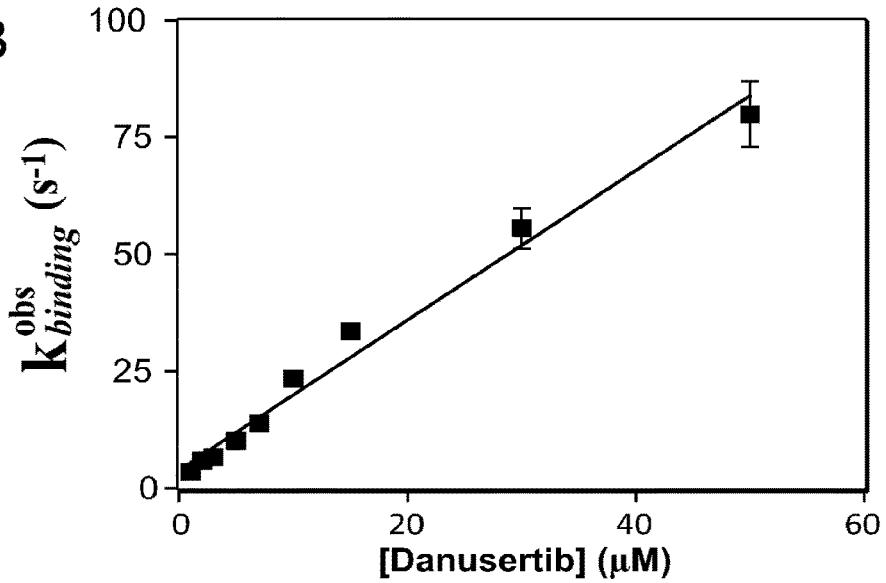
Figure 18C:
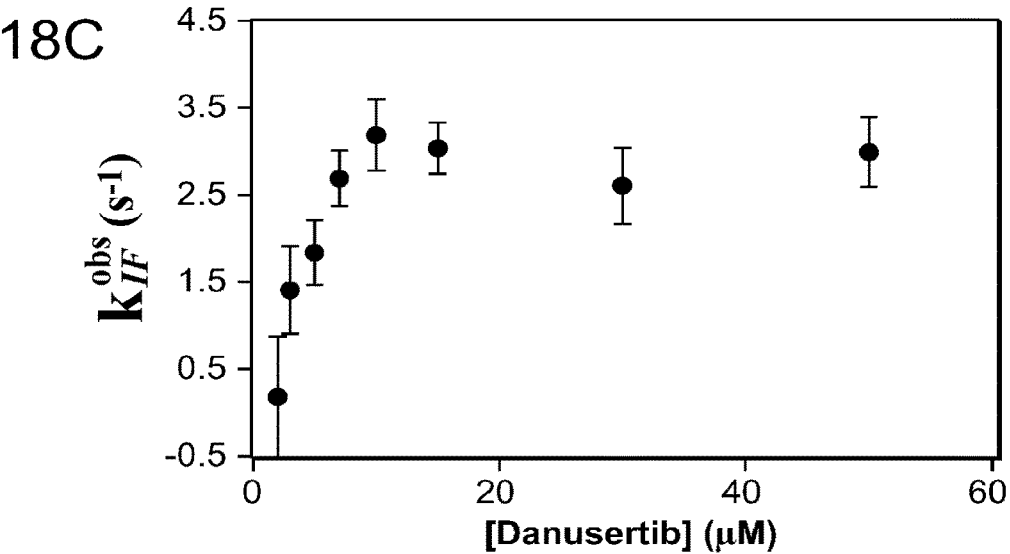
Figure 18D:
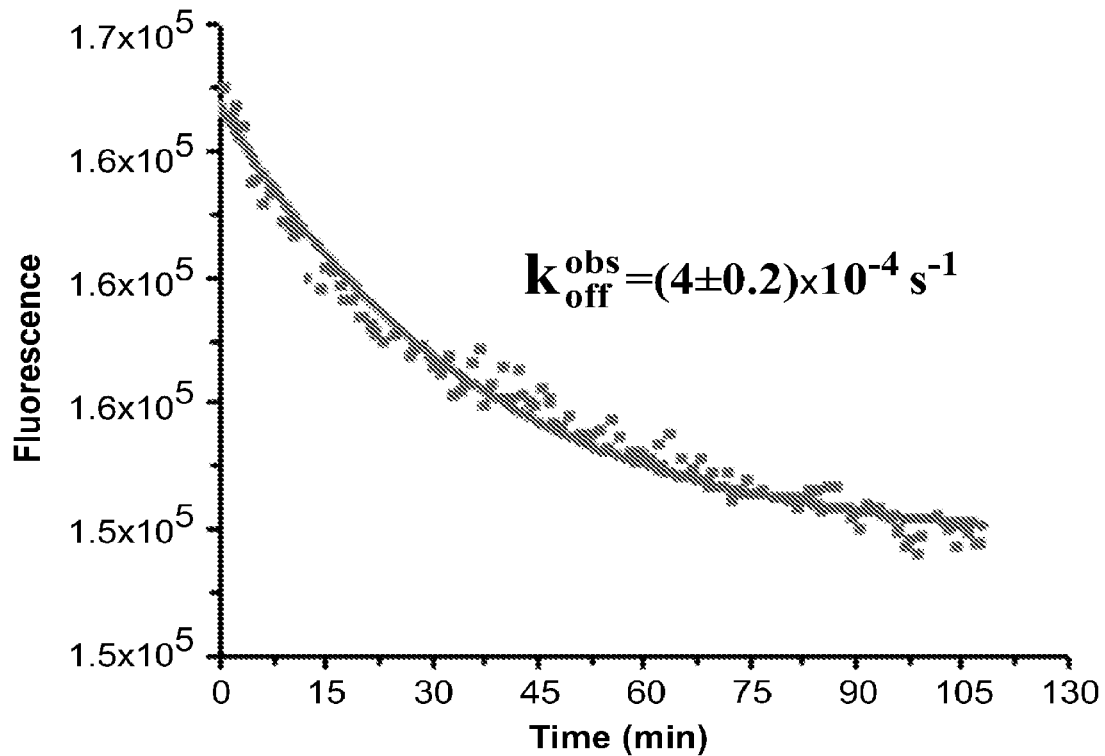
Figure 18E:
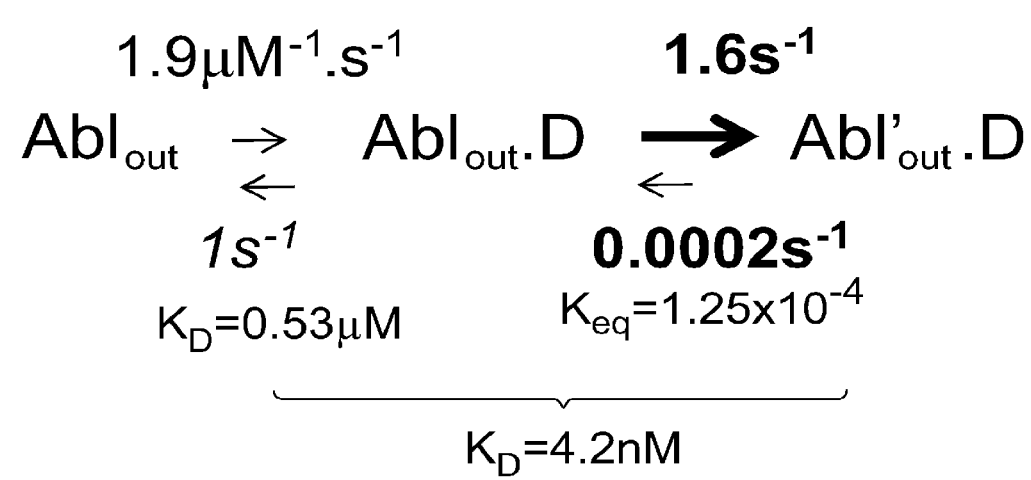
Figure 18G:
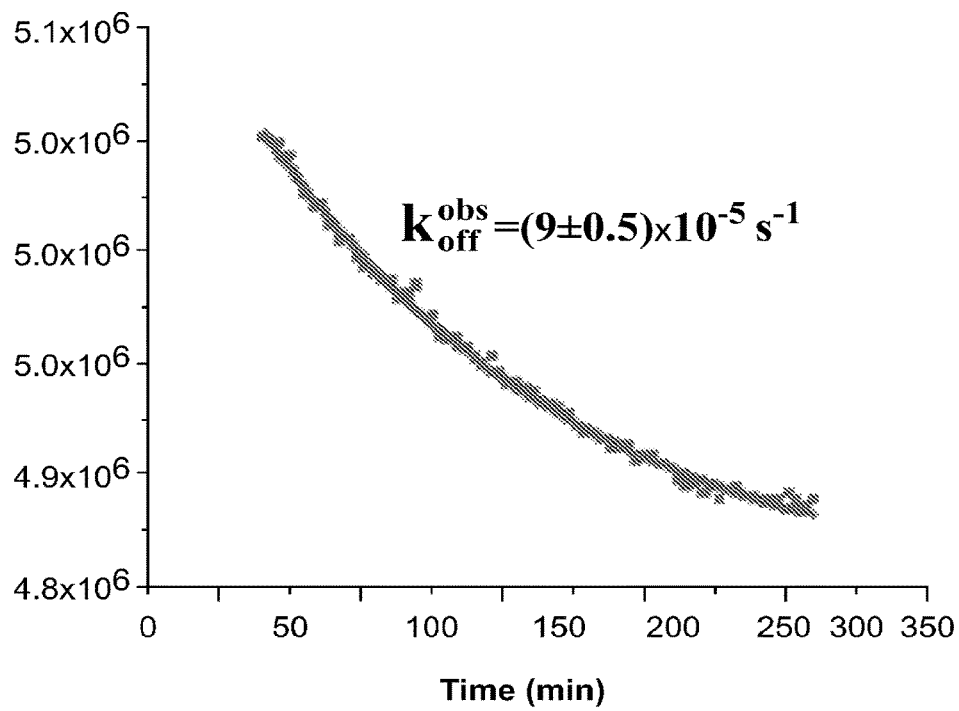
Figure 18H:
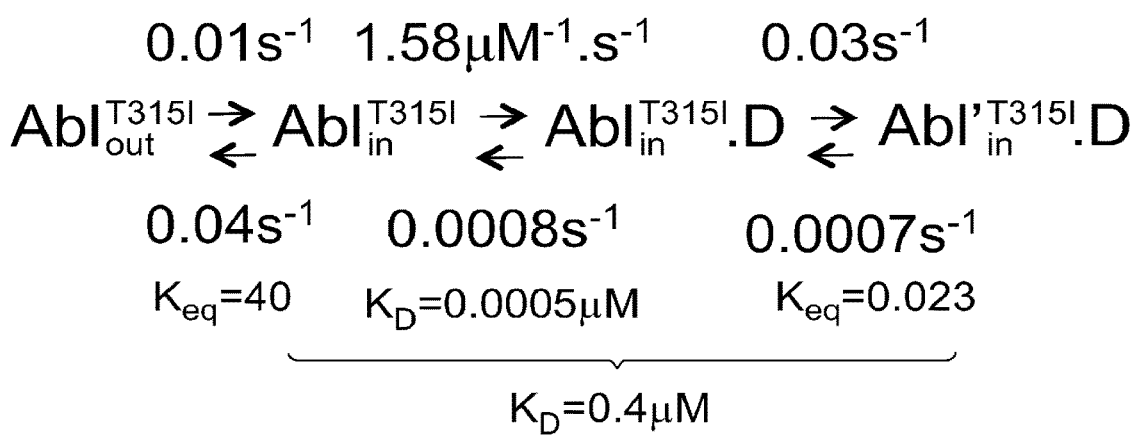
Figure 18I:
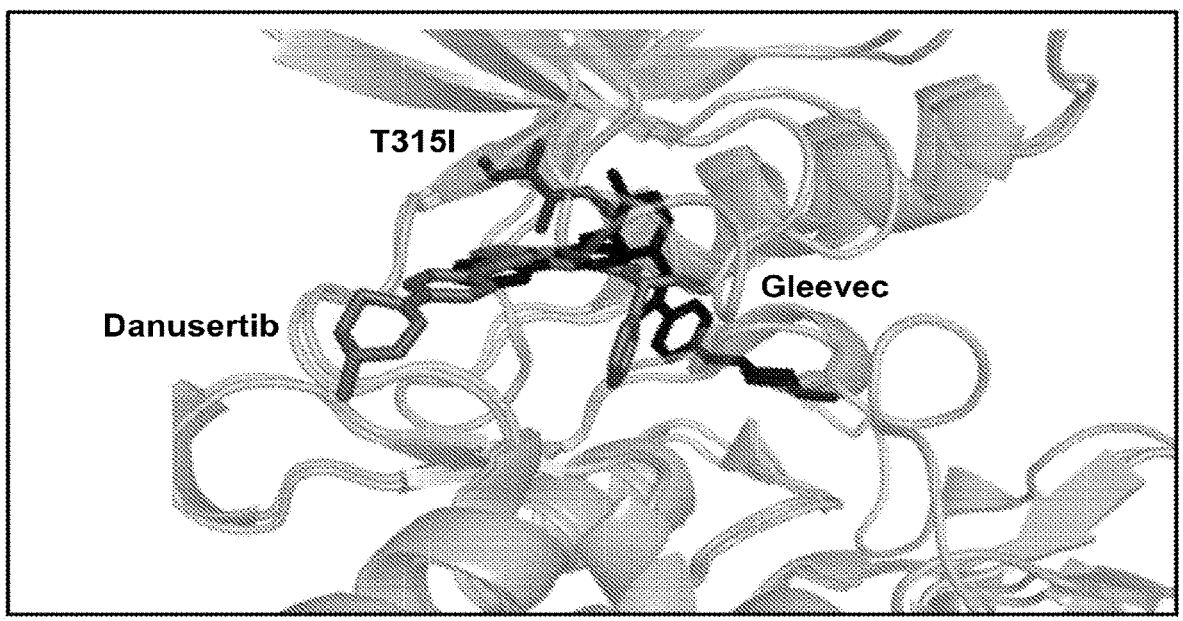
Figure 19A:
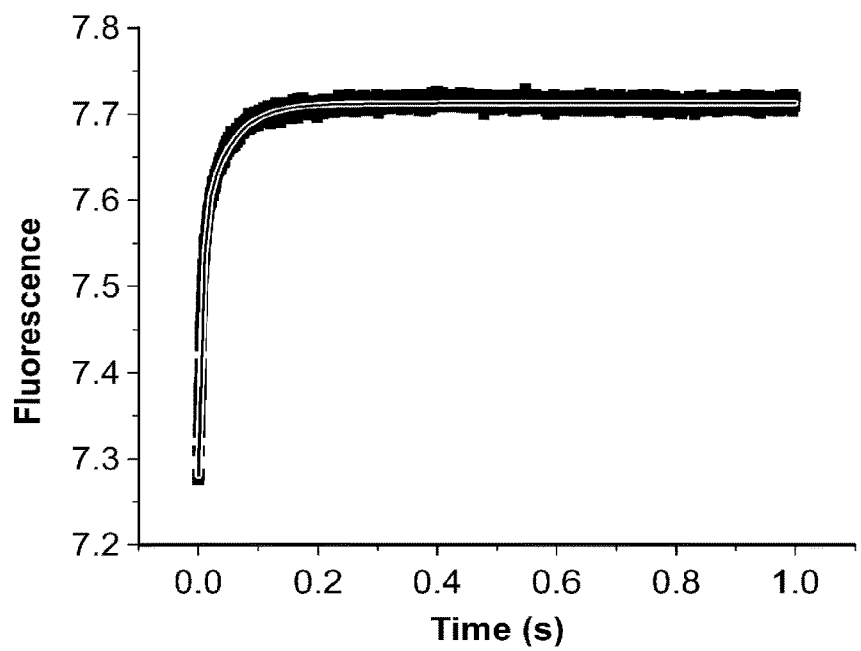
FIGS. 19A-19F are plots and schematics showing kinetics and binding scheme of MantATP to Aurora A wild-type at 10° C.
Figure 19B:
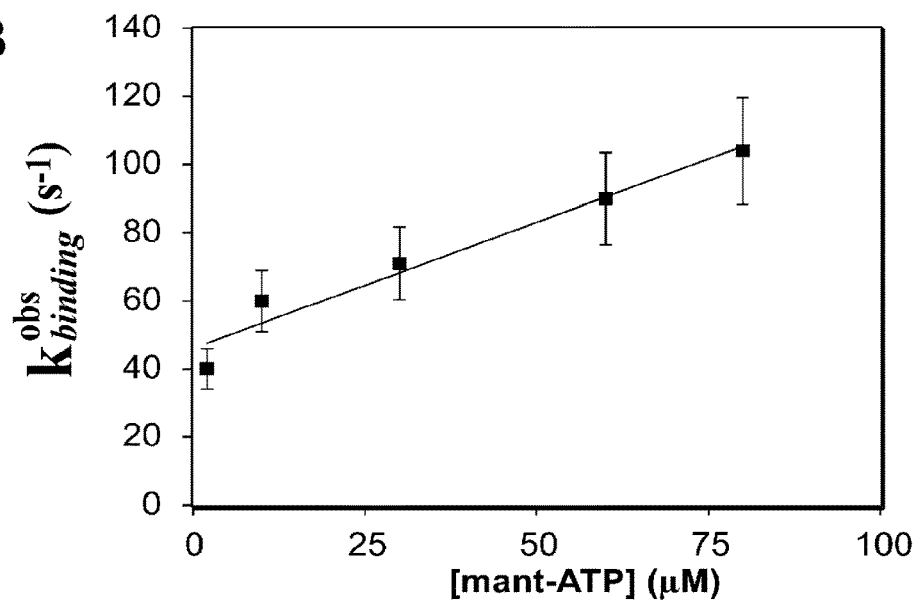
Figure 19C:
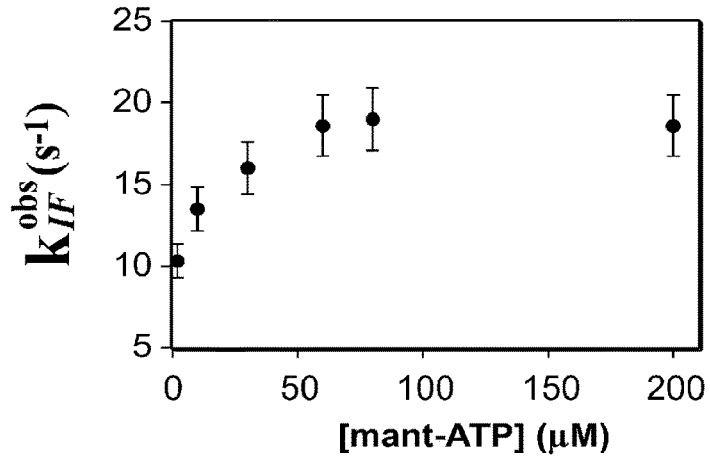
Figure 19D:
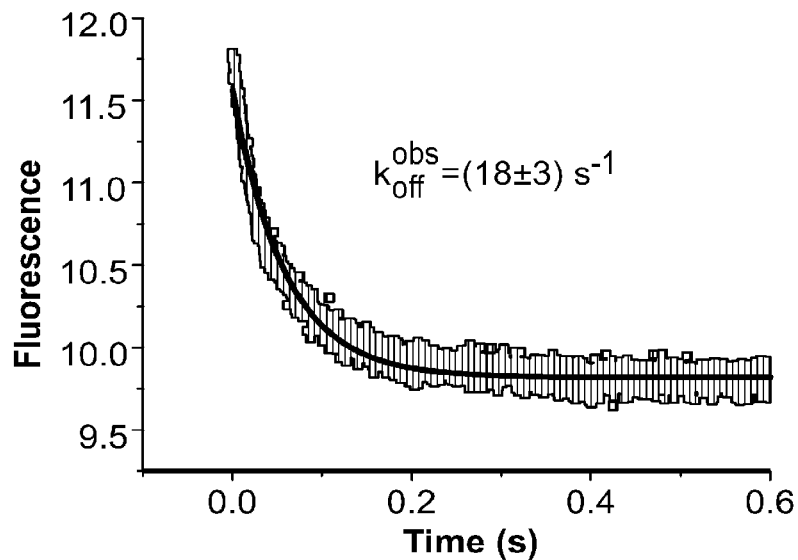
Figure 19E:
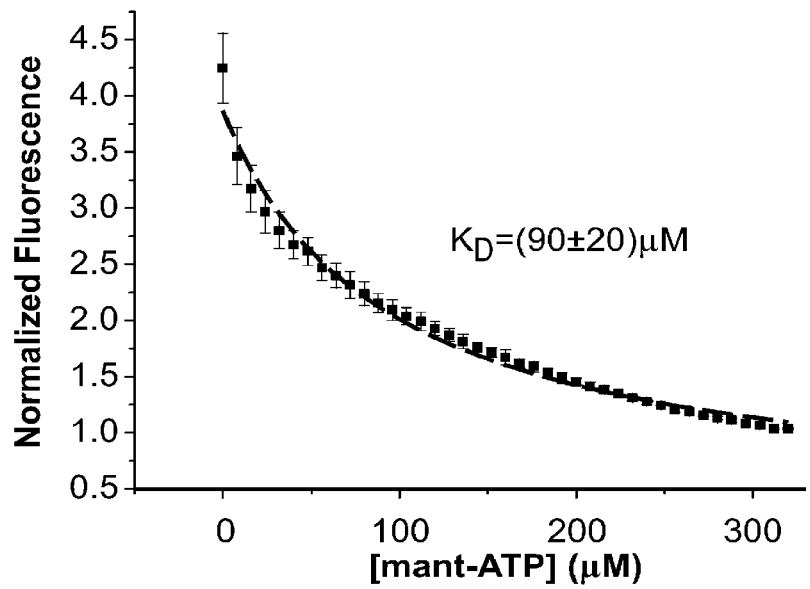

The T315I resistant mutation represents a serious therapeutic problem since second-generation tyrosine kinase inhibitors are ineffective (26). However, Danusertib, the drug used against Aurora A, and for which the kinetics of binding to Aurora was already described herein, has been shown to be effective against T315I Abl (FIG. 27A). In an effort to elucidate the underlying atomistic mechanism, a co-crystal structure of T315I Abl kinase bound to Danusertib (PDB code: 2V7A) was solved showing the inhibitor bound to an active conformation with a DFG-in loop conformation (25). However, results from the binding kinetics of Danusertib to wild-type and T315I Abl underscores the importance of these experiments in elucidating the underlying mechanism and illustrates the generality of an induced fit step for a tight affinity for drugs (FIGS. 18A-18I). The differences in affinity were not rooted in the DFG loop conformation as one might conclude from these X-ray structures, but always in the induced fit step (FIG. 18E; FIG. 18H). For both proteins, Danusertib binding was followed by a very slow induced fit step (FIG. 18C) that is far-shifted, thereby increasing the overall affinity by this coupled equilibrium (FIG. 19E;). Clearly, the nature of the induced fit step with Gleevec and Danusertib was different resulting in the ability for Danusertib to maintain high affinity for the gatekeeper mutant. Differences in the conformational changes after binding of the different drugs can be rationalized from the fact that these drugs extended to different parts of the protein upon binding.

Figure 19F:
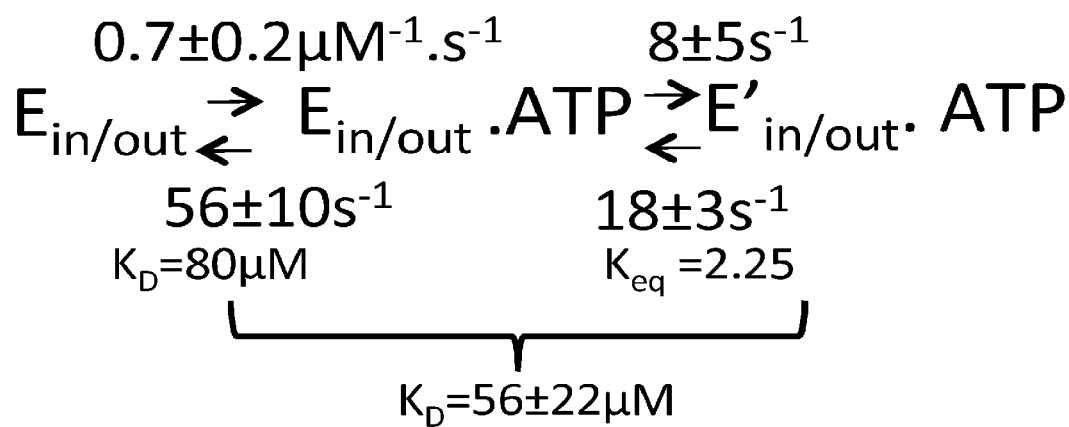

Inhibitors take advantage of built-in dynamics for ATP binding. The binding kinetics of the ATP-competitive inhibitors with the natural substrate ATP were compared (FIGS. 19A-19F). In order to measure stopped-flow kinetics for ATP binding FRET was measured by exciting Trp in Aurora A and detecting fluorescence transfer on Mant-ATP. It was found that ATP could bind to either the DFG -in or -out conformation and that nucleotide binding (FIG. 19B) was also followed by an induced fit step (FIG. 19C). Importantly, the latter conformational change was much faster and not as far-shifted compared to the inhibitor-bound states (FIG. 19F). Faster conformational changes are of course a prerequisite for efficient turnover; whereas very slow conformational changes particularly the reverse induced fit reaction is at the heart of action for an efficient drug because it results in tight binding and a long lifetime of the drug on the target. In summary, binding of different ligands to the ATP binding site, such as nucleotides or ATP-competitive inhibitors, is comprised by the physical binding step followed by an induced fit step. The nature of the induced fit step varies by definition for the different ligands since it happens as a result of ligand binding.

Additional Characterization of Danusertib and AT9283 Binding to Aurora A

FIG. 38, FIG. 39, FIG. 40, FIG. 41, FIG. 42, FIGS. 43A-43C, FIGS. 44A-44B, and FIG. 45 provide further characterization and elucidation of the binding mechanism and kinetics of binding of AT9283 and Danusertib to Aurora A. AT9283 binds to the "DFG_in" conformation whereas Danusertib binds to the "DFG_out" conformation. Results herein provide a finer characterization of the binding mechanism, kinetics, and energy landscape of the conformational selection step and induced fit step of binding to the active site of Aurora A.

Discussion

A central issue for drug design is to understand in detail the target/inhibitor interactions. This difficult task has primarily been tackled by comparing X-ray structures of the apo and inhibitor-bound targets, and by docking methods. Here it is revealed why the oversimplification in such a "two-state static view" cannot explain inhibitor affinity and specificity because the energy landscape of ligand binding is more complex even on the level of kinetically distinct states. In other words, both the apo enzyme and the ligand bound states were comprised of two conformations that could be experimentally distinguished because their interconversion was slower than microseconds. Crucially, the relative energies of these interconverting conformations dictated the overall affinity for the inhibitors. It was found that for kinase inhibitors, conformational selection and induced fit (37; 38) are at play. Strikingly, a far-shifted induced fit step was found to be the key step for all tight binders, and not the previously favored conformational selection of the DFG-in and -out structures. This mechanism seems to be general for different kinases and its inhibitors therefore providing a platform for future computational and experimental efforts in rational drug design. The "use" of a far-shifted induced fit step for a good drug is logical for three reasons: (i) it increases the affinity for the drug by this coupled equilibrium, (ii) it increases the residence time of the drug on the target via the slow reverse rate of the induced fit, and (iii) it is specific for each drug because it happens after the drug binding. The increased drug residence time has significant pharmacological advantages because it leads to a longer biological effect, a decrease of side effects and a lower risk of metabolic drug modification. Such inhibitors have long been described as slow tight-binding inhibitors.

Data described herein further deliver direct experimental information about the extensively discussed DFG-flip in kinases (33; 39-41). Dephosphorylated Aurora A, previously proposed to be exclusively in the inactive state, adopted both the DFG-out inactive and DFG-in active conformations in the same mother liquor. The existence of this equilibrium in solution was further substantiated by NMR and finally quantified using stopped-flow kinetics of drug binding. These new findings unambiguously establish the nature of this DFG flip both structurally and kinetically and resolve the longstanding question of its role for drug affinity.

The platform developed herein to monitor the detailed steps for drug binding delivered unexpected insight into the mechanism of drug resistance for the clinically common Abl gatekeeper mutation. It was found that the binding of Gleevec was not sterically hindered by the T315I mutation as previously described, but that this mutation severely affected the crucial induced fit step. Ponatinib (Ariad Pharmaceuticals) was approved in 2013 as second-line CML treatment, and was the only licensed tyrosine kinase inhibitor that binds to the T315I mutated kinase successfully (42). However, recently, the Food and Drug Administration (FDA) suspended Ponatinib distribution due to patients safety concern. Danusertib, originally used as Aurora inhibitor, has been proposed as a potential novel second-line inhibitor against this resistance mutation and indeed it was found that for this drug the induced fit step stayed intact, consequently preserving tight binding. Without intending to be bound by theory, it is believed that this is due the fact that the nature of the induced fit step is different for Danusertib and Gleevec because they are able to interact with different parts of the protein.

Results described herein exemplify why rational drug design is so challenging. The characterization of the complete free energy landscape of drug binding is needed, which will require more sophisticated computational approaches guided by experimental data such as provided in our study. A good illustration of this point are the computational reports focusing on the DFG flip as the key determinant responsible for Gleevec selectivity that now have been ruled out by kinetic measurements. The data herein suggest that future energy calculation should be focusing on the induced fit step. Clearly more experimental data for a series of inhibitors are essential to guide energy difference calculations. There is a large conformational space available for specific inhibitors even for kinases with very similar folds since the action does not happen on a single structure but on a complex energy landscape that is different for each kinase. It has been shown here that the inhibitors take advantage of the inherent plasticity of the enzymes that evolved for its activity and regulation.

References—Example 2

[1] Carvajal, R. D., Tse, A., & Schwartz, G. K. (2006) Aurora kinases: new targets for cancer therapy. Clinical cancer research: an official journal of the American Association for Cancer Research 12 (23): 6869-6875.
[2] Gautschi, O. et al. (2008) Aurora kinases as anticancer drug targets. Clinical cancer research: an official journal of the American Association for Cancer Research 14 (6): 1639-1648.
[3] Katayama, H. & Sen, S. (2010) Aurora kinase inhibitors as anticancer molecules. Biochimica et biophysica acta 1799 (10-12): 829-839.
[4] Hopkins, A. L. & Groom, C. R. (2002) The druggable genome. Nature reviews. Drug discovery 1 (9): 727-730.
[5] Cohen, P. (2002) Protein kinases—the major drug targets of the twenty-first century? Nature reviews. Drug discovery 1 (4): 309-315.
[6] Iqbal, N. & Iqbal, N. (2014) Imatinib: a breakthrough of targeted therapy in cancer. Chemotherapy research and practice 2014: 357027.
[7] Taylor, S. S., Keshwani, M. M., Steichen, J. M., & Kornev, A. P. (2012) Evolution of the eukaryotic protein kinases as dynamic molecular switches. Philosophical transactions of the Royal Society of London. Series B, Biological sciences 367 (1602): 2517-2528.
[8] Lovera, S. et al. (2012) The different flexibility of c-Src and c-Abl kinases regulates the accessibility of a druggable inactive conformation. Journal of the American Chemical Society 134 (5): 2496-2499.
[9] Fu, J., Bian, M., Jiang, Q., & Zhang, C. (2007) Roles of Aurora kinases in mitosis and tumorigenesis. Molecular cancer research: MCR 5 (1): 1-10.
[10] Marumoto, T., Zhang, D., & Saya, H. (2005) Aurora-A—a guardian of poles. Nature reviews. Cancer 5 (1): 42-50.
[11] Lukasiewicz, K. B. & Lingle, W. L. (2009) Aurora A, centrosome structure, and the centrosome cycle. Environmental and molecular mutagenesis 50 (8): 602-619.
[12] Nikonova, A. S., Astsaturov, I., Serebriiskii, I. G., Dunbrack, R. L., Jr., & Golemis, E. A. (2013) Aurora A kinase (AURKA) in normal and pathological cell division. Cellular and molecular life sciences: CMLS 70 (4): 661-687.
[13] Lok, W., Klein, R. Q., & Saif, M. W. (2010) Aurora kinase inhibitors as anti-cancer therapy. Anti-cancer drugs 21 (4): 339-350.
[14] Marzo, I. & Naval, J. (2013) Antimitotic drugs in cancer chemotherapy: promises and pitfalls. Biochemical pharmacology 86 (6): 703-710.
[15] Heron, N. M. et al. (2006) SAR and inhibitor complex structure determination of a novel class of potent and specific Aurora kinase inhibitors. Bioorganic & medicinal chemistry letters 16 (5): 1320-1323.
[16] Dodson, C. A. et al. (2010) Crystal structure of an Aurora-A mutant that mimics Aurora-B bound to MLN8054: insights into selectivity and drug design. The Biochemical journal 427 (1): 19-28.
[17] Fancelli, D. et al. (2006) 1,4,5,6-tetrahydropyrrolo[3,4-c]pyrazoles: identification of a potent Aurora kinase inhibitor with a favorable antitumor kinase inhibition profile. Journal of medicinal chemistry 49 (24): 7247-7251.
[18] Zhao, B. et al. (2008) Modulation of kinase-inhibitor interactions by auxiliary protein binding: crystallography studies on Aurora A interactions with VX-680 and with TPX2. Protein science: a publication of the Protein Society 17 (10): 1791-1797.
[19] Fraedrich, K. et al. (2012) Targeting aurora kinases with danusertib (PHA-739358) inhibits growth of liver metastases from gastroenteropancreatic neuroendocrine tumors in an orthotopic xenograft model. Clinical cancer research: an official journal of the American Association for Cancer Research 18 (17): 4621-4632.
[20] Carpinelli, P. et al. (2007) PHA-739358, a potent inhibitor of Aurora kinases with a selective target inhibition profile relevant to cancer. Molecular cancer therapeutics 6 (12 Pt 1): 3158-3168.
[21] Kollareddy, M. et al. (2012) Aurora kinase inhibitors: progress towards the clinic. Investigational new drugs 30 (6): 2411-2432.
[22] Steeghs, N. et al. (2009) Phase I pharmacokinetic and pharmacodynamic study of the aurora kinase inhibitor danusertib in patients with advanced or metastatic solid tumors. Journal of clinical oncology: official journal of the American Society of Clinical Oncology 27 (30): 5094-5101.
[23] Gontarewicz, A. et al. (2008) Simultaneous targeting of Aurora kinases and Bcr-Abl kinase by the small molecule inhibitor PHA-739358 is effective against imatinib-resistant BCR-ABL mutations including T315I. Blood 111 (8): 4355-4364.
[24] Martinelli, G. et al. (2009) Aurora kinase inhibitors: which role in the treatment of chronic myelogenous leukemia patients resistant to imatinib? Hematology Reports (formerly Hematology Reviews) 1 (1).
[25] Modugno, M. et al. (2007) Crystal structure of the T315I Abl mutant in complex with the aurora kinases inhibitor PHA-739358. Cancer research 67 (17): 7987-7990.
[26] Zuccotto, F., Ardini, E., Casale, E., & Angiolini, M. (2010) Through the "gatekeeper door": exploiting the active kinase conformation. Journal of medicinal chemistry 53 (7): 2681-2694.
[27] Lin, Y. L., Meng, Y., Jiang, W., & Roux, B. (2013) Explaining why Gleevec is a specific and potent inhibitor of Abl kinase. Proceedings of the National Academy of Sciences of the United States of America 110 (5): 1664-1669.

[28] Kornev, A. P. & Taylor, S. S. (2010) Defining the conserved internal architecture of a protein kinase. Biochimica et biophysica acta 1804 (3): 440-444.

[29] Zorba, A. et al. (2014) Molecular mechanism of Aurora A kinase autophosphorylation and its allosteric activation by TPX2. eLife 3: e02667.

[30] Bayliss, R., Sardon, T., Vernos, I., & Conti, E. (2003) Structural basis of Aurora-A activation by TPX2 at the mitotic spindle. Molecular cell 12 (4): 851-862.

[31] Chen, C. et al. (2014) Identification of a major determinant for serine-threonine kinase phosphoacceptor specificity. Molecular cell 53 (1): 140-147.

[32] Long, G. J., Rosen, J. F., & Schanne, F. A. (1994) Lead activation of protein kinase C from rat brain. Determination of free calcium, lead, and zinc by 19F NMR. The Journal of biological chemistry 269 (2): 834-837.

[33] Reddy, E. P. & Aggarwal, A. K. (2012) The ins and outs of bcr-abl inhibition. Genes & cancer 3 (5-6): 447-454.

[34] Barouch-Bentov, R. & Sauer, K. (2011) Mechanisms of drug resistance in kinases. Expert opinion on investigational drugs 20 (2): 153-208.

[35] Corbin, A. S., La Rosee, P., Stoffregen, E. P., Druker, B. J., & Deininger, M. W. (2003) Several Bcr-Abl kinase domain mutants associated with imatinib mesylate resistance remain sensitive to imatinib. Blood 101 (11): 4611-4614.

[36] Nagar, B. et al. (2003) Structural basis for the autoinhibition of c-Abl tyrosine kinase. Cell 112 (6): 859-871.

[37] Changeux, J. P. & Edelstein, S. (2011) Conformational selection or induced fit? 50 years of debate resolved. F1000 biology reports 3: 19.

[38] Nussinov, R. & Tsai, C. J. (2013) Allostery in disease and in drug discovery. Cell 153 (2): 293-305.

[39] Martin, M. P. et al. (2012) A novel mechanism by which small molecule inhibitors induce the DFG flip in Aurora A. ACS chemical biology 7 (4): 698-706.

[40] Shan, Y. et al. (2009) A conserved protonation-dependent switch controls drug binding in the Abl kinase. Proceedings of the National Academy of Sciences of the United States of America 106 (1): 139-144.

[41] Ranjitkar, P., Brock, A. M., & Maly, D. J. (2010) Affinity reagents that target a specific inactive form of protein kinases. Chemistry & biology 17 (2): 195-206.

[42] Shah, N. P. (2011) Ponatinib: targeting the T315I mutation in chronic myelogenous leukemia. Clinical advances in hematology & oncology: H&O 9 (12): 925-926.

[43] Crowley, P. B., Kyne, C., & Monteith, W. B. (2012) Simple and inexpensive incorporation of 19F-tryptophan for protein NMR spectroscopy. Chemical communications 48 (86): 10681-10683.

Example 3

Evolution of an Allosteric Activation Mechanism Enables Fine-Tuning of Aurora Kinase Activity Despite a myriad of cellular events being governed by allostery, evolution of this process is yet a fairly unexplored territory. The main difficulty relies in finding the right model system that would span a large evolutionary window for unbiasedly assessing meaningful interactions. In the present study, Ancestral Sequence Reconstruction was used to resurrect ancestors of two co-localizing proteins, Aurora kinase and its allosteric activator, TPX2. Isothermal Titration calorimetry (ITC) and High Performance Liquid Chromatography (HPLC)-based assays were used to assess the degree of interaction and allosteric activation of Aurora kinase by TPX2 from different evolutionary periods. It was observed that a binding event was necessary and sufficient for driving interaction of these proteins and that Aurora kinase evolved to feel the effects of TPX2. This showed a regulation mechanism whereby phosphorylation of Aurora kinase preceded allosteric activation by TPX2, and proved to be a more-elegant, higher-order fine-tuning of Aurora kinase in higher, complex organisms.

Introduction

Allostery is the process by which a subset of spatially clustered amino acids can cooperatively influence the behavior of a different subset of amino acids, remote from the interaction site. This phenomenon governs many crucial cellular signaling processes ranging from oxygen transport [1], to synaptic transmission [2], to modulation of catalytic rates of enzymes [3, 4].

Despite the importance of allostery in living organisms, a mechanistic understanding of the evolution of this process has proven extremely challenging to obtain. The first technical difficulty arises in uncoupling meaningful interactions given the rugged energy landscape of coevolution. The second challenge pertains to choosing the right model system that could span a large evolutionary window. Most recently, this latter point was addressed by Coyle et al. [5] where proteins spanning 1 billion years of evolution (from *S. pombe* to *S. cerevisiae*) were studied. However, works similar to the one mentioned above are few and far in between.

The question of how allosteric modulators and their partners coevolved is explored herein. Kuriyan and Eisenberg put forth an elegant theory to coevolution: colocalization of proteins, either through recombination or compartmentalization, gives the opportunity for nonspecific surface residue contacts to evolve into productive interactions [6]. A question of why is it that some surface residues provide productive coevolution basins while others don't was put forth. Ranganathan's lab addressed this question through SCA (Statistical Coupling Analysis), a tool that infers evolution based on sequence alignments of multiple proteins from varying organisms [7-9]. Through SCA, they showed that (a) overall, evolution of amino acids in a protein was a weakly coupled process (most aminoacids evolve independently of each-other) but that (b) several hotspots, typically accounting for 10-30% of aminoacids, were most responsible for coevolution [8]. Thus, the hotspots became the productive basins that Kuriyan and Eisenberg were referring to while discussing coevolution of allostery. Although very elegant in nature, most of the evolution of allostery remains theoretical given the technical challenges mentioned above.

In the current work, the hypothesis set forth by Kuriyan, Eisenberg and Ranganathan was experimentally addressed through a novel approach: the study of coevolution of allostery based on Ancestral Sequence Reconstruction (ASR). Not only did this method allow a look at a significantly larger evolutionary window (4+ billion years to present), but it also resolved the problem of finding the optimal model organism since our work is done using an *E. coli*-based expression system. Having addressed these two technical challenges, an in-depth mechanistic study of a coevolving set of proteins whose interaction is governed by allostery was conducted: that of Aurora A, an oncogenic Ser/Thr kinase, and its allosteric activator, Targeting Protein for Xklp2, TPX2. Aberrant levels of Aurora A lead to improper centrosome maturation, abnormal spindle formation, problems signaling mitotic entry and cancerous growth [10-27]. TPX2 targets Aurora A to the spindle microtubules and allosterically activates the protein by inducing an active conformation of the dephosphorylated, lowly-active form of the kinase [28, 29] and causes a conformational rearrangement of the phosphorylated, active Aurora A which leads to protection of the phosphate group on T288 from dephosphorylation [30]. Therefore, a mechanistic understanding of the coevolution of allostery in Aurora A-TPX2 could help identify hotspots in both of these proteins that could later be explored for much sought-after Aurora A inhibitors.

To this goal, Aurora and TPX2 ancestors were resurrected from different evolutionary periods. Two of the four Aurora ancestors ($Aur_{ANC1}$ and $Aur_{ANC2}$) belonged to a period in time where TPX2 was not present. This was not surprising given that Aurora is a significantly older protein that TPX2, first appearing in protists (single-cell eukaryotes) while the oldest annotated sequence for TPX2 that is available, belongs to the plants and animals split. ITC was used to biophysically characterize the interaction between ancestral and modern day Aurora kinases and TPX2. Having assessed the degree of binding, activity assays were then performed to evaluate the potential allosteric effect of TPX2 on Aurora kinases.

The following observations were made. First, all resurrected Aurora ancestors were active on their own, with the phosphorylated form of these kinases being exceedingly more active than the dephosphorylated form, as expected. Second, $Aur_{ANC1}$ and $Aur_{ANC2}$ from the pre-canonical-TPX2 era could bind weakly but could not sense the allosteric effect of either the ancestral or the modern TPX2. Third, $Aur_{ANC3}$ and $Aur_{ANC4}$ could bind to ancestral and modern TPX2s with similar affinity, however, their response to the allosteric activation by TPX2 was incremental. Walking along the evolutionary timescale from younger to older canocical-TPX2-era Auroras ($Aur_{ANC3} \rightarrow Aur_{ANC4} \rightarrow Aur_{Amodern}$), the fold increase in kinase activity due to the presence of TPX2 went from 2→6→16 fold.

Remarkably, this suggested an adaptation on the energy landscape of Aurora whereby binding to TPX2 preceded the ability of Aurora kinase to "feel" the allosteric effects of TPX2. To further test this hypothesis, two novel mutant Aurora kinases were generated where binding to TPX2 was either diminished (Y199H/T288V $Aur_{Amodern}$) or enhanced (H199Y/T288V $Aur_{ANC3}$), but the response to TPX2 did not change. In other words, once saturated with TPX2, Y199H/T288V $Aur_{Amodern}$ felt the same increase in allosteric activation by TPX2. Analogously, H199Y/T288V $Aur_{ANC3}$, despite its increased binding affinity to TPX2, did not experience an increase in allosteric activation.

Through these experiments, Aurora ancestors were used to guide in the discovery of Y199 as a hotspot in the Aurora A-TPX2 interaction: Y199 contributed significantly to the heat of interaction between these partners, but it did not affect activation by allostery. Data herein thus provide a novel approach to studying coevolution of allostery. They also show that allosteric regulation by TPX2 followed phosphorylation as an additional mechanism of fine-tuning Aurora kinase activity. The data herein is also in line with the Kuriyan-Eisenberg-Ranagathan model whereby a small subset of amino acids contribute to the overall binding between partner proteins.

The results described herein were obtained using the following methods and materials.

Cloning and Purification of Aurora A Kinase

TEV-cleavable, His6-tagged Aurora A kinase, either modern (residues 122-403) or ancestral constructs (residues 133-403 in equivalent Aurora A numbering), were cloned into pET28a and expressed in Rosetta 2 (DE3) *E. coli* cells (Stratagene) for 13-15 h at 21° C. Cells were centrifuged at 5000 rpm for 15 min, resuspended in Buffer A, and sonicated in the presence of EDTA-free protease inhibitor cocktail and DNAse for 4 min (20 s on, 20 s off, 3.0 V). Lysates thus obtained were filtered using a 0.22 m filtering unit and passed through a NiNTA column. The protein was eluted at 20% Buffer B and Aurora A kinase fractions were pooled and TEV-cleaved overnight at 4° C. in a 5 kDa dialysis cassette that was exchanged against buffer C. Cleaved Aurora A was passed through another nickel column to remove any uncleaved reactants and His6-TEV-protease, and then purified to homogeneity through a 26/60 S200 size exclusion column. Protein thus produced was aliquoted and flash-frozen before being stored at −80° C. and used for kinase assays. Mutant modern Aurora $A^{122-403}$ T288V, ancestral Aurora $A^{133-403}$ T288V, modern Aurora $A^{122-403}$ Y199H/T288V and ancestral Aurora $A^{133-403}$ H199Y/T288V were also purified the same way.

The buffers used were: Buffer A: 50 mM TrisHCl (pH 8.0), 300 mM NaCl, 20 mM imidazole, 20 mM $MgCl_2$, 10% (v/v) glycerol. Buffer B: 50 mM TrisHCl (pH 8.0), 300 mM NaCl, 500 mM imidazole, 20 mM $MgCl_2$, 10% (v/v) glycerol. Buffer C: 20 mM TrisHCl (pH 7.0), 200 mM NaCl, 20 mM $MgCl_2$, 5 mM TCEP, 10% (v/v) glycerol. Typical yields were 8-10 mg of phosphorylated Aurora A and 20-25 mg of T288V mutants of Aurora A (including Y199H or H199Y mutants mentioned above), for either modern or ancestral protein per liter of *E. coli* culture.

Thrombin-cleavable, His6-tagged, GB1-fused TPX2, either modern or ancestral constructs (residues 1-45), were cloned into pET28a and expressed in Rosetta 2 (DE3) *E. coli* cells (Stratagene) for 5 h at 37° C. Cells were pelleted, resuspended, sonicated, centrifuged, and then passed through a first Ni2+ column as discussed above. The protein was eluted at 20% Buffer B and TPX2 fractions were pooled and thrombin-cleaved overnight at 4° C. in a 2 kDa dialysis cassette that was exchanged against buffer C. Cleaved TPX2 was passed through a tandem benzamidine-nickel column so as to remove any uncleaved reactants as well as thrombin, and then purified to homogeneity through a 26/60 S200 size exclusion column. TPX2 thus produced was aliquoted and flash-frozen before being stored at −80° C. and used for kinase assays. Typical yields were 50-60 mg of TPX2 per liter of *E. coli* culture.

In Vitro Kinase Assays

Aurora A, either modern or ancestral, either phosphorylated or T288V mutant protein was mixed with Kemptide (LRRASLG) in the absence or presence of TPX2 in kinase buffer (20 mM TrisHCl, 200 mM NaCl, 3% (v/v) glycerol, 20 mM $MgCl_2$, 1 mM TCEP, pH 7.50). TPX2 concentrations varied depending on the experiment. Please refer to the figure legends for more detail. The Kemptide substrate comprises the consensus sequence for Aurora A ([R/K/N]-R-X-[S/T]-B where B is any hydrophobic residue with the exception of Pro [34-36]. Kemptide was ordered through Genscript. The reaction was initiated with the addition of 5 mM ATP. 5 L timepoints were collected, resuspended in 10 L 6% (v/v) trichloroacetic acid (in water) to quench the reaction and neutralized with 50 L 100 mM $KH_2PO_4$, pH 8.0 to provide the appropriate pH for nucleotide separation. The mixture was then passed through a 0.22 m SpinX column to remove any protein precipitation. Reverse Phase High Performance Liquid Chromatography (RP-HPLC) and an ACE 5 C18-AR, 100 Å pore size column, was used to separate nucleotides (data not shown) as well as peptides. For peptide runs the optimal injection volume for analysis was 20 L. Nucleotide runs were routinely performed to ensure no unproductive hydrolysis was occurring during the experiment. An isocratic elution run in 100 mM $KH_2PO_4$, pH 6.0, was performed for this purpose. For the peptide runs, a gradient of 0-30% of elution buffer lasting 10 min at 0.4 ml/min was sufficient to separate phosphorylated from non-phosphorylated species. The running buffer was 0.1% TFA (v/v) in water whereas the elution buffer was 100% acetonitrile.

Isothermal Titration Calorimetry

All titrations were carried out using Nano ITC (TA instruments) and analyzed via the NanoAnalyze software using the independent fit model. Injectant was added in 1 L volume, every 180 s, with a constant stirring speed at 350 rpm and at 25° C. Prior to ITC titration, both protein and peptide were dialyzed/resuspended in 20 mM TrisHCl, 200 mM NaCl, 10% (v/v) glycerol, 1 mM TCEP, pH 7.50. The concentrations used for each of the runs are shown in FIGS. 35A-35C.

The results of the experiments herein are now described.

Results & Discussion

Aurora ancestors are active and precede TPX2 ancestors in the evolution timescale. Two modes of activation of Aurora A kinase are currently accepted: phosphorylation of a conserved activation loop residue (T288) and allosteric activation through binding of TPX2. Previously, it was shown that allosteric activation was preferentially skewed for the lowly-active, dephosphorylated form of Aurora A [31]. It is hypothesized that activation by TPX2 was a recent evolutionary adaptation in the regulation of Aurora A, one that followed phosphorylation. In the study herein, the evolution of allostery between these two proteins was investigated.

Figure 30A:
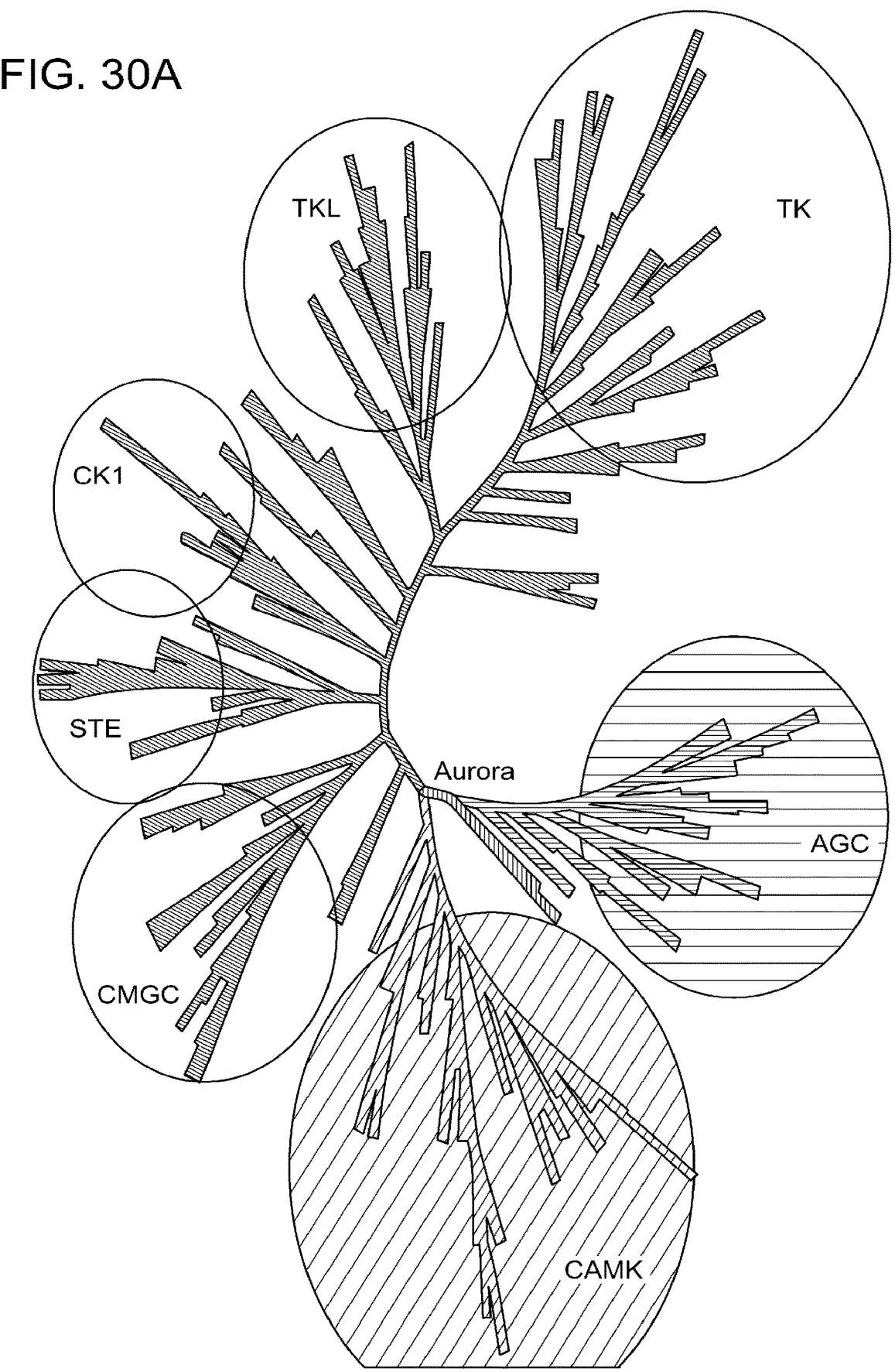
FIGS. 30A-30C are diagrams and plots showing ancestral Aurora A kinases have different activity.
Figure 30B:
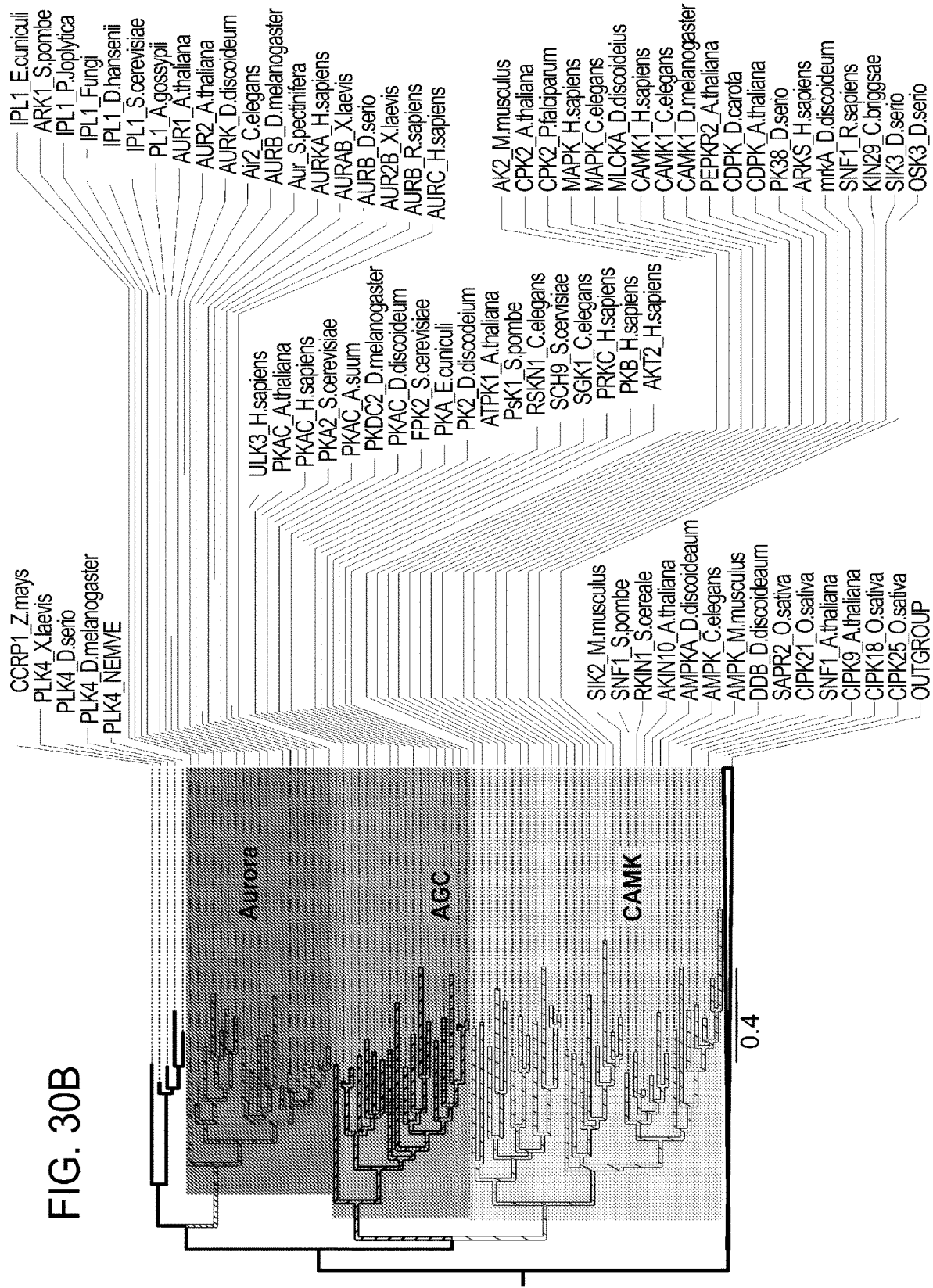

A closer look at the Manning tree (FIG. 30A), showed that Aurora kinases (red branch) were an old branch of the kinome and similar to the AGC family of proteins. Modern day Aurora sequences from various organisms were aligned and that alignment was used to generate a Bayesian-based phylogenetic tree (FIG. 30B). AGC and CAMK families were also used to increase the robustness of our alignment and XX was used as the outgroup. Subsequently, this tree was the input for PAML [32] to generate ancestral proteins. Similarly, to generate the TPX2 ancestors TPX2 from various organisms were aligned and WVD2 was used as the outgroup (FIG. 34).

Figure 30C:
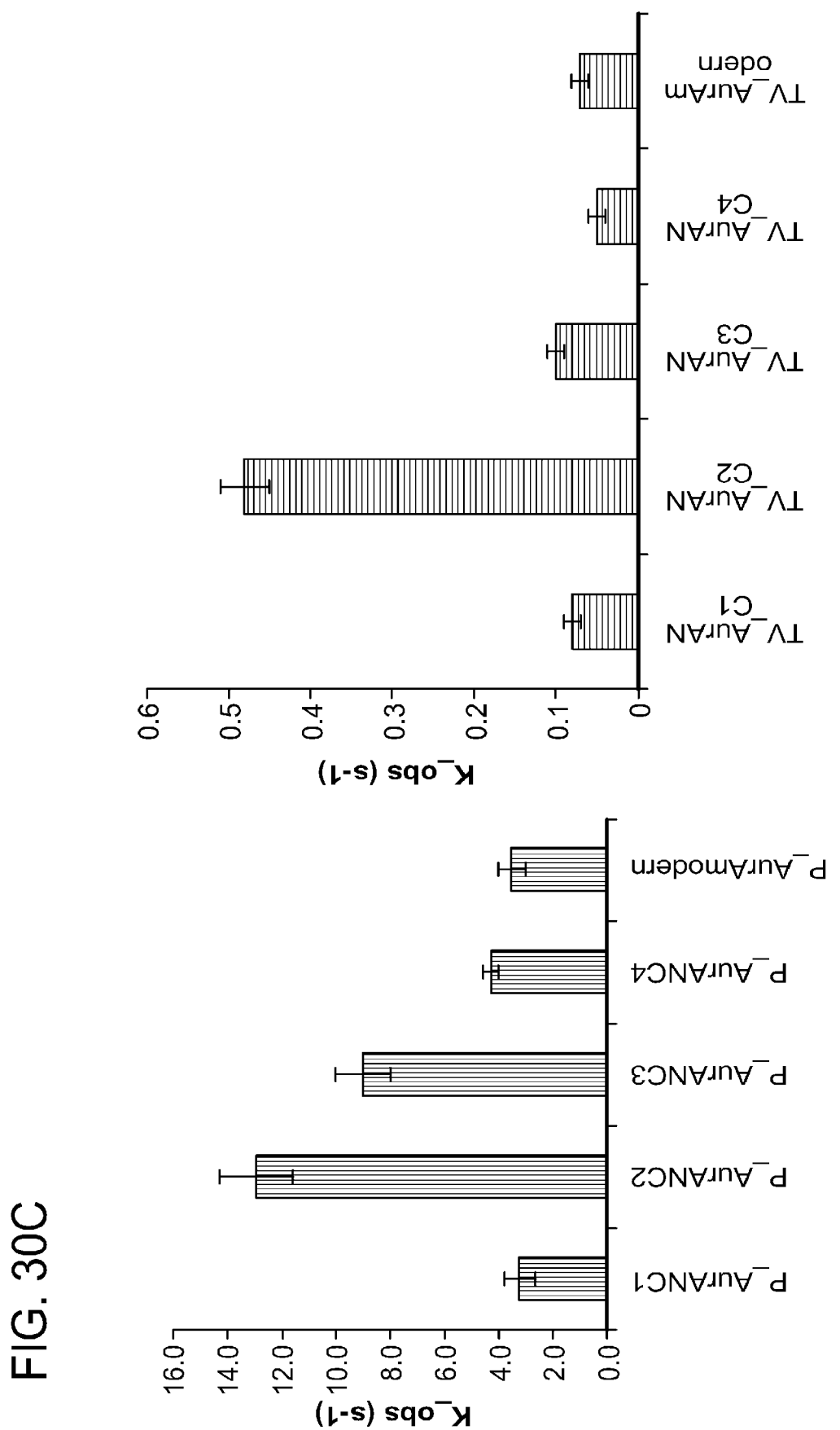

Four ancestors of Aurora kinase ($Aur_{ANC1-4}$) were resurrected. Reverse Phase High Performance Liquid Chromatography (RP-HPLC) was used to test the activity of these ancestors towards a model substrate peptide Kemptide (LR-RASLG, where the phosphorylated residue is bolded). These proteins had activities comparable to that of modern Aurora A, both in their phosphorylated forms (FIG. 30C, left) and their dephosphorylated-like form (T288V mutant Aurora kinases, FIG. 30C, right).

Aurora kinases are older and were present long before a canonical TPX2 protein existed (FIG. 31). In fact, there are currently no annotated TPX2 sequences in the database that pre-date the split between plants and animals. On the other hand, Aurora kinase sequences go back in time as far as Encephalitozoon cuniculi, a microsporidian—an intracellular parasite—and a single-cell Eukaryote informally known as a protist [33]. Thus, two of the four resurrected Aurora kinases ($Aur_{ANC1}$ and $Aur_{ANC2}$), belong to an evolutionary period prior to the appearance of a canonical TPX2 motif.

Aurora Ancestors That Postdate the Appearance of TPX2, Bind Tightly and are Allosterically Activated by TPX2

To test whether modern or ancestral Aurora or TPX2 proteins interact with each-other, Isothermal Titration calorimetry was used to quantify the extent of binding of these proteins (FIG. 32A and FIGS. 35A-35C). It was found that a weak, non-quantifiable interaction signal between Aurora ancestors that predated TPX2 ($Aur_{ANC1}$ and $Aur_{ANC2}$) and TPX2 from either ancestral sequence reconstruction or modern day protein. Curiously, younger Aurora ancestors ($Aur_{ANC3}$ and $Aur_{ANC4}$) that coincided in evolutionary time with the presence of TPX2, could bind tightly and rather indiscriminately to TPX2 with Kd's comparable to that of the modern protein. This seemed to suggest that the Aurora-TPX2 binding event did not significantly evolve past the plant-animal evolutionary split, which was when TPX2 first appeared.

Having established the existence of the Aurora-TPX2 interaction, next allosteric activation by TPX2, or perhaps lack thereof, was sought be quantified. Since the dynamic range of TPX2 on Aurora A is larger for its dephosphorylated-like form, T288V mutants of Aurora were used to observe the fold increase in activity of these mutants in the presence of TPX2. It was not expected that TPX2 ancestors ($TPX2_{ANC3-4}$) would allosterically increase the activity of Aurora ancestors of the pre-canonical-TPX2 era ($Aur_{ANC1}$ and $Aur_{ANC2}$). Conversely, it was expected that younger Aurora ancestors ($Aur_{ANC3}$ and $Aur_{ANC4}$) would respond to the allosteric effect of TPX2. This is in fact what was observed. $Aur_{ANC1}$ and $Aur_{ANC2}$ did not experience an increase in the rate of Kemptide phosphorylation in the presence of $TPX2_{ANC3}$, the TPX2 ancestor that was closest to them. On the other hand, younger Aurora ancestors experienced an incremental increase (2×→6×→16×) in allosteric activation by TPX2 the closer the move towards modern-day Aurora was (FIG. 32B).

Given that Aurora kinases that postdate the appearance of TPX2 ($Aur_{ANC3}$ and $Aur_{ANC4}$) can bind with similar affinity to TPX2 from different evolutionary periods, next the allosteric increase in rate by mismatched pairs of Aurora and TPX2 was investigated (FIG. 32C and FIG. 36). Even with the mismatched pairs, the effect of allosteric activation by TPX2 gradually increased moving from older to younger Auroras of the evolutionary timescale.

Initiation of an Aurora-TPX2 Binding Event Preceded Evolution of Aurora to Respond to the Allosteric Effect of TPX2.

The data thus far hinted at a model whereby a productive Aurora-TPX2 binding event needed to first be established for Aurora to later evolve to "feel" the allosteric activation effect of TPX2. To test this hypothesis a residue was looked for, a potential binding "hotspot" in Aurora that, once mutated, could either increase or decrease binding to TPX2 without effecting modulation in allosteric activation.

The structure of dephosphorylated Aurora A bound to TPX2 was used to identify key residues in Aurora A that made extensive contacts with TPX2. The evolution of these residues in time was looked at and it was determined Y199 was a potential TPX2-binding hotspot since this residue was a His in Aurora ancestors that predated the appearance of TPX2 (FIG. 33A; FIG. 33B; FIG. 33C). In fact, Y199H weakened the binding of modern Aurora A to modern TPX2 by approximately 20 fold, clearly suggesting the significant implication of the residue in the overall Aurora A-TPX2 heat of interaction (FIG. 33B). As hypothesized, once saturated with TPX2 however, this Y199H mutant was still capable of fully responding to the allosteric activation by modern TPX2 (FIG. 33B).

Analogously, the opposite mutation (H199Y) in $Aur_{ANC2}$ significantly increased the binding of a pre-TPX2 era Aurora ancestor to modern TPX2. However, although binding was more tightly established, $Aur_{ANC2}$ could not be allosterically activated by TPX2.

Conclusions

Exploitation of allostery in regulating protein kinase activity is particularly fascinating given that kinases share remarkable structural similarity, yet they are affected by allosteric modulators with astounding selectivity. This raises the question of how allosteric modulators and their target protein kinases coevolved.

In the present study, Ancestral Sequence Reconstruction and an *E. coli*-based expression system were used to resurrect ancestral Aurora kinase and TPX2 and study their coevolution. It was observed that Aurora ancestors that existed before the canonical TPX2 came around, bound very weakly to and were not allosterically activated by, TPX2. Aurora ancestors that existed around the same time that TPX2 existed, bound with similar affinity to TPX2 and were differentially regulated with the younger ANCs being more responsive to the effect of TPX2. These findings suggest a model whereby a binding event needed to occur prior to Aurora kinase evolving to respond to the allosteric effect of TPX2. This model suggests that allosteric regulation by TPX2 postdated phosphorylation as an additional mechanism in fine-tuning Aurora kinase activity.

References—Example 3

1. Fischer, S., K. W. Olsen, K. Nam, and M. Karplus, Unsuspected pathway of the allosteric transition in hemoglobin. Proc Natl Acad Sci USA, 2011. 108(14): p. 5608-13.
2. Hogg, R. C., B. Buisson, and D. Bertrand, Allosteric modulation of ligand-gated ion channels. Biochem Pharmacol, 2005. 70(9): p. 1267-76.
3. Benkovic, S. J. and S. Hammes-Schiffer, A perspective on enzyme catalysis. Science, 2003. 301(5637): p. 1196-202.
4. Eisenmesser, E. Z., O. Millet, W. Labeikovsky, D. M. Korzhnev, M. Wolf-Watz, D. A. Bosco, J. J. Skalicky, L. E. Kay, and D. Kern, Intrinsic dynamics of an enzyme underlies catalysis. Nature, 2005. 438(7064): p. 117-21.
5. Coyle, S. M., J. Flores, and W. A. Lim, Exploitation of latent allostery enables the evolution of new modes of MAP kinase regulation. Cell, 2013. 154(4): p. 875-87.
6. Kuriyan, J. and D. Eisenberg, The origin of protein interactions and allostery in colocalization. Nature, 2007. 450(7172): p. 983-90.
7. Halabi, N., O. Rivoire, S. Leibler, and R. Ranganathan, Protein sectors: evolutionary units of three-dimensional structure. Cell, 2009. 138(4): p. 774-86.
8. Reynolds, K. A., R. N. McLaughlin, and R. Ranganathan, Hot spots for allosteric regulation on protein surfaces. Cell, 2011. 147(7): p. 1564-75.
9. Suel, G. M., S. W. Lockless, M. A. Wall, and R. Ranganathan, Evolutionarily conserved networks of residues mediate allosteric communication in proteins. Nat Struct Biol, 2003. 10(1): p. 59-69.
10. Macurek, L., A. Lindqvist, D. Lim, M. A. Lampson, R. Klompmaker, R. Freire, C. Clouin, S. S. Taylor, M. B. Yaffe, and R. H. Medema, Polo-like kinase-1 is activated by aurora A to promote checkpoint recovery. Nature, 2008. 455(7209): p. 119-23.
11. Seki, A., J. A. Coppinger, C. Y. Jang, J. R. Yates, and G. Fang, Bora and the kinase Aurora a cooperatively activate the kinase Plk1 and control mitotic entry. Science, 2008. 320(5883): p. 1655-8.
12. Hannak, E., M. Kirkham, A. A. Hyman, and K. Oegema, Aurora-A kinase is required for centrosome maturation in *Caenorhabditis elegans*. J Cell Biol, 2001. 155(7): p. 1109-16.
13. Toji, S., N. Yabuta, T. Hosomi, S. Nishihara, T. Kobayashi, S. Suzuki, K. Tamai, and H. Nojima, The centrosomal protein Lats2 is a phosphorylation target of Aurora-A kinase. Genes Cells, 2004. 9(5): p. 383-97.
14. Abe, Y., M. Ohsugi, K. Haraguchi, J. Fujimoto, and T. Yamamoto, LATS2-Ajuba complex regulates gamma-tubulin recruitment to centrosomes and spindle organization during mitosis. FEBS Lett, 2006. 580(3): p. 782-8.
15. Mori, D., Y. Yano, K. Toyo-oka, N. Yoshida, M. Yamada, M. Muramatsu, D. Zhang, H. Saya, Y. Y. Toyoshima, K. Kinoshita, A. Wynshaw-Boris, and S. Hirotsune, NDEL1 phosphorylation by Aurora-A kinase is essential for centrosomal maturation, separation, and TACC3 recruitment. Mol Cell Biol, 2007. 27(1): p. 352-67.
16. Glover, D. M., M. H. Leibowitz, D. A. McLean, and H. Parry, Mutations in aurora prevent centrosome separation leading to the formation of monopolar spindles. Cell, 1995. 81(1): p. 95-105.
17. Giet, R., D. McLean, S. Descamps, M. J. Lee, J. W. Raff, C. Prigent, and D. M. Glover, *Drosophila* Aurora A kinase is required to localize D-TACC to centrosomes and to regulate astral microtubules. J Cell Biol, 2002. 156(3): p. 437-51.
18. Kapitein, L. C., E. J. Peterman, B. H. Kwok, J. H. Kim, T. M. Kapoor, and C. F. Schmidt, The bipolar mitotic kinesin Eg5 moves on both microtubules that it crosslinks. Nature, 2005. 435(7038): p. 114-8.
19. Tsai, M. Y. and Y. Zheng, Aurora A kinase-coated beads function as microtubule-organizing centers and enhance RanGTP-induced spindle assembly. Curr Biol, 2005. 15(23): p. 2156-63.
20. Koffa, M. D., C. M. Casanova, R. Santarella, T. Kocher, M. Wilm, and I. W. Mattaj, HURP is part of a Ran-dependent complex involved in spindle formation. Curr Biol, 2006. 16(8): p. 743-54.
21. Wong, J., R. Lerrigo, C. Y. Jang, and G. Fang, Aurora A regulates the activity of HURP by controlling the accessibility of its microtubule-binding domain. Mol Biol Cell, 2008. 19(5): p. 2083-91.
22. Zhang, X., S. C. Ems-McClung, and C. E. Walczak, Aurora A phosphorylates MCAK to control ran-dependent spindle bipolarity. Mol Biol Cell, 2008. 19(7): p. 2752-65.
23. Venoux, M., J. Basbous, C. Berthenet, C. Prigent, A. Fernandez, N. J. Lamb, and S. Rouquier, ASAP is a novel substrate of the oncogenic mitotic kinase Aurora-A: phosphorylation on Ser625 is essential to spindle formation and mitosis. Hum Mol Genet, 2008. 17(2): p. 215-24.
24. Sen, S., H. Zhou, and R. A. White, A putative serine/threonine kinase encoding gene BTAK on chromosome 20q13 is amplified and overexpressed in human breast cancer cell lines. Oncogene, 1997. 14(18): p. 2195-200.
25. Zhou, H., J. Kuang, L. Zhong, W. L. Kuo, J. W. Gray, A. Sahin, B. R. Brinkley, and S. Sen, Tumour amplified kinase STK15/BTAK induces centrosome amplification, aneuploidy and transformation. Nat Genet, 1998. 20(2): p. 189-93.
26. Kallioniemi, A., O. P. Kallioniemi, J. Piper, M. Tanner, T. Stokke, L. Chen, H. S. Smith, D. Pinkel, J. W. Gray, and F. M. Waldman, Detection and mapping of amplified DNA sequences in breast cancer by comparative genomic hybridization. Proc Natl Acad Sci USA, 1994. 91(6): p. 2156-60.
27. Jeng, Y. M., S. Y. Peng, C. Y. Lin, and H. C. Hsu, Overexpression and amplification of Aurora-A in hepatocellular carcinoma. Clin Cancer Res, 2004. 10(6): p. 2065-71.
28. Kufer, T., H. Silljé, R. Körner, O. Gruss, P. Meraldi, and E. Nigg, Human TPX2 is required for targeting Aurora-A kinase to the spindle. The Journal of cell biology, 2002. 158(4): p. 617-640.
29. Giubettini, M., I. A. Asteriti, J. Scrofani, M. De Luca, C. Lindon, P. Lavia, and G. Guarguaglini, Control of Aurora-A stability through interaction with TPX2. J Cell Sci, 2011. 124(Pt 1): p. 113-22.
30. Bayliss, R., T. Sardon, I. Vernos, and E. Conti, Structural basis of Aurora-A activation by TPX2 at the mitotic spindle. Mol Cell, 2003. 12(4): p. 851-62.
31. Zorba, A., V. Buosi, S. Kutter, N. Kern, F. Pontiggia, Y. J. Cho, and D. Kern, Molecular mechanism of Aurora A kinase autophosphorylation and its allosteric activation by TPX2. Elife, 2014. 3: p. e02667.
32. Yang, Z., PAML 4: phylogenetic analysis by maximum likelihood. Mol Biol Evol, 2007. 24(8): p. 1586-91.
33. Hedges, S. B., The origin and evolution of model organisms. Nat Rev Genet, 2002. 3(11): p. 838-49.
34. Ferrari, S., O. Marin, M. A. Pagano, F. Meggio, D. Hess, M. El-Shemerly, A. Krystyniak, and L. A. Pinna, Aurora-A site specificity: a study with synthetic peptide substrates. Biochem J, 2005. 390(Pt 1): p. 293-302.
35. Ohashi, S., G. Sakashita, R. Ban, M. Nagasawa, H. Matsuzaki, Y. Murata, H. Taniguchi, H. Shima, K. Furukawa, and T. Urano, Phospho-regulation of human protein kinase Aurora-A: analysis using anti-phospho-Thr288 monoclonal antibodies. Oncogene, 2006. 25(59): p. 7691-702.
36. Sardon, T., R. A. Pache, A. Stein, H. Molina, I. Vernos, and P. Aloy, Uncovering new substrates for Aurora A kinase. EMBO Rep, 2010. 11(12): p. 977-84.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of selecting an inhibitor of a target protein having an active site, the method comprising
measuring stability of an induced fit conformation (E*-I) of a candidate agent contacted to the active site of the target protein, wherein the measuring comprises
performing fast fluorescence binding kinetics of the binding of the candidate agent to the target protein, determining an observed binding rate ($k_{fast}$) and an induced fit binding rate ($k_{slow}$) from the fast fluorescence binding kinetics data as a function of candidate concentration, extracting from $k_{fast}$ and $k_{slow}$ microscope rate constants for conformational selection steps and induced fit steps in binding of the candidate agent to the target protein, and providing a kinetic binding scheme for the candidate agent to the target protein that includes the conformational selection steps and induced fit steps,
performing NMR titrations using 1H 15N or 1H 13C HSQC spectra on the target protein with and without bound candidate agent to determine flexible portions of the target protein which undergo conformational change upon binding of the candidate agent, and
performing in silico simulation combining the kinetic binding scheme determined by the fast fluorescence binding kinetics and the conformational change in the flexible portions of the target protein determined by the dynamic NMR, wherein the in silico simulation includes target protein motions on picosecond, microsecond and millisecond timescales to determine the flexibility of the target protein and the stability of the induced fit conformation (E*-I),
wherein the candidate agent is selected as the inhibitor of the target protein when the determined stability of the induced fit conformation (E*-I) of the candidate agent contacted to the active site increased by at least about 1 kcal/mol compared to a reference stability.

2. The method of claim 1, wherein the reference stability is the stability of an induced fit conformation (E*-I) of a pre-selected lead agent, a natural substrate of the protein, or a natural ligand of the protein or an analog thereof contacted to the active site of the protein.

3. The method of claim 1, further comprising
further optimizing the candidate agent by identifying a modified form of the candidate agent having an increased stability of an induced fit conformation of the modified form of candidate agent contacted to the active site of the protein relative to a second reference stability.

4. The method of claim 1, wherein the candidate agent induces a conformational change in the target protein during an induced fit step subsequent to primary binding of the agent to the target protein; and/or wherein contacting the target protein with the candidate agent results in an equilibrium that is far-shifted to an induced fit step or induced fit conformation.

5. The method of claim 1, wherein an induced fit step or induced fit conformation (E*-I) is identified by detecting a rate having a non-linear dependence on candidate agent concentration.

6. The method of claim 1, wherein the candidate agent is a pre-selected lead agent is selected from a conventional screen of a library of agents or from an in silico simulation.

7. The method of claim 1, wherein the candidate agent is a small molecule, polypeptide, peptide, or peptide mimetic.

8. The method of claim 1, wherein the fast fluorescence binding kinetics is a stopped flow experiment.

9. The method of claim 1, further comprising, prior to measuring the stability of the induced fit conformation (E*-I) of the candidate agent contacted to the active site of the protein, measuring an overall affinity of the candidate agent for the active site of the protein using fluorescence, ITC, or SPR, and wherein the binding scheme includes the overall affinity.

10. The method of claim 1, further comprising calculating ancestral protein sequences and incorporating evolution of amino acid changes into the in silico simulation.

11. The method of claim 1, wherein the target protein is a kinase.

12. The method of claim 11, wherein the kinase is an Aurora A kinase.

13. The method of claim 1, wherein binding in the fast fluorescence binding kinetics is monitored as changes in tryptophan fluorescence, and wherein the target protein in the NMR is labeled on tryptophan side chains.

14. The method of claim 1, further comprising performing one-dimensional NMR on target protein containing 19F-labeled tryptophans, and using the on-dimensional NMR data to reduce exchange broadening and improve sensitivity in the HSQC spectra.

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial sequence
<220> FEATURE:
<223> OTHER INFORMATION: standard peptide

<400> SEQUENCE: 1

Glu Ala Ile Tyr Ala Ala Pro Phe Ala Lys Lys Lys
1               5                   10
```